(12) United States Patent
Battista et al.

(10) Patent No.: US 7,582,649 B2
(45) Date of Patent: *Sep. 1, 2009

(54) HYDROXY ALKYL SUBSTITUTED 1,3,8-TRIAZASPIRO[4.5]DECAN-4-ONE DERIVATIVES USEFUL FOR THE TREATMENT OF ORL-1 RECEPTOR MEDIATED DISORDERS

(75) Inventors: Kathleen Battista, Ewing, NJ (US); Gilles Bignan, Bridgewater, NJ (US); Peter J. Connolly, New Providence, NJ (US); Allen B. Reitz, Lansdale, PA (US); Tina Morgan Ross, Royerford, PA (US); Malcolm Scott, Telford, PA (US); Steven A. Middleton, Flemington, NJ (US); Michael Orsini, Somerset, NJ (US)

(73) Assignee: Janssen Pharmaceutica, NV, Beerse (BE)

(*) Notice: Subject to any disclaimer, the term of this patent is extended or adjusted under 35 U.S.C. 154(b) by 481 days.

This patent is subject to a terminal disclaimer.

(21) Appl. No.: 11/242,654

(22) Filed: Oct. 4, 2005

(65) Prior Publication Data

US 2006/0030577 A1    Feb. 9, 2006

Related U.S. Application Data

(63) Continuation of application No. 10/656,934, filed on Sep. 5, 2003, now Pat. No. 7,081,463.

(60) Provisional application No. 60/409,134, filed on Sep. 9, 2002.

(51) Int. Cl.
*A61K 31/438* (2006.01)
*C07D 471/10* (2006.01)

(52) U.S. Cl. .......................... 514/278; 546/20
(58) Field of Classification Search ................. 514/278, 514/231.5; 546/20
See application file for complete search history.

(56) References Cited

U.S. PATENT DOCUMENTS

| | | | |
|---|---|---|---|
| 3,238,216 A | 3/1966 | Paul Adriaan | |
| 3,839,340 A | 10/1974 | Scharpf | |
| 4,329,353 A | 5/1982 | Stokbroekx et al. | |
| 5,739,336 A | 4/1998 | Weinhardt et al. | |
| 6,043,366 A | 3/2000 | Adam et al. | |
| 6,060,482 A | 5/2000 | Heine et al. | |
| 6,071,925 A | 6/2000 | Adam et al. | |
| 6,113,527 A | 9/2000 | Adam et al. | |
| 6,262,066 B1 | 7/2001 | Tulshian et al. | |
| 6,277,991 B1 | 8/2001 | Hohlweg et al. | |
| 6,777,421 B2 | 8/2004 | Jordan et al. | |
| 7,081,463 B2 * | 7/2006 | Battista et al. ............... | 514/278 |

2003/0109539 A1    6/2003   Jordan et al.

FOREIGN PATENT DOCUMENTS

| | | |
|---|---|---|
| EP | 0856514 B1 | 8/1998 |
| EP | 0921125 B1 | 6/1999 |
| EP | 0997464 B1 | 2/2005 |
| WO | 93/12789 | 8/1993 |
| WO | 95/07294 | 3/1995 |
| WO | 97/07212 | 2/1997 |
| WO | 99/59997 | 11/1999 |
| WO | 00/06545 | 2/2000 |
| WO | 01/07050 A1 | 2/2001 |
| WO | 01/36418 A1 | 5/2001 |
| WO | 01/39723 A2 | 6/2001 |
| WO | 01/46192 A1 | 6/2001 |
| WO | 01/94346 A1 | 12/2001 |
| WO | 01/96337 A1 | 12/2001 |
| WO | 02/083673 A1 | 10/2002 |
| WO | 02/085355 A1 | 10/2002 |
| WO | 03/010168 B1 | 6/2003 |

OTHER PUBLICATIONS

Kiesewetter, D. et al., "Syntheses and D.sub.2 Receptor Affinities of Derivatives of Spiperone Containing Aliphatic Halogens" *Appl. Radiat. Isot.*1986, 37(12), 1181-1188.

(Continued)

*Primary Examiner*—Charanjit S Aulakh

(57) ABSTRACT

The present invention is directed to novel hydroxy alkyl substituted 1,3,8-triazaspiro[4.5]decan-4-one derivatives of the general formula

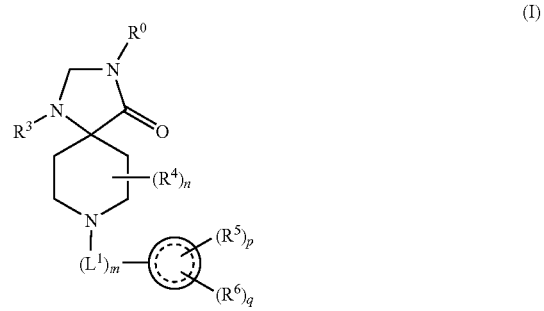

wherein all variables are as defined herein, useful in the treatment of disorders and conditions mediated by the ORL-1 G-protein coupled receptor. More particularly, the compounds of the present invention are useful in the treatment of disorders and conditions such as anxiety, depression, panic, dementia, mania, bipolar disorder, substance abuse, neuropathic pain, acute pain, chronic pain, migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorder (ADHD), Alzheimer's disease, for improved cognition or memory and for mood stabilization.

14 Claims, No Drawings

OTHER PUBLICATIONS

Chalon, S. et al "Iodoethylspiperone, a New Potential Agent for Exploration of Central Dopamine D.sub.2 Receptors: Synthesis and Preliminary In Vivo Study" *Nucl. Med. Bio.*1990, 17(4), 389-395.

Satyamurthy, N. et al., "3-(2'[.sup.18 F]Fluoroethyl)spiperone, a Potent Dopamine Antagonist: Synthesis, Structural Analysis and In-vivo Utilization in Humans" *Appl. Radiat. Isot.* 1990, 41(2), 113-129.

Rver S. et al., "High-Affinity, Non-Peptide Agonists for the ORL1 (Orphanin FQ/Nociceptin) Receptor" *J. Med. Chem.*, 2000, 43, 1329-1338.

Jenck, Francois et al., "A synthetic agonist at the orphanin FQ/nociceptin receptor ORL1: Anxiolytic profile in the rat," *PNAS*, Apr. 25, 2000, vol. 97, No. 9, pp. 4938-4953.

Thomsen, Christian et al. "(8-Naphthalen-1-ylmethyl-4-oxo-1-phenyl-1,3,8-triaza-spiro[4.5]- dec-3-yl- )-acetic acid methyl ester (NNC 63-0532) is a novel potent nociceptin receptor agonist," *British Journal of Pharmacology*, 2000,131, 903-908.

Calo, Girolamo, et al., Pharmacology of nociceptin and its receptor: a novel theurapeutic target. *Briti.J. Of Pharm.* 2000, 129, 1261-1283.

Poulain, R. et al., "From Hit to Lead. Combining Two Complementary Methods for Focused Library Design. Application to .mu. Opiate Ligands" *J. Med. Chem.* 2001, 44, 3378-3390.

Poulain, R. et al., "From Hit to Lead. Analyzing Structure--Profile Relationship" *J.Med. Chem.* 2001, 44, 3391-3401.

Ronzoni, Silvano et al., "Lead generation and lead optimization approaches in the discovery of selective, non-peptide ORL-1 receptor agonists and antagonists," *Exp. Opin. Ther. Patents*, 2001, (11) 4, pp. 525-546.

Calo, G. et al., "Pharmacological Profile of Nociceptin/Orphanin FQ Receptors" *Clinical and Experimental Pharmacology and Physiology*; 2002, 29, 223-228.

Zaveri, Nurulain, "Peptide and nonpeptide ligands for the nociceptin/orphanin FQ receptor ORL1: Research tools and potential therapeutic agents," *Life Sciences* 73 2003, pp. 663-678.

* cited by examiner

HYDROXY ALKYL SUBSTITUTED 1,3,8-TRIAZASPIRO[4.5]DECAN-4-ONE DERIVATIVES USEFUL FOR THE TREATMENT OF ORL-1 RECEPTOR MEDIATED DISORDERS

CROSS REFERENCE TO RELATED APPLICATIONS

This application is a continuation of U.S. application Ser. No. 10/656,934 filed on Sep. 5, 2003 now U.S. Pat. No. 7,081,463, which claims benefit of nonprovisional of U.S. Application No. 60/409,134 filed on Sep. 9, 2002, the complete disclosures of aforesaid applications being incorporated herein by reference.

FIELD OF THE INVENTION

The present invention is directed to novel hydroxy alkyl substituted 1,3,8-triazaspiro[4.5]decan-4-one derivatives useful in the treatment of disorders and conditions mediated by the ORL-1 G-protein coupled receptor. More particularly, the compounds of the present invention are useful in the treatment of disorders and conditions such as anxiety, depression, panic, mania, dementia, bipolar disorder, substance abuse, neuropathic pain, acute pain, chronic pain, migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorder (ADHD), Alzheimer's disease, for improved cognition or memory and for mood stabilization.

BACKGROUND OF THE INVENTION

The ORL-1 (orphan opioid receptor) G-protein coupled receptor, also known as the nociceptin receptor, was first reported in 1994, and was discovered based on its homology with the classic delta- (OP-1), mu- (OP-3), and kappa- (OP-2) opioid receptors. The ORL-1 G-protein coupled receptor does not bind opioid ligands with high affinity. The amino acid sequence of ORL-1 is 47% identical to the opioid receptors overall, and 64% identical in the transmembrane domains. (*Nature*, 1995, 377, 532.)

The endogenous ligand of ORL-1, known as nociceptin, a highly basic 17 amino acid peptide, was isolated from tissue extracts in 1995. It was named both nociceptin, because it increased sensitivity to pain when injected into mouse brain, and orphanin FQ (OFQ) because of the terminal phenylalanine (F) and glutamine (Q) residues that flank the peptide on the N- and C-termini respectively. (WO97/07212)

Nociceptin binding to ORL-1 receptors causes inhibition of cAMP synthesis, inhibition of voltage-gated calcium channels, and activation of potassium conductance. In vivo, nociceptin produces a variety of pharmacological effects that at times oppose those of the opioids, including hyperalgesia and inhibition of morphine-induced analgesia. Mutant mice lacking nociceptin receptors show better performance in learning and memory tasks. These mutant mice also have normal responses to painful stimuli.

The ORL-1 receptor is widely distributed/expressed throughout the human body, including in the brain and spinal cord. In the spinal cord, the ORL-1 receptor exists in both the dorsal and ventral horns, and precursor mRNA has been found in the superficial lamina of the dorsal horn, where primary afferent fibers of nociceptors terminate. Therefore, the ORL-1 has an important role in nociception transmission in the spinal cord. This was confirmed in recent studies wherein nociceptin, when given to mice by i.c.v. injection, induced hyperalgesia and decreased locomotor activity. (*Brit. J. Pharmacol.* 2000, 129, 1261.)

Ito, et al., in EP 0997464 disclose 1,3,8-triazaspiro[4.5]decan-4-one compounds as ORL-1 receptor agonists, useful as analgesics or the like in mammalian subjects.

Hohlweg et al., in PCT publication WO 01/36418 disclose triazaspirodecanones with high affinity for opioid receptor subtypes useful in the treatment of migraine, non-insulin dependent diabetes mellitus, sepsis, inflammation, incontinence and/or vasomotor disturbances.

Tulshian et al. in PCT publication WO00/06545 disclose high affinity ligands for the nociceptin receptor ORL-1 and the use of said compounds as nociceptin receptor inhibitors useful in the treatment of pain, anxiety, cough, asthma, depression and alcohol abuse.

Higgins, et al., in European Forum of Neuroscience 2000, Brighton, U.K., Jun. 24-28, 2000, Poster 077.22 disclosed, 8-[(1R,3aS)-2,3,3a,4,5,6-hexahydro-1H-phenalen-1-yl]-1-phenyl-1,3,8-triazaspiro[4.5]decan-4-one useful as cognition enhancers.

We now describe novel small molecule modulators of the ORL-1 receptor, useful for the treatment of disorders and conditions mediated by the ORL-1 receptor, such as anxiety, depression, panic, dementia, mania, bipolar disorder, substance abuse, neuropathic pain, acute pain, chronic pain, migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorders (ADHD), Alzheimer's disease, for improved cognition or memory and for mood stabilization.

SUMMARY OF THE INVENTION

The present invention is directed to compounds of the general formula (I)

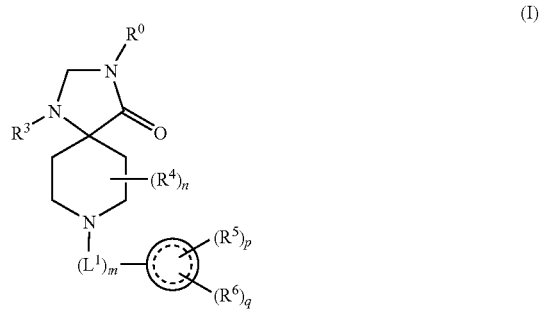

wherein
R$^0$ is selected from the group consisting of

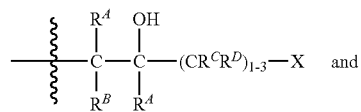

and

-continued

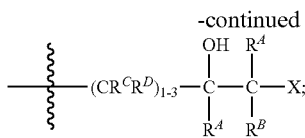

each $R^A$ and $R^B$ is independently selected from the group consisting of hydrogen and $C_{1-4}$alkyl;

each $R^C$ and $R^D$ is independently selected from the group consisting of hydrogen, hydroxy, carboxy, $C_{1-4}$alkyl, $C_{1-4}$alkoxy, nitro, cyano, $N(R^E)_2$, aryl, $arC_{1-4}$alkyl, heteroaryl or heterocycloalkyl; wherein the aryl, $arC_{1-4}$alkyl, heteroaryl or heterocycloalkyl substituent is optionally substituted with one or more substituents independently selected from hydroxy, carboxy, $C_{1-4}$alkyl, $C_{1-4}$alkoxy, nitro, cyano or $N(R^E)_2$;

each $R^E$ is independently selected from the group consisting of hydrogen and $C_{1-4}$alkyl;

X is selected from the group consisting of —$NR^1R^2$, —C(O)—$NR^1R^2$, —$NR^1$—C(O)—$R^2$, —$OR^1$, —$SR^1$, —$SOR^1$, —$SO_2R^1$, —S—($C_{2-4}$alkyl)-$NR^1R^2$, —S—($C_{2-4}$alkyl)-$NR^1$—C(O)O—C(CH$_3$)$_3$, —SO—($C_{1-4}$alkyl)-$NR^1R^2$ and —$SO_2$—($C_{1-4}$alkyl)-$NR^1R^2$; wherein the alkyl portion of the —S—($C_{2-4}$alkyl)-$NR^1R^2$, —SO—($C_{1-4}$alkyl)-$NR^1R^2$ or —$SO_2$—($C_{1-4}$alkyl)-$NR^1R^2$ group is optionally substituted with one or more substituents independently selected from carboxy, hydroxy, hydroxy$C_{1-4}$alkyl, $C_{1-4}$alkyl, $C_{1-4}$alkoxycarbonyl or —$CONR^1R^2$;

each $R^1$ and $R^2$ is independently selected from the group consisting of hydrogen, $C_{1-8}$alkyl, $C_{1-8}$alkoxy, $C_{1-8}$alkoxycarbonyl, cycloalkyl, cycloalkyl-$C_{1-4}$alkyl, partially unsaturated carbocyclyl, partially unsaturated carbocyclyl-$C_{1-4}$alkyl, aryl, $arC_{1-4}$alkyl, $arC_{1-4}$alkoxy, heteroaryl, heteroaryl-$C_{1-4}$alkyl, heterocycloalkyl, heterocycloalkyl-$C_{1-4}$alkyl, —C(O)—$C_{1-6}$alkyl, —C(O)-aryl, —C(O)-$arC_{1-4}$alkyl, —C(O)-heteroaryl, —C(O)-heterocycloalkyl, —C(O)O-cycloalkyl and —C(O)O-aryl, —C(O)O-$arC_{1-4}$alkyl, —C(O)O-(partially unsaturated carbocyclyl), C(O)-heteroaryl, —C(O)O-heterocycloalkyl; wherein the $C_{1-8}$alkyl, cycloalkyl, partially unsaturated carbocyclyl, aryl, $arC_{1-4}$alkyl, heteroaryl or heterocycloalkyl group, whether alone or part of a substituent group, is optionally substituted with one or more substituents independently selected from halogen, hydroxy, carboxy, $C_{1-4}$alkyl, $C_{1-4}$alkoxy, trifluoromethyl, trifluoromethoxy, nitro, cyano, C(O)—$C_{1-4}$alkyl, $C_{1-4}$alkoxycarbonyl, $N(R^E)_2$, $N(R^E)_2$—$C_{1-4}$alkyl, $N(R^E)$—C(O)C(CH$_3$)$_3$, —$C_{1-4}$alkyl-$N(R^E)$C(O)O—$C_{1-4}$alkyl and —$N(R^E)$C(O)O—$C_{1-4}$alkyl, aryl, aryloxy, cycloalkyl, heteroaryl, aryl substituted heteroarylaminosulfonyl or $C_{1-6}$alkylthio;

alternatively when $R^1$ and $R^2$ are both bound to the same nitrogen atom, $R^1$ and $R^2$ are taken together with the nitrogen atom to which they are bound to form a heteroaryl or heterocycloalkyl group; wherein the heteroaryl or heterocycloalkyl group is optionally substituted with one or more substituents independently selected from halogen, hydroxy, carboxy, $C_{1-4}$alkyl, hydroxy substituted $C_{1-4}$alkyl, $C_{1-4}$alkoxy, $C_{1-4}$alkoxycarbonyl, trifluoromethyl, trifluoromethoxy, nitro, cyano, $N(R^E)_2$, aryl, $arC_{1-4}$alkyl, heteroaryl, heterocycloalkyl, di($C_{1-6}$)alkylamino-carbonyl, $C_{1-4}$alkoxycarbonyl-$N(R^E)$— or arylamino-$C_{1-4}$alkyl; wherein the aryl, $arC_{1-4}$alkyl, heteroaryl or heterocycloalkyl substituent is optionally further substituted with one or more substituents independently selected from halogen, hydroxy, carboxy, $C_{1-4}$alkyl, $C_{1-4}$alkoxy, trifluoromethyl, trifluoromethoxy, nitro, cyano, $N(R^E)_2$, phenyl or substituted phenyl; wherein the substituents on the phenyl are one or more independently selected from halogen, hydroxy, carboxy, $C_{1-4}$alkyl, $C_{1-4}$alkoxy, trifluoromethyl, trifluoromethoxy, nitro, cyano or $N(R^E)_2$;

$R^3$ is selected from the group consisting of aryl, $arC_{1-6}$alkyl and heteroaryl; wherein the aryl, $arC_{1-6}$alkyl or heteroaryl group is optionally substituted with one or more substituents independently selected from halogen, hydroxy, carboxy, $C_{1-4}$alkyl, $C_{1-4}$alkoxy, trifluoromethyl, trifluoromethoxy, nitro, cyano or $N(R^E)_2$;

n is an integer from 0 to 2;

$R^4$ is selected from the group consisting of hydroxy, $C_{1-4}$alkyl and hydroxy substituted $C_{1-4}$alkyl;

m is an integer from 0 to 1;

$L^1$ is selected from the group consisting of $C_{1-6}$alkyl and $C_{3-6}$alkenyl; wherein the double bond of the $C_{3-6}$alkenyl group is at least one carbon atom removed from the attachment point to the N atom; and wherein the $C_{1-6}$alkyl or $C_{3-6}$alkenyl group is optionally substituted with one to two substituents independently selected from hydroxy, fluoro, $C_{1-6}$alkyl, fluorinated $C_{1-6}$alkyl or $C_{1-6}$alkoxy;

is selected from the group consisting of cycloalkyl, partially unsaturated carbocyclyl, aryl, heteroaryl and heterocycloalkyl;

p is an integer from 0 to 5;

$R^5$ is selected from the group consisting of hydroxy, carboxy, halogen, $C_{1-6}$alkyl, hydroxy substituted $C_{1-6}$alkyl, $C_{1-6}$alkoxy, nitro, cyano, $NR^1R^2$, trifluoromethyl, trifluoromethoxy, $C_{1-4}$alkoxycarbonyl, —SO—$NR^1R^2$, —$S_2$—$NR^1R^2$ and —C(O)—$NR^1R^2$;

q is an integer from 0 to 1;

$R^6$ is selected from the group consisting of -($L^2$)$_{0-1}$-$R^7$;

$L^2$ is selected from the group consisting of —$C_{1-6}$alkyl-, —$C_{2-4}$alkenyl-, —$C_{2-6}$alkynyl-, —O—, —S—, —NH—, —N($C_{1-4}$alkyl)-, —$C_{1-6}$alkyl-O—, —$C_{1-6}$alkyl-S—, —O—$C_{1-6}$alkyl-, —S—$C_{1-6}$alkyl-, —O—$C_{2-6}$alkyl-O—, —S—$C_{2-6}$alkyl-S—, —$SO_2$—, —$SO_2$NH—, —$SO_2$N($C_{1-4}$alkyl)-, —NH—$SO_2$—, —N($C_{1-4}$alkyl)-$SO_2$—, —C(O)O— and —O—C(O)—;

$R^7$ is selected from the group consisting of aryl, partially unsaturated carbocyclyl, cycloalkyl, heteroaryl and heterocycloalkyl; wherein the aryl, partially unsaturated carbocyclyl, cycloalkyl, heteroaryl or heterocycloalkyl group is optionally substituted with one or more substituents independently selected from hydroxy, carboxy, halogen, $C_{1-6}$alkyl, $C_{1-6}$alkoxy, nitro, cyano, $N(R^E)_2$, trifluoromethyl, trifluoromethoxy, $C_{1-4}$alkoxycarbonyl, —$SO_2$—$N(R^E)_2$ and —C(O)—$N(R^E)_2$;

or a pharmaceutically acceptable salt thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating disorders and conditions mediated by the ORL-1 receptor in a subject in need thereof comprising administering to the subject a therapeutically effective amount of any of the compounds or pharmaceutical compositions described above.

An example of the invention is a method of treating a condition selected from the group consisting of anxiety, depression, panic, mania, dementia, bipolar disorder, substance abuse, neuropathic pain, acute pain, chronic pain migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorder (ADHD), Alzheimer's disease, for improved cognition or memory and for mood stabilization, in a subject in need thereof comprising administering to the subject a therapeutically effective amount of any of the compounds or pharmaceutical compositions described above.

Another example of the invention is the use of any of the compounds described herein in the preparation of a medicament for treating: (a) anxiety, (b) depression, (c) panic, (d) mania, (e) dementia, (f) bipolar disorder, (g) substance abuse (h) neuropathic pain, (i) acute pain, (j) chronic pain, (k) migraine, (l) asthma, (m) cough, (n) psychosis, (o) schizophrenia, (p) epilepsy, (q) hypertension, (r) obesity, (s) eating disorders, (t) cravings, (u) diabetes), (v) cardiac arrhythmia, (w) irritable bowel syndrome, (x) Crohn's disease, (uy) urinary incontinence, (z) adrenal disorders, (aa) attention deficit disorder (ADD), (bb) attention deficit hyperactivity disorder (ADHD), (cc) Alzheimer's disease, for (dd) improved cognition, (ee) improved memory and (ff) mood stabilization, in a subject in need thereof.

The present invention is further directed to a compound of formula (E)

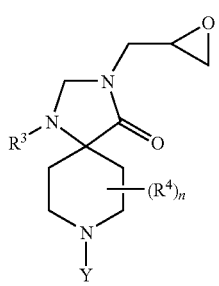

wherein $R^3$ is selected from the group consisting of aryl, ar$C_{1-6}$alkyl and heteroaryl; wherein the aryl, ar$C_{1-6}$alkyl or heteroaryl group is optionally substituted with one or more substituents independently selected from halogen, hydroxy, carboxy, $C_{1-4}$alkyl, $C_{1-4}$alkoxy, trifluoromethyl, trifluoromethoxy, nitro, cyano or $N(R^E)_2$;

wherein each $R^E$ is independently selected from hydrogen or $C_{1-4}$alkyl;

n is an integer from 0 to 2;

$R^4$ is selected from the group consisting of hydroxy, $C_{1-4}$alkyl and hydroxy substituted $C_{1-4}$alkyl;

Y is selected from the group consisting of hydrogen, $C_{1-4}$alkyl, t-butoxycarbonyl and

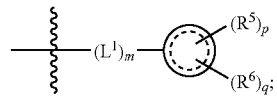

m is an integer from 0 to 1;

$L^1$ is selected from the group consisting of $C_{1-6}$alkyl and $C_{3-6}$alkenyl; wherein the double bond of the $C_{3-6}$alkenyl group is at least one carbon atom removed from the attachment point to the N atom; and wherein the $C_{1-6}$alkyl or $C_{3-6}$alkenyl group is optionally substituted with one to two substituents independently selected from hydroxy, fluoro, $C_{1-6}$alkyl, fluorinated $C_{1-6}$alkyl or $C_{1-6}$alkoxy;

is selected from the group consisting of cycloalkyl, partially unsaturated carbocyclyl, aryl, heteroaryl and heterocycloalkyl;

p is an integer from 0 to 5;

$R^5$ is selected from the group consisting of hydroxy, carboxy, halogen, $C_{1-6}$alkyl, hydroxy substituted $C_{1-6}$alkyl, $C_{1-6}$alkoxy, nitro, cyano, $NR^1R^2$, trifluoromethyl, trifluoromethoxy, $C_{1-4}$alkoxycarbonyl, —SO—$NR^1R^2$, —$SO_2$—$NR^1R^2$ and —C(O)—$NR^1R^2$;

q is an integer from 0 to 1;

$R^6$ is selected from the group consisting of -$(L^2)_{0-1}$-$R^7$;

$L^2$ is selected from the group consisting of —$C_{1-6}$alkyl-, —$C_{2-4}$alkenyl-, —$C_{2-6}$alkynyl-, —O—, —S—, —NH—, —N($C_{1-4}$alkyl)-, —$C_{1-6}$alkyl-O—, —$C_{1-6}$alkyl-S—, —O—$C_{1-6}$alkyl-, —S—$C_{1-6}$alkyl-, —O—$C_{2-6}$alkyl-O—, —S—$C_{2-6}$alkyl-S—, —$SO_2$—, —$SO_2$NH—, —$SO_2$N($C_{1-4}$alkyl)-, —NH—$SO_2$—, —N($C_{1-4}$alkyl)-$SO_2$—, —C(O)—O— and —O—C(O)—;

$R^7$ is selected from the group consisting of aryl, partially unsaturated carbocyclyl, cycloalkyl, heteroaryl and heterocycloalkyl; wherein the aryl, partially unsaturated carbocyclyl, cycloalkyl, heteroaryl or heterocycloalkyl group is optionally substituted with one or more substituents independently selected from hydroxy, carboxy, halogen, $C_{1-6}$alkyl, $C_{1-6}$alkoxy, nitro, cyano, $N(R^E)_2$, trifluoromethyl, trifluoromethoxy, $C_{1-4}$alkoxycarbonyl, —$SO_2$—$N(R^E)_2$ and —C(O)—$N(R^E)_2$;

or a pharmaceutically acceptable salt thereof.

DETAILED DESCRIPTION OF THE INVENTION

The present invention provides hydroxy alkyl substituted 1,3,8-triazaspiro[4.5]decan-4-one derivatives useful for the treatment of disorders and conditions mediated by the ORL-1 receptor. More particularly, the compounds of the present invention are of the general formula (I)

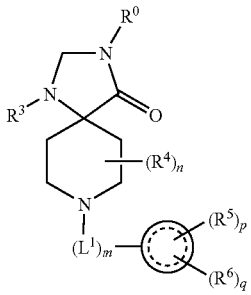

wherein $R^0$, $R^3$, n, $R^4$, m, $L^1$,

, p, $R^5$, q and $R^6$ are as herein defined, or a pharmaceutically acceptable salt thereof. The compounds of formula (I) are useful in the treatment of disorders mediated by the ORL-1 receptor. The compound of formula (I) are further useful for the treatment of disorders associated with the adrenal gland.

More particularly, the compound of formula (I) are useful in the treatment of anxiety, depression, panic, mania, dementia, bipolar disorder, substance abuse, neuropathic pain, acute pain, chronic pain migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorder (ADHD), Alzheimer's disease, for improved cognition or memory and for mood stabilization. Preferably, the compounds of formula (I) are useful in the treatment of anxiety, depression, substance abuse, neuropathic pain, acute pain, chronic pain, migraine, cough, hypertension, cardiac arrhythmia, irritable bowel syndrome and Crohn's disease.

In an embodiment of the present invention are compounds of formula (I) wherein $R^0$ is selected from the group consisting of

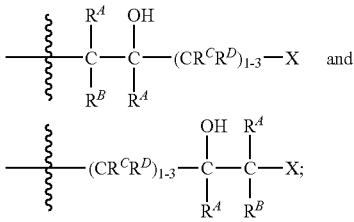

each $R^A$ and $R^B$ is independently selected from the group consisting of hydrogen and $C_{1-4}$alkyl;

each $R^C$ and $R^D$ is independently selected from the group consisting of hydrogen, hydroxy, carboxy, $C_{1-4}$alkyl, $C_{1-4}$alkoxy, nitro, cyano, $N(R^E)_2$, aryl, $arC_{1-4}$alkyl, heteroaryl or heterocycloalkyl; wherein the aryl, $arC_{1-4}$alkyl, heteroaryl or heterocycloalkyl substituent is optionally substituted with one or more substituents independently selected from hydroxy, carboxy, $C_{1-4}$alkyl, $C_{1-4}$alkoxy, nitro, cyano or $N(R^E)_2$;

each $R^E$ is independently selected from the group consisting of hydrogen and $C_{1-4}$alkyl;

X is selected from the group consisting of —$NR^1R^2$, —C(O)—$NR^1R^2$, —$NR^1$—C(O)—$R^2$, —$OR^1$, —$SR^1$, —$SOR^1$, —$SO_2R^1$, —S—($C_{2-4}$alkyl)-$NR^1R^2$, —S—($C_{2-4}$alkyl)-$NR^1$—C(O)O—C(CH$_3$)$_3$, —SO—($C_{1-4}$alkyl)-$NR^1R^2$ and —$SO_2$—($C_{1-4}$alkyl)-$NR^1R^2$; wherein the alkyl portion of the —S—($C_{2-4}$alkyl)-$NR^1R^2$, —SO—($C_{1-4}$alkyl)-$NR^1R^2$ or —$SO_2$—($C_{1-4}$alkyl)-$NR^1R^2$ group is optionally substituted with one or more substituents independently selected from carboxy, hydroxy, hydroxy$C_{1-4}$alkyl, $C_{1-4}$alkyl, $C_{1-4}$alkoxycarbonyl or —$CONR^1R^2$;

each $R^1$ and $R^2$ is independently selected from the group consisting of hydrogen, $C_{1-8}$alkyl, $C_{1-8}$alkoxy, cycloalkyl, cycloalkyl-$C_{1-4}$alkyl, partially unsaturated carbocyclyl, aryl, $arC_{1-4}$alkyl, $arC_{1-4}$alkoxy, heteroaryl, heteroaryl-$C_{1-4}$alkyl, heterocycloalkyl, heterocycloalkyl-$C_{1-4}$alkyl, —C(O)—$C_{1-6}$alkyl, —C(O)-aryl, —C(O)-$arC_{1-4}$alkyl, —C(O)-heteroaryl and —C(O)-heterocycloalkyl; wherein the $C_{1-8}$alkyl, cycloalkyl, partially unsaturated carbocyclyl, aryl, $arC_{1-4}$alkyl, heteroaryl or heterocycloalkyl group, whether alone or part of a substituent group, is optionally substituted with one or more substituents independently selected from halogen, hydroxy, carboxy, $C_{1-4}$alkyl, $C_{1-4}$alkoxy, trifluoromethyl, trifluoromethoxy, nitro, cyano, C(O)—$C_{1-4}$alkyl, $C_{1-4}$alkoxycarbonyl, $N(R^E)_2$, $N(R^E)_2$—$C_{1-4}$alkyl, $N(R^E)$—C(O)C(CH$_3$)$_3$, aryl, aryloxy, cycloalkyl, heteroaryl, aryl substituted heteroarylaminosulfonyl or $C_{1-6}$alkylthio;

alternatively when $R^1$ and $R^2$ are both bound to the same nitrogen atom, $R^1$ and $R^2$ are taken together with the nitrogen atom to which they are bound to form a heteroaryl or heterocycloalkyl group; wherein the heteroaryl or heterocycloalkyl group is optionally substituted with one or more substituents independently selected from halogen, hydroxy, carboxy, $C_{1-4}$alkyl, $C_{1-4}$alkoxy, $C_{1-4}$alkoxycarbonyl, trifluoromethyl, trifluoromethoxy, nitro, cyano, $N(R^E)_2$, aryl, $arC_{1-4}$alkyl, heteroaryl, heterocycloalkyl, di($C_{1-6}$)alkylamino-carbonyl, t-butoxycarbonyl or arylamino-$C_{1-4}$alkyl; wherein the aryl, $arC_{1-4}$alkyl, heteroaryl or heterocycloalkyl substituent is optionally further substituted with one or more substituents independently selected from halogen, hydroxy, carboxy, $C_{1-4}$alkyl, $C_{1-4}$alkoxy, trifluoromethyl, trifluoromethoxy, nitro, cyano, $N(R^E)_2$ or substituted phenyl; wherein the substituents on the phenyl are one or more independently selected from halogen, hydroxy, carboxy, $C_{1-4}$alkyl, $C_{1-4}$alkoxy, trifluoromethyl, trifluoromethoxy, nitro, cyano or $N(R^E)_2$;

$R^3$ is selected from the group consisting of aryl, $arC_{1-6}$alkyl and heteroaryl; wherein the aryl, $arC_{1-6}$alkyl or heteroaryl group is optionally substituted with one or more substituents independently selected from halogen, hydroxy, carboxy, $C_{1-4}$alkyl, $C_{1-4}$alkoxy, trifluoromethyl, trifluoromethoxy, nitro, cyano or $N(R^E)_2$;

n is an integer from 0 to 2;

$R^4$ is selected from the group consisting of hydroxy, $C_{1-4}$alkyl and hydroxy substituted $C_{1-4}$alkyl;

m is an integer from 0 to 1;

$L^1$ is selected from the group consisting of $C_{1-6}$alkyl and $C_{3-6}$alkenyl; wherein the double bond of the $C_{3-6}$alkenyl group is at least one carbon atom removed from the attachment point to the N atom; and wherein the $C_{1-6}$alkyl or $C_{3-6}$alkenyl group is optionally substituted with one to two substituents independently selected from hydroxy, fluoro, $C_{1-6}$alkyl, fluorinated $C_{1-6}$alkyl or $C_{1-6}$alkoxy;

is selected from the group consisting of cycloalkyl, partially unsaturated carbocyclyl, aryl, heteroaryl and heterocycloalkyl;

p is an integer from 0 to 5;

$R^5$ is selected from the group consisting of hydroxy, carboxy, halogen, $C_{1-6}$alkyl, $C_{1-6}$alkoxy, nitro, cyano, $NR^1R^2$, trifluoromethyl, trifluoromethoxy, $C_{1-4}$alkoxycarbonyl, —SO—$NR^1R^2$, —$SO_2$—$NR^1R^2$ and —C(O)—$NR^1R^2$;

q is an integer from 0 to 1;

$R^6$ is selected from the group consisting of -$(L^2)_{0-1}$-$R^7$;

$L^2$ is selected from the group consisting of —$C_{1-6}$alkyl-, —$C_{2-4}$alkenyl-, -$C_{2-6}$alkynyl-, —O—, —S—, —NH—, —N($C_{1-4}$alkyl)-, —$C_{1-6}$alkyl-O—, —$C_{1-6}$alkyl-S—, —O—$C_{1-6}$alkyl-, —S—$C_{1-6}$alkyl-, —O—$C_{2-6}$alkyl-O—, —S—$C_{2-6}$alkyl-S—, —$SO_2$—, —$SO_2$NH—, —$SO_2$N($C_{1-4}$alkyl)-, —NH—$SO_2$—, —N($C_{1-4}$alkyl)-$SO_2$—, —C(O)—O— and —O—C(O)—;

$R^7$ is selected from the group consisting of aryl, partially unsaturated carbocyclyl, cycloalkyl, heteroaryl and heterocycloalkyl; wherein the aryl, partially unsaturated carbocyclyl, cycloalkyl, heteroaryl or heterocycloalkyl group is optionally substituted with one or more substituents independently selected from hydroxy, carboxy, halogen, $C_{1-6}$alkyl, $C_{1-6}$alkoxy, nitro, cyano, $N(R^E)_2$, trifluoromethyl, trifluoromethoxy, $C_{1-4}$alkoxycarbonyl, —$SO_2$—$N(R^E)_2$ and —C(O)—$N(R^E)_2$;

and pharmaceutically acceptable salts thereof.

In an embodiment of the present invention are compounds of the formula (E)

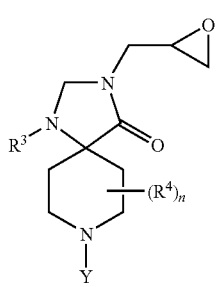

(E)

wherein $R^3$, n, $R^4$, and Y are as herein defined, or a pharmaceutically acceptable salt thereof. The compounds of formula (E) are useful as intermediates in the preparation of compounds of formula (I).

In an embodiment of the present invention are compounds of formula (E) wherein $R^3$ is selected from the group consisting of aryl, ar$C_{1-6}$alkyl and heteroaryl; wherein the aryl, ar$C_{1-6}$alkyl or heteroaryl group is optionally substituted with one or more substituents independently selected from halogen, hydroxy, carboxy, $C_{1-4}$alkyl, $C_{1-4}$alkoxy, trifluoromethyl, trifluoromethoxy, nitro, cyano or $N(R^E)_2$; wherein each $R^E$ is independently selected from hydrogen or $C_{1-4}$alkyl;

n is an integer from 0 to 2;

$R^4$ is selected from the group consisting of hydroxy, $C_{1-4}$alkyl and hydroxy substituted $C_{1-4}$alkyl;

Y is selected from the group consisting of hydrogen, $C_{1-4}$alkyl, t-butoxycarbonyl and

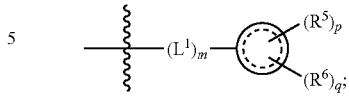

m is an integer from 0 to 1;

$L^1$ is selected from the group consisting of $C_{1-6}$alkyl and $C_{3-6}$alkenyl; wherein the double bond of the $C_{3-6}$alkenyl group is at least one carbon atom removed from the attachment point to the N atom; and wherein the $C_{1-6}$alkyl or $C_{3-6}$alkenyl group is optionally substituted with one to two substituents independently selected from hydroxy, fluoro, $C_{1-6}$alkyl, fluorinated $C_{1-6}$alkyl or $C_{1-6}$alkoxy;

is selected from the group consisting of cycloalkyl, partially unsaturated carbocyclyl, aryl, heteroaryl and heterocycloalkyl;

p is an integer from 0 to 5;

$R^5$ is selected from the group consisting of hydroxy, carboxy, halogen, $C_{1-6}$alkyl, $C_{1-6}$alkoxy, nitro, cyano, $NR^1R^2$, trifluoromethyl, trifluoromethoxy, $C_{1-4}$alkoxycarbonyl, —SO—$NR^1R^2$, —$SO_2$—$NR^1R^2$ and —C(O)—$NR^1R^2$;

q is an integer from 0 to 1;

$R^6$ is selected from the group consisting of -$(L^2)_{0-1}$-$R^7$;

$L^2$ is selected from the group consisting of —$C_{1-6}$alkyl-, —$C_{2-4}$alkenyl-, —$C_{2-6}$alkynyl-, —O—, —S—, —NH—, —N($C_{1-4}$alkyl)-, —$C_{1-6}$alkyl-O—, —$C_{1-6}$alkyl-S—, —O—$C_{1-6}$alkyl-, —S—$C_{1-6}$alkyl-, —O—$C_{2-6}$alkyl-O—, —S—$C_{2-6}$alkyl-S—, —$SO_2$—, —$SO_2$NH—, —$SO_2$N($C_{1-4}$alkyl)-, —NH—$SO_2$—, —N($C_{1-4}$alkyl)-$SO_2$—, —C(O)—O— and —O—C(O)—;

$R^7$ is selected from the group consisting of aryl, partially unsaturated carbocyclyl, cycloalkyl, heteroaryl and heterocycloalkyl; wherein the aryl, partially unsaturated carbocyclyl, cycloalkyl, heteroaryl or heterocycloalkyl group is optionally substituted with one or more substituents independently selected from hydroxy, carboxy, halogen, $C_{1-6}$alkyl, $C_{1-6}$alkoxy, nitro, cyano, $N(R^E)_2$, trifluoromethyl, trifluoromethoxy, $C_{1-4}$alkoxycarbonyl, —$SO_2$—$N(R^E)_2$ and —C(O)—$N(R^E)_2$;

and pharmaceutically acceptable salts thereof.

In an embodiment of the present invention are compounds of the formula (Ia)

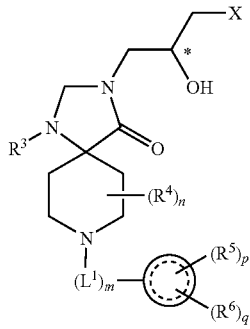

wherein X, $R^3$, n, $R^4$, m, $L^1$,

, p, $R^5$, q and $R^6$ are as herein defined, or a pharmaceutically acceptable salt thereof. The compounds of formula (I) are useful in the treatment of disorders mediated by the ORL-1 receptor.

In an embodiment of the present invention is a compound of formula (I) wherein the binding of the compound to the ORL-1 receptor is 10 fold greater than the binding of the compound to the μ opioid (OP-3) receptor. In another embodiment of the present invention is a compound of formula (I) wherein the binding of the compound to the ORL-1 receptor is 100 fold greater, preferably 500 fold greater, more preferably 1000 fold greater, than the binding of the compound to the μ opioid (OP-3) receptor.

In an embodiment of the present invention is a compound of formula (I) wherein the compound's measured $IC_{50}$ to the ORL-1 receptor is less than or equal to about 100 nM, preferably less than or equal to about 50 nM. In another embodiment of the present invention is a compound of formula (I) wherein the compound's measured Ki to the ORL-1 receptor is less than or equal to about 100 nM, preferably less than or equal to about 50 nM.

In an embodiment of the present invention $R^o$ is

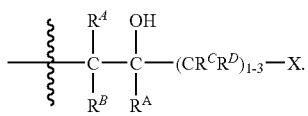

In another embodiment of the present invention, $R^o$ is

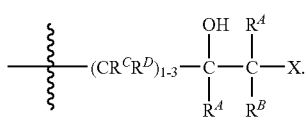

In yet another embodiment of the present invention, $R^o$ is

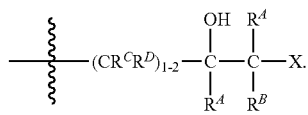

Preferably, $R^o$ is selected from the group consisting of

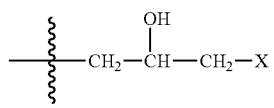

and

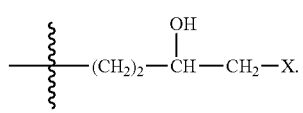

More preferably, $R^o$ is

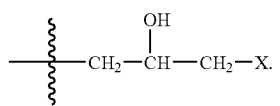

In yet another embodiment of the present invention, $R^o$ is

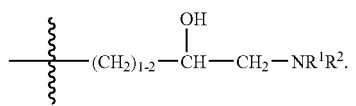

Preferably, $R^o$ is

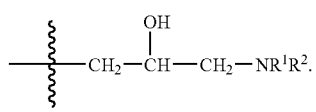

In an embodiment of the present invention, the hydroxy group on the

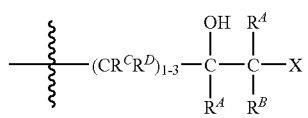

group is present in the R stereo-configuration. In another embodiment of the present invention, the hydroxy group on the

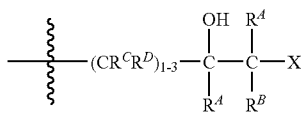

group is present in the S stereo-configuration.

In an embodiment of the present invention $R^A$ and $R^B$ are each independently selected from hydrogen, methyl and ethyl, preferably $R^A$ and $R^B$ are each hydrogen. In another embodiment of the present invention $R^C$ and $R^D$ are each independently selected from hydrogen and $C_{1-4}$alkyl, preferably $R^C$ and $R^D$ are each hydrogen. In yet another embodiment of the present invention $R^E$ is selected from the group consisting of hydrogen, methyl and ethyl, preferably $R^E$ is hydrogen.

In an embodiment of the present invention X is selected from the group consisting of $-NR^1R^2$, $-C(O)-NR^1R^2$, $-NR^1-C(O)-R^2$, $-OR^1$, $-SR^1$, $-SO-R^1$, $-SO_2-R^1$, $-S-(C_{2-4}alkyl)-NR^1R^2$, $-SO-(C_{1-4}alkyl)-NR^1R^2$, $-SO_2-(C_{1-4}alkyl)-NR^1R^2$ wherein the alkyl portion of the $-S-(C_{2-4}alkyl)-NR^1R^2$, $-S-(C_{1-4}alkyl)-NR^1-C(O)O-C(CH_3)_3$, $-SO-(C_{1-4}alkyl)-NR^1R^2$ or $-SO_2-(C_{1-4}alkyl)-NR^1R^2$ group is optionally substituted with one to two substituents independently selected from $C_{1-4}$alkyl, hydroxy$C_{1-4}$alkyl, $C_{1-4}$alkoxycarbonyl or carboxy. Preferably, X is selected from the group consisting of $-NR^1R^2$, $-OR^1$, $-SR^1$, $-S-(C_{2-4}alkyl)-NR^1-C(O)O-C(CH_3)_3$, $-S-(C_{2-4}alkyl)-NR^1R^2$ wherein the alkyl portion of the $-S-(C_{2-4}alkyl)-NR^1R^2$ or $-S-(C_{2-4}alkyl)-NR^1-C(O)O-C(CH_3)_3$ group is optionally substituted with a carboxy or $C_{1-4}$alkoxycarbonyl group. More preferably, X is selected from the group consisting of $-NR^1R^2$, $-OR^1$, $-SR^1$, $-S-CH_2CH(CO_2H)-NH-C(O)-CH_3$ and $-S-CH_2CH(CO_2H)-NH-C(O)O-C(CH_3)_3$. More preferably still, X is selected from the group consisting of $-NR^1R^2$, $-SR^1$ and $-S-CH_2CH(CO_2H)-NH-C(O)-CH_3$.

In an embodiment of the present invention $R^1$ is selected from the group consisting of hydrogen, $C_{1-4}$alkyl, $C_{1-4}$alkoxy, $C_{1-4}$alkoxycarbonyl, aryl, ar$C_{1-4}$alkyl, ar$C_{1-4}$alkyloxy, heteroaryl, heteroaryl-alkyl, heterocycloalkyl, heterocycloalkyl-alkyl, cycloalkyl-alkyl, $C(O)-C_{1-4}$alkyl and $-C(O)$-heteroaryl; wherein the $C_{1-4}$alkyl, aryl, ar$C_{1-4}$alkyl, heteroaryl, heterocycloalkyl or cycloalkyl group, whether alone or part of a substituent group, is optionally substituted with one to three substituents independently selected from halogen, hydroxy, carboxy, $C_{1-4}$alkyl, $C_{1-4}$alkoxy, $C_{1-4}$alkoxycarbonyl, $N(R^E)_2$, $N(R^E)_2-C_{1-4}$alkyl, $N(R^E)-C(O)OC(CH_3)_3$, nitro, trifluoromethyl, trifluoromethoxy, phenyl, phenoxy, heteroaryl, cycloalkyl, 1-phenyl-pyrazol-2-yl-aminosulfonyl or $C_{1-4}$alkylthio. Preferably, In an embodiment of the present invention $R^1$ is selected from the group consisting of hydrogen, $C_{1-4}$alkyl, $C_{1-4}$alkoxy, aryl, ar$C_{1-4}$alkyl, ar$C_{1-4}$alkyloxy, heteroaryl, heteroaryl-alkyl, heterocycloalkyl, heterocycloalkyl-alkyl, cycloalkyl-alkyl, $C(O)-C_{1-4}$alkyl and $-C(O)$-heteroaryl; wherein the $C_{1-4}$alkyl, aryl, ar$C_{1-4}$alkyl, heteroaryl, heterocycloalkyl or cycloalkyl group, whether alone or part of a substituent group, is optionally substituted with one to three substituents independently selected from halogen, hydroxy, carboxy, $C_{1-4}$alkyl, $C_{1-4}$alkoxy, $C_{1-4}$alkoxycarbonyl, $N(R^E)_2$, $N(R^E)_2-C_{1-4}$alkyl, $N(R^E)-C(O)OC(CH_3)_3$, nitro, trifluoromethyl, trifluoromethoxy, phenyl, phenoxy, heteroaryl, cycloalkyl, 1-phenyl-pyrazol-2-yl-aminosulfonyl or $C_{1-4}$alkylthio.

In another embodiment of the present invention, $R^1$ is selected from the group consisting of hydrogen, $C_{1-4}$alkyl, ar$C_{1-4}$alkyl, $C_{1-4}$alkoxycarbonyl and $C(O)-C_{1-4}$alkyl; wherein the $C_{1-4}$alkyl, ar$C_{1-4}$alkyl or aryl group, whether alone or part of a substituent group, is optionally substituted with one to two substituents independently selected from carboxy, $C_{1-4}$alkyl, $C_{1-4}$alkoxy, $C_{1-4}$alkoxycarbonyl, $N(R^E)_2$, $N(R^E)_2-C_{1-4}$alkyl or $N(R^E)-C(O)OC(CH_3)_3$. Preferably, $R^1$ is selected from the group consisting of hydrogen, $C_{1-4}$alkyl, ar$C_{1-4}$alkyl and $C(O)-C_{1-4}$alkyl; wherein the $C_{1-4}$alkyl, ar$C_{1-4}$alkyl or aryl group, whether alone or part of a substituent group, is optionally substituted with one to two substituents independently selected from carboxy, $C_{1-4}$alkyl, $C_{1-4}$alkoxy, $C_{1-4}$alkoxycarbonyl, $N(R^E)_2$, $N(R^E)_2-C_{1-4}$alkyl or $N(R^E)-C(O)OC(CH_3)_3$.

In another embodiment of the present invention, $R^1$ is selected from the group consisting of hydrogen, methyl, ethyl, n-propyl, n-butyl, t-butyl, amino-n-propyl, dimethylaminoethyl, benzyl, phenylethyl, 4-methyl-benzyl,

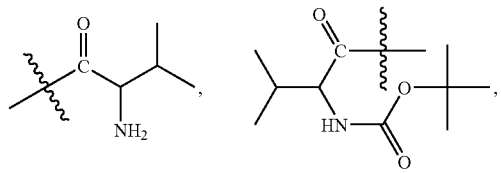

2-(3,4-dimethoxy-phenyl)ethyl, 3-methylphenyl, 2-amino-2-methoxycarbonyl-ethyl, ethoxy-carbonyl-methyl, t-butoxycarbonyl, and

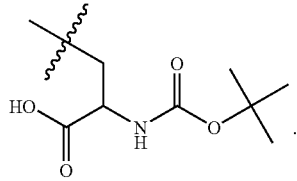

Preferably, $R^1$ is selected from the group consisting of hydrogen, methyl, n-propyl, n-butyl, t-butyl, dimethylaminoethyl, benzyl, 4-methyl-benzyl,

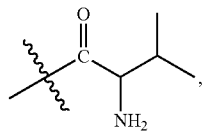

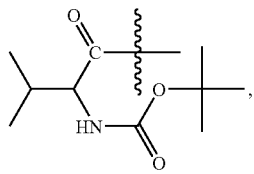

2-(3,4-dimethoxy-phenyl)ethyl, 3-methylphenyl, 2-amino-2-methoxycarbonyl-ethyl and

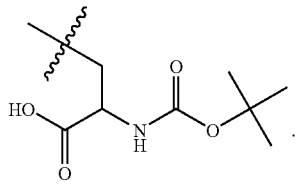

In another embodiment of the present invention, $R^1$ is selected from the group consisting of hydrogen, methyl, ethyl, n-propyl, n-butyl, t-butyl, dimethylaminoethyl, benzyl, phenylethyl,

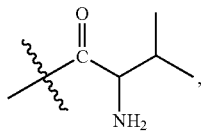

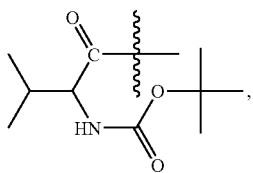

3-methyl-phenyl, 2-(3,4-dimethoxyphenyl)-ethyl, ethoxycarbonyl-methyl, dimethylamino-ethyl and 2-amino-2-methoxycarbonyl-ethyl. Preferably, $R^1$ is selected from the group consisting of hydrogen, methyl, ethyl, n-propyl, n-butyl, t-butyl, dimethylaminoethyl, benzyl,

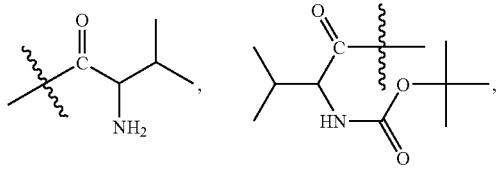

3-methyl-phenyl and 2-amino-2-methoxycarbonyl-ethyl.

In yet another embodiment of the present invention, $R^1$ is selected from the group consisting of hydrogen, methyl, ethyl, n-propyl, n-butyl, t-butyl, dimethylaminoethyl, benzyl, phenylethyl, 2-(3,4-dimethoxyphenyl)-ethyl, dimethylamino-ethyl, ethoxy-carbonyl-methyl,

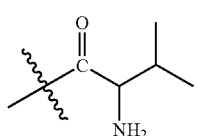 and 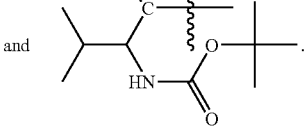

Preferably, $R^1$ is selected from the group consisting of hydrogen, methyl, ethyl, n-propyl, n-butyl, t-butyl, dimethylaminoethyl, benzyl,

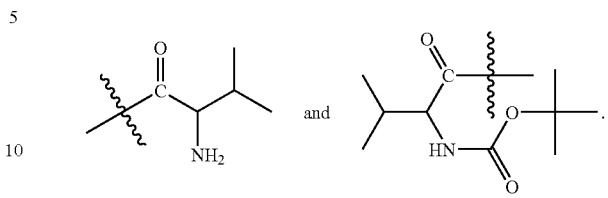

In another embodiment of the present invention $R^1$ is selected from the group consisting of hydrogen, t-butoxycarbonyl, 2-(3,4-dimethoxyphenyl)-ethyl, 1-(3,4-dimethoxyphenyl)-n-ethyl and amino-n-propyl. In yet another embodiment of the present invention $R^1$ is selected from the group consisting of hydrogen, t-butoxycarbonyl and amino-n-propyl.

In an embodiment of the present invention $R^2$ is selected from the group consisting of hydrogen, $C_{1-4}$alkyl, $C_{1-4}$alkoxy, cycloalkyl, cycloalkyl-$C_{1-4}$alkyl, aryl, ar$C_{1-4}$alkyl, ar$C_{1-4}$alkyloxy, partially unsaturated carbocyclyl, particularly unsaturated carbocyclyl-$C_{1-4}$alkyl, heteroaryl, heteroaryl-$C_{1-4}$ alkyl, heterocycloalkyl, heterocycloalkyl-$C_{1-4}$alkyl, —C(O)—$C_{1-4}$alkyl, —C(O)-aryl, —C(O)-ar$C_{1-4}$alkyl, —C(O)-heteroaryl, —C(O)-heterocycloalkyl, —C(O)O-cycloalkyl and —C(OO)—$C_{1-4}$alkyl; wherein the $C_{1-4}$alkyl, aryl, ar$C_{1-4}$alkyl, partially unsaturated carbocyclyl, heteroaryl, heterocycloalkyl or cycloalkyl group, whether alone or part of a substituent group, is optionally substituted with one to three substituents independently selected from halogen, hydroxy, carboxy, $C_{1-4}$alkyl, $C_{1-4}$alkoxy, $C_{1-4}$alkoxycarbonyl, $N(R^E)_2$, $N(R^E)_2$—$C_{1-4}$alkyl, $(CH_3)_3COC(O)$—N$(R^E)$—$C_{1-4}$-alkyl, nitro, cyano, trifluoromethyl, trifluoromethoxy, phenyl, phenoxy, heteroaryl, cycloalkyl, 1-phenyl substituted heteroaryl-aminosulfonyl, —C(O)—$C_{1-4}$alkyl or $C_{1-4}$alkylthio. Preferably, $R^2$ is selected from the group consisting of hydrogen, $C_{1-4}$alkyl, $C_{1-4}$alkoxy, cycloalkyl-$C_{1-4}$alkyl, aryl, ar$C_{1-4}$alkyl, ar$C_{1-4}$alkyloxy, partially unsaturated carbocyclyl, heteroaryl, heteroaryl-$C_{1-4}$ alkyl, heterocycloalkyl, heterocycloalkyl-$C_{1-4}$alkyl, —C(O)—$C_{1-4}$alkyl, —C(O)-aryl, —C(O)-ar$C_{1-4}$alkyl, —C(O)-heteroaryl and —C(O)-heterocycloalkyl; wherein the $C_{1-4}$alkyl, aryl, ar$C_{1-4}$alkyl, partially unsaturated carbocyclyl, heteroaryl, heterocycloalkyl or cycloalkyl group, whether alone or part of a substituent group, is optionally substituted with one to three substituents independently selected from halogen, hydroxy, carboxy, $C_{1-4}$alkyl, $C_{1-4}$alkoxy, $C_{1-4}$alkoxycarbonyl, $N(R^E)_2$, $N(R^E)_2$—$C_{1-4}$alkyl, nitro, cyano, trifluoromethyl, trifluoromethoxy, phenyl, phenoxy, heteroaryl, cycloalkyl, 1-phenyl substituted heteroaryl-aminosulfonyl, —C(O)—$C_{1-4}$alkyl or $C_{1-4}$alkylthio.

In an embodiment of the present invention, $R^2$ is selected from the group consisting of hydrogen, $C_{1-4}$alkyl, $C_{1-4}$alkoxy, cycloalkyl, aryl, ar$C_{1-4}$alkyl, ar$C_{1-4}$alkyloxy, partially unsaturated carbocyclyl, partially unsaturated carbocyclyl-$C_{1-4}$ alkyl, heteroaryl, heteroaryl-$C_{1-4}$alkyl, heterocycloalkyl, heterocycloalkyl-$C_{1-4}$alkyl, cycloalkyl-$C_{1-4}$alkyl, —C(O)ar$C_{1-4}$ alkyl, —C(O)-heteroaryl, —C(OO)-cycloalkyl and —C(O)O—$C_{1-4}$alkyl; wherein the $C_{1-4}$alkyl, aryl, ar$C_{1-4}$alkyl, partially unsaturated carbocyclyl, heteroaryl, heterocycloalkyl or cycloalkyl group, whether alone or part of a substituent group, is optionally substituted with one to three substituents independently selected from halogen, hydroxy, carboxy, $C_{1-4}$alkyl, $C_{1-4}$alkoxy, $C_{1-4}$alkoxycarbonyl, $N(R^E)_2$, N(R$^E$)$_2$—C$_{1-4}$alkyl, alkyl, nitro, trifluoromethyl, trifluoromethoxy, phenyl, phenoxy, heteroaryl, cycloalkyl, 1-phenyl-pyrazol-2-yl-aminosulfonyl or C$_{1-4}$alkylthio. Preferably, R$^2$ is selected from the group consisting of hydrogen, C$_{1-4}$alkyl, C$_{1-4}$alkoxy, aryl, arC$_{1-4}$alkyl, arC$_{1-4}$alkyloxy, partially unsaturated carbocyclyl, heteroaryl, heteroaryl-alkyl, heterocycloalkyl, heterocycloalkyl-alkyl, cycloalkyl-alkyl and —C(O)-heteroaryl; wherein the C$_{1-4}$alkyl, aryl, arC$_{1-4}$ alkyl, partially unsaturated carbocyclyl, heteroaryl, heterocycloalkyl or cycloalkyl group, whether alone or part of a substituent group, is optionally substituted with one to three substituents independently selected from halogen, hydroxy, carboxy, C$_{1-4}$alkyl, C$_{1-4}$alkoxy, C$_{1-4}$alkoxycarbonyl, N(R$^E$)$_2$, N(R$^E$)$_2$—C$_{1-4}$alkyl, nitro, trifluoromethyl, trifluoromethoxy, phenyl, phenoxy, heteroaryl, cycloalkyl, 1-phenyl-pyrazol-2-yl-aminosulfonyl or C$_{1-4}$alkylthio.

In an embodiment of the present invention, R$^2$ is selected from the group consisting of hydrogen, methyl, methoxy, ethyl, carboxy-methyl, methoxycarbonylmethyl, 2,2,2-trifluoroethyl, ethoxy, dimethylaminoethyl, t-butoxycarbonylamino-ethyl, n-butyl, t-butyl, n-propyl, 3-hydroxy-n-propyl, 3-methoxy-n-propyl, methylamino-n-propyl, dimethylamino-n-propyl, di(n-butyl)amino-n-propyl, t-butoxycarbonylamino-n-propyl, 3-phenyl-n-propyl, 3-(2-pyridyl)-n-propyl, t-butoxycarbonyl, cyclopropyl, phenyl, 4-fluorophenyl, 4-methylphenyl, 3,4-dimethoxyphenyl, 2-aminophenyl, 4-biphenyl, 2-ethoxyphenyl, 4-((1-phenyl-pyrazol-2-yl)-aminosulfonyl)-phenyl, 4-cyclohexylphenyl, 4-(aminoethyl) phenyl, 4-(t-butoxycarbonylamino-ethyl)-phenyl, —CH (CH$_3$)-phenyl, benzyl, benzyloxy, 2-methylbenzyl, 3-methylbenzyl, 4-methylbenzyl, 2-methoxybenzyl, 3-methoxybenzyl, 4-methoxybenzyl, 2-ethoxybenzyl, 3-ethoxybenzyl, 2-bromobenzyl, 3-bromobenzyl, 4-bromobenzyl, 3-chlorobenzyl, 4-chlorobenzyl), 3-iodobenzyl, 2-fluorobenzyl, 3-fluorobenzyl, 4-fluorobenzyl, 2-trifluoromethylbenzyl, 3-trifluoromethylbenzyl, 4-trifluoromethylbenzyl, 4-trifluoromethoxybenzyl, 4-methoxycarbonylbenzyl, 2,3-dimethoxybenzyl, 2,4-dichlorobenzyl, 3,4-dichlorobenzyl, 2,4-difluorobenzyl, 2,5-difluorobenzyl, 3,4-difluorobenzyl, 3,4,5-trimethoxybenzyl, 2,4,6-trimethoxybenzyl, 4-carboxybenzyl, 3-nitrobenzyl, 4-nitrobenzyl, 2,4-dimethoxybenzyl, 3,4-dimethoxybenzyl, 3,5-dimethoxybenzyl, 3,4-difluorobenzyl, 3,5-di(trifluoromethyl)benzyl, 4-(dimethylamino) benzyl, 2-phenylethyl, 2-(4-bromophenyl)ethyl, 2-(3-methoxyphenyl)ethyl, 2-(4-methoxyphenyl)ethyl, 2-(3,4-dimethoxyphenyl)ethyl, 2-(2-nitro-4,5-dimethoxyphenyl) ethyl, 3-(4-morpholinyl)-n-propyl, 2-(4-morpholinyl)ethyl, 2-(4-imidazolyl)ethyl, 1-adamantanyl, 1-adamantanyl-methyl, (2,5-dimethoxy-2,5-dihydro-fur-2-yl)methyl, 2-pyridyl, 3-pyridyl, 4-pyridyl, 2-pyridyl-methyl, 3-pyridyl-methyl, 4-pyridyl-methyl, 2-(3,4-dimethyl-pyridyl), 2-(5-bromopyridyl), 2-(4,6-dimethyl-pyridyl), 2-(5-methyl-pyridyl), 3-(6-methoxy-pyridyl), 6-methylthio-2-pyridyl-carbonyl, thienyl-methyl, 2-thienylethyl, 4-pyridinyl, 1-naphthyl, 1-naphthyl-methyl, 1-(3,4-methylenedioxyphenyl)methyl, 2-(3,4-methylenedioxyphenyl)ethyl, 1-phenyl-2-(t-butoxycarbonyl)ethyl, —C(O)—C(OCH$_3$)(CF$_3$)-phenyl, —C(O)O-(2-isopropyl-5-methyl-cyclohexyl), 1-(4-ethoxycarbonyl-piperidinyl), 2-(3H-imidazol-4-yl)ethyl, 2-(1,2,3,4-tetrahydro-isoquinolinyl), 2-furyl-methyl,

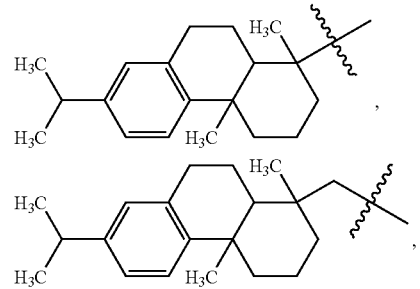

2S-hydroxy-S-cyclopentyl-methyl, 2S-hydroxy-S-cyclohexyl-methyl, 2S-hydroxy-S-cycloheptyl-methyl, 2-phenoxy-ethyl, 2-(2-pyridyl)-ethyl, 2-(6-fluoro-2-indolyl)ethyl and 2-phenyl-cyclopropyl. Preferably, R$^2$ is selected from the group consisting of hydrogen, methyl, methoxy, ethyl, carboxy-methyl, ethoxycarbonylmethyl, 2,2,2,-trifluoroethyl, ethoxy, dimethylaminoethyl, n-butyl, t-butyl, n-propyl, di(n-butyl)amino-n-propyl, 3-phenyl-n-propyl, 3-(2-pyridyl)-n-propyl, phenyl, 4-biphenyl, 2-ethoxyphenyl, 4-((1-phenyl-pyrazol-2-yl)-aminosulfonyl)-phenyl, 4-cyclohexylphenyl, 4-(aminoethyl)phenyl, benzyl, benzyloxy, 2-methylbenzyl, 3-methylbenzyl, 4-methylbenzyl, 2-methoxybenzyl, 3-methoxybenzyl, 4-methoxybenzyl, 2-ethoxybenzyl, 3-ethoxybenzyl, 2-bromobenzyl, 3-bromobenzyl, 4-bromobenzyl, 3-chlorobenzyl, 4-chlorobenzyl), 3-iodobenzyl, 2-fluorobenzyl, 3-fluorobenzyl, 4-fluorobenzyl, 2-trifluoromethylbenzyl, 3-trifluoromethylbenzyl, 4-trifluoromethylbenzyl, 4-trifluoromethoxybenzyl, 4-methoxycarbonylbenzyl, 2,3-dimethoxybenzyl, 2,4-dichlorobenzyl, 3,4-dichlorobenzyl, 2,4-difluorobenzyl, 2,5-difluorobenzyl, 3,4-difluorobenzyl, 3,4,5-trimethoxybenzyl, 2,4,6-trimethoxybenzyl, 4-carboxybenzyl, 3-nitrobenzyl, 4-nitrobenzyl, 2,4-dimethoxybenzyl, 3,4-dimethoxybenzyl, 3,5-dimethoxybenzyl, 3,4-difluorobenzyl, 3,5-di(trifluoromethyl)benzyl, 4-(dimethylamino) benzyl, 2-phenylethyl, 2-(4-bromophenyl)ethyl, 2-(3-methoxyphenyl)ethyl, 2-(4-methoxyphenyl)ethyl, 2-(3,4-dimethoxyphenyl)ethyl, 2-(2-nitro-4,5-dimethoxyphenyl) ethyl, 3-(4-morpholinyl)-n-propyl, 2-(4-morpholinyl)ethyl, 2-(4-imidazolyl)ethyl, 1-adamantanyl, 1-adamantanyl-methyl, (2,5-dimethoxy-2,5-dihydro-fur-2-yl)methyl, 2-pyridyl, 3-pyridyl, 4-pyridyl, 2-pyridyl-methyl, 3-pyridyl-methyl, 4-pyridyl-methyl, 2-(3,4-dimethyl-pyridyl), 2-(5-bromopyridyl), 2-(4,6-dimethyl-pyridyl), 2-(5-methyl-pyridyl), 3-(6-methoxy-pyridyl), 6-methylthio-2-pyridyl-carbonyl, 2-thienylethyl, 1-naphthyl, 1-naphthyl-methyl, 1-(3,4-methylenedioxyphenyl)methyl, 2-(3,4-methylenedioxyphenyl)ethyl, 1-phenyl-2-(t-butoxycarbonyl)ethyl, 2-(1,2,3,4-tetrahydro-isoquinolinyl), 2-furyl-methyl,

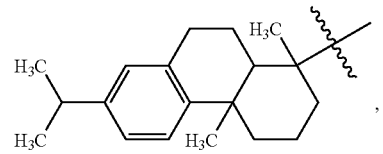

2S-hydroxy-S-cyclopentyl-methyl, 2S-hydroxy-S-cyclohexyl-methyl, 2S-hydroxy-S-cycloheptyl-methyl, 2-phenoxy-ethyl, 2-(2-pyridyl)-ethyl, 2-(6-fluoro-2-indolyl)ethyl and 2-phenyl-cyclopropyl.

In an embodiment of the present invention, $R^2$ is selected from the group consisting of hydrogen, methyl, methoxy, ethyl, ethoxycarbonyl-methyl, 2,2,2-trifluoroethyl, ethoxy, dimethylaminoethyl, n-butyl, t-butyl, n-propyl, di(n-butyl)amino-n-propyl, 3-phenyl-n-propyl, 3-(2-pyridyl)-n-propyl, cyclopropyl, phenyl, 4-fluorophenyl, 4-methylphenyl, 2-aminophenyl, 4-(t-butoxycarbonylamino-ethyl)-phenyl, 3,4-dimethoxyphenyl, 4-biphenyl, 2-ethoxyphenyl, 4-((1-phenyl-pyrazol-2-yl)-aminosulfonyl)-phenyl, 4-(aminoethyl)-phenyl, benzyl, benzyloxy, 2-methylbenzyl, 3-methylbenzyl, 4-methylbenzyl, 2-methoxybenzyl, 3-methoxybenzyl, 4-methoxybenzyl, 2-ethoxybenzyl, 3-ethoxybenzyl, 2-bromobenzyl, 3-bromobenzyl, 4-bromobenzyl, 3-chlorobenzyl, 4-chlorobenzyl, 3-iodobenzyl, 2-fluorobenzyl, 3-fluorobenzyl, 4-fluorobenzyl, 2-trifluoromethylbenzyl, 3-trifluoromethylbenzyl, 4-trifluoromethylbenzyl, 4-trifluoromethoxybenzyl, 4-methoxycarbonyl-benzyl, 2,3-dimethoxybenzyl, 2,4-dichlorobenzyl, 3,4-dichlorobenzyl, 2,4-difluorobenzyl, 2,5-difluorobenzyl, 3,4-difluorobenzyl, 3,4,5-trimethoxybenzyl, 2,4,6-trimethoxybenzyl, 4-carboxybenzyl, 3-nitrobenzyl, 4-nitrobenzyl, 2,4-dimethoxybenzyl, 3,4-dimethoxybenzyl, 3,5-dimethoxybenzyl, 3,4-difluorobenzyl, 3,5-di(trifluoromethyl)-benzyl, 2-phenylethyl, 2-(4-bromophenyl)ethyl, 2-(3-methoxyphenyl)ethyl, 2-(4-methoxyphenyl)ethyl, 2-(3,4-dimethoxyphenyl)ethyl, 2-(2-nitro-4,5-dimethoxy-phenyl)ethyl, 3-(4-morpholinyl)-n-propyl, 2-(4-morpholinyl)ethyl, 2-(4-imidazolyl)ethyl, adamantanyl, 1-adamantanyl-methyl, 2-(2,5-dimethoxy-2,5-dihydro-furyl)methyl, 2-pyridyl, 3-pyridyl, 4-pyridyl, 2-pyridyl-methyl, 3-pyridyl-methyl, 4-pyridyl-methyl, 2-(3,4-dimethyl-pyridyl), 2-(5-bromopyridyl), 2-(4,6-dimethyl-pyridyl), 2-(5-methyl-pyridyl), 3-(6-methoxy-pyridyl), thienylmethyl, 2-thienylethyl, 1-naphthyl, 1-naphthyl-methyl, 1-(3,4-methylenedioxyphenyl)methyl, 2-(3,4-methylenedioxyphenyl)ethyl, 2-furyl-methyl,

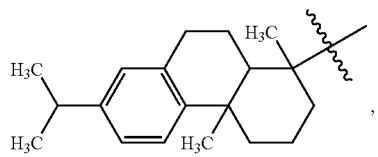

2S-hydroxy-S-cyclopentyl-methyl, 2S-hydroxy-S-cyclohexyl-methyl, 2S-hydroxy-S-cycloheptyl-methyl, 2-phenoxy-ethyl and 2-(6-fluoro-2-indolyl)-ethyl. Preferably still, $R^2$ is selected from the group consisting of hydrogen, methyl, methoxy, ethyl, ethoxycarbonyl-methyl, 2,2,2-trifluoroethyl, ethoxy, dimethylaminoethyl, n-butyl, t-butyl, n-propyl, di(n-butyl)amino-n-propyl, 3-phenyl-n-propyl, 3-(2-pyridyl)-n-propyl, phenyl, 4-biphenyl, 2-ethoxyphenyl, 4-((1-phenyl-pyrazol-2-yl)-aminosulfonyl)-phenyl, 4-(aminoethyl)-phenyl, benzyl, benzyloxy, 2-methylbenzyl, 3-methylbenzyl, 4-methylbenzyl, 2-methoxybenzyl, 3-methoxybenzyl, 4-methoxybenzyl, 2-ethoxybenzyl, 3-ethoxybenzyl, 2-bromobenzyl, 3-bromobenzyl, 4-bromobenzyl, 3-chlorobenzyl, 4-chlorobenzyl, 3-iodobenzyl, 2-fluorobenzyl, 3-fluorobenzyl, 4-fluorobenzyl, 2-trifluoromethylbenzyl, 3-trifluoromethylbenzyl, 4-trifluoromethylbenzyl, 4-trifluoromethoxybenzyl, 4-methoxycarbonyl-benzyl, 2,3-dimethoxybenzyl, 2,4-dichlorobenzyl, 3,4-dichlorobenzyl, 2,4-difluorobenzyl, 2,5-difluorobenzyl, 3,4-difluorobenzyl, 3,4,5-trimethoxybenzyl, 2,4,6-trimethoxybenzyl, 4-carboxybenzyl, 3-nitrobenzyl, 4-nitrobenzyl, 2,4-dimethoxybenzyl, 3,4-dimethoxybenzyl, 3,5-dimethoxybenzyl, 3,4-difluorobenzyl, 3,5-di(trifluoromethyl)-benzyl, 2-phenylethyl, 2-(4-bromophenyl)ethyl, 2-(3-methoxyphenyl)ethyl, 2-(4-methoxyphenyl)ethyl, 2-(3,4-dimethoxyphenyl)ethyl, 2-(2-nitro-4,5-dimethoxy-phenyl)ethyl, 3-(4-morpholinyl)-n-propyl, 2-(4-morpholinyl)ethyl, 2-(4-imidazolyl)ethyl, adamantanyl, 1-adamantanyl-methyl, 2-(2,5-dimethoxy-2,5-dihydro-furyl)methyl, 2-pyridyl, 3-pyridyl, 4-pyridyl, 2-pyridyl-methyl, 3-pyridyl-methyl, 4-pyridyl-methyl, 2-(3,4-dimethyl-pyridyl), 2-(5-bromopyridyl), 2-(4,6-dimethyl-pyridyl), 2-(5-methyl-pyridyl), 3-(6-methoxy-pyridyl), 2-thienylethyl, 1-naphthyl, 1-naphthyl-methyl, 1-(3,4-methylenedioxyphenyl)methyl, 2-(3,4-methylenedioxyphenyl)ethyl, 2-furyl-methyl,

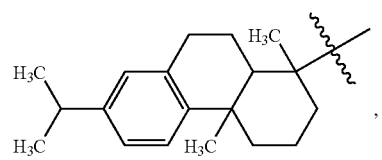

2S-hydroxy-S-cyclopentyl-methyl, 2S-hydroxy-S-cyclohexyl-methyl, 2S-hydroxy-S-cycloheptyl-methyl, 2-phenoxy-ethyl and 2-(6-fluoro-2-indolyl)-ethyl.

In an embodiment of the present invention, $R^2$ is selected from the group consisting of hydrogen, methyl, methoxy, ethyl, ethoxycarbonyl-methyl, ethoxy, dimethylaminoethyl, n-butyl, n-propyl, di(n-butyl)amino-n-propyl, 3-phenyl-n-propyl, 3-(2-pyridyl)-n-propyl, cyclopropyl, phenyl, 4-fluorophenyl, 4-methylphenyl, 2-aminophenyl, 3,4-dimethoxyphenyl, 4-(t-butoxycarbonylamino-ethyl)-phenyl, 4-biphenyl, 2-ethoxyphenyl, 4-((1-phenyl-pyrazol-2-yl)-aminosulfonyl)-phenyl, 4-(aminoethyl)-phenyl, benzyl, benzyloxy, 2-methylbenzyl, 3-methylbenzyl, 4-methylbenzyl, 2-methoxybenzyl, 3-methoxybenzyl, 4-methoxybenzyl, 2-ethoxybenzyl, 3-ethoxybenzyl, 2-bromobenzyl, 3-bromobenzyl, 4-bromobenzyl, 3-chlorobenzyl, 4-chlorobenzyl, 3-iodobenzyl, 2-fluorobenzyl, 3-fluorobenzyl, 4-fluorobenzyl, 2-trifluoromethylbenzyl, 3-trifluoromethylbenzyl, 4-trifluoromethylbenzyl, 4-trifluoromethoxybenzyl, 4-methoxycarbonyl-benzyl, 2,3-dimethoxybenzyl, 2,4-dichlorobenzyl, 3,4-dichlorobenzyl, 2,4-difluorobenzyl, 2,5-difluorobenzyl, 3,4,5-trimethoxybenzyl, 2,4,6-trimethoxybenzyl, 3-nitrobenzyl, 4-nitrobenzyl, 2,4-dimethoxybenzyl, 3,4-dimethoxybenzyl, 3,5-dimethoxybenzyl, 3,4-difluorobenzyl, 3,5-di(trifluoromethyl)-benzyl, 2-phenylethyl, 2-(4-bromophenyl)ethyl, 2-(3-methoxyphenyl)ethyl, 2-(4-methoxyphenyl)ethyl, 2-(3,4-dimethoxyphenyl)ethyl, 2-(2-nitro-4,5-dimethoxy-phenyl)ethyl, 3-(4-morpholinyl)-n-propyl, 2-(4-morpholinyl)ethyl, 2-(4-imidazolyl)ethyl, 1-adamantanyl, 1-adamantanyl-methyl, 2-(2,5-dimethoxy-2,5-dihydro-furyl)methyl, 2-pyridyl, 3-pyridyl, 4-pyridyl, 2-pyridyl-methyl, 3-pyridyl-methyl, 4-pyridyl-methyl, 2-(3,4-dimethyl-pyridyl), 2-(5-bromopyridyl), 2-(4,6-dimethyl-pyridyl), 2-(5-methyl-pyridyl), 3-(6-methoxy-pyridyl), thienylmethyl, 2-thienylethyl, 1-naphthyl, 1-naphthyl-methyl, 1-(3,4-methylenedioxyphenyl)methyl, 2-(3,4-methylenedioxyphenyl)ethyl, 2-furyl-methyl,

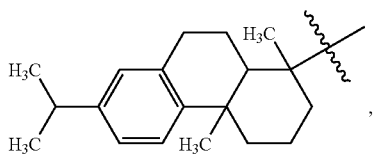

2S-hydroxy-S-cyclopentyl-methyl, 2S-hydroxy-S-cyclohexyl-methyl, 2S-hydroxy-S-cycloheptyl-methyl and 2-phenoxy-ethyl. Preferably, $R^2$ is selected from the group consisting of hydrogen, methyl, methoxy, ethyl, ethoxycarbonyl-methyl, ethoxy, dimethylaminoethyl, n-butyl, n-propyl, di(n-butyl)amino-n-propyl, 3-phenyl-n-propyl, 3-(2-pyridyl)-n-propyl, 4-biphenyl, 2-ethoxyphenyl, 4-((1-phenyl-pyrazol-2-yl)-aminosulfonyl)-phenyl, 4-(aminoethyl)-phenyl, benzyl, benzyloxy, 2-methylbenzyl, 3-methylbenzyl, 4-methylbenzyl, 2-methoxybenzyl, 3-methoxybenzyl, 4-methoxybenzyl, 2-ethoxybenzyl, 3-ethoxybenzyl, 2-bromobenzyl, 3-bromobenzyl, 4-bromobenzyl, 2-chlorobenzyl, 4-chlorobenzyl, 3-iodobenzyl, 2-fluorobenzyl, 3-fluorobenzyl, 4-fluorobenzyl, 2-trifluoromethylbenzyl, 3-trifluoromethylbenzyl, 4-trifluoromethylbenzyl, 4-trifluoromethoxybenzyl, 4-methoxycarbonyl-benzyl, 2,3-dimethoxybenzyl, 2,4-dichlorobenzyl, 3,4-dichlorobenzyl, 2,4-difluorobenzyl, 2,5-difluorobenzyl, 3,4,5-trimethoxybenzyl, 2,4,6-trimethoxybenzyl, 3-nitrobenzyl, 4-nitrobenzyl, 2,4-dimethoxybenzyl, 3,4-dimethoxybenzyl, 3,5-dimethoxybenzyl, 3,4-difluorobenzyl, 3,5-di(trifluoromethyl)-benzyl, 2-phenylethyl, 2-(4-bromophenyl)ethyl, 2-(3-methoxyphenyl)ethyl, 2-(4-methoxyphenyl)ethyl, 2-(3,4-dimethoxyphenyl)ethyl, 2-(2-nitro-4,5-dimethoxy-phenyl)ethyl, 3-(4-morpholinyl)-n-propyl, 2-(4-morpholinyl)ethyl, 2-(4-imidazolyl)ethyl, 1-adamantanyl, 1-adamantanyl-methyl, 2-(2,5-dimethoxy-2,5-dihydrofuryl)methyl, 2-pyridyl, 3-pyridyl, 4-pyridyl, 2-pyridyl-methyl, 3-pyridyl-methyl, 4-pyridyl-methyl, 2-(3,4-dimethylpyridyl), 2-(5-bromopyridyl), 2-(4,6-dimethyl-pyridyl), 2-(5-methyl-pyridyl), 3-(6-methoxy-pyridyl), 2-thienylethyl, 1-naphthyl, 1-naphthyl-methyl, 1-(3,4-methylenedioxyphenyl)methyl, 2-(3,4-methylenedioxyphenyl)ethyl, 2-furylmethyl,

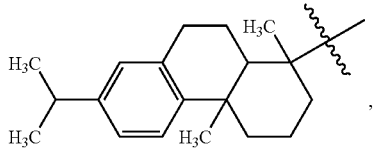

2S-hydroxy-S-cyclopentyl-methyl, 2S-hydroxy-S-cyclohexyl-methyl, 2S-hydroxy-S-cycloheptyl-methyl and 2-phenoxy-ethyl.

In an embodiment of the present invention $R^2$ is selected from the group consisting of hydrogen, methyl, n-butyl, 3-hydroxy-n-propyl, 3-methoxy-n-propyl, methylamino-n-propyl, dimethylamino-n-propyl, t-butoxycarbonylamino-n-propyl, N-methyl-N-t-butoxycarbonyl-amino-n-ethyl, 3-nitrobenzyl, 4-methoxycarbonyl-benzyl, —CH(CH$_3$)-phenyl, 4-pyridinyl, 1-(4-ethoxycarbonyl-piperidinyl) and 2-(3H-imidazol-4-yl)-ethyl.

Preferably, $R^2$ is selected from the group consisting of hydrogen, methyl, n-butyl, 3-hydroxy-n-propyl, 3-methoxy-n-propyl, methylamino-n-propyl, dimethylamino-n-propyl, N-methyl-N-t-butoxycarbonyl-amino-n-ethyl, 3-nitrobenzyl, 4-methoxycarbonyl-benzyl, —CH(CH$_3$)-phenyl, 4-pyridinyl and 2-(3H-imidazol-4-yl)-ethyl.

In an embodiment of the present invention, when $R^1$ and $R^2$ are both bound to the same nitrogen atom, $R^1$ and $R^2$ are taken together with the nitrogen atom to which they are bound to form a heteroaryl or heterocycloalkyl group; wherein the heteroaryl or heterocycloalkyl is optionally substituted with one to three substituents independently selected from halogen, hydroxy, carboxy, $C_{1-4}$alkyl, hydroxy substituted $C_{1-4}$alkyl, $C_{1-4}$alkoxy, $C_{1-4}$alkoxycarbonyl, trifluoromethyl, trifluoromethoxy, nitro, cyano, $N(R^E)_2$, phenyl, ar$C_{1-4}$alkyl, heterocycloalkyl, di($C_{1-4}$alkyl)amino-carbonyl, $C_{1-4}$alkoxycarbonylamino or phenylamino-$C_{1-4}$alkyl; wherein the phenyl or ar$C_{1-4}$alkyl substituent on the heteroaryl or heterocycloalkyl group is optionally substituted with one or two substituents independently selected from halogen, hydroxy, carboxy, $C_{1-4}$alkyl, $C_{1-4}$alkoxy, trifluoromethyl, trifluoromethoxy, nitro, cyano, $N(R^E)_2$ or substituted phenyl; wherein the substituents on the phenyl are one to three independently selected from halogen. Preferably, when $R^1$ and $R^2$ are both bound to the same nitrogen atom, $R^1$ and $R^2$ are taken together with the nitrogen atom to which they are bound to form a heteroaryl or heterocycloalkyl group; wherein the heteroaryl or heterocycloalkyl is optionally substituted with one to three substituents independently selected from halogen, hydroxy, carboxy, $C_{1-4}$alkyl, $C_{1-4}$alkoxy, $C_{1-4}$alkoxycarbonyl, trifluoromethyl, trifluoromethoxy, nitro, cyano, $N(R^E)_2$, phenyl, ar$C_{1-4}$alkyl, heterocycloalkyl, di($C_{1-4}$alkyl) amino-carbonyl, or phenylamino-$C_{1-4}$alkyl; wherein the phenyl or ar$C_{1-4}$alkyl substituent on the heteroaryl or heterocycloalkyl group is optionally substituted with one or two substituents independently selected from halogen, hydroxy, carboxy, $C_{1-4}$alkyl, $C_{1-4}$alkoxy, trifluoromethyl, trifluoromethoxy, nitro, cyano, $N(R^E)_2$ or substituted phenyl; wherein the substituents on the phenyl are one to three independently selected from halogen.

In an embodiment of the present invention, when $R^1$ and $R^2$ are both bound to the same nitrogen atom, $R^1$ and $R^2$ are taken together with the nitrogen atom to which they are bound to form a group selected from heterocycloalkyl and heteroaryl; wherein the heteroaryl or heterocycloalkyl is optionally substituted with one or more substituents independently selected from hydroxy, carboxy, $C_{1-4}$alkyl, hydroxy substituted $C_{1-4}$alkyl, $C_{1-4}$alkoxy, phenyl, ar$C_{1-4}$alkyl, heterocycloalkyl, $C_{1-4}$alkoxycarbonyl, amino, $C_{1-4}$alkylamino, di($C_{1-4}$alkyl) amino, di($C_{1-4}$alkyl)amino-carbonyl, t-butoxycarbonyl, t-butoxycarbonylamino or phenylamino-$C_{1-4}$alkyl; wherein the phenyl or ar$C_{1-4}$alkyl substituent is optionally substituted with one or two substituents independently selected from chloro, trifluoromethyl or chlorophenyl. Preferably, when $R^1$ and $R^2$ are both bound to the same nitrogen atom, $R^1$ and $R^2$ are taken together with the nitrogen atom to which they are bound to form a group selected from heterocycloalkyl and heteroaryl; wherein the heteroaryl or heterocycloalkyl is optionally substituted with one or more substituents independently selected from $C_{1-4}$alkyl, $C_{1-4}$alkoxy, phenyl, ar$C_{1-4}$alkyl, heterocycloalkyl, $C_{1-4}$alkoxycarbonyl, di($C_{1-4}$alkyl) amino-carbonyl or phenylamino-$C_{1-4}$alkyl; wherein the phenyl or ar$C_{1-4}$alkyl substituent is optionally substituted with one or two substituents independently selected from trifluoromethyl or chlorophenyl.

In an embodiment of the present invention, when $R^1$ and $R^2$ are both bound to the same nitrogen atom, $R^1$ and $R^2$ are taken together with the nitrogen atom to which they are bound to form a group selected from 1-morpholinyl, 1-(4-(3-trifluoromethyl-phenyl)-piperazinyl), 1-(4-piperidinyl-piperidinyl), 1-(4-pyrrolidinyl-piperidinyl), 1-(4-phenyl-piperidinyl), 1-(3-hydroxy-piperidinyl), 1-(4-hydroxy-piperidinyl), 1-(3-hydroxymethyl-piperidinyl), 1-(3,5-dimethyl-piperidinyl), 1-(4-dimethylamino-piperidinyl), 1-(4-(3,4-methylenedioxyphenylmethyl)-piperazinyl), 1-(3-(diethylaminocarbonyl)-piperidinyl), 1-(4-t-butoxycarbonylamino-piperidinyl), 1-(2,3-dihydro-1H-pyrrolyl), 1-(4-[(4-chlorophenyl)-phenyl-methyl]-piperazinyl), 2-(1,2,3,4-tetrahydro-isoquinolinyl), 1-(4-t-butoxycarbonyl-piperazinyl), 2-(1,2,3,4-tetrahydro-6,7-dimethoxy-isoquinolinyl), 4-(2,6-dimethyl-morpholinyl), 1-(4-benzyl-piperazinyl), 1-pyrrolidinyl, 1-(2,3,-dihydro-pyrrolidinyl), 1-(3-hydroxy-pyrrolidinyl), 1-(3-(S)-hydroxy-pyrrolidinyl), 1-piperidinyl, 1-(3-ethoxycarbonyl-piperidinyl), 1-(4-ethoxycarbonyl-piperidinyl), 1-imidazolyl, 1-(2-(phenylamino-methyl)-N-pyrrolidinyl), 1-(3-(R)-dimethylamino-pyrrolidinyl), 1-(3-(R)-hydroxy-pyrrolidinyl), 1-(3,4-dihydroxy-2,5-bis-hydrooxymethyl-pyrrolidinyl), 1-(3-(R)-t-butoxycarbonylamino-pyrrolidinyl), 1-(3-(S)-ethylamino-pyrrolidinyl), 1-(3-(R)-amino-pyrrolidinyl), 1-(3-(S)-amino-pyrrolidinyl), 1-(3-(R)-methylamino-pyrrolidinyl), 1-(3-(S)-methylamino-pyrrolidinyl), 1-(3-(N-methyl-N-t-butoxycarbonyl-amino)-pyrrolidinyl) or 1-(2-(3,5-dichlorophenyl)-3-methyl-5-carboxy-1,2,4-triazolyl). Preferably, when $R^1$ and $R^2$ are both bound to the same nitrogen atom, $R^1$ and $R^2$ are taken together with the nitrogen atom to which they are bound to form a group selected from 1-(4-(3-trifluoromethyl-phenyl)-piperazinyl), 1-(4-piperidinyl-piperidinyl), 1-(4-(3,4-methylenedioxyphenylmethyl)-piperazinyl), 1-(3-(diethylaminocarbonyl)-piperidinyl), 1-(2,3-dihydro-1H-pyrrolyl), 1-(4-[(4-chlorophenyl)-phenyl-methyl]-piperazinyl), 2-(1,2,3,4-tetrahydro-isoquinolinyl), 1-(4-t-butoxycarbonyl-piperazinyl), 2-(1,2,3,4-tetrahydro-6,7-dimethoxy-isoquinolinyl), 4-(2,6-dimethyl-morpholinyl), 1-(4-benzyl-piperazinyl), 1-pyrrolidinyl, 1-piperidinyl, 1-(4-ethoxycarbonyl-piperidinyl), 1-imidazolyl and 1-(2-(phenylamino-methyl)-N-pyrrolidinyl).

In an embodiment of the present invention, when $R^1$ and $R^2$ are both bound to the same nitrogen atom, $R^1$ and $R^2$ are taken together with the nitrogen atom to which they are bound to form a group selected from 1-(4-(3-trifluoromethyl-phenyl)-piperazinyl), 1-(4-phenyl-piperidinyl), 1-(4-piperidinyl-piperidinyl), 1-(4-(3,4-methylenedioxyphenyl-methyl)-piperazinyl), 1-(3-(diethylaminocarbonyl)-piperidinyl), 1-(4-[(4-chlorophenyl)-phenylmethyl]-piperiazinyl), 2-(1,2,3,4-tetrahydro-isoquinolinyl), 1-(4-t-butoxycarbonyl-piperazinyl), 2-(1,2,3,4-tetrahydro-6,7-dimethoxy-isoquinolinyl), 4-(2,6-dimethyl-morpholinyl), 1-(4-benzyl-piperazinyl), 1-morpholinyl, 1-pyrrolidinyl, 1-(2,3-dihydro-pyrrolidinyl), 1-piperidinyl, 1-(3,5-dimethyl-piperidinyl), 1-(3-hydroxymethyl-piperidinyl), 1-(3-ethoxycarbonyl-piperidinyl), 1-(4-(ethoxycarbonyl)-piperidinyl), 1-imidazolyl and 1-(2-(phenylamino-methyl)-N-pyrrolidinyl). Preferably, when $R^1$ and $R^2$ are both bound to the same nitrogen atom, $R^1$ and $R^2$ are taken together with the nitrogen atom to which they are bound to form a group selected from 1-(4-(3-trifluoromethyl-phenyl)-piperazinyl), 1-(4-piperidinyl-piperidinyl), 1-(4-(3,4-methylenedioxyphenyl-methyl)-piperazinyl), 1-(3-(diethylaminocarbonyl)-piperidinyl), 1-(4-[(4-chlorophenyl)-phenylmethyl]-piperiazinyl), 2-(1,2,3,4-tetrahydro-isoquinolinyl), 1-(4-t-butoxycarbonyl-piperazinyl), 2-(1,2,3,4-tetrahydro-6,7-dimethoxy-isoquinolinyl), 4-(2,6-dimethyl-morpholinyl), 1-(4-benzyl-piperazinyl), 1-pyrrolidinyl, 1-piperidinyl, 1-(4-(ethoxycarbonyl)-piperidinyl), 1-imidazolyl and 1-(2-(phenylamino-methyl)-N-pyrrolidinyl).

In an embodiment of the present invention, when $R^1$ and $R^2$ are both bound to the same nitrogen atom, $R^1$ and $R^2$ are taken together with the nitrogen atom to which they are bound to form a group selected from 1-(4-(3-trifluoromethyl-phenyl)-piperazinyl), 1-(4-phenyl-piperidinyl), 1-(4-piperidinyl-piperidinyl), 1-(4-(3,4-methylenedioxyphenyl-methyl)-piperazinyl), 1-(3-(diethylaminocarbonyl)-piperidinyl), 1-(4-[(4-chlorophenyl)-phenylmethyl]-piperiazinyl), 2-(1,2,3,4-tetrahydro-isoquinolinyl), 1-(4-t-butoxycarbonyl-piperazinyl), 2-(1,2,3,4-tetrahydro-6,7-dimethoxy-isoquinolinyl), 4-(2,6-dimethyl-morpholinyl), 1-(4-benzyl-piperazinyl), 1-(3,5-dimethyl-piperidinyl), 1-(3-hydroxymethyl-piperidinyl), 1-(3-ethoxycarbonyl-piperidinyl), 1-(4-(ethoxycarbonyl)-piperidinyl), 1-piperidinyl, 1-morpholinyl, 1-pyrrolidinyl, 1-imidazolyl, 1-(2,3-dihydro-pyrrolidinyl), and 1-(2-(phenylamino-methyl)-N-pyrrolidinyl). Preferably, when $R^1$ and $R^2$ are both bound to the same nitrogen atom, $R^1$ and $R^2$ are taken together with the nitrogen atom to which they are bound to form a group selected from 1-(4-(3-trifluoromethyl-phenyl)-piperazinyl), 1-(4-piperidinyl-piperidinyl), 1-(4-(3,4-methylenedioxyphenyl-methyl)-piperazinyl), 1-(3-(diethylaminocarbonyl)-piperidinyl), 1-(4-[(4-chlorophenyl)-phenylmethyl]-piperiazinyl), 2-(1,2,3,4-tetrahydro-isoquinolinyl), 1-(4-t-butoxycarbonyl-piperazinyl), 2-(1,2,3,4-tetrahydro-6,7-dimethoxy-isoquinolinyl), 4-(2,6-dimethyl-morpholinyl), 1-(4-benzyl-piperazinyl), 1-(4-(ethoxycarbonyl)-piperidinyl), 1-piperidinyl, 1-imidazolyl and 1-(2-(phenylamino-methyl)-N-pyrrolidinyl).

In an embodiment of the present invention, when $R^1$ and $R^2$ are both bound to the same nitrogen atom, $R^1$ and $R^2$ are taken together with the nitrogen atom to which they are bound to form a group selected from 2-(1,2,3,4-tetrahydro-6,7-dimethoxy-isoquinolinyl), 1-(4-[(4-chlorophenyl)-phenylmethyl]-piperazinyl), 1-pyrrolidinyl, 1-(3-hydroxy-pyrrolidinyl), 1-(3-(R)-hydroxy-pyrrolidinyl), 1-(4-hydroxy-piperidinyl), 1-(3-(R)-dimethylamino-pyrrolidinyl), 1-(4-t-butoxycarbonylamino-pyrrolidinyl), 1-(3-(R)-t-butoxycarbonylamino-pyrrolidinyl), 1-(3-(R)-amino-pyrrolidinyl), 1-(3-(S)-amino-pyrrolidinyl), 1-(3-(R)-methylamino-pyrrolidinyl), 1-(3-(S)-ethylamino-pyrrolidinyl), 1-(4-dimethylamino-pyrrolidinyl), 1-(3-(N-methyl-N-t-butoxycarbonyl-amino-pyrrolidinyl) or 1-(2-(3,5-dichlorophenyl)-3-methyl-5-carboxy-1,2,4-triazolyl). Preferably, when $R^1$ and $R^2$ are both bound to the same nitrogen atom, $R^1$ and $R^2$ are taken together with the nitrogen atom to which they are bound to form a group selected from 2-(1,2,3,4-tetrahydro-6,7-dimethoxy-isoquinolinyl), 1-(4-[(4-chlorophenyl)-phenyl-methyl]-piperazinyl), 1-pyrrolidinyl, 1-(3-hydroxy-pyrrolidinyl), 1-(3-(R)-hydroxy-pyrrolidinyl), 1-(4-hydroxy-piperidinyl), 1-(3-(R)-dimethylamino-pyrrolidinyl), 1-(4-t-butoxycarbonylamino-pyrrolidinyl), 1-(3-(R)-t-butoxycarbonylamino-pyrrolidinyl), 1-(3-(R)-amino-pyrrolidinyl), 1-(3-(S)-amino-pyrrolidinyl), 1-(3-(S)-methylamino-pyrrolidinyl), 1-(3-(R)-methylamino-pyrrolidinyl), 1-(3-(S)-ethylamino-pyrrolidinyl), 1-(4-dimethylamino-pyrrolidinyl), 1-(3-(N-methyl-N-t-butoxycarbonyl-amino-pyrrolidinyl) or 1-(2-(3,5-dichlorophenyl)-3-methyl-5-carboxy-1,2,4-triazolyl).

In an embodiment of the present invention, n is an integer from 0 to 1, preferably n is 0. In an embodiment of the present invention m is 0. In another embodiment of the present invention m is 1.

In an embodiment of the present invention p is an integer from 0 to 2, preferably p is an integer from 0 to 1. In an embodiment of the present invention q is 0. In another embodiment of the present invention, q is 1.

In an embodiment of the present invention, $R^3$ is selected from the group consisting of aryl and $arC_{1-4}$alkyl; wherein the aryl or $arC_{1-4}$alkyl group is optionally substituted with one to three substituents independently selected from halogen, hydroxy, carboxy, $C_{1-4}$alkyl, $C_{1-4}$alkoxy, trifluoromethyl, trifluoromethoxy, nitro, cyano or $N(R^E)_2$. Preferably, $R^3$ is aryl; wherein the aryl group is optionally substituted with one or more substituents independently selected from halogen. More preferably, $R^3$ is selected from the group consisting of phenyl and 4-fluorophenyl.

In an embodiment of the present invention, $L^1$ is $C_{1-4}$alkyl; wherein the $C_{1-4}$alkyl group is optionally substituted with one to two substituents independently selected from hydroxy, fluoro, $C_{1-4}$alkyl, fluorinated $C_{1-4}$alkyl or $C_{1-4}$alkoxy. Preferably, $L^1$ is unsubstituted $C_{1-4}$alkyl. More preferably, $L^1$ is selected from the group consisting of —$CH_2$—, —CH($CH_3$)— and —$CH_2CH_2$—. More preferably still, $L^1$ is —$CH_2$— or —$CH_2CH_2$—;

In an embodiment of the present invention,

is selected from the group consisting of partially unsaturated carbocyclyl, cycloalkyl, aryl, heterocycloalkyl and heteroaryl.

In another embodiment of the present invention,

is selected from the group consisting of cyclooctyl, 1-acenaphthenyl, R-1-acenaphthenyl, S-1-acenaphthenyl, cyclohexyl, phenyl, 1-naphthyl, 2-naphthyl, 1,2,3,4-tetrahydro-naphthyl, 2-thienyl, benzothienyl, 4,5,6,7-tetrahydrobenzothienyl, bicyclo[3.1.1]hepten-2-yl, bicyclo[3.1.1]heptyl and (3aS)-2,3,3a,4,5,6-hexahydro-1H-phenalen-1-yl. Preferably,

is selected from the group consisting of cyclooctyl, 1-acenaphthenyl, R-1-acenaphthenyl, S-1-acenaphthenyl, cyclohexyl, phenyl, 1-naphthyl, 2-naphthyl, 2-thienyl and (3aS)-2,3,3a,4,5,6-hexahydro-1H-phenalen-1-yl.

In another embodiment of the present invention,

is selected from the group consisting of cyclooctyl, 1-acenaphthenyl, R-1-acenaphthenyl, S-1-acenaphthenyl, cyclohexyl, phenyl, 1-naphthyl and (3a-S)-2,3,3a,4,5,6-hexahydro-1H-phenalen-2-yl.

In another embodiment of the present invention,

is selected from the group consisting of cyclooctyl, 1-naphthyl, 1-acenaphthenyl, R-1-acenaphthenyl, S-1-acenaphthenyl, bicyclo[3.1.1]hepten-2-yl and (3aS)-2,3,3a,4,5,6-hexahydro-1H-phenalen-1-yl.

In an embodiment of the present invention, $R^5$ is selected from the group consisting of hydroxy, carboxy, halogen, $C_{1-4}$alkyl, $C_{1-4}$alkoxy, nitro, cyano, $N(R^E)_2$, trifluoromethyl, trifluoromethoxy, $C_{1-4}$alkoxycarbonyl, —SO—$N(R^E)_2$, —$SO_2$—$N(R^E)_2$ and —C(O)—$N(R^E)_2$.

In another embodiment of the present invention, $R^5$ is selected from the group consisting of halogen, $C_{1-4}$alkyl and trifluoromethyl. Preferably, $R^5$ is selected from the group consisting of chloro, methyl, n-propyl and trifluoromethyl.

In another embodiment of the present invention, $R^5$ is selected from the group consisting of methyl, n-propyl, chloro and trifluoromethyl. Preferably, $R^5$ is selected from the group consisting of methyl, n-propyl and trifluoromethyl. More preferably, $R^5$ is selected from the group consisting of methyl and n-propyl. In yet another embodiment of the present invention, $R^5$ is methyl.

In an embodiment of the present invention $R^6$ is -$(L^2)_0$-$R^7$. In another embodiment of the present invention, $R^6$ is -$(L^2)_1$-$R^7$ and $L^2$ is selected from the group consisting of —$C_{1-4}$alkyl-, —O—, —S—, —$N(R^E)$—, —C(O)O— and —O—C(O)—.

In an embodiment of the present invention, $R^7$ is selected from the group consisting of cycloalkyl, aryl, heteroaryl and heterocycloalkyl; wherein the aryl, heteroaryl or heterocycloalkyl group is optionally substituted with one to two substituents independently selected from hydroxy, carboxy, halogen, $C_{1-4}$alkyl, $C_{1-4}$alkoxy, nitro, cyano, $N(R^E)_2$, trifluoromethyl, trifluoromethoxy or $C_{1-4}$alkoxycarbonyl. Preferably, $R^7$ is selected from the group consisting of aryl and heteroaryl. More preferably, $R^7$ is selected from the group consisting of phenyl and 2-thienyl. More preferably still, $R^7$ is 2-thienyl.

In an embodiment of the present invention is a compound of formula (I) selected from the group consisting of
8-(R) acenaphthen-1-yl-3-(3-amino-2-(S)-hydroxy-propyl)-1-(4-fluoro-phenyl)-1,3,8-triaza-spiro[4.5]decan-4-one;
8-(R) acenaphthen-1-yl-3-(3-amino-2-(R)-hydroxy-propyl)-1-(4-fluoro-phenyl)-1,3,8-triaza-spiro[4.5]decan-4-one;
8-(R)-Acenaphthen-1-yl-3-(3-dimethylamino-2-(R)-hydroxy-propyl)-1-(4-fluoro-phenyl)-1,3,8-triaza-spiro[4.5]decan-4-one;
3-(3-Amino-2-(R)-hydroxy-propyl)-1-(4-fluoro-phenyl)-8-(8-methyl-naphthalen-1-ylmethyl)-1,3,8-triaza-spiro[4.5]decan-4-one;
3-(3-Dimethylamino-2-(R)-hydroxy-propyl)-1-(4-fluoro-phenyl)-8-(8-methyl-naphthalen-1-ylmethyl)-1,3,8-triaza-spiro[4.5]decan-4-one;
8-(R)-Acenaphthen-1-yl-1-(4-fluoro-phenyl)-3-[2-(R)-hydroxy-3-(3-hydroxymethyl-piperidin-1-yl)-propyl]-1,3,8-triaza-spiro[4.5]decan-4-one;
3-(3-Amino-2-(R)-hydroxy-propyl)-8-cyclooctyl-1-(4-fluoro-phenyl)-1,3,8-triaza-spiro[4.5]decan-4-one;
3-(3-Amino-2-(R)-hydroxy-propyl)-1-(4-fluoro-phenyl)-8-1-(S)-(3aS)-(2,3,3a,4,5,6-hexahydro-1H-phenalen-1-yl)-1,3,8-triaza-spiro[4.5]decan-4-one;

1-(4-Fluoro-phenyl)-3-[2-(R)-hydroxy-3-(3-hydroxy-propylamino)-propyl]-8-(8-methyl-naphthalen-1-ylmethyl)-1,3,8-triaza-spiro[4.5]decan-4-one;

1-(4-Fluoro-phenyl)-3-[2-(R)-hydroxy-3-(3-methylamino-propylamino)-propyl]-8-(8-methyl-naphthalen-1-ylmethyl)-1,3,8-triaza-spiro[4.5]decan-4-one;

3-[3-(3-Dimethylamino-propylamino)-2-(R)-hydroxy-propyl]-1-(4-fluoro-phenyl)-8-(8-methyl-naphthalen-1-ylmethyl)-1,3,8-triaza-spiro[4.5]decan-4-one and pharmaceutically acceptable salts thereof.

With regard to compounds of formula (E), in an embodiment of the present invention Y is selected from the group consisting of hydrogen, $C_{1-4}$alkyl and t-butoxycarbonyl, preferably, $C_{1-4}$alkyl or t-butoxycarbonyl, more preferably ethyl. In another embodiment of the present invention Y is

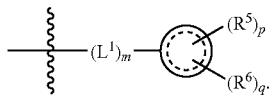

Additional embodiments of the present invention, include those wherein the substituents selected for one or more of the variables defined herein (i.e. $R^0$, $R^3$, n, $R^4$, m, $L^1$,

p, $R^5$, q, $R^6$ and Y) are independently selected to be any individual substituent or any subset of substituents selected from the complete list as defined herein.

As used herein, unless otherwise noted, "halogen" shall mean chlorine, bromine, fluorine and iodine.

As used herein, the term "alkyl", whether used alone or as part of a substituent group, include straight and branched alkyl chain, preferably comprising one to eight carbon atoms. For example, alkyl radicals include methyl, ethyl, propyl, isopropyl, butyl, isobutyl, sec-butyl, t-butyl, pentyl and the like. As used herein, the term. "lower alkyl" shall mean a straight or branched alkyl chain comprising one to four carbon atoms. Suitable examples of a lower alkyl group include methyl, ethyl, propyl, isopropyl, butyl, t-butyl, and the like.

As used herein, unless otherwise noted, the term "hydroxy substituted alkyl" shall mean any straight or branched alkyl chain which is substituted with one or more hydroxy groups, for example hydroxymethyl, 1-hydroxy-eth-2-yl, and the like. Preferably, the alkyl chain is substituted with one to three hydroxy groups, more preferably one hydroxy group.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "aryl" shall refer to unsubstituted carbocyclic aromatic groups such as phenyl, naphthyl, and the like.

As used herein, unless otherwise noted, "ar$C_{1-4}$alkyl" shall mean any lower alkyl group (i.e. $C_{1-4}$alkyl group) substituted with an aryl group such as phenyl, naphthyl and the like. Suitable examples of an ar$C_{1-4}$alkyl group include, benzyl, 2-phenylethyl (i.e. Phenyl-$CH_2$—$CH_2$—), 3-phenyl-n-propyl (i.e. Phenyl-$CH_2$—$CH_2$—$CH_2$—), naphthyl-methyl, and the like.

As used herein, unless otherwise noted, the term "acyl" shall mean a radical formed from an organic acid by removal of the hydroxy group. Suitable example include acetyl, benzoyl, and the like.

As used herein, unless otherwise noted, the term "cycloalkyl" shall mean any stable three to fourteen membered monocyclic, bicyclic, tricyclic or bridged carbon based, saturated ring system, for example cyclopropyl, cyclobutyl, cyclopentyl, cyclohexyl, cycloheptyl, cyclooctyl, adamantanyl, bicyclo[3.1.1]heptyl, and the like.

As used herein, unless otherwise noted, the term "carbocyclyl" shall mean four to fourteen membered, preferably five to thirteen membered, more preferably five to ten membered monocyclic, bicyclic or tricyclic, carbon based ring structure. Similarly, unless otherwise noted, the term "partially unsaturated carbocyclyl" shall mean any five to fourteen, preferably five to thirteen, more preferably five to ten, membered monocyclic, bicyclic or tricyclic, carbon based ring structure containing at least one unsaturated (double or triple) bond. Suitable examples of partially unsaturated carbocyclyl groups include 1,2,3,4-tetrahydronaphthyl, cyclohexen-1-yl, 1-acenaphthenyl,

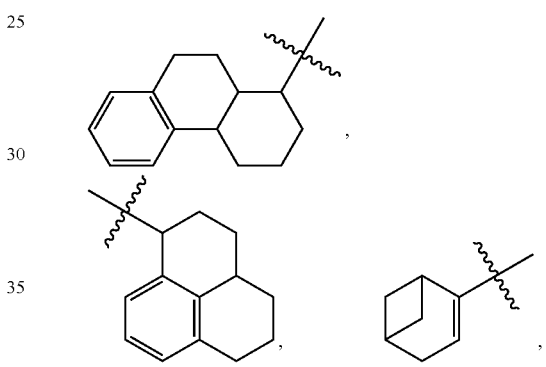

and the like.

As used herein, unless otherwise noted, "heteroaryl" shall denote any five to seven, preferably five to six, membered monocyclic aromatic ring structure containing at least one heteroatom selected from the group consisting of O, N and S, optionally containing one to three additional heteroatoms independently selected from the group consisting of O, N and S; or a nine to ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, pyrazolyl, isoxazolyl, thiazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like. Preferred heteroaryl groups include thienyl, pyridyl, furyl, imidazolyl, pyrazolyl, pyrrolyl, indolyl and quinolinyl.

One skilled in the art will recognize that wherein the heteroaryl group contains one or more nitrogen atoms, said heteroaryl group may optionally be present as or within a substituent group in a quaternary form, for example as in 1-(2-(3,5-dichlorophenyl)-3-methyl-5-carboxy-1,2,4-triazolyl), a substituent of the formula

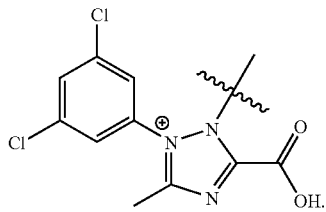

As used herein, the term "heterocycloalkyl" shall denote any five to seven, preferably five to six, membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, 1,2,3,4-tetrahydroisoquinolinyl, 1,2,3,4-tetrahydroquinolinyl, 4,5,6,7-tetrahydro-benzo[b]thienyl and the like. Preferred heterocycloalkyl groups include pyrrolidinyl, piperidinyl, piperazinyl, morpholinyl, 1,2,3,4-tetrahydroisoquinolinyl, 4,5,6,7-tetrahydro-benzo[b]thienyl, 3,4-methylenedioxyphenyl and 3,4-dihydro-2H-benzo[b][1,4]dioxepine.

As used herein, the name "1-acenaphthenyl" shall mean a substituent group of the formula

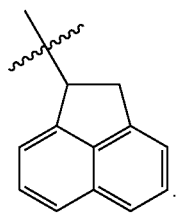

As used herein, the name "2-(3,4-methylenedioxyphenyl) ethyl" shall mean a substituent group of the formula

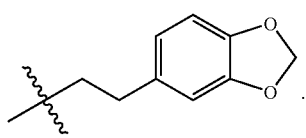

As used herein, the name "2-(1,2,3,4-tetrahydro-6,7-dimethoxy-isoquinolinyl)" shall mean a substituent group of the formula

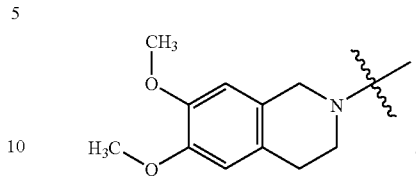

As used herein, the name "2,3,3a,4,5,6-hexahydro-1H-phenalen-1-yl" shall mean a substituent group of the formula

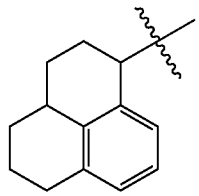

As used herein, the name "oxarinyl-methyl" shall mean a substituent group of the formula

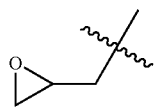

As used herein, the name "6,6-dimethyl-bicyclo[3.1.1]heptyl" shall mean a substituent group of the formula

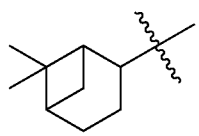

As used herein, the name "6,6-dimethyl-bicyclo[3.1.1]hept-2-enyl" shall mean a substituent group of the formula

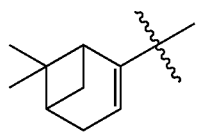

As used herein, the notation "*" shall denote the presence of a stereogenic center.

When a particular group is "substituted" (e.g., alkyl, aryl, carbocyclyl, heterocycloalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula

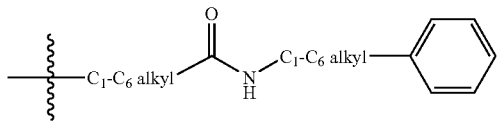

Abbreviations used in the specification, particularly the Schemes and Examples, are as follows:

| | |
|---|---|
| AcCN = | Acetonitrile |
| BINAP = | 2,2'-Bis(diphenylphosphino)-1,1'-binaphthyl |
| Boc = | t-Butoxycarbonyl |
| CBz = | benzyloxycarbonyl (C$_6$H$_5$—CH$_2$—O—C(O)—) |
| DAMGO = | Tyr-D-Ala-Gly-N-methyl-Phe-Gly-ol |
| DCC = | N,N-dicyclohexylcarbodiimide |
| DCE = | Dichloroethane |
| DCM = | Dichloromethane |
| DIPEA or DIEA = | Diisopropylethylamine |
| DMF = | N,N-Dimethylformamide |
| DME = | 1,2-dimethoxyethane |
| DMSO = | Dimethylsulfoxide |
| DPDPE = | Tyr-D-Pen-Gly-p-Chloro-Phe-D-Pen[Disulfide Bridge: 2-5] |
| EDCI = | 1-(3-dimethylaminopropyl)-3-ethylcarbodiimide hydrochloride |
| EDTA = | Ethylenediaminetetraacetic acid |
| EGTA = | Ethylene glycol-O,O'-bis(2-aminoethyl)-N,N,N',N'-tetracacetic acid |
| EtOAc = | Ethyl acetate |
| Fmoc = | 9-Fluorenylmethoxycarbonyl |
| HBTU = | O-(1H-Benzotriazol-1-yl)-N,N,N',N'-tetramethyluronium hexafluorophosphate |
| hex = | Hexane |
| HPLC = | High Pressure Liquid Chromatography |
| KO-t-Bu = | Potassium t-butoxide |
| LiHMDS = | Lithium bis(trimethylsilyl)amide |
| mCPBA = | meta-chloroperoxybenzoic acid |
| MeCN = | Acetonitrile |
| Ms = | mesyl or methanesulfonyl group |
| µW = | Microwave |
| NaHMDS = | Sodium bis(trimethylsilyl)amide |
| NatBuO or tBuONa = | Sodium t-butoxide |
| NMP = | N-methyl-2-pyrrolidinone |
| Pd$_2$(dba)$_3$ = | Tris(dibenzylideneacetone) dipalladium (0) |
| Pd(OAc)$_2$ = | Palladium (II) acetate |
| Pd(PPh$_3$)$_4$ = | tetrakis(triphenylphosphine)palladium(0) |
| PdCl$_2$(PPh$_3$)$_2$ or Pd(PPh$_3$)$_2$Cl$_2$ = | di(chloro)di(triphenylphosphine)palladium(0) |
| P(tBu)$_3$ = | Tri-t-butyl phosphine |
| PEI = | Polyethylimine |
| TEA or Et$_3$N = | Triethylamine |
| TFA = | Trifluoroacetic acid |
| THF = | Tetrahydrofuran |
| TLC = | Thin Layer Chromatography |
| TNE Buffer = | 50 mM Tris-HCl, pH 7.4 + 5 mM EDTA + 150 mM NaCl |
| Tris HCl = | Tris[hydroxymethyl]aminomethyl hydrochloride |
| Ts = | Tosyl or p-toluenesulfonyl group |
| U69593 = | (+)-(5α,7α,8β)-N-methyl-N-7-(1-pyrrolidinyl)-1-oxaspiro[4.5]dec-8-yl] benzene acetamide |

As used herein, unless otherwise noted, the term "eating disorders" shall mean any disorder associated with eating. Suitable examples include, but are not limited to anorexia nervosa, bulimia, binge eating, food cravings, and the like.

As used herein, unless otherwise noted, the term "adrenal disorders" shall mean disorders mediated by the adrenal gland. Suitable examples include, but are not limited to Cushing's syndrome, Addison's disease, and the like.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, carnsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, tosylate, triethiodide and valerate.

The compounds of formula (I) of the present invention may be prepared according to the processes described in more detail herein. More particularly, the compounds of formula (I) may be prepared through intermediates of formula (M1) or (M2), as outlined in Scheme 1.

Scheme 1

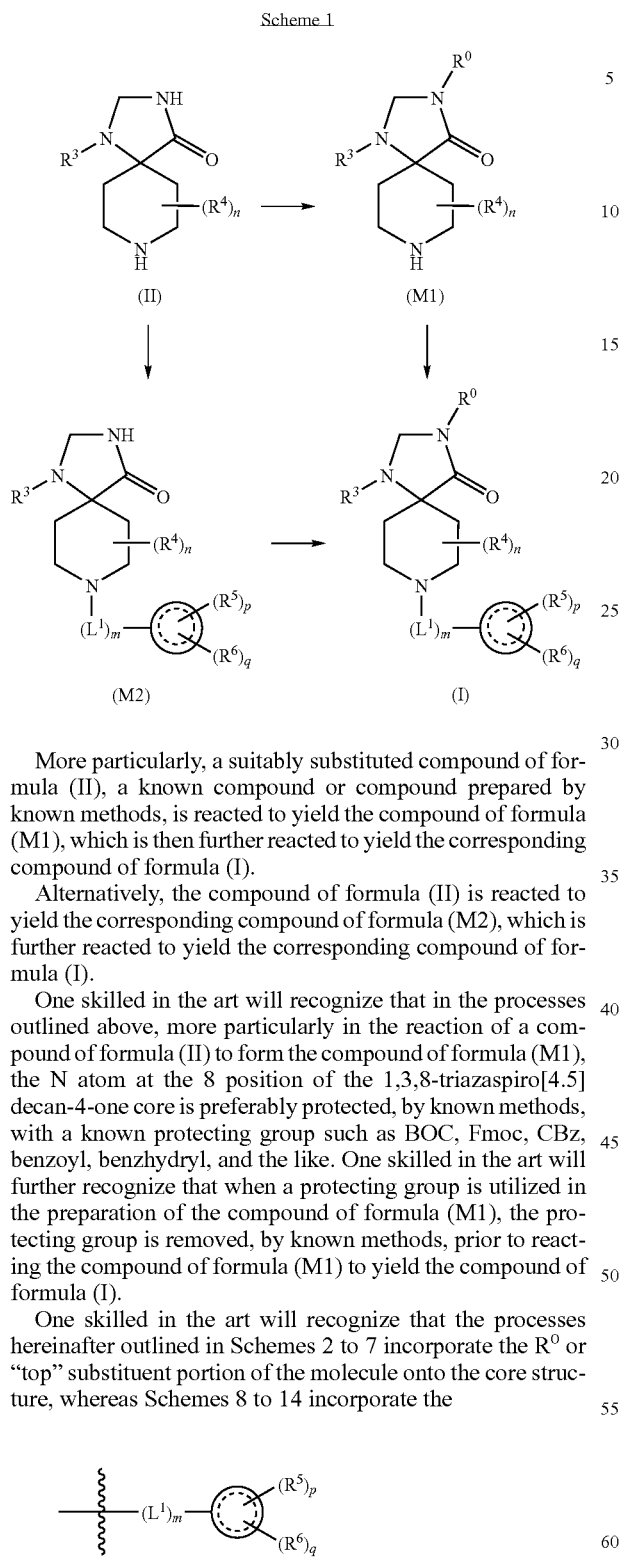

More particularly, a suitably substituted compound of formula (II), a known compound or compound prepared by known methods, is reacted to yield the compound of formula (M1), which is then further reacted to yield the corresponding compound of formula (I).

Alternatively, the compound of formula (II) is reacted to yield the corresponding compound of formula (M2), which is further reacted to yield the corresponding compound of formula (I).

One skilled in the art will recognize that in the processes outlined above, more particularly in the reaction of a compound of formula (II) to form the compound of formula (M1), the N atom at the 8 position of the 1,3,8-triazaspiro[4.5]decan-4-one core is preferably protected, by known methods, with a known protecting group such as BOC, Fmoc, CBz, benzoyl, benzhydryl, and the like. One skilled in the art will further recognize that when a protecting group is utilized in the preparation of the compound of formula (M1), the protecting group is removed, by known methods, prior to reacting the compound of formula (M1) to yield the compound of formula (I).

One skilled in the art will recognize that the processes hereinafter outlined in Schemes 2 to 7 incorporate the $R^O$ or "top" substituent portion of the molecule onto the core structure, whereas Schemes 8 to 14 incorporate the or "bottom" substituent portion of the molecule onto the core structure. One skilled in the art will further recognize that the top and bottom substituent portions may be incorporated into the compound of formula (I) in any order which yields the desired product.

Compounds of formula (M1) wherein $R^O$ is —$CR^AR^B$—CH(OH)—$CR^CR^D$—X and X is $NR^1R^2$ may be prepared from a suitably substituted compound of formula (II) according to the process outlined in Scheme 2.

Scheme 2

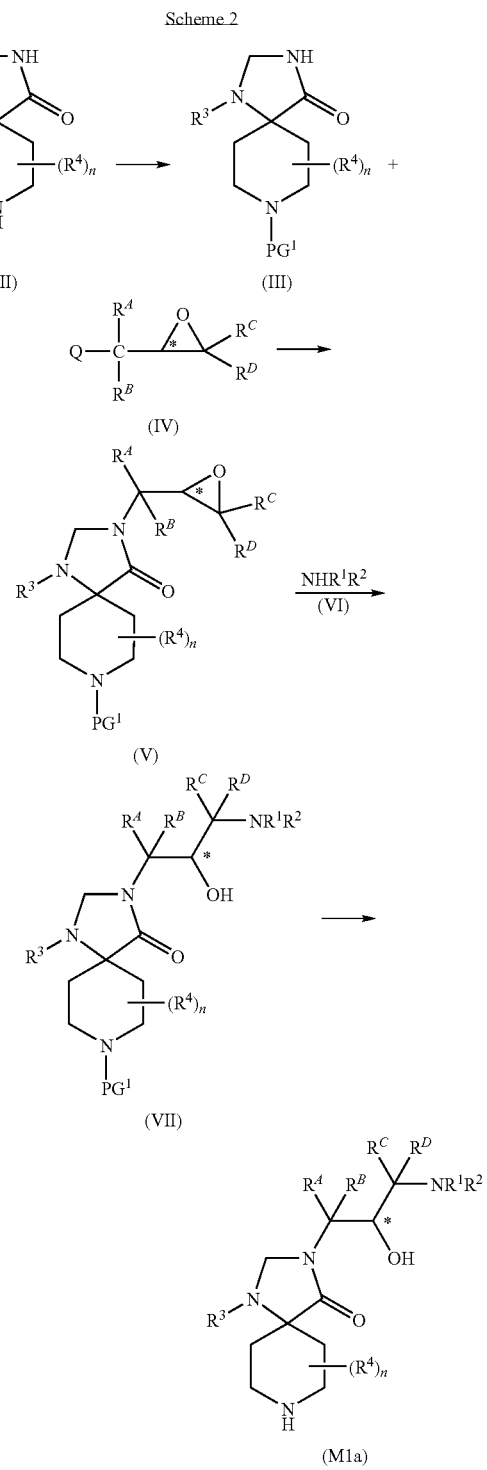

Accordingly, a suitably substituted compound of formula (II), is protected by known methods, with a suitably protecting group $PG^1$, such as t-butoxycarbonyl (BOC), CBz, Fmoc, benzhydryl, triphenylmethyl, 4-methoxybenzyl, benzoyl, and the like, to yield the corresponding compound of formula (III).

The compound of formula (III) is reacted with a suitable substituted compound of formula (IV) wherein Q is a suitable leaving group such as Cl, Br, I, tosylate, mesylate, and the like, a known compound or compound prepared by known methods, in the presence of a base such as NaH, KO-t-Bu, $K_2CO_3$, NaHMDS, LiHMDS, and the like, in an organic solvent such as NMP, DMF, THF, and the like, to yield the corresponding compound of formula (V).

The compound of formula (V) is reacted with a suitably substituted amine of formula (VI), a known compound or compound prepared by known methods, in an organic solvent such as ethanol, acetonitrile, methanol, isopropanol, and the like, to yield the corresponding compound of formula (VII).

The compound of formula (VII) is de-protected by known methods, to yield the corresponding compound of formula (M1a).

One skilled in the art will recognize that in the preparation of compounds of formula (I) and (M1a) as in Scheme 2 above (i.e. in reactions where the oxarinyl group is opened with a suitably substituted compound of formula (VI)), the stereo-configuration of the hydroxy group will be determined by the stereo-configuration of the compound of formula (IV), with the naming (R or S) of the stereo-center based on chemical nomenclature rules. Thus, for example, wherein the process outlined in Scheme 2 above $R^1$, $R^2$, $R^A$, $R^B$, $R_C$ and $R^D$ are each hydrogen, the compound of formula (IV) is 2-(R)-chloromethyl-oxirane, then the compound of formula (M1a) will have the hydroxy group in the (R) position.

Compounds of formula (M1a) wherein $R^0$ is

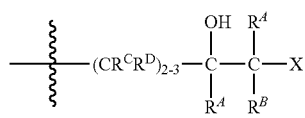

may be similarly prepared according to the process outlined in Scheme 2 above, with substitution of a suitably substituted compound of formula (VIII)

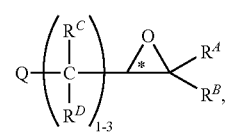

(VIII)

wherein Q is a suitable leaving group as previously defined, a known compound or compound prepared by known methods, for the compound (IV).

Compounds of formula (M1) wherein X is —O—$R^1$ may be prepared from a suitably substituted compound of formula (V) according to the process outlined in Scheme 3.

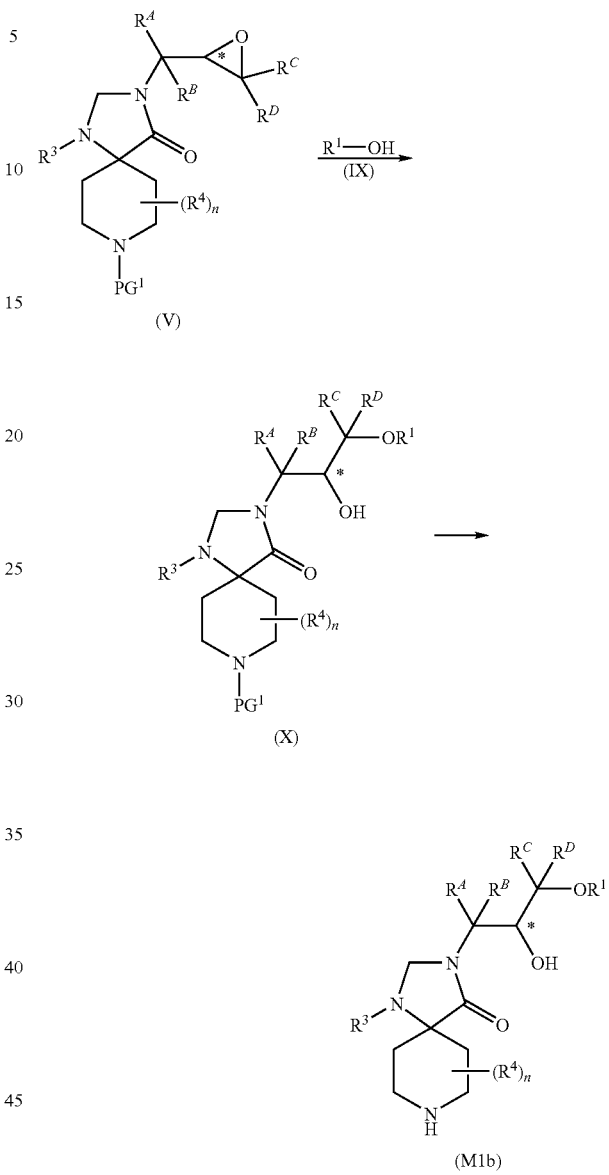

Accordingly, a suitably substituted compound of formula (V), is reacted with suitably substituted compound of formula (IX), a known compound or compound prepared by known methods, in the presence of a base such as NaH, KH, sodium trimethylsilylamide, TEA, DIPEA, and the like, wherein the base is present in amount equal to or greater than about one molar equivalent, in an organic solvent such as THF, NMP, DMF, and the like, to yield the corresponding compound of formula (X).

The compound of formula (X) is de-protected, by known methods, to yield the corresponding compound of formula (M1b).

Compounds of formula (M1) wherein X is selected from the group consisting of —S—$R^1$, —SO—$R^1$ or —$SO_2$—$R^1$ may be prepared from a suitably substituted compound of formula (V) according to the process outlined in Scheme 4.

Scheme 4

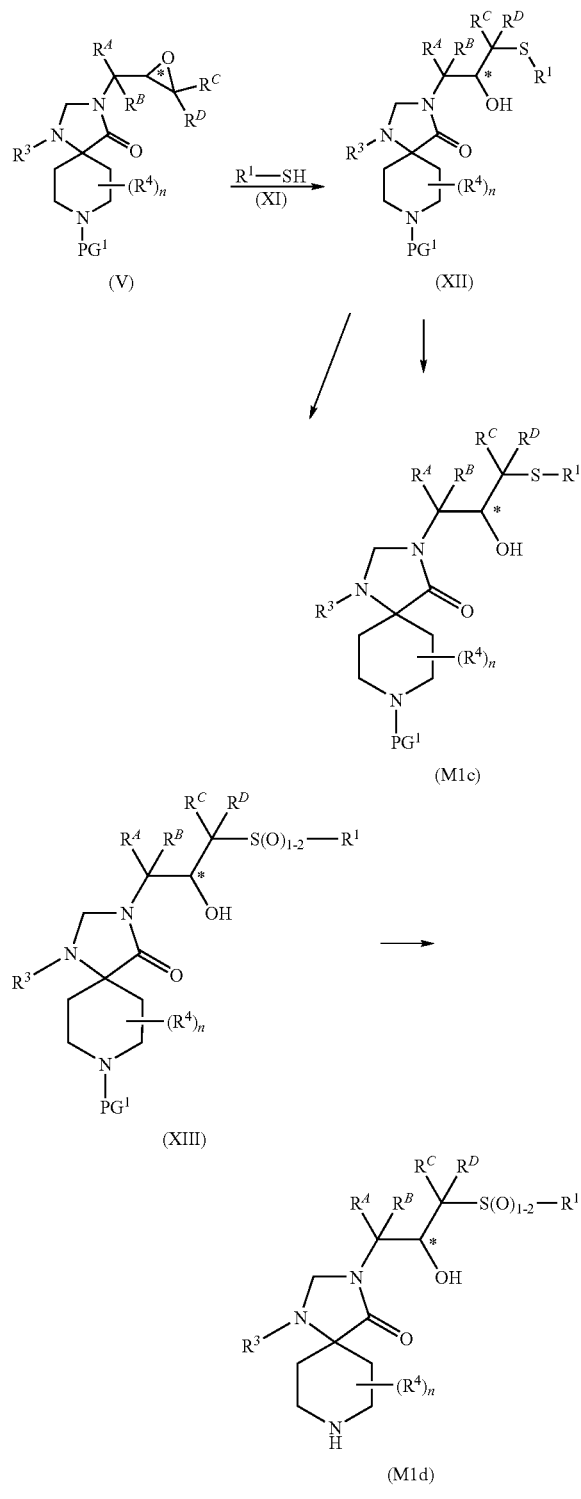

at an elevated temperature in the range of about room temperature to about 100° C., preferably at a temperature of about 50 to about 100° C., to yield the corresponding compound of formula (XII).

The compound of formula (XII) is de-protected by known methods, to yield the corresponding compound of formula (M1c), wherein X is —S—$R^1$.

Alternatively, the compound of formula (XII) is oxidized with an oxidizing agent such as hydrogen peroxide, mCPBA, and the like, according to known methods, to yield the corresponding compound of formula (XIII).

The compound of formula (XIII) is de-protected by known methods, to yield the corresponding compound of formula (M1d), wherein X is —SO—$R^1$ or —$SO_2$—$R^1$.

One skilled in the art will recognize that in the processes described in Scheme 4 above, the $PG^1$ protecting group on the N atom at the 8-position of the 1,3,8-triazaspiro[4.5]decan-4-one is not mandatory (but may be preferred), as the reactions will yield the desired compounds even in the absence of protection of the N atom.

One skilled in the art will recognize that compounds of formula (M1) wherein X is selected from —S-(alkyl)-$NR^1R^2$, —SO-(alkyl)-$NR^1R^2$ or —$SO_2$-(alkyl)-$NR^1R^2$ may be similarly prepared according to the process outlined in Scheme 4 above, with substitution of a suitably substituted compound of formula (XIV)

HS-(alkyl)-$NR^1R^2$       (XIV), a known compound or compound prepared by known methods, for the compound of formula (XI).

Compounds of formula (M1) wherein X is —$NR^1$—C(O)—$R^2$ may be prepared according to the process outlined in Scheme 5.

Scheme 5

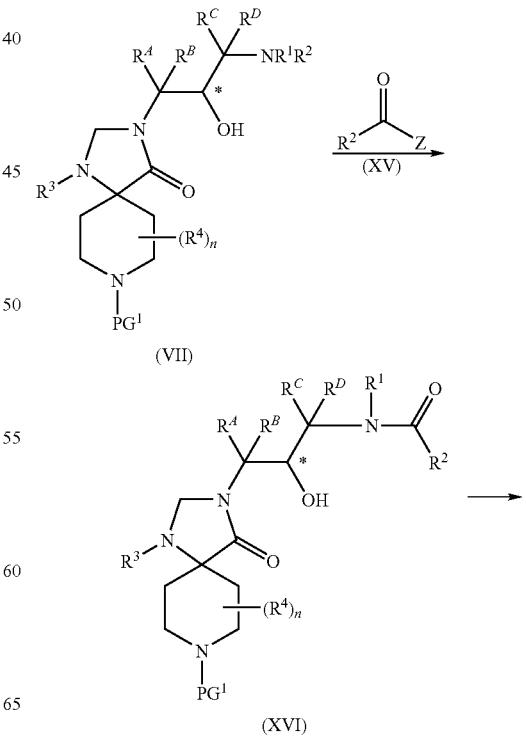

Accordingly, a suitably substituted compound of formula (V) is reacted with a suitably substituted compound of formula (XI), a known compound or compound prepared by known methods, in the presence of a base such as TEA, DIPEA, and the like, in a protic solvent such as ethanol, methanol, NMP, and the like, or a mixture thereof, preferably -continued

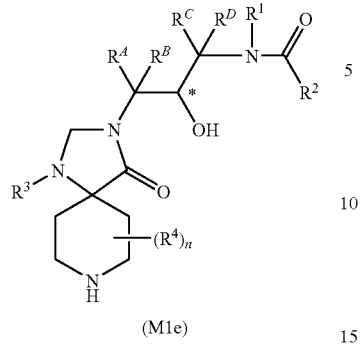

(M1e)

Accordingly, a suitably substituted compound of formula (VII), wherein $R^1$ is hydrogen, is reacted with a suitably substituted compound of formula (XV), wherein Z is Cl, Br or OH, a known compound or compound prepared by known methods, in the presence of a base such as TEA, DIPEA, pyridine, and the like, wherein the base is present in an amount equal to or greater than about one molar equivalent, in an organic solvent such as THF, DMF, NMP, DCM, and the like, preferably at room temperature, to yield the corresponding compound of formula (XVI). Wherein the compound of formula (XV) Z is OH, the compound of formula (VII) is reacted with the compound of formula (XV) in the presence of a coupling agent such as HBTU, DCC, and the like.

The compound of formula (XVI) is de-protected by known methods, to yield the corresponding compound of formula (M1e).

Compounds of formula (M1) wherein X is —C(O)—$NR^1NR^2$ may be prepared according to the process outlined in Scheme 6.

Scheme 6

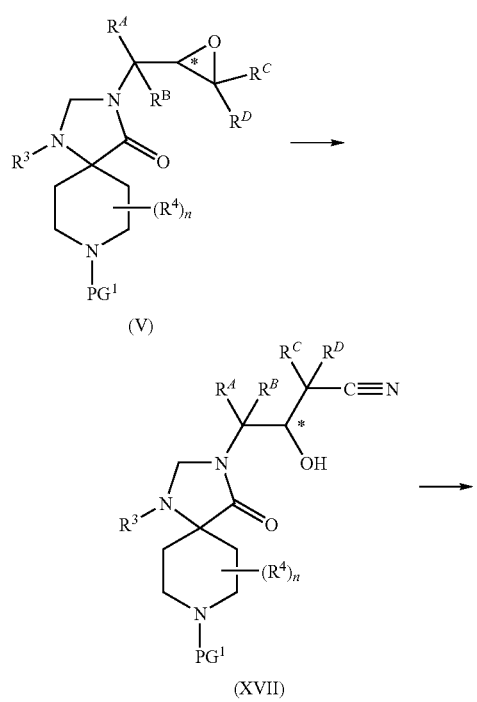

-continued

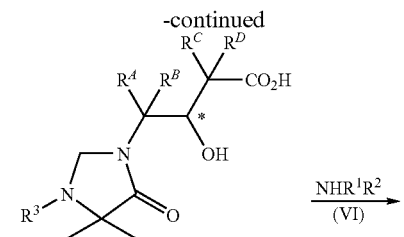

(XVIII)

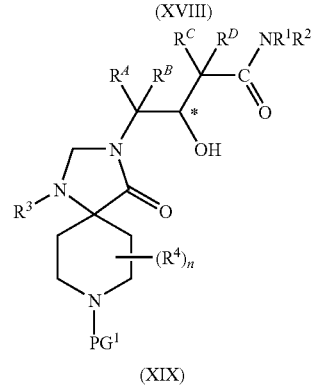

(XIX)

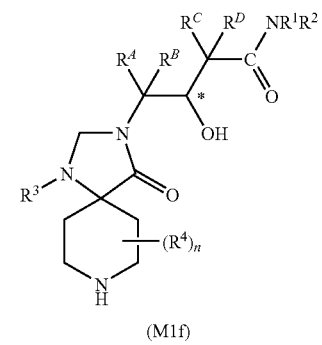

(M1f)

Accordingly, a suitably substituted compound of formula (V) is reacted with potassium cyanide, in a co-solvent such as methanol-water, and the like, preferably at room temperature, to yield the corresponding compound of formula (XVII).

The compound of formula (XVII) is reacted with a base such as KOH, NaOH, and the like or with an acid such as $H_2SO_4$, HCl, and the like, or $NaBH_4$ in the presence of $AlCl_3$, to yield the corresponding compound of formula (XVIII).

The compound of formula (XVIII) is reacted with a suitably substituted compound of formula (VI), a known compound or compound prepared by known methods, in the presence of a coupling agent such as DCC, EDCl, and the like, in an organic solvent such as $CH_2Cl_2$, THF, DMF, and the like, to yield the corresponding compound of formula (XIX).

The compound of formula (XIX) is de-protected by known methods, to yield the corresponding compound of formula (M1f).

Alternatively, the compound of formula (XVII) is reacted with a suitably substituted alcohol, a compound of the formula $R^1$—OH, a known compound or compound prepared by known methods, in the presence of an acid such as acetic acid, $H_2SO_4$, HCl, and the like, to yield the corresponding compound of formula (M1) wherein X is $C(O)NHR^1$. One skilled in the art will recognize that compounds of formula (M1) wherein X is C(O)N(R$^1$)$_2$ may be similarly prepared by reacting the compound of formula (XVII) with a suitably substituted alcohol of the formula R$^1$—OH, in the presence of an acid such as H$_2$SO$_4$, HCl, and the like, wherein the alcohol of formula R$^1$—OH is present in an excess amount.

Compounds of formula (M1a) wherein R$^0$ is

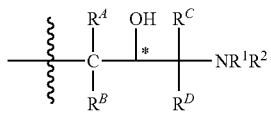

may alternatively be prepared according to the process outlined in Scheme 7.

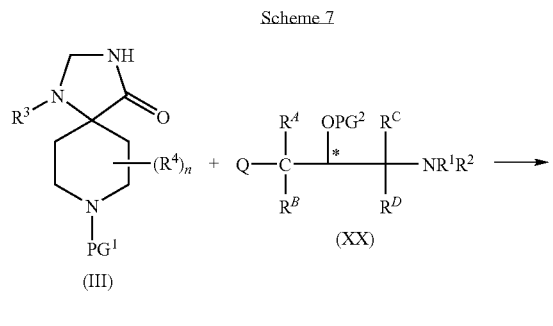

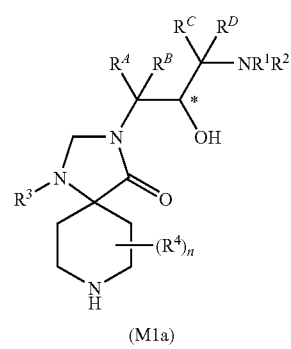

Accordingly, a suitably substituted compound of formula (III), is reacted with a suitably substituted compound of formula (XX), wherein Q is a suitable leaving group such as Cl, Br, I, tosylate, mesylate, and the like, and wherein PG$^2$ is a suitably protecting group such as benzyl, acyl, and the like, a known compound or compound prepared by known methods, in the presence of a base such as NaH, KO-t-Bu, K$_2$CO$_3$, NaHMDS, LiHMDS, and the like, in an organic solvent such as NMP, DMF, THF, and the like, to yield the corresponding compound of formula (XXI).

The compound of formula (XXI) is de-protected by known methods, to yield the corresponding compound of formula (M1a). One skilled in the art will recognize that the protecting groups PG$^1$ and PG$^2$ on the compound of formula (XXI) may be removed simultaneously or sequentially, in any order, by known methods.

One skilled in the art will recognize, that compounds of formula (M1) wherein R$^0$ is selected from the group consisting of

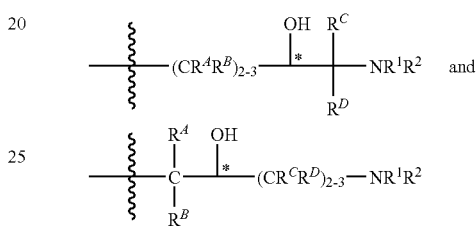 and

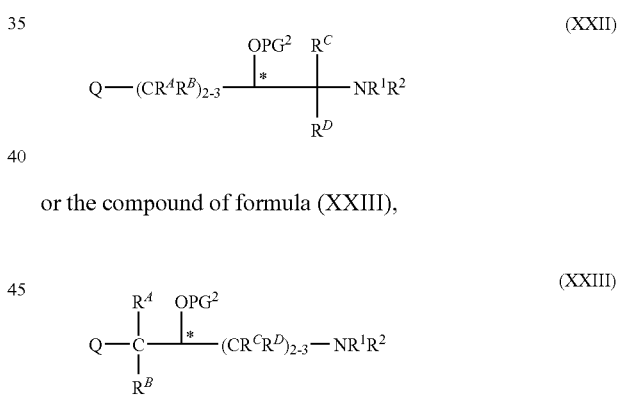

may be similarly prepared according to the process outlined in Scheme 7 above, with selection and substitution of a suitably substituted compound of formula (XXII)

(XXII)

$$Q—(CR^AR^B)_{2\text{-}3}\overset{OPG^2}{\underset{R^D}{\overset{R^C}{\vert}}}—NR^1R^2$$

or the compound of formula (XXIII), (XXIII)

$$Q—\overset{R^A}{\underset{R^B}{\overset{\vert}{C}}}\overset{OPG^2}{\underset{\phantom{R}}{\vert}}(CR^CR^D)_{2\text{-}3}—NR^1R^2$$

respectively, for the compound of formula (XX).

One skilled in the art will recognize that the processes outlined in Schemes 2 to 7 above may be similarly applied to the preparation of compounds of formula (I) with substitution of a suitably substituted compound of formula (M2) for the compound of formula (II).

Compounds of formula (M2), wherein m is an integer from 0 to 1, provided that when

is aryl or heteroaryl, then m is 1, may be prepared according to the process outlined in Scheme 8.

Scheme 8

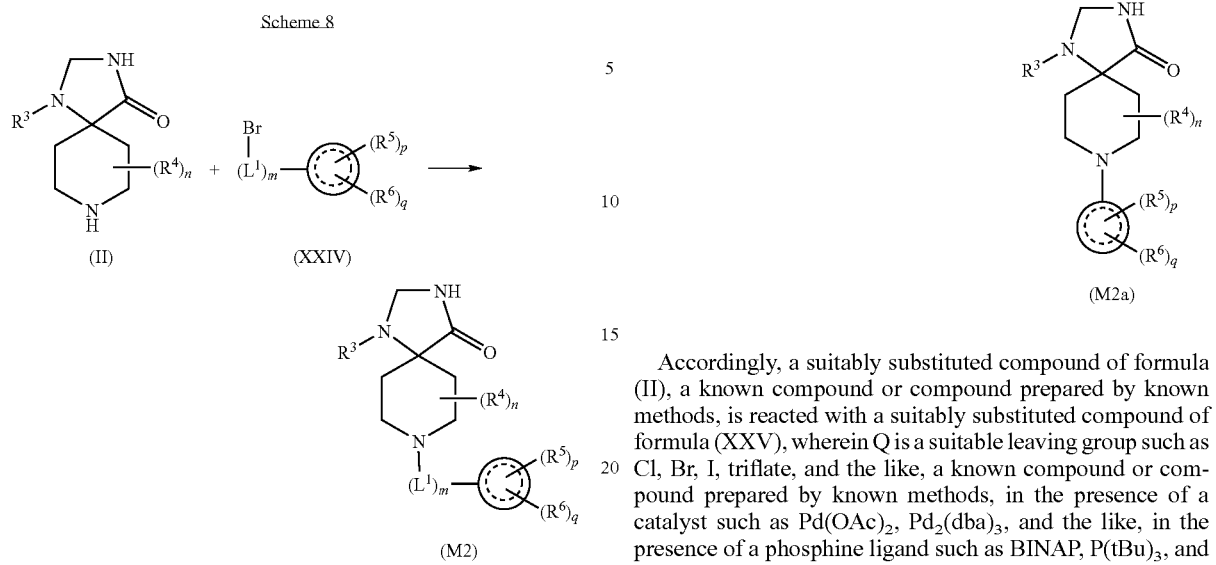

Accordingly, a suitably substituted compound of formula (II), a known compound or compound prepared by known methods, is reacted with a suitably substituted compound of formula (XXIV), a known compound or compound prepared by known methods, in the presence of a base such as TEA, DIPEA, pyridine, $Na_2CO_3$, $K_2CO_3$, and the like, wherein the base is present in an amount equal to or greater than about one molar equivalent, in an organic solvent such as DMF, DMSO, NMP, and the like, to yield the corresponding compound of formula (M2).

Compounds of formula (M2) wherein m is 0 and

is aryl or heteroaryl may be prepared according to the process outlined in Scheme 9.

Scheme 9

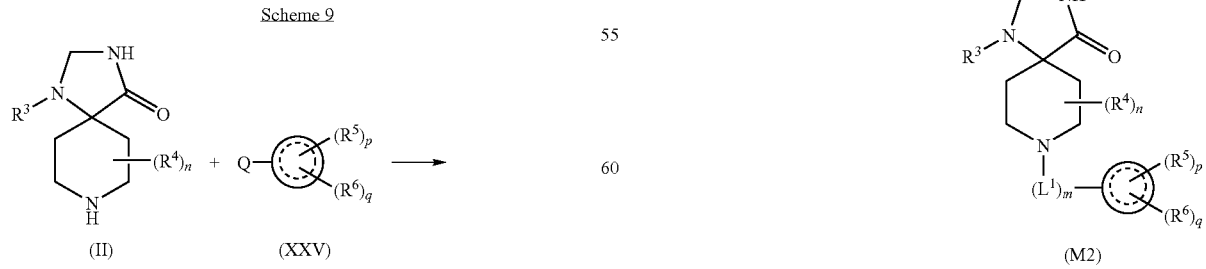

Accordingly, a suitably substituted compound of formula (II), a known compound or compound prepared by known methods, is reacted with a suitably substituted compound of formula (XXV), wherein Q is a suitable leaving group such as Cl, Br, I, triflate, and the like, a known compound or compound prepared by known methods, in the presence of a catalyst such as $Pd(OAc)_2$, $Pd_2(dba)_3$, and the like, in the presence of a phosphine ligand such as BINAP, $P(tBu)_3$, and the like, in the presence of a base such as $Na_2CO_3$, tBuONa, and the like, in an organic solvent such as toluene, dioxane, and the like, preferably at an elevated temperature in the range of about 30 to about 120° C., to yield the corresponding compound of formula (M2a).

Compounds of formula (M2) may alternatively be prepared according to the process outlined in Scheme 10.

Scheme 10

Accordingly, a suitably substituted compound of formula (II), a known compound or compound prepared by known methods, is reacted with a suitably substituted compound of formula (XXVI), a known compound or compound prepared by known methods, in the presence of a base such as TEA, DIPEA, pyridine, Na$_2$CO$_3$, K$_2$CO$_3$, and the like, wherein the base is present in an amount equal to or greater than about one molar equivalent, in an organic solvent such as DMF, DMSO, NMP, and the like, to yield the corresponding compound of formula (XXVII).

The compound of formula (XXVII) is reacted with a suitably substituted boronic acid, a compound of formula (XXVIII), a known compound or compound prepared by known methods, in the presence of a catalyst such as Pd(PPh$_3$)$_4$, Pd(PPh$_3$)$_2$Cl$_2$, and the like, in the presence of a base such as Na$_2$CO$_3$, K$_3$PO$_4$, and the like, in a non-protic organic solvent or mixture thereof, such as toluene, DME, DMF, and the like, or a mixture thereof such as toluene/ethanol, and the like, to yield the corresponding compound of formula (M2).

One skilled in the art will recognize that for compounds of formula (XXVI), the Br may alternatively be replaced with an I or triflate.

Compounds of formula (M2) wherein m is 1, L$^1$ is C$_{1-6}$alkyl or C$_{3-6}$alkenyl, R$^6$ is (L$^2$)$_0$-R$^7$ and R$^7$ is an aryl or heteroaryl group may be prepared according to the process outlined in Scheme 11.

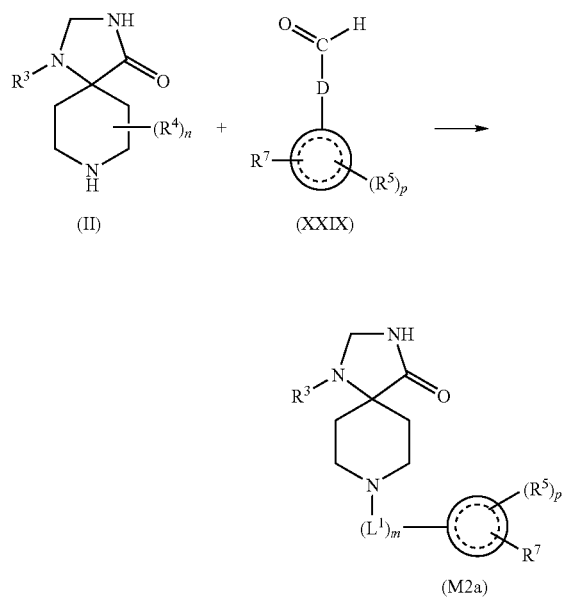

Accordingly, a suitably substituted compound of formula (II), a known compound or compound prepared by known methods, is reacted with a suitably substituted aldehyde, a compound of formula (XXIX), wherein D is C$_{1-5}$alkyl or C$_{2-5}$alkenyl, a known compound or compound prepared by known methods, in the presence of a reducing agent such as sodium triacetoxyborohydride, sodium cyanoborohydride, and the like, in the presence of an acid such as acetic acid, and the like, in an organic solvent such as DCE, THF, acetonitrile, and the like, to yield the corresponding compound of formula (M2a).

Compounds of formula (XXIX) may be prepared according to the processes outlined in Scheme 12.

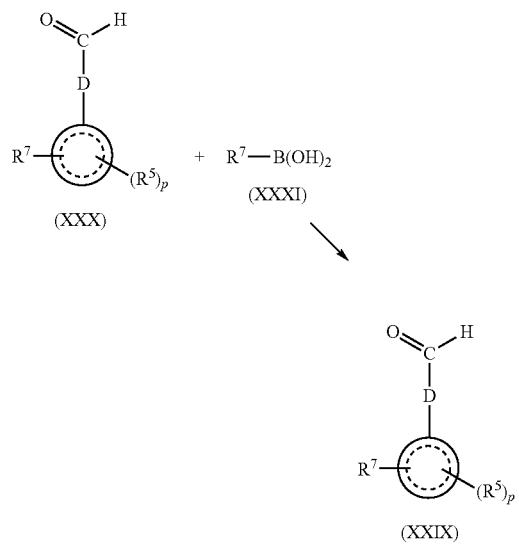

Accordingly, a suitably substituted compound of formula (XXX), wherein D is C$_{1-5}$alkyl or C$_{2-5}$alkenyl, a known compound or compound prepared by known methods, is reacted with a suitably substituted boronic acid, a compound of formula (XXXI), a known compound or compound prepared by known methods, in the presence of a catalyst such as Pd(PPh$_3$)$_4$, Pd(PPh$_3$)$_2$Cl$_2$, and the like, in the presence of a base such as Na$_2$CO$_3$, NaHCO$_3$, K$_3$PO$_4$, and the like, in a non-protic organic solvent or mixture thereof such as toluene, toluene/ethanol, DME, DMF, benzene, and the like, to yield the corresponding compound of formula (XXIX).

Alternatively, a suitably substituted compound of formula (XXXII), wherein D is C$_{1-5}$alkyl or C$_{2-5}$alkenyl, a known compound or compound prepared by known methods, is reacted with a suitably substituted compound of formula (XXXIII), a known compound or compound prepared by known methods, in the presence of a catalyst such as Pd(PPh$_3$)$_4$, PdCl$_2$(PPh$_3$)$_2$, and the like, in the presence of a base such as aqueous NaHCO$_3$, Na$_2$CO$_3$, K$_3$PO$_4$, and the like, in an organic solvent such as DME, DMF, toluene, benzene, and the like, to yield the corresponding compound of formula (XXIX).

One skilled in the art will recognize that for compounds of formula (XXXI) and/or compounds of formula (XXXIII), the Br may alternatively be replaced with an I or triflate.

Compounds of formula (M2) wherein q is 1, R$^6$ is (L$^2$)$_1$-R$^7$ and L$^2$ is —O— may be prepared according to the process outlined in Scheme 13.

Scheme 13

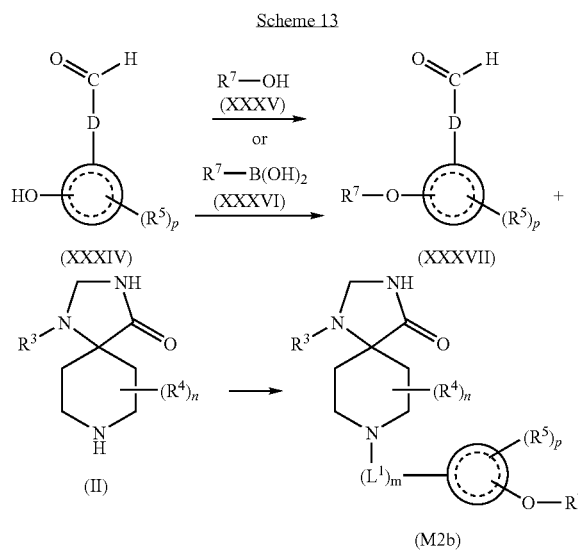

Accordingly, a suitably substituted compound of formula (XXXIV), wherein D is $C_{1-5}$alkyl or $C_{2-5}$alkenyl, a known compound or compound prepared by known methods, is reacted with a suitably substituted alcohol, a compound of formula (XXXV), a known compound or compound prepared by known methods, in the presence of an activating agent such as tributylphosphine, triphenylphosphine, diphenyl-2-pyridylphosphine, and the like, in an anhydrous organic solvent such as benzene, THF, DCM, and the like, (via a Mitsunobu reaction) in the presence of a dehydrating agent such as 1,1'-(azodicarbonyl)dipiperidine, diethylazodicarboxylate, diisopropylazodicarboxylate, and the like, to yield the corresponding compound of formula (XXXVII).

Alternatively, the compound of formula (XXXVII) may be prepared by reacting a compound of formula (XXXIV) with a compound of formula (XXXV), wherein the hydroxy (OH) group on the compound of formula (XXXV) is replaced with a fluoro, bromo or triflate, in the presence of a base such as $K_2CO_3$, sodium carbonate, sodium bicarbonate, and the like, in a dipolar aprotic solvent such as $(CH_3)_2NCOCH_3$, DMF, DMSO, and the like.

Alternatively, the compound of formula (XXXIV) is reacted with a suitably substituted boronic acid, a compound of formula (XXXVI), a known compound or compound prepared by known methods, in the presence of a catalyst such as copper (II) acetate, and the like, in the presence of an base such as TEA, pyridine, and the like, in the presence of molecular sieves, preferably 4 Angstrom molecular sieves, in an organic solvent such as DCM, DCE, and the like, preferably at ambient temperature, to yield the corresponding compound of formula (XXXVII).

The compound of formula (XXXVII) is reacted with a suitably substituted compound of formula (II), a known compound or compound prepared by known methods, in the presence of a reducing agent such as sodium triacetoxyborohydride, sodium cyanoborohydride, and the like, in an organic solvent such as DCE, THF, acetonitrile, and the like, to yield the corresponding compound of formula (M2b).

One skilled in the art will recognize that compounds of formula (M2) wherein $L^2$ is —S— may similarly be prepared according to the process outlined above with appropriate selection and substitution of suitably substituted starting materials (e.g. substitution of the OH group on the compound of formula (XXXIV) with Cl or Br and substitution of a suitably substituted compound of the formula $R^7$—SH for the compound of formula (XXXV), preferably in the presence of a copper catalyst, according to known methods. The sulfur group may then be further oxidized with a suitable oxidizing agent such as hydrogen peroxide, mCPBA, and the like, according to known methods, to yield the corresponding compound wherein $L^2$ is selected from —SO— or —$SO_2$—.

Compounds of formula (M2) wherein $R^6$ is -$L^2$-$R^7$ and $L^2$ is $C_{2-4}$alkenyl may be prepared according to the process outlined in Scheme 14.

Scheme 14

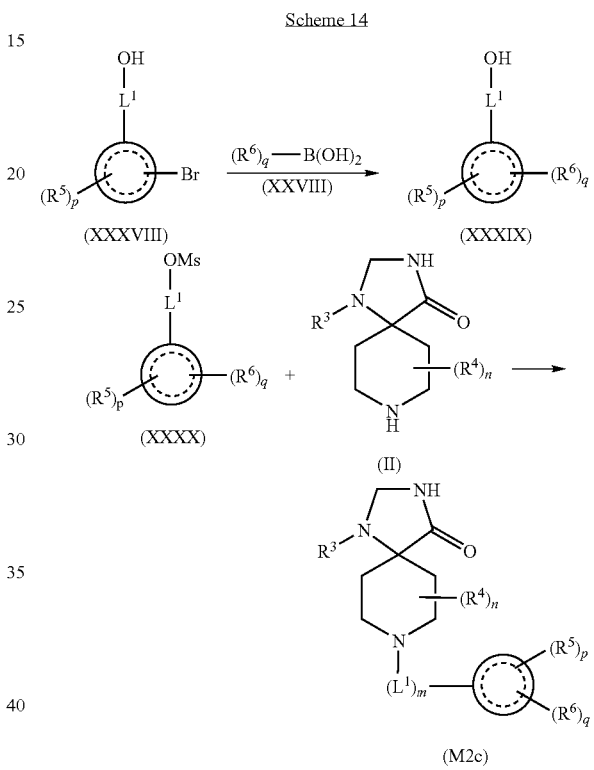

Accordingly, a suitably substituted compound of formula (XXXVIII), a known compound or compound prepared by known methods, is reacted with a suitably substituted boronic acid, a compound of formula (XXVIII), a known compound or compound prepared by known methods, in the presence of a catalyst such as $Pd(PPh_3)_4$, $Pd(PPh_3)_2Cl_2$, and the like, in the presence of a base such as $NaHCO_3$, $K_2CO_3$, $Na_2CO_3$, and the like, to yield the corresponding compound of formula (XXXIX).

The compound of formula (XXXIX) is reacted with methanesulfonyl chloride, a known compound, in the presence of an organic base such as TEA, DIPEA, N-methylmorpholine, and the like, in an aprotic solvent such as DCM, THF, acetonitrile, $CHCl_3$, and the like, to yield the corresponding compound of formula (XXXX), wherein Ms is a mesyl group.

The compound of formula (XXXX) is reacted with a suitably substituted compound of formula (II), a known compound or compound prepared by known methods, in the presence of a reducing agent such as sodium triacetoxyborohydride, sodium cyanoborohydride, and the like, in an organic solvent such as DCM, DCE, THF, methanol, acetonitrile, and the like, to yield the corresponding compound of formula (M2c).

One skilled in the art will recognize that the processes outlined in Schemes 8 to 14 above may be similarly applied to the preparation of compounds of formula (I) with substitution of a suitably substituted compound of formula (M1) for the compound of formula (II).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs*. ed. H. Bundgaard, Elsevier, 1985.

Following the procedures described herein, representative compounds of the present invention were prepared as listed in Tables 1-8. In the Tables below, the column headed with a * shall define the stereochemical configuration of the bond denoted with the "*" symbol in the general structure at the head of the table. In addition to "R" and "S" designations, racemic mixtures will be denoted with the term "Rac". For the

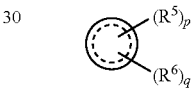

substituent, the stereoconfiguration is racemic, unless otherwise noted with an "R" or "S". In the columns headed $(L^1)_m$, a listing of "absent" shall mean that m is 0.

TABLE 1

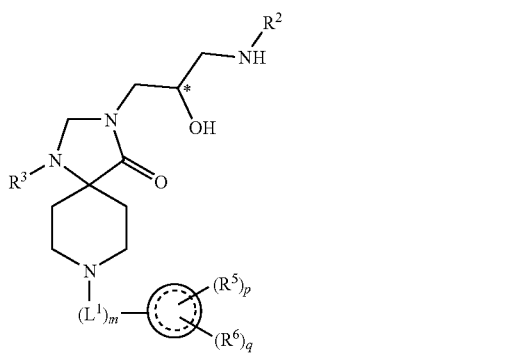

| ID# | * | $R^2$ | $R^3$ | $(L^1)_m$ | <img> |
|---|---|---|---|---|---|
| 1 | S | 2-(4-morpholinyl)ethyl | 4-fluorophenyl | $CH_2$ | cyclooctyl |
| 2 | R | 3,4-dimethoxy benzyl | 4-fluorophenyl | $CH_2$ | cyclooctyl |
| 3 | R | 3,5-di(trifluoromethyl)benzyl | 4-fluorophenyl | $CH_2$ | cyclooctyl |
| 4 | R | 2-(4-imidazolyl) ethyl | 4-fluorophenyl | $CH_2$ | cyclooctyl |
| 5 | R | 4-bromobenzyl | 4-fluorophenyl | $CH_2$ | cyclooctyl |
| 6 | R | 3,4-dimethoxy benzyl | 4-fluorophenyl | $CH_2$ | cyclooctyl |
| 7 | S | 2,4-difluorobenzyl | 4-fluorophenyl | $CH_2$ | cyclooctyl |

TABLE 1-continued

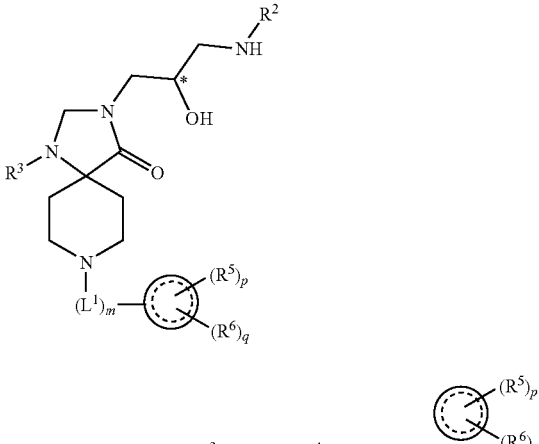

| ID# | * | R² | R³ | (L¹)ₘ | (R⁵)ₚ (R⁶)q |
|---|---|---|---|---|---|
| 8 | S | 2,4-dimethoxy benzyl | 4-fluorophenyl | CH₂ | cyclooctyl |
| 9 | S | 4-biphenyl | 4-fluorophenyl | CH₂ | cyclooctyl |
| 10 | S | 2-ethoxybenzyl | 4-fluorophenyl | CH₂ | cyclooctyl |
| 11 | S | 2-phenylethyl | 4-fluorophenyl | CH₂ | cyclooctyl |
| 12 | S | 2,5-difluorobenzyl | 4-fluorophenyl | CH₂ | cyclooctyl |
| 13 | S | 2-(5-bromopyridyl) | 4-fluorophenyl | CH₂ | cyclooctyl |
| 14 | S | 2-methoxybenzyl | 4-fluorophenyl | CH₂ | cyclooctyl |
| 15 | S | 4-bromobenzyl | 4-fluorophenyl | CH₂ | cyclooctyl |
| 16 | S | 3,5-di(trifluoro methyl)benzyl | 4-fluorophenyl | CH₂ | cyclooctyl |
| 17 | S | 1-adamantanyl-methyl | 4-fluorophenyl | CH₂ | cyclooctyl |
| 18 | S | 3-methylbenzyl | 4-fluorophenyl | CH₂ | cyclooctyl |
| 19 | S | 2-(2,5-dimethoxy-2,5-dihydro-furyl)-methyl | 4-fluorophenyl | CH₂ | cyclooctyl |
| 20 | S | 3-bromobenzyl | 4-fluorophenyl | CH₂ | cyclooctyl |
| 21 | S | 3-chlorobenzyl | 4-fluorophenyl | CH₂ | cyclooctyl |
| 22 | S | 3,4-dimethoxy benzyl | 4-fluorophenyl | CH₂ | cyclooctyl |
| 23 | S | 4-nitrobenzyl | 4-fluorophenyl | CH₂ | cyclooctyl |
| 24 | S | 4-pyridyl | 4-fluorophenyl | CH₂ | cyclooctyl |
| 25 | S | 3,5-dimethoxy-benzyl | 4-fluorophenyl | CH₂ | cyclooctyl |
| 26 | S | 2-(2-thienyl)ethyl | 4-fluorophenyl | CH₂ | cyclooctyl |
| 27 | S | 2-methylbenzyl | 4-fluorophenyl | CH₂ | cyclooctyl |
| 28 | S | 2-(4-imidazolyl)-ethyl | 4-fluorophenyl | CH₂ | cyclooctyl |
| 29 | S | 4-trifluoromethyl benzyl | 4-fluorophenyl | CH₂ | cyclooctyl |
| 30 | S | 2-(4-bromophenyl) ethyl | 4-fluorophenyl | CH₂ | cyclooctyl |
| 31 | S | 2,4-dichlorobenzyl | 4-fluorophenyl | CH₂ | cyclooctyl |
| 32 | S | 3-pyridylmethyl | 4-fluorophenyl | CH₂ | cyclooctyl |
| 33 | S | 3-trifluoromethyl benzyl | 4-fluorophenyl | CH₂ | cyclooctyl |
| 34 | S | 2-(4-methoxy-phenyl)ethyl | 4-fluorophenyl | CH₂ | cyclooctyl |
| 35 | S | 3-methoxybenzyl | 4-fluorophenyl | CH₂ | cyclooctyl |
| 36 | S | 4-pyridyl | 4-fluorophenyl | CH₂ | cyclooctyl |
| 38 | S | 2-(3,4-dimethoxy phenyl)ethyl | 4-fluorophenyl | CH₂ | cyclooctyl |
| 39 | S | 2-pyridylmethyl | 4-fluorophenyl | CH₂ | cyclooctyl |
| 40 | S | 1-naphthyl | 4-fluorophenyl | CH₂ | cyclooctyl |
| 41 | S | 4-methylbenzyl | 4-fluorophenyl | CH₂ | cyclooctyl |
| 42 | S | 2-(3,5-dimethyl-pyridyl) | 4-fluorophenyl | CH₂ | cyclooctyl |
| 43 | S | 3,4,5-trimethoxy-benzyl | 4-fluorophenyl | CH₂ | cyclooctyl |
| 44 | S | 2-bromobenzyl | 4-fluorophenyl | CH₂ | cyclooctyl |
| 45 | S | 2,3-dimethoxy benzyl | 4-fluorophenyl | CH₂ | cyclooctyl |
| 46 | S | 3,4-dichlorobenzyl | 4-fluorophenyl | CH₂ | cyclooctyl |
| 47 | R | 2-(4-morpholinyl) ethyl | 4-fluorophenyl | absent | 1-acenaphthenyl |
| 48 | S | 2-(3,4-dimethoxy-phenyl)ethyl | 4-fluorophenyl | absent | 1-acenaphthenyl |
| 49 | S | 2-(3,4-dimethoxy-phenyl)ethyl | 4-fluorophenyl | absent | 4-n-propyl-cyclohexyl |
| 50 | S | 2-(4-morpholinyl) ethyl | 4-fluorophenyl | CH₂CH₂ | phenyl |

TABLE 1-continued

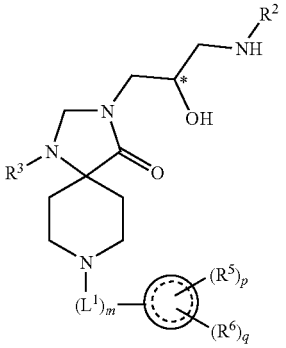

| ID# | * | R² | R³ | (L¹)ₘ | (R⁵)ₚ / (R⁶)q |
|---|---|---|---|---|---|
| 51 | S | 2-(3,4-dimethoxy-phenyl)ethyl | 4-fluorophenyl | CH₂CH₂ | phenyl |
| 52 | Rac | 2-(3,4-dimethoxy-phenyl)ethyl | phenyl | absent | 1-acenaphthenyl |
| 53 | R | 2-(4-morpholinyl)ethyl | phenyl | absent | 1-acenaphthenyl |
| 251 | S | 2-(4-morpholinyl)ethyl | 4-fluorophenyl | CH₂ | 1-naphthyl |
| 253 | S | 2-(3,4-dimethoxy-phenyl)ethyl | 4-fluorophenyl | CH₂ | 1-naphthyl |
| 254 | S | 2-(3,4-methylene dioxyphenyl)ethyl | 4-fluorophenyl | CH₂ | 1-naphthyl |
| 255 | S | 2-(2-nitro-4,5-dimethoxy-phenyl)ethyl | 4-fluorophenyl | CH₂ | 1-naphthyl |
| 259 | S | 2-(4-morpholinyl)ethyl | 4-fluorophenyl | CH₂ | 2-naphthyl |
| 261 | S | 2-(3,4-dimethoxy-phenyl)ethyl | 4-fluorophenyl | CH₂ | 2-naphthyl |
| 262 | S | 2-(3,4-methylene dioxyphenyl)ethyl | 4-fluorophenyl | CH₂ | 2-naphthyl |
| 265 | S | 2-(4-morpholinyl)ethyl | 4-fluorophenyl | CH₂ | 4-chlorophenyl |
| 267 | R | 2-(3,4-dimethoxy-phenyl)ethyl | 4-fluorophenyl | CH₂ | 4-chlorophenyl |
| 268 | R | 2-(3,4-methylene dioxyphenyl)ethyl | 4-fluorophenyl | CH₂ | 4-chlorophenyl |
| 269 | R | 2-(2-nitro-4,5-dimethoxy-phenyl)ethyl | 4-fluorophenyl | CH₂ | 4-chlorophenyl |
| 271 | R | 2-(3,4-methylene dioxyphenyl)ethyl | 4-fluorophenyl | absent | 1-acenaphthenyl |
| 276 | S | 2-(2-nitro-4,5-dimethoxy-phenyl)ethyl | 4-fluorophenyl | absent | 1-acenaphthenyl |
| 279 | S | 1-(t-butoxy-carbonyl)-2-phenylethyl | 4-fluorophenyl | CH₂ | cyclooctyl |
| 281 | S | 2-ethoxy-phenyl | 4-fluorophenyl | CH₂ | cyclooctyl |
| 282 | S | 4-((1-phenyl-pyrazol-2-yl)-aminosulfonyl)phenyl | 4-fluorophenyl | CH₂ | cyclooctyl |
| 285 | S | 4-cyclohexyl-phenyl | 4-fluorophenyl | CH₂ | cyclooctyl |
| 292 | S | 2-(3,4-dimethoxy-phenyl)ethyl | 4-fluorophenyl | CH₂ | 5-phenyl-2-thienyl |
| 293 | S | 2-(4-morpholinyl)ethyl | 4-fluorophenyl | CH₂ | 5-phenyl-2-thienyl |
| 298 | R | 2-(4-morpholinyl)ethyl | 4-fluorophenyl | absent | 1-acenaphthenyl |
| 300 | R | 2-(3,4-dimethoxy-phenyl)ethyl | 4-fluorophenyl | absent | 1-acenaphthenyl |
| 307 | S | 3,4-dimethoxy-benzyl | 4-fluorophenyl | absent | 1-acenaphthenyl |
| 308 | S | 4-nitrobenzyl | 4-fluorophenyl | absent | 1-acenaphthenyl |
| 309 | S | 2-(1,2,3,4-tetrahydro-isoquinolinyl) | 4-fluorophenyl | absent | 1-acenaphthenyl |
| 310 | S | 4-biphenyl | 4-fluorophenyl | absent | 1-acenaphthenyl |
| 311 | S | 2-furylmethyl | 4-fluorophenyl | absent | 1-acenaphthenyl |

TABLE 1-continued

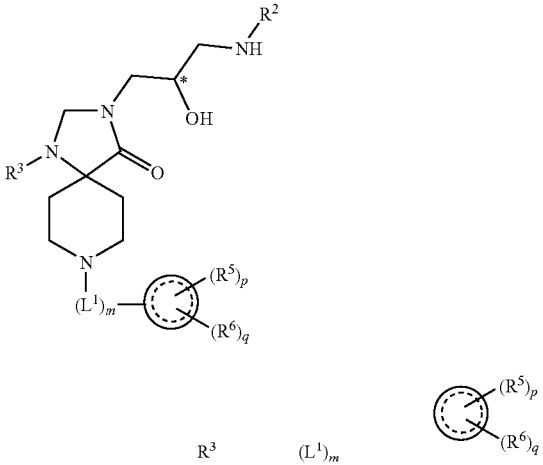

| ID# | * | R² | R³ | (L¹)ₘ | (R⁵)ₚ (R⁶)_q |
|---|---|---|---|---|---|
| 312 | S | 3-iodobenzyl | 4-fluorophenyl | absent | 1-acenaphthenyl |
| 314 | S | 3,4-difluorobenzyl | 4-fluorophenyl | absent | 1-acenaphthenyl |
| 315 | S | 3-bromobenzyl | 4-fluorophenyl | absent | 1-acenaphthenyl |
| 316 | S | 4-chlorobenzyl | 4-fluorophenyl | absent | 1-acenaphthenyl |
| 317 | S | 4-methoxybenzyl | 4-fluorophenyl | absent | 1-acenaphthenyl |
| 318 | S | 2-methoxybenzyl | 4-fluorophenyl | absent | 1-acenaphthenyl |
| 319 | S | 3,5-di(trifluoromethyl)benzyl | 4-fluorophenyl | absent | 1-acenaphthenyl |
| 320 | S | 3,4,5-trimethoxybenzyl | 4-fluorophenyl | absent | 1-acenaphthenyl |
| 321 | S | 3-fluorobenzyl | 4-fluorophenyl | absent | 1-acenaphthenyl |
| 322 | S | 3-methoxybenzyl | 4-fluorophenyl | absent | 1-acenaphthenyl |
| 323 | S | 2-(4-methoxyphenyl)ethyl | 4-fluorophenyl | absent | 1-acenaphthenyl |
| 324 | S | 3,5-dimethoxybenzyl | 4-fluorophenyl | absent | 1-acenaphthenyl |
| 325 | S | 4-methyl-benzyl | 4-fluorophenyl | absent | 1-acenaphthenyl |
| 326 | S | 3-(phenyl)-n-propyl | 4-fluorophenyl | absent | 1-acenaphthenyl |
| 327 | S | 4-pyridyl | 4-fluorophenyl | absent | 1-acenaphthenyl |
| 328 | S | 4-trifluoromethoxybenzyl | 4-fluorophenyl | absent | 1-acenaphthenyl |
| 329 | S | 2-(phenoxy)ethyl | 4-fluorophenyl | absent | 1-acenaphthenyl |
| 330 | S | 2-methyl-benzyl | 4-fluorophenyl | absent | 1-acenaphthenyl |
| 331 | S | 2,3-dimethoxybenzyl | 4-fluorophenyl | absent | 1-acenaphthenyl |
| 338 | S | 3-di(n-butyl)amino-n-propyl | 4-fluorophenyl | absent | 1-acenaphthenyl |
| 341 | S | 2-phenylethyl | 4-fluorophenyl | absent | 1-acenaphthenyl |
| 342 | S | 2,5-difluoro-benzyl | 4-fluorophenyl | absent | 1-acenaphthenyl |
| 343 | S | 3,4-dichloro-benzyl | 4-fluorophenyl | absent | 1-acenaphthenyl |
| 344 | S | 3-trifluoromethyl benzyl | 4-fluorophenyl | absent | 1-acenaphthenyl |
| 345 | S | benzyl | 4-fluorophenyl | absent | 1-acenaphthenyl |
| 346 | S | 2-fluoro-benzyl | 4-fluorophenyl | absent | 1-acenaphthenyl |
| 347 | S | 4-trifluoromethyl benzyl | 4-fluorophenyl | absent | 1-acenaphthenyl |
| 348 | S | 4-methoxycarbonyl-benzyl | 4-fluorophenyl | absent | 1-acenaphthenyl |
| 349 | S | 2,4-dimethoxybenzyl | 4-fluorophenyl | absent | 1-acenaphthenyl |
| 350 | S | 3-chlorobenzyl | 4-fluorophenyl | absent | 1-acenaphthenyl |
| 351 | S | 3-ethoxybenzyl | 4-fluorophenyl | absent | 1-acenaphthenyl |
| 352 | S | 4-bromobenzyl | 4-fluorophenyl | absent | 1-acenaphthenyl |
| 353 | S | 3-methylbenzyl | 4-fluorophenyl | absent | 1-acenaphthenyl |
| 354 | S | 4-fluorobenzyl | 4-fluorophenyl | absent | 1-acenaphthenyl |
| 355 | S | 2-bromobenzyl | 4-fluorophenyl | absent | 1-acenaphthenyl |
| 356 | S | 2-(3,4-methylenedioxyphenyl)ethyl | 4-fluorophenyl | absent | 1-acenaphthenyl |
| 358 | S | 2,4-difluorobenzyl | 4-fluorophenyl | absent | 1-acenaphthenyl |
| 365 | S | 2-(4-bromophenyl)ethyl | 4-fluorophenyl | absent | 1-acenaphthenyl |
| 366 | S | 3-pyridyl-methyl | 4-fluorophenyl | absent | 1-acenaphthenyl |
| 367 | S | 2,4,6-trimethoxybenzyl | 4-fluorophenyl | absent | 1-acenaphthenyl |
| 368 | S | 2,4-dichlorobenzyl | 4-fluorophenyl | absent | 1-acenaphthenyl |
| 370 | S | 3-nitrobenzyl | 4-fluorophenyl | absent | 1-acenaphthenyl |
| 371 | S | 1-naphthyl-methyl | 4-fluorophenyl | absent | 1-acenaphthenyl |
| 372 | S | 2-(2-thienyl)ethyl | 4-fluorophenyl | absent | 1-acenaphthenyl |

TABLE 1-continued

| ID# | * | R² | R³ | (L¹)ₘ | (R⁵)ₚ / (R⁶)_q |
|---|---|---|---|---|---|
| 373 | S | 2-trifluoromethyl benzyl | 4-fluorophenyl | absent | 1-acenaphthenyl |
| 385 | R | 2-(3,4-dimethoxy-phenyl)ethyl | 4-fluorophenyl | CH₂ | 1-(8-methyl-naphtyl) |
| 386 | S | 2-(3,4-dimethoxy-phenyl)ethyl | 4-fluorophenyl | CH₂ | 1-(8-methyl-naphtyl) |
| 387 | R | 2-(4-morpholinyl)ethyl | 4-fluorophenyl | CH₂ | 1-(8-methyl-naphtyl) |
| 374 | S | 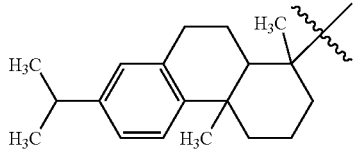 | 4-fluorophenyl | absent | 1-acenaphthenyl |
| 375 | S | 2-(4,6-dimethyl)-pyridyl | 4-fluorophenyl | absent | 1-acenaphthenyl |
| 376 | S | 4-pyridyl-methyl | 4-fluorophenyl | absent | 1-acenaphthenyl |
| 378 | R | 2-pyridyl-methyl | 4-fluorophenyl | absent | 1-acenaphthenyl |
| 379 | R | 4-pyridyl | 4-fluorophenyl | absent | 1-acenaphthenyl |
| 380 | R | 3-(6-methoxy-pyridyl) | 4-fluorophenyl | absent | 1-acenaphthenyl |
| 381 | R | 3-pyridyl | 4-fluorophenyl | absent | 1-acenaphthenyl |
| 383 | R | 2-(5-methyl-pyridyl) | 4-fluorophenyl | absent | 1-acenaphthenyl |
| 390 | R | 2-(3,4-methylene dioxyphenyl)ethyl | 4-fluorophenyl | CH₂ | 1-(8-methyl-naphthyl) |
| 392 | R | 4-methoxybenzyl | 4-fluorophenyl | CH₂ | 1-(8-methyl-naphthyl) |
| 393 | R | 4-pyridyl | 4-fluorophenyl | CH₂ | 1-(8-methyl-naphthyl) |
| 396 | S | 2-(4-morpholinyl)ethyl | 4-fluorophenyl | CH₂ | 1-(8-methyl-naphthyl) |
| 398 | S | 4-methoxybenzyl | 4-fluorophenyl | CH₂ | 1-(8-methyl-naphthyl) |
| 418 | S | 2-(3,4-methylene dioxyphenyl)ethyl | 4-fluorophenyl | CH₂ | 1-(8-methyl-naphthyl) |
| 419 | S | 2-pyridyl | 4-fluorophenyl | absent | 1-acenaphthenyl |
| 420 | R | H | 4-fluorophenyl | absent | R-1-acenaphthenyl |
| 421 | R | 2-pyridyl | 4-fluorophenyl | absent | R-1-acenaphthenyl |
| 422 | S | H | 4-fluorophenyl | CH₂ | 1-(8-methyl-naphthyl) |
| 424 | S | H | 4-fluorophenyl | absent | R-1-acenaphthenyl |
| 425 | R | methyl | 4-fluorophenyl | absent | R-1-acenaphthenyl |
| 426 | R | H | 4-fluorophenyl | absent | S-1-acenaphthenyl |
| 427 | R | methyl | 4-fluorophenyl | absent | S-1-acenaphthenyl |
| 430 | S | H | 4-fluorophenyl | absent | S-1-acenaphthenyl |
| 431 | S | methyl | 4-fluorophenyl | absent | S-1-acenaphthenyl |
| 437 | S | methyl | 4-fluorophenyl | absent | R-1-acenaphthenyl |
| 438 | R | H | 4-fluorophenyl | CH₂ | 1-(8-methyl-naphthyl) |
| 443 | S | methoxy | 4-fluorophenyl | absent | R-1-acenaphthenyl |
| 444 | S | ethoxy | 4-fluorophenyl | absent | R-1-acenaphthenyl |
| 446 | R | 2-(3,4-methylene dioxyphenyl)ethyl | 4-fluorophenyl | absent | 1-acenaphthenyl |
| 448 | S | 2-phenoxyethyl | 4-fluorophenyl | absent | 1-acenaphthenyl |
| 451 | S | 4-(1-phenyl-2-pyrazolyl-amino-sulfonyl)phenyl | 4-fluorophenyl | CH₂ | cyclooctyl |
| 452 | S | 4-carboxy-benzyl | 4-fluorophenyl | CH₂ | cyclooctyl |
| 453 | S | H | 4-fluorophenyl | CH₂ | cyclooctyl |

TABLE 1-continued

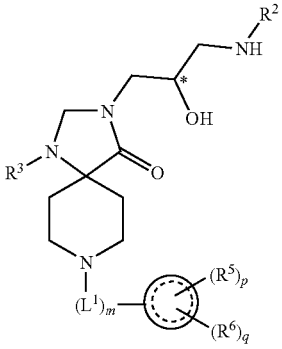

| ID# | * | R² | R³ | (L¹)ₘ | 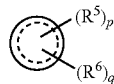 |
|---|---|---|---|---|---|
| 454 | S | n-butyl | 4-fluorophenyl | CH₂ | cyclooctyl |
| 458 | S | phenyl | 4-fluorophenyl | CH₂ | 2-trifluoromethyl-6-chloro-phenyl |
| 461 | R | 2-(2-nitro-4,5-dimethoxy-phenyl)ethyl | 4-fluorophenyl | absent | 1-acenaphthenyl |
| 463 | S | benzyloxy | 4-fluorophenyl | absent | R-1-acenaphthenyl |
| 464 | R | 4-(aminoethyl)-phenyl | 4-fluorophenyl | absent | S-1-acenaphthenyl |
| 600 | S | phenyl | 4-fluorophenyl | absent | R-1-acenaphthenyl |
| 601 | R | 4-(t-butoxycarbonyl-amino-ethyl)-phenyl | 4-fluorophenyl | absent | S-1-acenaphthenyl |
| 602 | S | 4-fluorophenyl | 4-fluorophenyl | absent | R-1-acenaphthenyl |
| 603 | S | 3,4-(dimethoxy)-phenyl | 4-fluorophenyl | absent | R-1-acenaphthenyl |
| 604 | S | 4-(methyl)-phenyl | 4-fluorophenyl | absent | R-1-acenaphthenyl |
| 605 | R | 2-(aminoethyl)-phenyl | 4-fluorophenyl | absent | S-1-acenaphthenyl |
| 606 | S | 1-cyclopropyl | 4-fluorophenyl | absent | R-1-acenaphthenyl |
| 607 | S | 1-Adamantanyl | 4-fluorophenyl | CH₂ | 3,5-bis-trifluoromethyl-phenyl |
| 608 | S | 4-pyridyl | 4-fluorophenyl | CH₂ | 3,5-bis-trifluoromethyl-phenyl |
| 609 | S | 1-(3-pyridyl)-methyl | 4-fluorophenyl | CH₂ | 3,5-bis-trifluoromethyl-phenyl |
| 610 | S | 3-di(n-butyl)amino-n-propyl | 4-fluorophenyl | CH₂ | 3,5-bis-trifluoromethyl-phenyl |
| 611 | R | 1-(3-pyridyl)-methyl | 4-fluorophenyl | absent | R-1-acenaphthenyl |
| 612 | S | 1-(4-pyridyl)-methyl | 4-fluorophenyl | absent | R-1-acenaphthenyl |
| 613 | S | 1-(3-pyridyl)-methyl | 4-fluorophenyl | absent | R-1-acenaphthenyl |
| 614 | S | 1-(2-thienyl)-methyl | 4-fluorophenyl | absent | R-1-acenaphthenyl |
| 615 | R | 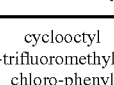 | 4-fluorophenyl | CH₂ | 1-(8-methyl-naphthyl) |
| 616 | S | H | 4-fluorophenyl | absent | cyclooctyl |
| 617 | S | 4-pyridinyl | 4-fluorophenyl | absent | cyclooctyl |
| 618 | S | 4-pyridinyl | 4-fluorophenyl | CH₂ | 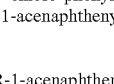 |
| 619 | S | H | 4-fluorophenyl | CH₂ | 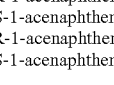 |

TABLE 1-continued

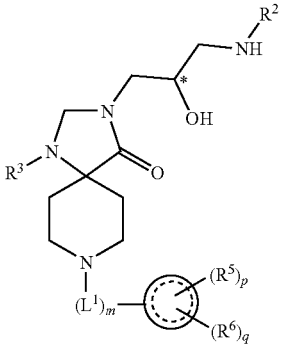

| ID# | * | R² | R³ | (L¹)ₘ | (R⁵)ₚ / (R⁶)q |
|---|---|---|---|---|---|
| 620 | R | H | 4-fluorophenyl | CH₂ | cyclooctyl |
| 621 | R | 4-pyridinyl | 4-fluorophenyl | CH₂ | cyclooctyl |
| 622 | S | 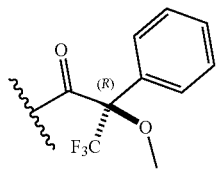 | 4-fluorophenyl | CH₂ | 1-(8-methyl-naphthyl) |
| 623 | R | H | 4-fluorophenyl | absent | cyclooctyl |
| 624 | R | n-butyl | 4-fluorophenyl | absent | cyclooctyl |
| 625 | R | 3-nitrobenzyl | 4-fluorophenyl | absent | cyclooctyl |
| 626 | R | 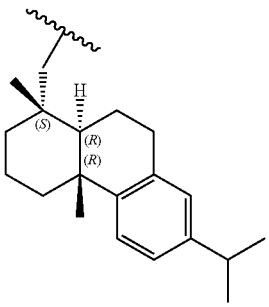 | 4-fluorophenyl | absent | cyclooctyl |
| 627 | R | 4-pyridinyl | 4-fluorophenyl | absent | cyclooctyl |
| 628 | R | 4-methoxycarbonyl-benzyl | 4-fluorophenyl | absent | cyclooctyl |
| 629 | R | 1-[2-(3H-imidazol-4-yl)-ethyl] | 4-fluorophenyl | absent | cyclooctyl |
| 630 | — | 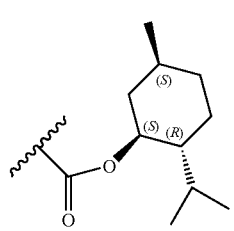 | 4-fluorophenyl | CH₂ | 1-(8-methyl-naphthyl) |
| 631 | R | C(O)O-t-butyl | 4-fluorophenyl | CH₂ | 1-(8-methyl-naphthyl) |
| 632 | R | H | 4-fluorophenyl | CH(CH₃) | 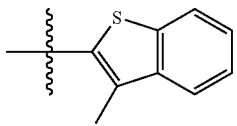 |

TABLE 1-continued

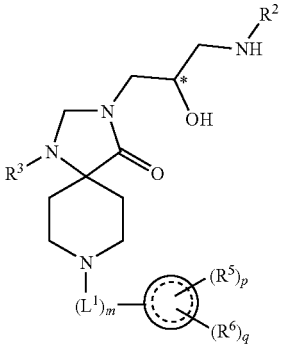

| ID# | * | R² | R³ | (L¹)ₘ | 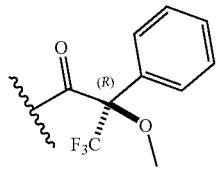 |
|---|---|---|---|---|---|
| 633 | S | dimethylamino-n-propyl | 4-fluorophenyl | CH₂ | cyclooctyl |
| 634 | S | 3-hydroxy-n-propyl | 4-fluorophenyl | CH₂ | cyclooctyl |
| 635 | R | 3-hydroxy-n-propyl | 4-fluorophenyl | CH₂ | cyclooctyl |
| 636 | R | dimethylamino-n-propyl | 4-fluorophenyl | CH₂ | cyclooctyl |
| 637 | S | 3-hydroxy-n-propyl | 4-fluorophenyl | absent | S-1-acenaphthenyl |
| 638 | S | dimethylamino-n-propyl | 4-fluorophenyl | absent | S-1-acenaphthenyl |
| 639 | R | 3-hydroxy-n-propyl | 4-fluorophenyl | absent | S-1-acenaphthenyl |
| 640 | R | H | phenyl | absent | 1S-(3a-S)-2,3,3a,4,5,6-hexahydro-1H-phenalen-1-yl |
| 641 | S | 3-methoxy-n-propyl | 4-fluorophenyl | absent | R-1-acenaphthenyl |
| 642 | S | 3-hydroxy-n-propyl | 4-fluorophenyl | absent | R-1-acenaphthenyl |
| 643 | R | 3-hydroxy-n-propyl | 4-fluorophenyl | absent | R-1-acenaphthenyl |
| 644 | R | 3-methoxy-n-propyl | 4-fluorophenyl | absent | R-1-acenaphthenyl |
| 645 | R | 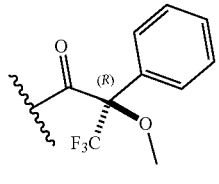 | 4-fluorophenyl | absent | R-1-acenaphthenyl |
| 646 | S |  | 4-fluorophenyl | absent | R-1-acenaphthenyl |
| 647 | R | dimethylamino-n-propyl | 4-fluorophenyl | absent | R-1-acenaphthenyl |
| 648 | S | methyl | 4-fluorophenyl | CH₂ | 1-(8-methyl-naphthyl) |
| 649 | S | 3-hydroxy-n-propyl | 4-fluorophenyl | CH₂ | 1-(8-methyl-naphthyl) |
| 650 | S | 3-methoxy-n-propyl | 4-fluorophenyl | CH₂ | 1-(8-methyl-naphthyl) |
| 651 | R | 3-hydroxy-n-propyl | 4-fluorophenyl | CH₂ | 1-(8-methyl-naphthyl) |
| 652 | R | 3-methoxy-n-propyl | 4-fluorophenyl | CH₂ | 1-(8-methyl-naphthyl) |
| 653 | S | dimethylamino-n-propyl | 4-fluorophenyl | CH₂ | 1-(8-methyl-naphthyl) |
| 654 | S | methylamino-n-propyl | 4-fluorophenyl | absent | S-1-acenaphthenyl |
| 655 | S | methylamino-n-propyl | 4-fluorophenyl | CH₂ | 1-(8-methyl-naphthyl) |
| 656 | R | methylamino-n-propyl | 4-fluorophenyl | CH₂ | 1-(8-methyl-naphthyl) |
| 657 | R | methylamino-n-propyl | 4-fluorophenyl | CH₂ | cyclooctyl |

TABLE 1-continued

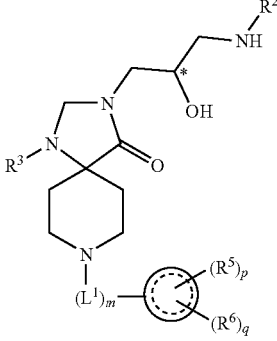

| ID# | * | R² | R³ | (L¹)ₘ | (R⁵)ₚ (R⁶)q |
|---|---|---|---|---|---|
| 658 | S | methylamino-n-propyl | phenyl | absent | 1S-(3a-S)-2,3,3a,4,5,6-hexahydro-1H-phenalen-1-yl |
| 659 | S | H | phenyl | absent | 1S-(3a-S)-2,3,3a,4,5,6-hexahydro-1H-phenalen-1-yl |
| 660 | R | methyl | 4-fluorophenyl | CH₂ | 1-(8-methyl-naphthyl) |
| 661 | R | methylamino-ethyl | 4-fluorophenyl | CH₂ | 1-(8-methyl-naphthyl) |
| 662 | R | 1-(4-ethoxycarbonyl-piperidinyl) | 4-fluorophenyl | CH₂ | 1-(8-methyl-naphthyl) |
| 663 | R | 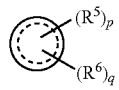 | 4-fluorophenyl | absent | S-1-acenaphthenyl |
| 664 | R | methylamino-n-propyl | 4-fluorophenyl | CH₂ | 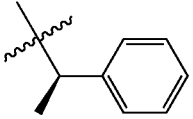 |
| 665 | R | t-butoxycarbonyl-amino-n-propyl | 4-fluorophenyl | CH₂ | 1-(8-methyl-naphthyl) |
| 666 | R | dimethylamino-n-propyl | 4-fluorophenyl | CH₂ | 1-(8-methyl-naphthyl) |
| 667 | R | N-methyl-N-t-butoxycarbonyl-amino-ethyl | 4-fluorophenyl | CH₂ | 1-(8-methyl-naphthyl) |

TABLE 2

[Chemical structure: spiro imidazolidinone-piperidine with R1, R2, R3, L1, R5, R6 substituents]

| ID# | * | R¹ | R² | R³ | (L¹)ₘ | (R⁵)ₚ / (R⁶)q ring |
|---|---|---|---|---|---|---|
| 54 | S | n-butyl | benzyl | phenyl | absent | (3a-S)-2,3,3a,4,5,6-hexahydro-1H-phenalen-2-yl |
| 55 | S | ethyl | 4-methyl benzyl | 4-fluoro-phenyl | absent | 1-acenaphthenyl |
| 56 | S | t-butyl | benzyl | 4-fluoro-phenyl | absent | 1-acenaphthenyl |
| 57 | S | ethyl | 4-methyl benzyl | 4-fluoro-phenyl | absent | 4-n-propyl-cyclohexyl |
| 58 | S | ethyl | 4-methyl benzyl | 4-fluoro-phenyl | CH₂CH₂ | phenyl |
| 59 | S | t-butyl | benzyl | 4-fluoro-phenyl | absent | 4-n-propyl-cyclohexyl |
| 60 | S | t-butyl | benzyl | 4-fluoro-phenyl | CH₂CH₂ | phenyl |
| 61 | Rac | ethyl | 4-methyl benzyl | phenyl | absent | 1-acenaphthenyl |
| 62 | Rac | t-butyl | benzyl | phenyl | absent | 1-acenaphthenyl |
| 63 | S | 2-(dimethyl amino)ethyl | benzyl | 4-fluoro-phenyl | CH₂ | cyclooctyl |
| 64 | S | n-butyl | benzyl | 4-fluoro-phenyl | CH₂ | cyclooctyl |
| 65 | S | benzyl | 2-phenyl-ethyl | 4-fluoro-phenyl | CH₂ | cyclooctyl |
| 78 | S | [C(=O)CH(NH₂)CH(CH₃)₂ – valinyl ketone group] | 4-methyl benzyl | 4-fluoro phenyl | CH₂ | cyclooctyl |
| 79 | S | [C(=O)CH(NHBoc)CH(CH₃)₂ – N-Boc-valinyl ketone group] | 4-methyl benzyl | 4-fluoro phenyl | CH₂ | cyclooctyl |
| 250 | S | t-butyl | benzyl | 4-fluoro phenyl | CH₂ | 1-naphthyl |
| 252 | S | ethyl | 4-methyl benzyl | 4-fluoro-phenyl | CH₂ | 1-naphthyl |
| 256 | S | methyl | 2-(3,4-dimethoxy-phenyl)ethyl | 4-fluoro-phenyl | CH₂ | 1-naphthyl |
| 258 | S | ethyl | 4-methyl benzyl | 4-fluoro-phenyl | CH₂ | 2-naphthyl |
| 260 | S | t-butyl | benzyl | 4-fluoro-phenyl | CH₂ | 2-naphthyl |

TABLE 2-continued

| ID# | * | R¹ | R² | R³ | (L¹)$_m$ | (R⁵)$_p$ / (R⁶)$_q$ |
|---|---|---|---|---|---|---|
| 263 | S | methyl | 2-(3,4-dimethoxy-phenyl)ethyl | 4-fluoro-phenyl | CH$_2$ | 2-naphthyl |
| 264 | S | ethyl | 4-methyl benzyl | 4-fluoro-phenyl | CH$_2$ | 4-chlorophenyl |
| 266 | S | t-butyl | benzyl | 4-fluoro-phenyl | CH$_2$ | 4-chlorophenyl |
| 270 | S | methyl | 2-(3,4-dimethoxy-phenyl)ethyl | 4-fluoro-phenyl | CH$_2$ | 4-chlorophenyl |
| 275 | S | methyl | 2-(3,4-dimethoxy-phenyl)ethyl | 4-fluoro-phenyl | absent | 1-acenaphthenyl |
| 280 | S | n-butyl | benzyl | 4-fluoro-phenyl | CH$_2$ | 2,3,4,5,6-pentamethyl-phenyl |
| 283 | S | methyl | 3-(2-pyridyl)-n-propyl | 4-fluoro-phenyl | CH$_2$ | cyclooctyl |
| 289 | S | benzyl | (1S,2S)-1-hydroxy-cyclopent-2-yl-methyl | 4-fluoro-phenyl | CH$_2$ | cyclooctyl |
| 290 | S | benzyl | (1S,2S)-1-hydroxy-cyclohex-2-yl-methyl | 4-fluoro-phenyl | CH$_2$ | cyclooctyl |
| 291 | S | benzyl | (1S,2S)-1-hydroxy-cyclohept-2-yl-methyl | 4-fluoro-phenyl | CH$_2$ | cyclooctyl |
| 294 | S | ethyl | 4-methyl benzyl | 4-fluoro-phenyl | CH$_2$ | 5-phenyl-2-thienyl |
| 295 | Rac | methyl | 2-(3,4-dimethoxy-phenyl)ethyl | 4-fluoro-phenyl | absent | 1-acenaphthenyl |
| 299 | R | t-butyl | benzyl | 4-fluoro-phenyl | absent | 1-acenaphthenyl |
| 305 | R | methyl | 2-(3,4-dimethoxy-phenyl)ethyl | 4-fluoro-phenyl | absent | 1-acenaphthenyl |
| 313 | S | benzyl | 2-phenylethyl | 4-fluoro-phenyl | absent | 1-acenaphthenyl |
| 339 | R | methyl | 2-(3,4-dimethoxy-phenyl)ethyl | 4-fluoro-phenyl | absent | R-1-acenaphthenyl |
| 340 | R | methyl | 2-(3,4-dimethoxy-phenyl)ethyl | 4-fluoro-phenyl | absent | S-1-acenaphthenyl |
| 362 | S | benzyl | benzyl | 4-fluoro-phenyl | absent | 1-acenaphthenyl |
| 364 | S | methyl | 2-(2-pyridyl)ethyl | 4-fluoro-phenyl | absent | 1-acenaphthenyl |
| 389 | R | t-butyl | benzyl | 4-fluoro-phenyl | CH$_2$ | 1-(8-methyl-naphthyl) |
| 391 | R | methyl | 2-(3,4-dimethoxy-phenyl)ethyl | 4-fluoro-phenyl | CH$_2$ | 1-(8-methyl-naphthyl) |

TABLE 2-continued

| ID# | * | R¹ | R² | R³ | (L¹)ₘ | (R⁵)ₚ (R⁶)q |
|---|---|---|---|---|---|---|
| 394 | S | ethyl | 4-methyl-benzyl | 4-fluoro-phenyl | CH₂ | 1-(8-methyl-naphthyl) |
| 395 | S | t-butyl | benzyl | 4-fluoro-phenyl | CH₂ | 1-(8-methyl-naphthyl) |
| 399 | S | methyl | 2-(3,4-dimethoxy-phenyl)ethyl | 4-fluoro-phenyl | CH₂ | 1-(8-methyl-naphthyl) |
| 423 | R | methyl | methyl | 4-fluoro-phenyl | absent | R-1-acenaphthenyl |
| 428 | R | methyl | methyl | 4-fluoro-phenyl | absent | S-1-acenaphthenyl |
| 429 | R | methyl | ethyl | 4-fluoro-phenyl | absent | S-1-acenaphthenyl |
| 432 | S | methyl | methyl | 4-fluoro-phenyl | absent | S-1-acenaphthenyl |
| 433 | S | methyl | ethyl | 4-fluoro-phenyl | absent | S-1-acenaphthenyl |
| 434 | R | methyl | ethyl | 4-fluoro-phenyl | absent | R-1-acenaphthenyl |
| 435 | S | methyl | methyl | 4-fluoro-phenyl | absent | R-1-acenaphthenyl |
| 436 | S | methyl | ethyl | 4-fluoro-phenyl | absent | R-1-acenaphthenyl |
| 439 | S | methyl | methyl | 4-fluoro-phenyl | CH₂ | 1-(8-methyl-naphthyl) |
| 440 | S | methyl | ethyl | 4-fluoro-phenyl | CH₂ | 1-(8-methyl-naphthyl) |
| 441 | R | methyl | methyl | 4-fluoro-phenyl | CH₂ | 1-(8-methyl-naphthyl) |
| 442 | R | methyl | ethyl | 4-fluoro-phenyl | CH₂ | 1-(8-methyl-naphthyl) |
| 455 | S | 4-methyl-benzyl | 6-methylthio-2-pyridyl-carbonyl | 4-fluoro-phenyl | CH₂ | cyclooctyl |
| 456 | S | n-butyl | benzyl | 4-fluoro-phenyl | CH₂ | 2-trifluoromethyl-6-chloro-phenyl |
| 457 | S | methyl | 2-(3,4-dimethoxy-phenyl)ethyl | 4-fluoro-phenyl | CH₂ | 2-trifluoromethyl-6-chloro-phenyl |
| 459 | S | benzyl | 2-(dimethyl-amino)ethyl | 4-fluoro-phenyl | CH₂ | 2-trifluoromethyl-6-chloro-phenyl |
| 462 | R | ethyl | 4-methyl-benzyl | 4-fluoro-phenyl | absent | 1-acenaphthenyl |
| 668 | S | ethyl | phenyl | 4-fluoro-phenyl | absent | R-1-acenaphthenyl |
| 669 | S | methyl | phenyl | 4-fluoro-phenyl | absent | R-1-acenaphthenyl |
| 670 | S | ethoxy-carbonyl-methyl | benzyl | 4-fluoro-phenyl | CH₂ | 3,5-bis-trifluoromethyl-phenyl |

TABLE 2-continued

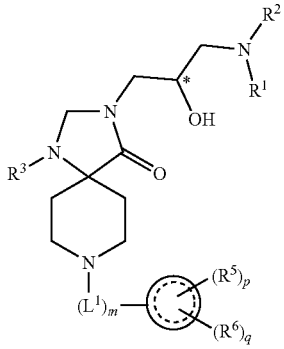

| ID# | * | R¹ | R² | R³ | (L¹)$_m$ | (R⁵)$_p$ / (R⁶)$_q$ |
|---|---|---|---|---|---|---|
| 671 | S | n-butyl | benzyl | 4-fluoro-phenyl | CH$_2$ | 3,5-bis-trifluoromethyl-phenyl |
| 672 | S | 1-phenyl-ethyl | benzyl | 4-fluoro-phenyl | CH$_2$ | 3,5-bis-trifluoromethyl-phenyl |
| 673 | S | 2-(3,4-dimethoxy-phenyl)-ethyl | methyl | 4-fluoro-phenyl | CH$_2$ | 3,5-bis-trifluoromethyl-phenyl |
| 674 | S | (dimethyl-amino)-ethyl | benzyl | 4-fluoro-phenyl | CH$_2$ | 3,5-bis-trifluoromethyl-phenyl |
| 675 | S | 2-(3,4-dimethoxy-phenyl)-ethyl | methyl | 4-fluoro-phenyl | absent | cyclooctyl |
| 676 | S | benzyl | n-butyl | 4-fluoro-phenyl | absent | cyclooctyl |
| 677 | S | benzyl | n-butyl | 4-fluoro-phenyl | CH$_2$ | 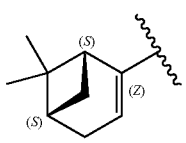 |
| 678 | R | 2-(3,4-dimethoxy-phenyl)-ethyl | methyl | 4-fluoro-phenyl | CH$_2$ | cyclooctyl |
| 679 | S | t-butoxy-carbonyl | methyl | 4-fluoro-phenyl | absent | R-1-acenaphthenyl |
| 680 | S | t-butoxy-carbonyl | methyl | 4-fluoro-phenyl | CH$_2$ | 1-(8-methyl-naphthyl) |
| 681 | R | amino-n-propyl | methyl | 4-fluoro-phenyl | CH$_2$ | 1-(8-methyl-naphthyl) |

TABLE 3

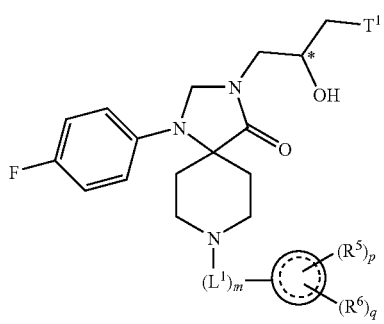

| ID# | * | T¹ (NR¹R² taken together) | 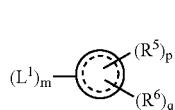 |
|---|---|---|---|
| 66 | S | 1-(4-(3-trifluoromethyl-phenyl)-piperazinyl) | cyclooctyl-methyl |
| 67 | S | 1-(4-piperidinyl-piperidinyl) | cyclooctyl-methyl |
| 68 | S | 1-(4-(3,4-methylenedioxyphenyl-methyl)-piperazinyl) | cyclooctyl-methyl |
| 69 | S | 1-(3-(diethylaminocarbonyl)-piperidinyl) | cyclooctyl-methyl |
| 70 | S | 1-(2,3-dihydro-1H-pyrrolyl) | cyclooctyl-methyl |
| 71 | S | 1-(4-[(4-chlorophenyl)-phenylmethyl]-piperazinyl) | cyclooctyl-methyl |
| 72 | S | 2-(1,2,3,4-tetrahydro-isoquinolinyl) | cyclooctyl-methyl |
| 73 | S | 1-(4-t-butoxycarbonyl-piperazinyl) | cyclooctyl-methyl |
| 74 | S | 2-(1,2,3,4-tetrahydro-6,7-dimethoxy-isoquinolinyl) | cyclooctyl-methyl |
| 75 | S | 4-(2,6-dimethyl-morpholinyl) | cyclooctyl-methyl |
| 76 | S | 1-(4-benzyl-piperazinyl) | cyclooctyl-methyl |
| 115 | S | 2-(1,2,3,4-tetrahydro-isoquinolinyl) | 2-(2-(2-thienyl)-phenyl)ethyl |
| 160 | R | 1-(4-t-butoxycarbonyl-piperazinyl) | 2-(2-(2-thienyl)-phenyl)ethyl |
| 165 | S | 1-(4-t-butoxycarbonyl-piperazinyl) | 2-(2-(2-thienyl)-phenyl)-ethyl |
| 166 | S | 2-(1,2,3,4-tetrahydro-6,7-dimethoxy-isoquinolinyl) | 2-(2-(2-thienyl)-phenyl)ethyl |
| 181 | R | 2-(1,2,3,4-tetrahydro-6,7-dimethoxy-isoquinolinyl) | 2-(2-(2-thienyl)-phenyl)ethyl |
| 183 | R | 1-pyrrolidinyl | 2-(2-(2-thienyl)-phenyl)ethyl |
| 188 | R | 1-(4-ethoxycarbonyl-piperidinyl) | 2-(2-(2-thienyl)-phenyl)-ethyl |
| 257 | S | 2-(1,2,3,4-tetrahydro-6,7-dimethoxy-isoquinolinyl) | 2-(2-(2-thienyl)-phenyl)ethyl |
| 284 | S | 1-(2S-(phenylamino-methyl)-pyrrolidinyl) | cyclooctyl-methyl |

TABLE 3-continued

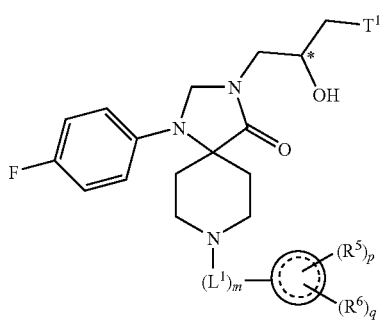

| ID# | * | T¹ (NR¹R² taken together) | 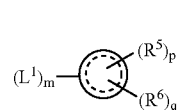 |
|---|---|---|---|
| 682 | S | 2-(1,2,3,4-tetrahydro-isoquinolinyl) | 3,5-bis-trifluoro-methyl-benzyl |
| 683 | S | 1-[4-(3-trifluoromethyl-phenyl)-piperazinyl] | 3,5-bis-trifluoro-methyl-benzyl |
| 684 | S | 1-(4-ethoxycarbonyl-piperidinyl) | 3,5-bis-trifluoro-methyl-benzyl |
| 685 | S | 1-(2,3-dihydro-pyrrolidinyl) | 3,5-bis-trifluoro-methyl-benzyl |
| 686 | S | 3-(diethylaminocarbonyl)-piperidinyl | 3,5-bis-trifluoro-methyl-benzyl |
| 687 | S | 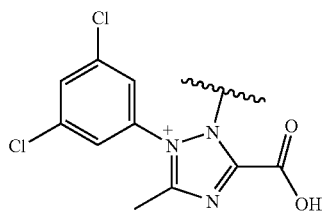 | cyclooctyl |
| 688 | R | 1-(3,4-dihydroxy-2,5-bis-hydroxymethyl-pyrrolidinyl) | cyclooctyl |
| 689 | R | 2-(1,2,3,4-tetrahydro-6,7-dimethoxy-isoquinolinyl) | cyclooctyl |
| 690 | R | 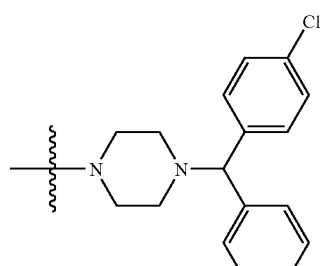 | cyclooctyl |

TABLE 4

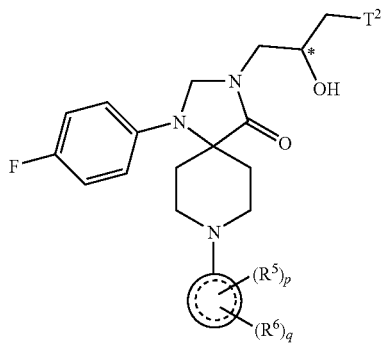

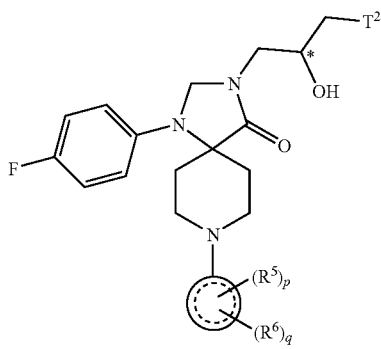

| ID# | * | T² (NR¹R² taken together) | (R⁵)p / (R⁶)q |
|---|---|---|---|
| 296 | R | 2-(1,2,3,4-tetrahydro-6,7-dimethoxy-isoquinolinyl) | 1-acenaphthenyl |
| 332 | S | 1-(4-benzyl-piperazinyl) | 1-acenaphthenyl |
| 333 | S | 1-(4-(3-trifluoromethyl-phenyl)-piperazinyl) | 1-acenaphthenyl |
| 334 | S | 1-(4-(1-piperidinyl)-piperidinyl) | 1-acenaphthenyl |
| 335 | S | 1-(4-(3,4-methylenedioxyphenyl-methyl)-piperazinyl) | 1-acenaphthenyl |
| 336 | S | 1-(3-(diethylaminocarbonyl)-piperidinyl) | 1-acenaphthenyl |
| 337 | S | 1-(4-[(4-chlorophenyl)-phenyl-methyl]-piperazinyl) | 1-acenaphthenyl |
| 360 | S | 1-(4-ethoxycarbonyl-piperidinyl) | 1-acenaphthenyl |
| 377 | S | 2-(1,2,3,4-tetrahydro-6,7-dimethoxy-isoquinolinyl) | 1-acenaphthenyl |
| 382 | R | 1-imidazolyl | 1-acenaphthenyl |
| 388 | S | 2-(1,2,3,4-tetrahydro-6,7-dimethoxy-isoquinolinyl) | 1-(8-methyl-naphthyl) |
| 445 | R | 2-(1,2,3,4-tetrahydro-6,7-dimethoxy-isoquinolinyl) | 1-acenaphthenyl |
| 465 | S | 1-piperidinyl | R-1-acenaphthenyl |
| 691 | S | 1-morpholinyl | R-1-acenaphthenyl |
| 692 | S | 1-pyrrolidinyl | R-1-acenaphthenyl |
| 693 | R | 1-(4-ethoxycarbonyl-piperidinyl) | R-1-acenaphthenyl |
| 694 | R | 1-(4-phenyl-piperidinyl) | R-1-acenaphthenyl |
| 695 | R | 1-(3-hydroxymethyl-piperidinyl) | R-1-acenaphthenyl |
| 696 | R | 1-(3-ethoxycarbonyl-piperidinyl) | R-1-acenaphthenyl |
| 697 | R | 1-piperidinyl | R-1-acenaphthenyl |
| 698 | R | 1-pyrrolidinyl | R-1-acenaphthenyl |
| 699 | S | 1-(3,5-dimethyl-piperidinyl) | R-1-acenaphthenyl |
| 700 | S | 1-(4-phenyl-piperidinyl) | R-1-acenaphthenyl |
| 701 | S | 1-(4-ethoxycarbonyl-piperidinyl) | R-1-acenaphthenyl |
| 702 | S | 1-(3-hydroxymethyl-piperidinyl) | R-1-acenaphthenyl |
| 703 | S | 1-(3,5-dimethyl-piperidinyl) | R-1-acenaphthenyl |
| 704 | S | 1-pyrrolidinyl | 1-(8-methyl-naphthyl) |
| 705 | R | 1-pyrrolidinyl | 1-(8-methyl-naphthyl) |
| 706 | R | 1-(3-(R)-hydroxy-pyrrolidinyl) | 1-(8-methyl-naphthyl) |
| 707 | R | 1-(3-hydroxy-piperidinyl) | 1-(8-methyl-naphthyl) |
| 708 | R | 1-(3-(R)-dimethylamino-pyrrolidinyl) | 1-(8-methyl-naphthyl) |
| 709 | R | 1-(4-hydroxy-piperidinyl) | 1-(8-methyl-naphthyl) |
| 710 | R | 1-(3-(R)-t-butoxycarbonylamino-pyrrolidinyl) | 1-(8-methyl-naphthyl) |
| 711 | R | 1-(4-t-butoxycarbonylamino-piperidinyl) | 1-(8-methyl-naphthyl) |
| 712 | R | 1-(3-hydroxy-pyrrolidinyl) | 1-(8-methyl-naphthyl) |
| 713 | R | 1-(4-pyrrolidinyl-piperidinyl) | 1-(8-methyl-naphthyl) |
| 714 | R | 1-(3-(S)-hydroxy-pyrrolidinyl) | 1-(8-methyl-naphthyl) |
| 715 | R | 1-((3-(S)-ethylamino)pyrrolidinyl) | 1-(8-methyl-naphthyl) |
| 716 | R | 1-(3-(R)-amino-pyrrolidinyl) | 1-(8-methyl-naphthyl) |
| 717 | R | 1-(3-(S)-amino-pyrrolidinyl) | 1-(8-methyl-naphthyl) |
| 718 | R | 1-(4-dimethylamino-piperidinyl) | 1-(8-methyl-naphthyl) |
| 719 | R | 1-(3-(R)-methylamino-pyrrolidinyl) | 1-(8-methyl-naphthyl) |
| 720 | R | 1-(3-(S)-methylamino-pyrrolidinyl) | 1-(8-methyl-naphthyl) |
| 721 | R | 1-(3-(N-methyl-N-t-butoxycarbonyl-amino)-pyrrolidinyl) | 1-(8-methyl-naphthyl) |

TABLE 5

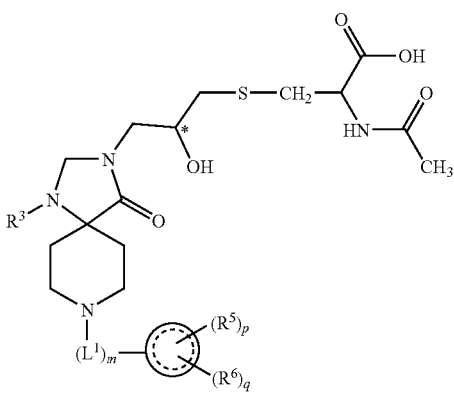

| ID# | * | R³ | (L¹)m | (R⁵)p / (R⁶)q |
|---|---|---|---|---|
| 100 | R | 4-fluorophenyl | CH₂ | cyclooctyl |
| 101 | S | 4-fluorophenyl | absent | 1-acenaphthenyl |
| 102 | R | 4-fluorophenyl | CH₂CH₂ | phenyl |
| 103 | R | 4-fluorophenyl | absent | 4-n-propyl-cyclohexyl |
| 104 | Rac | phenyl | absent | 1-acenaphthenyl |
| 179 | R | phenyl | CH₂CH₂ | 2-(2-thienyl)-phenyl |
| 447 | R | 4-fluorophenyl | CH₂ | cyclooctyl |

TABLE 6
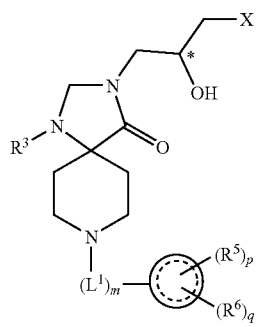
| ID# | * | X | R³ | (L¹)ₘ | (R⁵)ₚ (R⁶)q |
|---|---|---|---|---|---|
| 105 | R | 2-(3,4-dimethoxy phenyl)-ethyloxy | 4-fluoro phenyl | CH₂ | cyclooctyl |
| 106 | R | 2-(3,4-dimethoxy phenyl)-ethyloxy | phenyl | CH₂CH₂ | 2-(2-thienyl)-phenyl |
| 107 | R | 3-methylphenylthio | phenyl | CH₂CH₂ | 2-(2-thienyl)-phenyl |
| 108 | R | 3-methylphenylthio | 4-fluoro phenyl | CH₂ | cyclooctyl |
| 178 | S | 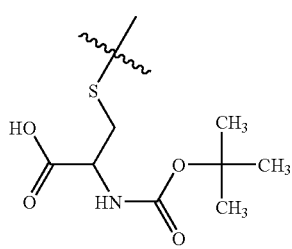 | phenyl | CH₂CH₂ | 2-(2-thienyl)-phenyl |
| 460 | R | 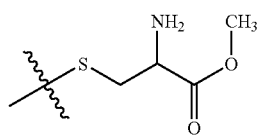 | 4-fluoro phenyl | CH₂ | cyclooctyl |

TABLE 7

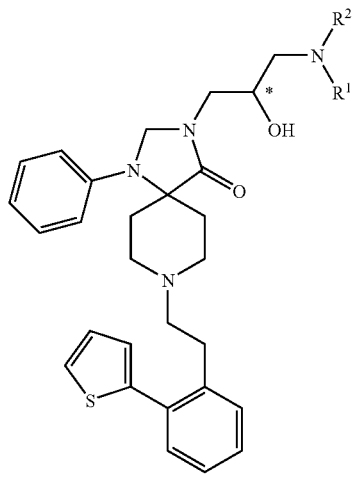

| ID No. | * | R¹ | R² |
|---|---|---|---|
| 110 | Rac | H | 3-(4-morpholinyl)-n-propyl |
| 111 | S | H | 3-(4-morpholinyl)-n-propyl |
| 112 | R | H | 3-(4-morpholinyl)-n-propyl |
| 113 | S | H | 3-chlorobenzyl |
| 114 | S | H | 2-ethoxybenzyl |
| 116 | S | H | (2,5-dimethoxy-2,5-dihydro-fur-2-yl)-methyl |
| 117 | S | n-butyl | benzyl |
| 118 | S | H | 2,5-difluorobenzyl |
| 119 | S | H | 2-phenyl-ethyl |
| 120 | S | H | 2-(5-bromo-pyridyl) |
| 121 | S | H | 3-iodobenzyl |
| 122 | 5 | H | 2,2,2-trifluoroethyl |
| 123 | 5 | H | 3-nitrobenzyl |
| 124 | S | H | 3,4-difluorobenzyl |
| 125 | S | H | 3-bromobenzyl |
| 126 | S | H | 4-chlorobenzyl |
| 127 | S | H | 4-methoxybenzyl |
| 128 | S | H | 3,4,5-trimethoxybenzyl |
| 129 | S | H | 2-(2-thienyl)ethyl |
| 130 | S | H | 3-methylbenzyl |
| 131 | S | H | 2-methoxybenzyl |
| 132 | S | H | benzyl |
| 133 | S | H | 4-bromobenzyl |
| 134 | S | H | 3,5-di(trifluoromethyl) benzyl |
| 135 | S | H | 2-(3-methoxyphenyl)ethyl |
| 136 | S | benzyl | 2-phenylethyl |
| 137 | R | H | 2-bromobenzyl |
| 138 | R | H | 2-(4-bromophenyl)ethyl |
| 139 | R | H | 4-(N,N-dimethylamino) benzyl |
| 140 | R | H | 4-methylbenzyl |
| 141 | R | H | 2-methylbenzyl |
| 142 | R | H | 2-(6-fluoro-2-indolyl)ethyl |
| 143 | R | H | 3-fluorobenzyl |
| 144 | R | H | 3-methoxybenzyl |
| 145 | R | H | 2-(4-methoxyphenyl)ethyl |
| 146 | R | H | 2-trifluoromethylbenzyl |
| 147 | R | H | 2-(4-imidazolyl)ethyl |
| 148 | R | H | 3,5-dimethoxybenzyl |
| 149 | R | H | t-butyl |
| 150 | R | H | 2-pyridyl-methyl |
| 151 | R | H | 2-(3,4-dimethoxyphenyl) ethyl |
| 152 | R | H | 2-fluorobenzyl |
| 153 | R | H | 3-trifluoromethylbenzyl |
| 154 | R | H | 4-pyridyl |
| 155 | R | H | 4-trifluoromethoxybenzyl |
| 156 | R | H | 2-phenyloxy-ethyl |
| 157 | R | H | 1-naphthyl-methyl |
| 158 | R | H | 4-fluorobenzyl |
| 159 | R | H | 4-trifluoromethylbenzyl |
| 161 | R | H | 4-pyridyl-methyl |
| 162 | R | H | 2,4-dichlorobenzyl |
| 163 | S | H | 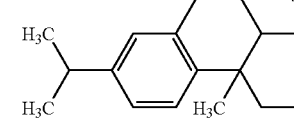 |
| 164 | S | benzyl | benzyl |
| 167 | S | H | 1-(3,4-methylene dioxyphenyl)methyl |
| 168 | S | benzyl | ethoxycarbonylmethyl |
| 169 | S | H | 2-phenyl-cyclopropyl |
| 170 | S | H | 4-methoxycarbonylbenzyl |
| 171 | S | benzyl | 2-(N,N-dimethylamino)ethyl |
| 173 | S | methyl | benzyl |
| 174 | S | ethyl | benzyl |
| 175 | R | benzyl | carboxymethyl |
| 176 | R | benzyl | 2-(N,N-dimethylamino)ethyl |
| 177 | R | n-butyl | benzyl |
| 180 | R | H | 2-phenyl-cyclopropyl |
| 182 | R | H | 4-methoxycarbonylbenzyl |
| 187 | R | H | 2-(2,5-dimethoxy-2,5-dihydro-fur-2-yl)-methyl |
| 189 | R | H | 2,4-dimethoxybenzyl |
| 190 | R | H | 4-biphenyl |
| 191 | R | benzyl | ethoxycarbonylmethyl |
| 192 | R | H | 4-methoxybenzyl |
| 193 | S | H | 2-methylbenzyl |
| 194 | S | H | 3,5-dimethoxybenzyl |
| 197 | S | H | 4-pyridyl |
| 198 | S | H | 2,4-dichlorobenzyl |
| 203 | S | H | 3,4-dimethoxybenzyl |
| 204 | R | H | 4-bromobenzyl |
| 205 | R | H | 3-methylbenzyl |
| 206 | R | H | 2-(2-thienyl)-ethyl |
| 208 | S | H | 3-nitrobenzyl |
| 209 | S | H | 2-bromobenzyl |
| 210 | S | H | 2-(4-imidazolyl)-ethyl |
| 211 | S | H | 2-(phenoxy)-ethyl |
| 215 | S | H | 2,3-dimethoxybenzyl |
| 216 | S | H | 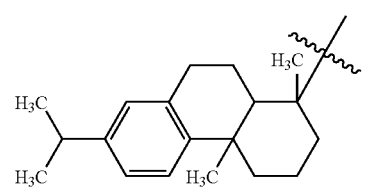 |

TABLE 7-continued

| ID No. | * | R¹ | R² |
|---|---|---|---|
| 217 | S | H | adamantanyl |
| 218 | S | H | n-propyl |
| 219 | S | n-propyl | n-propyl |
| 220 | S | benzyl | benzyl |
| 224 | S | H | 3-methoxybenzyl |
| 225 | S | H | 3-pyridyl-methyl |
| 227 | S | H | 2,4-difluorobenzyl |
| 228 | R | H | 2-methoxybenzyl |
| 229 | S | H | 3-(phenyl)-n-propyl |
| 230 | S | benzyl | 2-phenylethyl |

TABLE 8

| ID # | * | R² | R³ | $(L^1)_m$ | |
|---|---|---|---|---|---|
| 722 | S | H | 4-fluorophenyl | absent | R-1-acenaphthenyl |

Representative intermediates in the preparation of the compounds of the present invention are as listed in Tables 9 and 10. Wherein Table 9, A is listed as oxarinyl-methyl with no indication of the stereo-configuration, the oxarinyl-methyl group was present as racemate.

TABLE 9

| ID # | A | R³ | $(L^1)_m$ | |
|---|---|---|---|---|
| 500 | H | 4-fluorophenyl | absent | 1-acenaphthenyl |
| 501 | H | 4-fluorophenyl | CH₂—CH(CH₃)—CH₂ | phenyl |
| 502 | H | 4-fluorophenyl | CH₂CH₃ | |
| 503 | H | 4-fluorophenyl | CH₂CH₂ | phenyl |
| 504 | H | 4-fluorophenyl | absent | 4-n-propyl-cyclohexyl |
| 505 | H | 4-fluorophenyl | C(O)O-t-butyl | |
| 506 | H | 4-fluorophenyl | CH₂ | 2-naphthyl |
| 507 | H | 4-fluorophenyl | CH₂ | 1-naphthyl |
| 508 | H | 4-fluorophenyl | CH₂ | 4-chlorophenyl |
| 521 | H | 4-fluorophenyl | CH₂ | 4-quinolinyl |
| 522 | H | 4-fluorophenyl | CH₂ | 8-quinolinyl |
| 544 | H | 4-fluorophenyl | absent | 1,3,4-trihydro-2-naphthyl |
| 546 | H | 4-fluorophenyl | CH₂ | 5-phenyl-2-thienyl |

TABLE 9-continued

| ID # | A | R³ | (L¹)ₘ | (R⁵)ₚ / (R⁶)q |
|---|---|---|---|---|
| 547 | H | 4-fluorophenyl | CH₂ | 1-(8-methyl-naphthyl) |
| 548 | H | 4-fluorophenyl | CH₂ | 1-(4-methyl-naphthyl) |
| 549 | H | 4-fluorophenyl | absent | 2-hydroxy-cycloheptyl |
| 551 | H | 4-fluorophenyl | CH₂ | 1-(2-methyl-naphthyl) |
| 555 | H | 4-fluorophenyl | absent | R-1-acenaphthenyl |
| 556 | H | 4-fluorophenyl | absent | S-1-acenaphthenyl |
| 509 | oxiranyl-methyl | phenyl | absent | 1-acenaphthenyl |
| 510 | R-oxiranyl-methyl | 4-fluorophenyl | absent | 4-n-propyl-cyclohexyl |
| 511 | R-oxiranyl-methyl | 4-fluorophenyl | CH₂CH₂ | phenyl |
| 512 | oxiranyl-methyl | 4-fluorophenyl | absent | 1-acenaphthenyl |
| 513 | R-oxiranyl-methyl | 4-fluorophenyl | CH₂ | 4-chlorophenyl |
| 514 | R-oxiranyl-methyl | 4-fluorophenyl | CH₂ | 1-naphthyl |
| 516 | R-oxiranyl-methyl | 4-fluorophenyl | C(O)O-t-butyl | absent |
| 517 | S-oxiranyl-methyl | 4-fluorophenyl | C(O)O-t-butyl | absent |
| 518 | oxiranyl-methyl | phenyl | CH₂CH₂ | 2-(2-thienyl) phenyl |
| 519 | S-oxiranyl-methyl | phenyl | CH₂CH₂ | 2-(2-thienyl) phenyl |
| 520 | R-oxiranyl-methyl | phenyl | CH₂CH₂ | 2-(2-thienyl) phenyl |
| 540 | R-oxiranyl-methyl | 4-fluorophenyl | CH₂ | cyclooctyl |
| 541 | R-oxiranyl-methyl | 4-fluorophenyl | CH₂ | 5-phenyl-2-thienyl |
| 542 | S-oxiranyl-methyl | 4-fluorophenyl | CH₂ | 2-naphthyl |
| 543 | S-oxiranyl-methyl | 4-fluorophenyl | CH₂CH₃ | absent |
| 550 | S-oxiranyl-methyl | 4-fluorophenyl | CH₂ | 1-(8-methyl-naphthyl) |
| 552 | methoxy carbonyl-methyl | 4-fluorophenyl | CH₂ | 1-(8-methyl-naphthyl) |
| 553 | R-oxiranyl-methyl | 4-fluorophenyl | CH₂ | 1-(8-methyl-naphthyl) |
| 554 | R-2,3-dihydroxy-n-propyl | 4-fluorophenyl | CH₂ | 1-(8-methyl-naphthyl) |
| 564 | S-oxiranyl-methyl | 4-fluorophenyl | absent | R-1-acenaphthenyl |
| 565 | R-oxiranyl-methyl | 4-fluorophenyl | absent | R-1-acenaphthenyl |
| 566 | S-oxiranyl-methyl | 4-fluorophenyl | absent | S-1-acenaphthenyl |

TABLE 9-continued

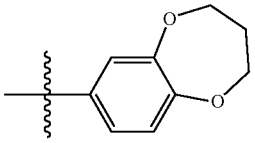

| ID # | A | R³ | (L¹)ₘ | (R⁵)ₚ / (R⁶)q |
|---|---|---|---|---|
| 567 | R-oxiranyl-methyl | 4-fluorophenyl | absent | S-1-acenaphthenyl |
| 568 | 2R-hydroxy-3-ethoxy-n-propyl | 4-fluorophenyl | absent | 1-acenaphthenyl |
| 569 | 2R-hydroxy-3-ethoxy-n-propyl | 4-fluorophenyl | absent | S-1-acenaphthenyl |
| 570 | 2S-hydroxy-3-ethoxy-n-propyl | 4-fluorophenyl | absent | R-1-acenaphthenyl |
| 571 | 2R-hydroxy-3-ethoxy-n-propyl | 4-fluorophenyl | absent | R-1-acenaphthenyl |
| 572 | H | 4-fluorophenyl | CH₂ | 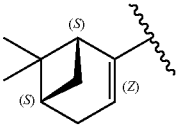 |
| 573 | H | 4-fluorophenyl | CH₂ | 3-(2H)-chromenyl |
| 576 | oxiranyl-methyl | phenyl | absent | 1-acenaphthenyl |
| 578 | R-oxiranyl-methyl | 4-fluorophenyl | CH₂ | 2-trifluoromethyl-6-chloro-phenyl |
| 579 | 3-chloro-2S-hydroxy-n-propyl | 4-fluorophenyl | absent | R-1-acenaphthenyl |
| 580 | S-oxiranyl-methyl | 4-fluorophenyl | CH₂ | cyclooctyl |
| 581 | H | phenyl | CH₂CH₂ | 2-(2-thienyl)-phenyl |
| 582 | H | 4-fluorophenyl | CH₂ | cyclooctyl |
| 583 | H | 4-fluorophenyl | CH₂ | 2,3,4,5,6-pentamethyl-phenyl |
| 584 | R-oxiranyl-methyl | 4-fluorophenyl | CH₂ | 2,3,4,5,6-pentamethyl-phenyl |
| 723 | R-oxiranyl-ethyl | 4-fluorophenyl | absent | R-1-acenaphthenyl |
| 725 | R-oxiranyl-methyl | 4-fluorophenyl | CH₂ | 2,3,4,5,6-pentamethylphenyl |
| 726 | H | 4-fluorophenyl | CH₂ | |

TABLE 9-continued
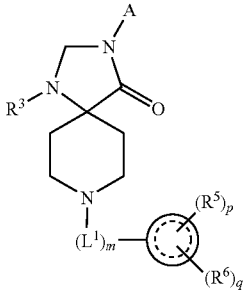
| ID # | A | R³ | (L¹)ₘ | 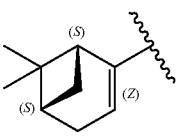 |
|---|---|---|---|---|
| 727 | R-oxiranyl-methyl | 4-fluorophenyl | CH₂ | 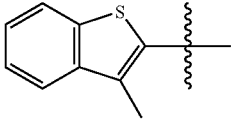 |
| 728 | H | 4-fluorophenyl | CH₂ | 1-(8-methyl-1,2,3,4-tetrahydro-naphthyl) |
| 729 | H | 4-fluorophenyl | CH(CH₃) | 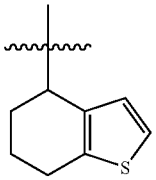 |
| 730 | H | 4-fluorophenyl | absent | 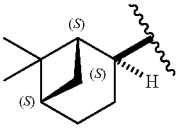 |
| 731 | S-oxiranyl-methyl | 4-fluorophenyl | absent | cyclooctyl |
| 732 | H | 4-fluorophenyl | CH₂ |  |
| 733 | H | 4-fluorophenyl | CH₂ | 1-[8-methoxy)-naphthyl] |
| 734 | H | 4-fluorophenyl | CH₂ | 1-[8-hydroxymethyl)-naphthyl] |
| 735 | H | 4-fluorophenyl | absent | cyclooctyl |

TABLE 10

| ID # | * | R¹ | R² | W |
|---|---|---|---|---|
| 523 | R | ethyl | 4-methylbenzyl | H |
| 524 | R | H | 2-(4-morpholinyl)-ethyl | H |
| 525 | R | t-butyl | benzyl | H |
| 526 | R | H | 2-(3,4-dimethoxy-phenyl)-ethyl | H |
| 527 | R | H | 2-(3,4-methylenedioxy phenyl)-ethyl | H |
| 528 | R | H | 2-(2-nitro-4,5-dimethoxy-phenyl)-ethyl | H |
| 529 | S | ethyl | 4-methylbenzyl | H |
| 530 | S | H | 2-(4-morpholinyl)-ethyl | H |
| 531 | S | t-butyl | benzyl | H |
| 532 | S | H | 2-(3,4-dimethoxy-phenyl)-ethyl | H |
| 533 | S | H | 2-(3,4-methylenedioxy phenyl)-ethyl | H |
| 534 | S | H | 2-(2-nitro-4,5-dimethoxy-phenyl)-ethyl | H |
| 535 | S | ethyl | 4-methylbenzyl | t-butoxycarbonyl |
| 536 | R | ethyl | 4-methylbenzyl | ethyl |
| 537 | R | H | 2-(4-morpholinyl)-ethyl | ethyl |
| 538 | R | t-butyl | benzyl | ethyl |
| 539 | R | H | 2-(3,4-dimethoxy-phenyl)-ethyl | ethyl |

Molecular weights for representative compounds of the present invention exemplified in Tables 1-10 above were measured using a Micromass Platform LC-Electrospray Mass Spectrometer, Chemical Ionization Spectrometer HP5989A or Agilent LC/MSD Electrospray Mass Spectrometer with results as listed in Table 11.

TABLE 11

| ID# | Theor. MW | M/e[MH+] |
|---|---|---|
| 1 | 559.77 | 560.8 |
| 2 | 596.78 | 597.7 |
| 3 | 672.73 | 673.6 |
| 4 | 540.72 | 541.7 |
| 5 | 615.63 | 617.9 |
| 6 | 610.81 | 611.8 |
| 7 | 572.71 | 573.3 |
| 8 | 596.78 | 597.5 |
| 9 | 598.8 | 599.5 |
| 10 | 580.78 | 581.5 |
| 11 | 550.76 | 551.5 |
| 12 | 572.71 | 573.5 |
| 13 | 602.60 | 604.3 |
| 14 | 566.76 | 567.5 |
| 15 | 615.60 | 617.4 |
| 16 | 672.73 | 673.5 |
| 17 | 594.85 | 595.5 |
| 18 | 550.76 | 551.5 |
| 19 | 588.76 | 589.5 |
| 20 | 615.63 | 617.4 |
| 21 | 571.18 | 571.5 |
| 22 | 596.78 | 597.5 |
| 23 | 581.73 | 582.5 |
| 24 | 537.72 | 538.4 |
| 25 | 596.78 | 597.2 |
| 26 | 556.79 | 557.4 |
| 27 | 550.76 | 552.4 |
| 28 | 540.72 | 541.5 |
| 29 | 604.73 | 605.5 |
| 30 | 629.65 | 630.5 |
| 31 | 605.62 | 607.3 |
| 32 | 537.72 | 538.4 |
| 33 | 604.73 | 605.4 |
| 34 | 566.76 | 567.5 |
| 35 | 566.76 | 567.7 |
| 36 | 523.69 | 523.9 |
| 38 | 610.81 | 611.5 |
| 39 | 537.72 | 538.5 |
| 40 | 586.79 | 587.4 |
| 41 | 550.76 | 551.4 |
| 42 | 551.75 | 551.5 |
| 43 | 626.81 | 627.4 |
| 44 | 615.63 | 616.4 |
| 45 | 596.78 | 597.3 |
| 46 | 605.62 | 607.4 |
| 47 | 587.70 | 588.3 |
| 48 | 638.70 | 639.3 |
| 49 | 610.81 | 611.4 |
| 50 | 539.63 | 540.3 |
| 51 | 590.74 | 591.3 |
| 52 | 621.00 | 622.0 |
| 53 | 569.00 | 570.0 |
| 54 | 620.88 | 621.5 |
| 55 | 606.70 | 607.3 |
| 56 | 620.80 | 621.3 |
| 57 | 578.81 | 579.5 |
| 58 | 558.74 | 559.3 |
| 59 | 592.84 | 593.4 |
| 60 | 572.77 | 573.3 |
| 61 | 588.00 | 589.0 |
| 62 | 602.00 | 603.0 |
| 63 | 607.28 | 608.3 |
| 64 | 592.84 | 593.5 |
| 65 | 640.88 | 641.5 |
| 66 | 659.81 | 660.1 |
| 67 | 597.86 | 598.2 |
| 68 | 649.85 | 650.1 |
| 69 | 613.86 | 614.3 |
| 70 | 498.68 | 499.5 |
| 71 | 716.38 | 717.4 |
| 72 | 562.77 | 563.5 |
| 73 | 615.83 | 616.4 |
| 74 | 622.82 | 623.2 |
| 75 | 544.75 | 545.4 |
| 76 | 605.84 | 606.2 |
| 78 | 649.89 | 650.2 |
| 79 | 750.01 | 751.5 |
| 100 | 592.77 | 593.8 |
| 101 | 620.70 | 621.3 |
| 102 | 572.70 | 573.3 |
| 103 | 592.77 | 593.3 |
| 104 | 602.70 | 603.0 |
| 105 | 611.79 | 612.4 |
| 106 | 655.86 | 656.4 |
| 107 | 597.84 | 598.4 |
| 108 | 553.78 | 554.6 |
| 110 | 617.85 | 618.3 |
| 111 | 617.85 | 618.3 |
| 112 | 617.85 | 618.3 |
| 113 | 615.24 | 615.3 |
| 114 | 624.85 | 625.3 |
| 115 | 606.83 | 607.3 |
| 116 | 632.82 | 633.3 |
| 117 | 636.90 | 637.4 |
| 118 | 616.78 | 617.3 |
| 119 | 594.80 | 595.3 |
| 120 | 646.65 | 648.2 |
| 121 | 706.68 | 707.2 |
| 122 | 572.69 | 573.3 |
| 123 | 625.79 | 626.3 |

TABLE 11-continued

| ID# | Theor. MW | M/e[MH+] |
|---|---|---|
| 124 | 616.77 | 617.3 |
| 125 | 659.68 | 661.2 |
| 126 | 615.30 | 615.3 |
| 127 | 610.82 | 611.3 |
| 128 | 670.87 | 671.3 |
| 129 | 600.85 | 601.2 |
| 130 | 594.82 | 595.3 |
| 131 | 610.82 | 611.3 |
| 132 | 580.79 | 581.2 |
| 133 | 659.69 | 661.2 |
| 134 | 716.79 | 717.2 |
| 135 | 624.85 | 625.3 |
| 136 | 684.94 | 685.3 |
| 137 | 659.69 | 661.2 |
| 138 | 673.72 | 675.3 |
| 139 | 623.86 | 624.4 |
| 140 | 594.82 | 595.4 |
| 141 | 594.82 | 595.4 |
| 142 | 651.85 | 652.3 |
| 143 | 598.78 | 599.3 |
| 144 | 610.82 | 611.3 |
| 145 | 624.85 | 625.3 |
| 146 | 648.80 | 649.3 |
| 147 | 584.76 | 585.3 |
| 148 | 640.85 | 641.3 |
| 149 | 546.77 | 547.3 |
| 150 | 581.78 | 582.3 |
| 151 | 654.87 | 655.5 |
| 152 | 598.78 | 599.3 |
| 153 | 648.79 | 649.3 |
| 154 | 567.75 | 568.3 |
| 155 | 664.79 | 665.3 |
| 156 | 610.82 | 611.3 |
| 157 | 630.85 | 631.3 |
| 158 | 598.78 | 599.3 |
| 159 | 648.80 | 649.3 |
| 160 | 659.89 | 660.4 |
| 161 | 581.78 | 582.3 |
| 162 | 649.68 | 651.1 |
| 163 | 759.11 | 759.1 |
| 164 | 670.82 | 671.4 |
| 165 | 659.89 | 660.5 |
| 166 | 666.88 | 667.4 |
| 167 | 624.80 | 625.4 |
| 168 | 666.88 | 667.4 |
| 169 | 606.83 | 607.5 |
| 170 | 638.83 | 639.4 |
| 171 | 651.92 | 653.0 |
| 173 | 594.80 | 595.8 |
| 174 | 608.85 | 609.9 |
| 175 | 638.83 | 639.6 |
| 176 | 651.92 | 652.9 |
| 177 | 636.90 | 637.6 |
| 178 | 694.91 | 695.8 |
| 179 | 636.90 | 637.6 |
| 180 | 606.83 | 607.9 |
| 181 | 666.88 | 667.8 |
| 182 | 638.83 | 639.8 |
| 183 | 544.76 | 545.7 |
| 187 | 632.82 | 633.9 |
| 188 | 630.85 | 631.9 |
| 189 | 640.85 | 641.9 |
| 190 | 642.86 | 643.8 |
| 191 | 666.88 | 667.8 |
| 192 | 610.82 | 611.9 |
| 193 | 594.82 | 595.8 |
| 194 | 640.85 | 641.9 |
| 197 | 567.75 | 568.8 |
| 198 | 649.68 | 651.6 |
| 203 | 640.85 | 641.7 |
| 204 | 659.69 | 662.0 |
| 205 | 594.82 | 595.9 |
| 206 | 600.85 | 601.7 |
| 208 | 625.79 | 626.8 |
| 209 | 659.69 | 661.2 |
| 210 | 584.79 | 585.8 |
| 211 | 610.82 | 611.8 |
| 215 | 640.85 | 641.7 |
| 216 | 759.11 | 759.7 |
| 217 | 638.92 | 639.8 |
| 218 | 532.75 | 533.6 |
| 219 | 574.83 | 575.9 |
| 220 | 670.92 | 671.7 |
| 224 | 610.82 | 611.8 |
| 225 | 581.78 | 582.7 |
| 227 | 616.78 | 617.7 |
| 228 | 610.82 | 611.8 |
| 229 | 608.85 | 609.7 |
| 230 | 684.94 | 685.7 |
| 250 | 608.79 | 609.3 |
| 251 | 575.72 | 576.3 |
| 252 | 594.76 | 595.3 |
| 253 | 626.76 | 627.3 |
| 254 | 610.72 | 611.2 |
| 255 | 671.76 | 672.3 |
| 256 | 640.79 | 641.4 |
| 257 | 638.77 | 639.3 |
| 258 | 594.76 | 595.3 |
| 259 | 575.72 | 576.3 |
| 260 | 608.79 | 609.3 |
| 261 | 626.76 | 627.3 |
| 262 | 610.72 | 611.2 |
| 263 | 640.78 | 641.4 |
| 264 | 579.15 | 579.3 |
| 265 | 560.10 | 560.2 |
| 266 | 593.17 | 593.3 |
| 267 | 611.15 | 691.2 |
| 268 | 595.10 | 595.2 |
| 269 | 656.14 | 656.2 |
| 270 | 625.17 | 625.3 |
| 271 | 622.72 | 623.2 |
| 275 | 652.80 | 653.4 |
| 276 | 683.79 | 684.3 |
| 279 | 650.88 | 651.3 |
| 280 | 628.88 | 629.2 |
| 281 | 566.77 | 567.5 |
| 282 | 743.95 | 744.1 |
| 283 | 565.75 | 566.4 |
| 284 | 605.85 | 605.9 |
| 285 | 604.86 | 605.3 |
| 289 | 634.89 | 635.3 |
| 290 | 648.91 | 649.2 |
| 291 | 662.94 | 663.3 |
| 292 | 658.84 | 659.2 |
| 293 | 607.80 | 608.3 |
| 294 | 626.84 | 627.3 |
| 295 | 634.82 | 635.4 |
| 296 | 650.80 | 651.3 |
| 298 | 587.74 | 588.3 |
| 299 | 620.82 | 621.4 |
| 300 | 638.79 | 639.3 |
| 305 | 652.82 | 653.3 |
| 307 | 624.76 | 625.3 |
| 308 | 609.71 | 610.3 |
| 309 | 619.79 | 620.3 |
| 310 | 626.78 | 627.3 |
| 311 | 554.67 | 555.4 |
| 312 | 690.61 | 691.2 |
| 313 | 668.86 | 669.3 |
| 314 | 600.69 | 601.3 |
| 315 | 643.61 | 643.6 |
| 316 | 599.15 | 599.2 |
| 317 | 594.74 | 595.3 |
| 318 | 594.74 | 595.3 |
| 319 | 700.71 | 701.2 |
| 320 | 654.79 | 655.3 |
| 321 | 582.70 | 583.3 |
| 322 | 594.74 | 595.3 |
| 323 | 608.76 | 609.3 |
| 324 | 624.76 | 625.3 |
| 325 | 578.74 | 579.3 |
| 326 | 592.76 | 593.4 |
| 327 | 551.67 | 552.3 |
| 328 | 648.71 | 649.3 |

TABLE 11-continued

| ID# | Theor. MW | M/e[MH+] |
|---|---|---|
| 329 | 594.74 | 595.3 |
| 330 | 578.74 | 579.0 |
| 331 | 624.76 | 625.3 |
| 332 | 633.82 | 634.3 |
| 333 | 687.79 | 688.3 |
| 334 | 625.84 | 626.4 |
| 335 | 677.83 | 678.3 |
| 336 | 641.84 | 642.5 |
| 337 | 744.36 | 744.3 |
| 338 | 643.90 | 644.4 |
| 339 | 652.82 | 653.4 |
| 340 | 652.82 | 653.4 |
| 341 | 578.74 | 579.3 |
| 342 | 600.69 | 601.3 |
| 343 | 633.60 | 633.2 |
| 344 | 632.71 | 634.0 |
| 345 | 564.71 | 565.3 |
| 346 | 582.70 | 583.3 |
| 347 | 632.71 | 634.0 |
| 348 | 622.75 | 623.2 |
| 349 | 624.76 | 625.3 |
| 350 | 599.15 | 599.2 |
| 351 | 608.76 | 609.3 |
| 352 | 643.10 | 643.2 |
| 353 | 578.74 | 579.3 |
| 354 | 584.72 | 583.3 |
| 355 | 643.61 | 645.2 |
| 356 | 608.72 | 609.0 |
| 358 | 600.69 | 601.0 |
| 360 | 614.77 | 615.0 |
| 362 | 654.84 | 655.3 |
| 364 | 593.75 | 594.2 |
| 365 | 657.63 | 659.2 |
| 366 | 565.70 | 566.2 |
| 367 | 654.79 | 655.3 |
| 368 | 633.60 | 635.2 |
| 370 | 609.71 | 610.3 |
| 371 | 614.77 | 615.3 |
| 372 | 584.76 | 595.3 |
| 373 | 632.71 | 633.3 |
| 374 | 743.03 | 743.6 |
| 375 | 579.72 | 580.3 |
| 376 | 565.70 | 566.2 |
| 377 | 650.80 | 651.3 |
| 378 | 551.67 | 552.2 |
| 379 | 551.67 | 552.2 |
| 380 | 581.70 | 582.2 |
| 381 | 551.67 | 552.3 |
| 382 | 525.63 | 526.2 |
| 383 | 565.70 | 566.2 |
| 385 | 640.81 | 641.4 |
| 386 | 640.81 | 641.4 |
| 387 | 589.76 | 590.4 |
| 388 | 652.82 | 653.4 |
| 389 | 622.83 | 623.4 |
| 390 | 624.76 | 625.3 |
| 391 | 654.83 | 655.3 |
| 392 | 596.75 | 597.3 |
| 393 | 553.69 | 554.2 |
| 394 | 608.81 | 609.4 |
| 395 | 622.83 | 623.4 |
| 396 | 589.76 | 590.4 |
| 398 | 596.75 | 597.3 |
| 399 | 654.83 | 655.3 |
| 418 | 624.76 | 625.3 |
| 419 | 551.67 | 552.3 |
| 420 | 474.58 | 475.2 |
| 421 | 551.67 | 552.3 |
| 422 | 476.6 | 477.3 |
| 423 | 502.64 | 503.3 |
| 424 | 474.58 | 475.2 |
| 425 | 488.61 | 489.3 |
| 426 | 474.58 | 475.2 |
| 427 | 488.61 | 489.3 |
| 428 | 502.64 | 503.3 |
| 429 | 516.66 | 517.3 |
| 430 | 474.58 | 475.2 |
| 431 | 488.61 | 489.3 |
| 432 | 502.64 | 503.3 |
| 433 | 516.66 | 517.3 |
| 434 | 516.66 | 517.3 |
| 435 | 502.64 | 503.3 |
| 436 | 516.66 | 517.3 |
| 437 | 488.61 | 489.3 |
| 438 | 476.6 | 477.3 |
| 439 | 504.65 | 505.4 |
| 440 | 518.68 | 519.3 |
| 441 | 504.65 | 505.4 |
| 442 | 518.68 | 519.3 |
| 443 | 504.61 | 505.2 |
| 444 | 518.64 | 519.3 |
| 445 | 650.80 | 651.3 |
| 446 | 622.75 | 623.2 |
| 447 | 592.78 | 593.4 |
| 448 | 594.74 | 595.3 |
| 451 | 743.95 | 744.1 |
| 452 | 580.75 | 581.5 |
| 453 | 446.61 | 447.9 |
| 454 | 502.72 | 503.2 |
| 455 | 701.95 | 702.0 |
| 456 | 661.19 | 662.5 |
| 457 | 693.19 | 694.0 |
| 458 | 591.05 | 592.0 |
| 459 | 676.20 | 677.4 |
| 460 | 564.77 | 565.2 |
| 461 | 683.79 | 684.3 |
| 462 | 606.79 | 607.3 |
| 463 | 580.71 | 581.3 |
| 464 | 593.75 | 594.3 |
| 465 | 542.70 | 543.3 |
| 500 | 401.49 | 402.2 |
| 501 | 367.47 | 368.2 |
| 502 | 277.34 | 278.2 |
| 503 | 353.44 | 354.2 |
| 504 | 373.52 | 374.2 |
| 505 | 349.41 | 372.0 |
| 506 | 389.48 | 390.1 |
| 507 | 389.48 | 390.1 |
| 508 | 373.86 | 374.1 |
| 509 | 439.56 | 440.2 |
| 510 | 409.51 | 410.2 |
| 511 | 429.58 | 430.3 |
| 512 | 457.55 | 458.3 |
| 513 | 429.93 | 430.2 |
| 514 | 445.54 | 446.3 |
| 516 | 405.47 | 428.3 |
| 517 | 405.47 | 428.3 |
| 518 | 473.65 | 474.1 |
| 519 | 473.65 | 474.1 |
| 520 | 473.65 | 474.1 |
| 521 | 390.45 | 391.2 |
| 522 | 390.45 | 391.0 |
| 523 | 454.58 | 455.0 |
| 524 | 435.54 | 436.0 |
| 525 | 468.61 | 469.0 |
| 526 | 486.58 | 487.0 |
| 527 | 470.54 | 471.0 |
| 528 | 531.58 | 532.0 |
| 529 | 454.48 | 544.0 |
| 530 | 435.54 | 436.0 |
| 531 | 468.61 | 469.0 |
| 532 | 486.58 | 488.0 |
| 533 | 470.54 | 471.0 |
| 534 | 531.58 | 532.0 |
| 535 | 554.70 | 555.3 |
| 536 | 482.65 | 483.3 |
| 537 | 463.60 | 464.3 |
| 538 | 496.67 | 497.4 |
| 539 | 514.65 | 515.2 |
| 540 | 429.58 | 430.5 |
| 541 | 477.61 | 478.2 |
| 542 | 445.54 | 446.3 |
| 543 | 333.41 | 334.2 |
| 544 | 379.48 | 380.2 |

TABLE 11-continued

| ID# | Theor. MW | M/e[MH+] |
|---|---|---|
| 546 | 421.54 | 422.1 |
| 547 | 403.50 | 404.2 |
| 548 | 403.50 | 404.2 |
| 549 | 361.46 | 362.3 |
| 550 | 459.57 | 460.2 |
| 551 | 403.50 | 404.2 |
| 552 | 475.57 | 476.2 |
| 553 | 459.57 | 460.2 |
| 554 | 477.58 | 478.2 |
| 555 | 401.49 | 402.1 |
| 556 | 401.49 | 402.1 |
| 564 | 457.55 | 458.3 |
| 565 | 457.55 | 458.3 |
| 566 | 457.55 | 458.3 |
| 567 | 457.55 | 548.3 |
| 568 | 503.62 | 504.3 |
| 569 | 503.62 | 504.3 |
| 570 | 503.62 | 504.3 |
| 571 | 503.62 | 504.3 |
| 572 | 411.48 | 412.2 |
| 573 | 393.47 | 394.2 |
| 576 | 439.56 | 458.3 |
| 578 | 497.92 | 498.9 |
| 579 | 494.01 | 494.2 |
| 581 | 417.58 | 418.1 |
| 582 | 373.52 | 374.1 |
| 583 | 409.55 | 410.5 |
| 584 | 465.62 | 466.1 |
| 600 | 550.68 | 551.7 |
| 601 | 693.87 | 694.9 |
| 602 | 568.67 | 569.7 |
| 603 | 610.74 | 611.7 |
| 604 | 564.71 | 565.7 |
| 605 | 593.75 | 594.8 |
| 606 | 514.65 | 515.7 |
| 607 | 696.76 | 697.8 |
| 608 | 625.59 | 626.6 |
| 609 | 639.62 | 640.6 |
| 610 | 717.82 | 718.8 |
| 611 | 565.7 | 566.7 |
| 612 | 565.7 | 566.7 |
| 613 | 565.7 | 566.7 |
| 614 | 570.73 | 571.7 |
| 615 | 692.76 | 693.8 |
| 616 | 432.59 | 433.6 |
| 617 | 509.67 | 510.7 |
| 618 | 533.7 | 534.7 |
| 619 | 456.61 | 457.6 |
| 620 | 446.61 | 447.6 |
| 621 | 523.7 | 524.7 |
| 622 | 692.76 | 693.8 |
| 623 | 432.59 | 433.6 |
| 624 | 488.69 | 489.7 |
| 625 | 567.71 | 568.7 |
| 626 | 701.03 | 702.0 |
| 627 | 509.67 | 510.7 |
| 628 | 580.75 | 581.8 |
| 629 | 526.7 | 527.7 |
| 630 | 658.86 | 659.9 |
| 631 | 576.72 | 577.7 |
| 632 | 496.65 | 497.7 |
| 633 | 531.76 | 532.8 |
| 634 | 504.69 | 505.7 |
| 635 | 504.69 | 505.7 |
| 636 | 531.76 | 532.8 |
| 637 | 532.66 | 533.7 |
| 638 | 559.73 | 560.7 |
| 639 | 532.73 | 533.7 |
| 640 | 474.65 | 475.7 |
| 641 | 546.69 | 547.7 |
| 642 | 532.66 | 533.7 |
| 643 | 532.66 | 533.7 |
| 644 | 546.69 | 547.7 |
| 645 | 690.74 | 691.7 |
| 646 | 690.74 | 691.7 |
| 647 | 559.73 | 560.7 |
| 648 | 490.63 | 491.6 |
| 649 | 534.68 | 535.7 |
| 650 | 548.71 | 549.7 |
| 651 | 534.68 | 535.7 |
| 652 | 235.13 | 236.1 |
| 653 | 430.5 | 431.5 |
| 654 | 545.71 | 546.7 |
| 655 | 547.72 | 548.7 |
| 656 | 547.72 | 548.7 |
| 657 | 517.74 | 518.7 |
| 658 | 545.77 | 546.8 |
| 659 | 474.65 | 475.7 |
| 660 | 490.63 | 491.6 |
| 661 | 533.7 | 534.7 |
| 662 | 631.8 | 632.8 |
| 663 | 578.74 | 579.7 |
| 664 | 529.75 | 530.8 |
| 665 | 633.81 | 634.8 |
| 666 | 561.75 | 562.8 |
| 667 | 633.80 | 634.2 |
| 668 | 578.74 | 579.7 |
| 669 | 564.71 | 565.7 |
| 670 | 724.73 | 725.7 |
| 671 | 694.74 | 695.7 |
| 672 | 742.79 | 743.8 |
| 673 | 726.74 | 727.7 |
| 674 | 709.76 | 710.8 |
| 675 | 610.82 | 611.8 |
| 676 | 578.82 | 579.8 |
| 677 | 602.84 | 603.8 |
| 678 | 564.74 | 565.7 |
| 679 | 645.82 | 646.8 |
| 680 | 647.84 | 648.8 |
| 681 | 547.72 | 548.7 |
| 682 | 664.67 | 665.7 |
| 683 | 761.71 | 762.7 |
| 684 | 688.69 | 689.7 |
| 685 | 600.58 | 601.6 |
| 686 | 715.76 | 716.8 |
| 687 | 688.66 | 689.7 |
| 688 | 578.73 | 579.7 |
| 689 | 608.8 | 609.8 |
| 690 | 702.36 | 703.4 |
| 691 | 544.68 | 545.7 |
| 692 | 528.68 | 529.7 |
| 693 | 614.77 | 615.8 |
| 694 | 618.8 | 619.8 |
| 695 | 572.73 | 573.7 |
| 696 | 614.77 | 615.8 |
| 697 | 542.7 | 543.7 |
| 698 | 528.68 | 529.7 |
| 699 | 570.76 | 571.8 |
| 700 | 618.8 | 619.8 |
| 701 | 614.77 | 615.8 |
| 702 | 572.73 | 573.7 |
| 703 | 570.76 | 571.8 |
| 704 | 530.69 | 531.7 |
| 705 | 530.69 | 531.7 |
| 706 | 546.69 | 547.7 |
| 707 | 560.72 | 561.7 |
| 708 | 573.76 | 574.8 |
| 709 | 560.72 | 561.7 |
| 710 | 645.82 | 646.8 |
| 711 | 659.85 | 660.9 |
| 712 | 546.69 | 547.7 |
| 713 | 613.83 | 614.8 |
| 714 | 546.60 | 647.7 |
| 715 | 573.76 | 574.8 |
| 716 | 545.71 | 546.7 |
| 717 | 545.71 | 546.7 |
| 718 | 587.79 | 588.8 |
| 719 | 559.73 | 560.7 |
| 720 | 559.73 | 560.7 |
| 721 | 659.85 | 660.9 |
| 722 | 488.61 | 489.6 |
| 723 | 471.58 | 472.6 |
| 725 | 465.62 | 466.6 |
| 726 | 383.51 | 384.5 |

TABLE 11-continued

| ID# | Theor. MW | M/e[MH+] |
|---|---|---|
| 727 | 439.58 | 440.6 |
| 728 | 407.54 | 408.5 |
| 729 | 423.56 | 424.6 |
| 730 | 385.51 | 386.5 |
| 731 | 415.56 | 416.6 |
| 732 | 385.53 | 386.4 |
| 733 | 433.53 | 434.5 |
| 734 | 419.5 | 420.5 |
| 735 | 359.49 | 360.5 |

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders mediated by the ORL-1 receptor described in the present invention may also be carried out using a pharmaceutical composition comprising any of the compounds as defined herein and a pharmaceutically acceptable carrier. The pharmaceutical composition may contain between about 1 mg and 1000 mg, preferably about 10 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

The compound of the present invention can also be administered via transdermal skin patches well known to those of ordinary skill in that art. To be administered in the form of a transdermal delivery system, the dosage administration will, of course, be continuous rather than intermittent throughout the dosage regimen.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyl-eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders mediated by the ORL-1 receptor is required.

The daily dosage of the products may be varied over a wide range from 1 to 1,000 mg per adult human per day. For oral administration, the compositions are preferably provided in the form of tablets containing, 0.5, 1.0, 5.0, 10.0, 15.0, 25.0, 50.0, 100, 250 and 500 milligrams of the active ingredient for the symptomatic adjustment of the dosage to the patient to be treated. An effective amount of the drug is ordinarily supplied at a dosage level of from about 0.01 mg/kg to about 30 mg/kg of body weight per day. Preferably, the range is from about 0.1 mg/kg to about 10 mg/kg of body weight per day, and especially from about 0.5 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

EXAMPLE 1

2-Thienylphenyl-2-ethanol

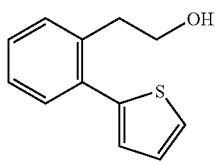

3-Bromophenethyl alcohol (4 ml, 29.8 mmol) was dissolved in 1,2-dimethoxyethane (225 mL) and mixed with tetrakistriphenylphosphine palladium[0] (2.6 g, 2.25 mmol) at room temperature. The reaction mixture was then added to a solution of 2-thienyl-boronic acid (12.6 g, 99 mmol) and 1N $NaHCO_3$ (90 mL). The reaction mixture was heated to reflux under nitrogen atmosphere for 48 hours. The reaction mixture was partitioned with water and ethyl acetate. The organic layer was dried with $MgSO_4$, filtered through a plug of silica and the solvent was evaporated in vacuo to yield a crude oil. The crude oil was purified via flash chromatography (30% EtOAc/hexane) to yield the title compounds as an oil.

MS (chemical ionization)=221 (M+$NH_4$) $^1$H NMR (300 MHz, $CDCl_3$) δ 1.3 (t, 1H), 3.0 (t, 2H), 3.75 (q, 2H), 7.0-7.4 (m, 7H)

EXAMPLE 2

Methane Sulfonic Acid 2-(2-thien-2-yl-phenyl)-ethyl Ester

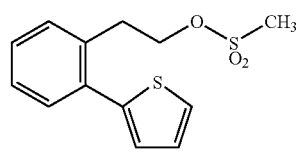

2-Thienylphenylethanol (13.6 mmol) and triethylamine (2.4 mL, 17.1 mmol) were dissolved in dichloromethane (50 mL). Methanesulfonylchloride (1.1 mL, 14 mmol) was then added slowly. The reaction mixture was stirred at room temperature for 1.5 hours. The reaction mixture was carefully partitioned with water and dichloromethane. The organic layer was dried with $Na_2SO_4$, filtered and the solvent evaporated in vacuo to yield the title compounds, which was used without further purification.

MS (chemical ionization)=300 (M+$NH_4$), 283 (MH+), 187, $^1$H NMR (300 MHz, $CDCl_3$) δ 2.8 (s, 3H), 3.2 (t, 2H), 4.3 (t, 2H), 7.0 (m, 1H), 7.1 (m, 1H), 7.2-7.5 (m, 5H)

EXAMPLE 3

1-Phenyl-8-[2-(2-thien-2-yl-phenyl)-ethyl]-1,3,8-triaza-spiro[4.5]decan-4-one Compound #581

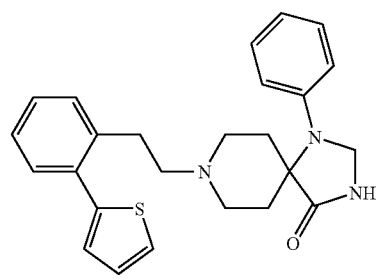

Methane sulfonic acid 2-(2-thien-2-yl-phenyl)-ethyl ester (23.14 mmol) was combined in NMP (100 mL) with 1-phenyl-1,3,8-triaza-spiro[4.5]decan-4-one (5.08 g, 22 mmol) and DIPEA (5.11 mL, 27.8 mmol) in a reaction tube which was sealed and heated to 70° C. overnight. The reaction mixture was partitioned with water and ethyl acetate. The organic layer was dried with $MgSO_4$, filtered and the solvent was evaporated in vacuo to yield a crude oil. The crude oil was purified via flash chromatography (5% methanol/$CH_2Cl_2$) to yield the title compound as a solid.

MS (electrospray)=418.1 (MH+), 313.0 $^1$H NMR (300 MHz, DMSO-$d_6$) δ 1.5 (d, 2H), 2.4 (m, 4H), 2.6 (m, 4H), 2.85 (m, 2H), 4.55 (s, 2H), 6.7-6.8 (m, 3H), 7.1-7.4 (m, 8H), 7.6 (s, 1H), 8.65 (s, 1H)

EXAMPLE 4

(R)-3-Oxiranylmethyl-1-phenyl-8-[2-(2-thien-2-yl-phenyl)-ethyl]-1,3,8-triaza-spiro[4.5]decan-4-one Compound #520

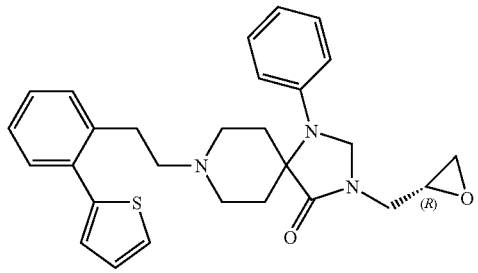

1-Phenyl-8-[2-(2-thien-2-yl-phenyl)-ethyl]-1,3,8-triaza-spiro[4.5]decan-4-one (0.7 g, 1.68 mmol) was dissolved in NMP (50 mL). To the mixture was then added sodium hydride (60% in mineral oil, 0.1, 2.52 mmol) and the reaction mixture stirred for 1 hour. S-(+)-epichlorohydrin (0.15 mL, 1.9 mmol) was then added to the reaction mixture. The reaction mixture was stirred overnight at room temperature. The reaction mixture was partitioned with saturated sodium bicarbonate and ethyl acetate. The organic layer was then partitioned with water. The organic layer was dried with MgSO$_4$, filtered and the solvent was evaporated in vacuo to yield a crude oil. The crude oil was purified via flash chromatography (80% EtOAc/hex) to yield the title compound as an oil.

MS (electrospray)=474.1 (MH+) $^1$H NMR (300 MHz, CDCl$_3$) δ 1.6 (t, 2H), 2.5-3.0 (m, 12H), 3.1-3.2 (m, 2H), 4.05 (d, 1H), 4.7 (d, 1H), 4.8 (d, 1H), 6.8 (m, 2H), 7.0 (m, 1H), 7.2-7.4 (m, 9H).

EXAMPLE 5

3-[2-(S)-Hydroxy-3-(3-morpholin-4-yl-propylamino)-propyl]-1-phenyl-8-[2-(2-thien-2-yl-phenyl)-ethyl]-1,3,8-triaza-spiro[4.5]decan-4-one Compound #111

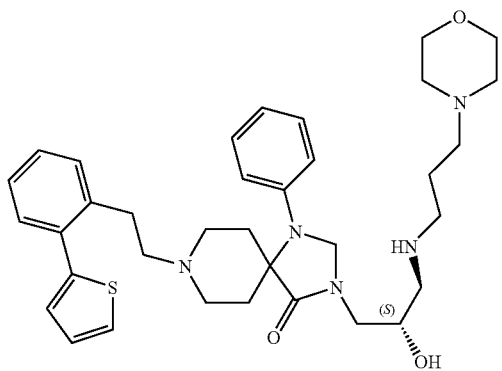

3-(R)-Oxiranylmethyl-1-phenyl-8-[2-(2-thien-2-yl-phenyl)-ethyl]-1,3,8-triaza-spiro[4.5]decan-4-one (0.1 g, 0.21 mmol) was dissolved in absolute ethanol (2 mL), mixed with 3-aminopropyl morpholino (90 μl, 0.63 mmol) and heated to 70° C. overnight. The solvent was evaporated and the resulting residue was purified by reverse phase chromatography (AcCN/water) to yield the title compounds as a trifluoroacetate salt, as a solid.

MS (electrospray)=618.3 (MH+) $^1$H NMR (300 MHz, CD$_3$OD) δ 2.0 (d, 2H), 2.2 (m, 2H), 2.72-2.88 (m, 2H), 3.0-4.3 (m, 23H), 4.8-5.05 (m, 6H), 6.8-7.5 (m, 12H).

EXAMPLE 6

(S)-3-Oxiranylmethyl-1-phenyl-8-[2-(2-thienyl-phenyl)-ethyl]-1,3,8-triazaspiro[4.5]decan-4-one Compound #519

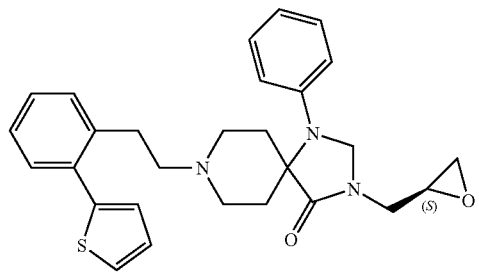

1-Phenyl-8-[2-(2-thienyl-phenyl)-ethyl]-1,3,8-triazaspiro[4.5]decan-4-one (0.13 g, 0.3 mmol) was dissolved in NMP (10 mL). To the mixture was then added sodium hydride (60% in mineral oil, 31 mg, 0.8 mmol) and the reaction mixture stirred for 1 hour. R-(−)-epichlorohydrin 927 μL, 0.35 mmol) was then added to the reaction mixture, which was then stirred overnight at room temperature. The reaction mixture was partitioned with saturated sodium bicarbonate and ethyl acetate. The organic layer was then partitioned with water. The organic layer was dried with MgSO$_4$, filtered and the solvent evaporated in vacuo to yield a crude oil. The crude oil was purified via flash chromatography (80% EtOAc/hexanes) to yield the title compound as an oil.

MS (electrospray)=474.1 (MH+) $^1$H NMR (300 MHz, CDCl$_3$) δ 1.65 (t, 2H), 2.0 (q, 1H), 2.4 (t, 1H), 2.5-3.0 (m, 11H), 3.2 (m, 1H), 3.3 (t, 1H), 4.0 (d, 1H), 4.7 (d, 1H), 4.8 (d, 1H), 6.9 (m, 2H), 7.0 (m, 1h), 7.15-7.4 (m, 9H).

EXAMPLE 7

3-[2-(R)-hydroxy-3-(3-morpholin-4-yl-propylamino)-propyl]-1-phenyl-8-[2-(2-thien-2-yl-phenyl)-ethyl]-1 3,8-triazaspiro[4.5]decan-4-one Compound #112

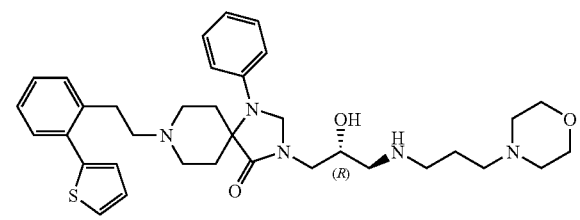

3-(S)-Oxiranylmethyl-1-phenyl-8-[2-(2-thien-2-yl-phenyl)-ethyl]-1,3,8-triazaspiro[4.5]decan-4-one (0.13 g, 0.27 mmol) was dissolved in absolute ethanol (2 mL), mixed with 3-aminopropylmorpholino (100 μL, 0.68 mmol) and heated with stirring at 70° C. overnight. The solvent was evaporated and the resulting residue was purified by reverse phase chromatography (Acetonitrile/water) to yield the title compound as a trifluoroacetate salt as a solid.

MS (electrospray)=618.3 (MH+) $^1$H NMR (300 MHz, CD$_3$OD) δ 2.0 (d, 2H), 2.2 (m, 2H), 2.75-2.9 (m, 2H), 3.0-4.3 (m, 23H), 4.8-5.05 (m, 6H), 6.8-7.5 (m, 12H).

EXAMPLE 8

1-bromo-acenaphthene

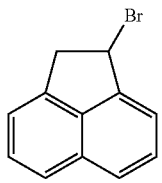

Acenaphthen-1-ol (88 mol) was dissolved in diethyl ether (150 mL) and cooled down to 0° C. Phosphorous tribromide (3.2 mL, 35 mmol) was then added slowly under nitrogen atmosphere. The reaction mixture was stirred for 30 minutes at room temperature and cooled to 0° C. The reaction mixture was partitioned with water and diethyl ether. The organic layer was dried over Na$_2$SO$_4$, filtered and the solvent evaporated in vacuo to yield the title compound as a yellow solid.

EXAMPLE 9

8-Acenaphthen-1-yl-1-(4-fluorophenyl)-1,3,8-triazaspiro[4.5]decan-4-one Compound # 500

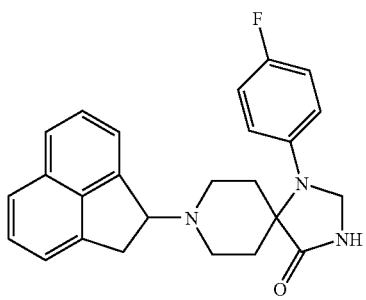

1-Bromo-acenaphthene (20.5 g, 87.9 mmol) and 1-(4-fluorophenyl)-1,3,8-triazaspiro[4.5]decan-4-one (9.15 g, 36.6 mmol) were dissolved in N,N-dimethylformamide (190 mL). Potassium carbonate (15.15 g, 110 mmol) was then added and the reaction mixture was stirred at room temperature under a nitrogen atmosphere for 18 hours. The reaction mixture was partitioned with water and diethyl ether. The title compound precipitated from the organic layer as an off-white solid.

$^1$H NMR (300 MHz, CDCl$_3$) δ7.68-7.66 (91H, m), 7.60 (1H, d, J=8.2 Hz), 7.53-7.49 (2H, m), 7.43 (1H, t, J=8.1 Hz), 7.26 (1H, d, J=7.8 Hz), 7.04-6.94 (4H, m), 6.67 (1H, br, s), 4.95 (1H, br, s), 4.66-4.63 (2H, m), 3.51 (1H, d), 3.34 (1H, dd J=7.6 and 17.5 Hz), 3.13-2.94 (2H, m), 2.83 (1H, br, s), 2.43 (1H, br, a), 2.24 (1H, m), 1.80-1.66 (3H, m) MS (ES$^+$) m/z 402.1 (M+H)$^+$ Chiral resolution: The racemate prepared as described above was resolved using a CHIRALCEL OD-H column with methanol as mobile phase and generated the two pure enantiomers R (RT=6.174 minutes, ee>99%) and S (RT=10.175 minutes, ee>99%).

EXAMPLE 10

1-(4-fluorophenyl)-8-(2-hydroxy-cycloheptyl)-1,3,8-triazaspiro[4.5]decan-4-one Compound #549

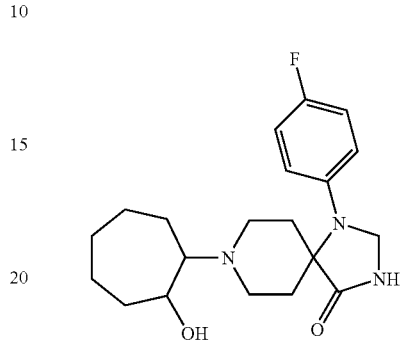

1-(4-fluorophenyl)-1,3,8-triazaspiro[4.5]decan-4-one (0.15 g, 0.6 mmol) was dissolved in dichloromethane (1 mL) and 1,2-dichloromethane (0.25 mL) under a nitrogen atmosphere. The reaction mixture was then added slowly at 0° C. to 1.9M triethyl aluminum in toluene (0.315 mL, 0.6 mmol). After stirring for 30 minutes at room temperature, to the reaction mixture was added slowly a solution of 8-oxa-bicyclo[5.1.0]octane (68 mg, 0.6 mmol) in dichloromethane (16 mL). The reaction mixture was stirred at room temperature under a nitrogen atmosphere for 13 days and then partitioned with 1N NaOH and DCM. The organic layer was dried over Na$_2$SO$_4$, filtered and the solvent evaporated in vacuo to yield a crude oil. The crude oil was purified via flash chromatography (2% methanol/DCM) to yield the title compound as an oil.

$^1$H NMR (300 MHz, CDCl$_3$) δ7.05-6.88 (4H, m), 4.69 (s, 2H), 3.44-3.31 (2H, m), 2.96-2.88 (1H, m), 2.73-2.69 (1H, m), 2.56-2.53 (1H, m), 2.42-2.17 (3H, m), 2.11-2.02 (1H, m), 1.94-1.87 (1H, m), 1.78 (1H, d), 1.72-1.19 (11H, m) MS (ES$^+$) m/z 362.3 (M+H)$^+$.

EXAMPLE 11

(R)-8-Acenaphthen-1-yl-1-(4-fluoro-phenyl)-3-(R)-oxiranylmethyl-1,3,8-triazaspiro[4.5]decan-4-one Compound #556

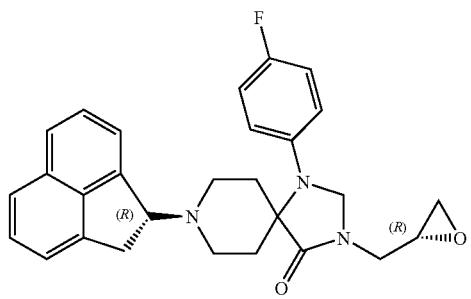

(R)-8-Acenaphthen-1-yl-1-(4-fluoro-phenyl)-1,3,8-triaza-spiro[4.5]decan-4-one (1.5 g, 3.736 mmol) was dissolved in N,N-dimethylformamide (10.0 mL). To the reaction mixture was then added at 0° C. sodium hydride (60% in mineral oil, 0.195 g, 4.856 mmol) under nitrogen atmosphere. The reaction mixture was stirred at 0° C. for 40 minutes and then warmed to room temperature. To the reaction mixture was then added (S)-epichlorhydrin (0.87 mL, 11.208 mmol). The reaction mixture was stirred at room temperature under nitrogen atmosphere for 18 hours and partitioned with water and ethyl acetate. The organic layer was dried with $Na_2SO_4$, filtered and the solvent evaporated in vacuo to yield a crude oil. The crude oil was purified via flash chromatography (1.5% methanol/dichloromethane) to yield the title compound as a foam.

$^1$H NMR (300 MHz, $CDCl_3$) δ 7.70-7.65 (1H, m), 7.60 (1H, d, J=8.2 Hz), 7.54-7.49 (2H, m), 7.44 (1H, t), 7.26 (1H, d), 7.05-6.93 (4H, m), 4.95 (1H, dd, J=3.4 and 7.8 Hz), 4.77-4.74 (1H, m), 4.66-4.64 (1H, m), 4.0 (1H, d, J=12.5 Hz), 3.56-3.32 (2H, m), 3.21-3.03 (4H, m), 2.83-2.80 (2H, m), 2.59-2.55 (1H, m), 2.46-2.30 (2H, m), 2.27-2.21 (1H, m), 1.77-1.60 (2H, m) MS (ES$^+$) m/z 458.3 (M+H)$^+$.

EXAMPLE 12

(R)-8-Acenaphthen-1-yl-3-(3-{[2-(3,4-dimethoxy-phenyl)-ethyl]-methyl-amino}-(R)-2-hydroxy-propyl)-1-(4-fluoro-phenyl)-1,3,8-triaza-spiro[4.5]decan-4-one Compound #339

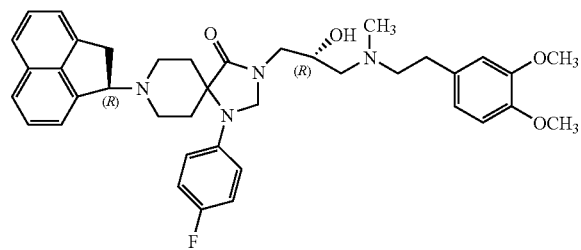

8-Acenaphthen-1-yl-1-(4-fluoro-phenyl)-3-(S)-oxiranylmethyl-1,3,8-triaza-spiro[4.5]decan-4-one (1.5 g, 3.28 mmol), [2-(3,4-dimethoxy-phenyl)-ethyl]-methyl-amine hydrochloride (2.3 g, 9.92 mmol) and N,N-diisopropylethylamine (5 mL, 28.7 mmol) were dissolved in ethanol (40 mL). The reaction mixture was heated at 80° C. for 18 hours, then cooled to room temperature and the solvent evaporated in vacuo to yield an oil. The oil was partitioned with water and ethyl acetate. The organic layer was dried with $Na_2SO_4$, filtered and the solvent evaporated in vacuo to yield a crude oil. The crude oil was purified via flash chromatography (2% [methanol in ammonia 2.0M]/dichloromethane) to yield the title compound as a foam.

Chiral resolution: Diastereoisomers were separated using a CHIRALCEL OD-H column with methanol as mobile phase and generated the two pure diastereoisomers R, R and R, S.

$^1$H NMR (300 MHz, $CDCl_3$) δ 7.69-7.65 (1H, m), 7.60 (1H, d, J=8.2 Hz), 7.54-7.50 (2H, m), 7.44 (1H, t), 7.27-7.25 (1H, m), 7.04-6.92 (4H, m), 6.77-6.64 (3H, m), 4.97-4.94 (1H, m), 4.79-4.71 (2H, m), 3.82 (3H, s), 3.81 (3H, s), 3.58-3.51 (3H, m), 3.38-3.02 (5H, m), 2.84-2.80 (1H, m), 2.77-2.53 (4H, m), 2.49-2.26 (7H, m), 1.76-1.59 (2H, m) MS (ES$^+$) m/z 653.4 (M+H)$^+$.

EXAMPLE 13

1-(4-Fluoro-phenyl)-8-naphthalen-1-ylmethyl-1,3,8-triaza-spiro[4.5]decan-4-one Compound #507

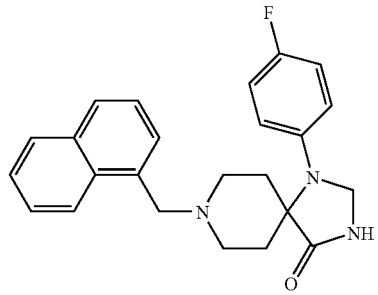

1-(4-Fluoro-phenyl)-1,3,8-triaza-spiro[4.5]decan-4-one (1.0 g, 4.01 mmol) and naphthalene-1-carbaldehyde (0.75 g, 4.81 mmol) were dissolved in dry tetrahydrofuran (60 mL). To the reaction mixture was then added at 0° C. sodium triacetoxyborohydride (1.27 g, 6.01 mmol) under nitrogen atmosphere and the reaction mixture was stirred at room temperature for 18 hours. The reaction mixture was then partitioned with 1N NaOH and ethyl acetate. The organic layer was washed with brine, dried with $Na_2SO_4$, filtered and the solvent evaporated in vacuo to yield a crude oil. The crude oil was purified via flash chromatography (3% methanol/dichloromethane) to yield the title compound as a solid.

$^1$H NMR (300 MHz, $CDCl_3$) δ 8.39-8.36 (1H, m), 7.87-7.75 (2H, m), 7.56-7.37 (4H, m), 6.99-6.85 (4H, m), 4.67 (2H, s), 3.97 (2H, s), 2.91-2.83 (4H, m), 2.42-2.31 (2H, m), 1.75-1.71 (2H, m) MS (ES$^+$) m/z 390.1 (M+H)$^+$.

EXAMPLE 14

1-(4-Fluoro-phenyl)-8-naphthalen-1-ylmethyl-(R)-3-oxiranylmethyl-1,3,8-triaza-spiro[4.5]decan-4-one Compound #514

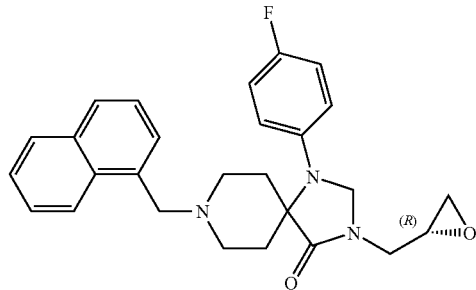

(R)-1-(4-Fluoro-phenyl)-8-naphthalen-1-ylmethyl-1,3,8-triaza-spiro[4.5]decan-4-one (0.218 g, 0.559 mmol) was dissolved in N,N-dimethylformamide (2.2 mL). To the reaction mixture was then added at 0° C. sodium hydride (60% in mineral oil, 30 mg, 0.727 mmol) under nitrogen atmosphere and the reaction mixture was stirred at 0° C. for 40 minutes. To the reaction mixture was then added (S)-epichlorhydrin (0.13 mL, 1.679 mmol) at 0° C. The reaction mixture was stirred at room temperature under nitrogen atmosphere for 18 hours and partitioned with water and ethyl acetate. The organic layer was washed with brine, dried with $Na_2SO_4$, filtered and the solvent evaporated in vacuo to yield a crude oil. The crude oil was purified via flash chromatography (2% methanol/dichloromethane) to yield the title compound as a solid.

$^1$H NMR (300 MHz, CDCl$_3$) δ8.38-8.35 (1H, m), 7.87-7.75 (2H, m), 7.56-7.37 (4H, m), 6.99-6.86 (4H, m), 4.78-4.65 (2H, m), 4.08-3.97 (3H, m), 3.21-3.12 (2H, m), 2.95-2.82 (5H, m), 2.61-2.59 (1H, m), 2.40-2.30 (2H, m), 1.72-1.59 (2H, m) MS (ES$^+$) m/z 446.3 (M+H)$^+$.

EXAMPLE 15

1-(4-Fluoro-phenyl)-8-(5-phenyl-thien-2-ylmethyl)-1,3,8-triaza-spiro[4.5]decan-4-one Compound #546

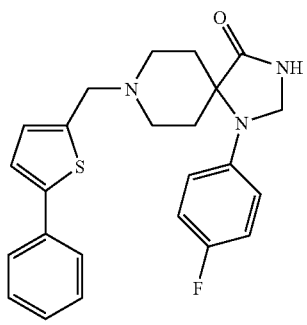

1-(4-Fluoro-phenyl)-1,3,8-triaza-spiro[4.5]decan-4-one (0.15 g, 0.601 mmol) and 5-phenyl-thienyl-2-carbaldehyde (0.136 g, 0.722 mmol) were dissolved in dry tetrahydrofuran (12 mL). To the reaction mixture was then added at 0° C. sodium triacetoxyborohydride (0.192 g, 0.902 mmol) under nitrogen atmosphere and the reaction mixture was stirred at room temperature for 18 hours. The reaction mixture was partitioned with 1N NaOH and ethyl acetate. The organic layer was washed with brine, dried with Na$_2$SO$_4$, filtered and the solvent evaporated in vacuo to yield a crude oil. The crude oil was purified via flash chromatography (2% methanol/dichloromethane) to yield the title compound as a solid.

$^1$H NMR (300 MHz, CDCl$_3$) δ7.59-7.56 (2H, m), 7.38-7.33 (2H, m), 7.27-7.22 (1H, m), 7.18-7.13 (1H, m), 7.05-6.92 (4H, m), 6.87 (1H, d, J=3.6 Hz), 6.26 (1H, br s), 4.67 (2H, s), 3.75 (2H, s), 2.87-2.78 (4H, m), 2.40-2.30 (2H, m), 1.76 (2H, d, J=14.1 Hz) MS (ES$^+$) m/z 422.1 (M+H)$^+$.

EXAMPLE 16

(R)-1-(4-Fluoro-phenyl)-3-oxiranylmethyl-8-(5-phenyl-thien-2-yl-methyl)-1,3,8-triaza-spiro[4.5]decan-4-one Compound #541

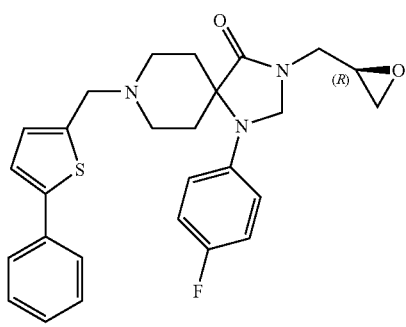

1-(4-Fluoro-phenyl)-8-(5-phenyl-thien-2-yl-methyl)-1,3,8-triaza-spiro[4.5]decan-4-one (0.105 g, 0.249 mmol) was dissolved in N,N-dimethylformamide (2.5 mL). To the reaction mixture was then added at 0° C. sodium hydride (60% in mineral oil, 13 mg, 0.323 mmol) under nitrogen atmosphere and the reaction mixture was stirred at 0° C. for 40 minutes. To the reaction mixture was then added (S)-epichlorhydrin (0.058 mL, 0.747 mmol) at 0° C. The reaction mixture was stirred at room temperature under nitrogen atmosphere for 18 hours and partitioned with water and ethyl acetate. The organic layer was washed with brine, dried with Na$_2$SO$_4$, filtered and the solvent evaporated in vacuo to yield a crude oil. The crude oil was purified via flash chromatography (2% methanol/dichloromethane) to yield the title compound as a solid.

$^1$H NMR (300 MHz, CDCl$_3$) δ7.59-7.55 (2H, m), 7.38-7.33 (2H, m), 7.27-7.22 (1H, m), 7.14 (1H, d, J=3.6 Hz), 7.05-6.92 (4H, m), 6.87 (1H, d, J=3.5 Hz), 4.77 (1H, d, J=4.8 Hz), 4.66 (1H, d, J=4.8 Hz), 4.06-3.99 (1H, m), 3.76 (2H, s), 3.20-3.13 (2H, m), 2.95-2.82 (3H, m), 2.60-2.58 (1H, m), 2.38-2.30 (2H, m), 1.75-1.67 (2H, m) MS (ES$^+$) m/z 478.2 (M+H)$^+$.

EXAMPLE 17

1-(4-Fluoro-phenyl)-8-(4-propyl-cyclohexyl)-1,3,8-triaza-spiro[4.5]decan-4-one Compound #504

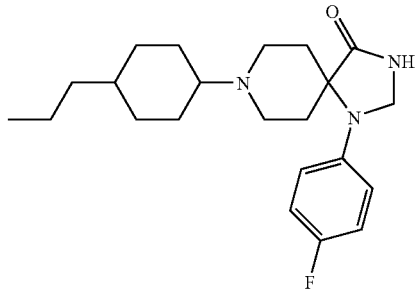

1-(4-Fluoro-phenyl)-1,3,8-triaza-spiro[4.5]decan-4-one (0.25 g, 1.00 mmol) was dissolved in dry toluene (10 mL). To the reaction mixture was then added 4-propyl-cyclohexanone (0.14 g, 1.00 mmol), powder molecular sieve 4A (0.5 g) and the reaction mixture was refluxing for 18 hours under nitrogen atmosphere. The reaction mixture was cooled to room temperature and filtered through Celite. The Celite cake was washed with dry dichloromethane and the combined filtrate evaporated in vacuo to dryness. The residue was dissolved in dry tetrahydrofuran (4 mL) and dry methanol (0.5 mL). To the solution was then added sodium cyanoborohydride (21 mg), the pH of the solution was adjusted to pH 4 with a few drops of glacial acetic acid and the reaction mixture was stirred for 48 hours at room temperature under nitrogen atmosphere. The reaction mixture was partitioned with 1N NaOH and ethyl acetate. The organic layer was dried with Na$_2$SO$_4$, filtered and the solvent evaporated in vacuo to yield a crude oil. The crude oil was purified via flash chromatography (gradient 2-4% methanol/dichloromethane) to yield the title compound.

¹H NMR (300 MHz, CDCl₃) δ7.02-6.93 (4H, m), 6.54 (1H, br d, J=9.1 Hz), 4.67 (2H, s), 3.05-2.70 (4H, m), 2.38-2.15 (3H, m), 1.9-1.11 (15H, m), 0.94-0.84 (3H, m) MS (ES⁺) m/z 374.0 (M+H)⁺.

EXAMPLE 18

1-Bromomethyl-8-methyl-naphthalene

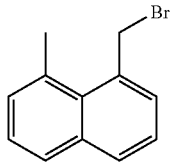

1,8-Dimethyl-naphthalene (1.30 g, 8.32 mmol) was dissolved in dry carbon tetrachloride (80 mL). To the reaction mixture was added N-bromosuccinimide (1.39 g, 7.82 mmol), dibenzoyl peroxide (6 mg, catalyst) and the reaction mixture was refluxing for 6 hours under nitrogen atmosphere. The reaction mixture was cooled to room temperature, a precipitate formed on cooling and the precipitate was separated by filtration. The filtrate was evaporated in vacuo to yield the title compound as a solid which was used in further steps without additional purification.

EXAMPLE 19

1-(4-Fluoro-phenyl)-8-(8-methyl-naphthalen-1-ylmethyl)-1,3,8-triaza-spiro[4.5]-decan-4-one Compound #547

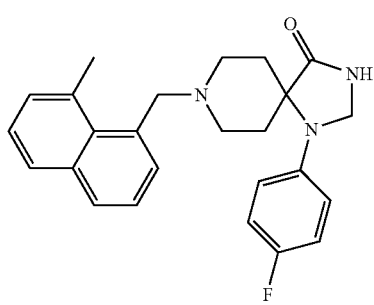

1-Bromomethyl-8-methyl-naphthalene (1.72 g, 7.31 mmol) and 1-(4-fluoro-phenyl)-1,3,8-triaza-spiro[4.5]decan-4-one (1.29 g, 5.17 mmol) were dissolved in N,N-dimethylformamide (50 mL). Potassium carbonate (2.4 g, 15.52 mmol) and potassium iodide (0.02 g) were added and the reaction mixture was stirred at 30° C. under nitrogen atmosphere for 18 hours. The reaction mixture was partitioned with water and ethyl acetate. The organic layer was washed with brine, dried with Na₂SO₄, filtered and the solvent evaporated in vacuo to yield a crude solid. The crude solid was recrystallized from diethyl ether to yield the title compound as a solid.
¹H NMR (300 MHz, CDCl₃) δ7.79-7.76 (1H, m), 7.72-7.69 (1H, m), 7.39-7.30 (4H, m), 6.98-6.92 (2H, m), 6.87-6.82 (2H, m), 6.24 (1H, br s), 4.66 (2H, s), 4.01 (2H, s), 3.12 (3H, s), 2.86-2.78 (4H, m), 2.33-2.23 (2H, m), 1.72 (2H, d, J=14.1 Hz) MS (ES⁺) m/z 404.2 (M+H)⁺.

EXAMPLE 20

1-(4-Fluoro-phenyl)-8-(8-methyl-naphthalen-1-ylmethyl)-3-(R)-oxiranylmethyl-1,3,8-triaza-spiro[4.5] decan-4-one Compound #553

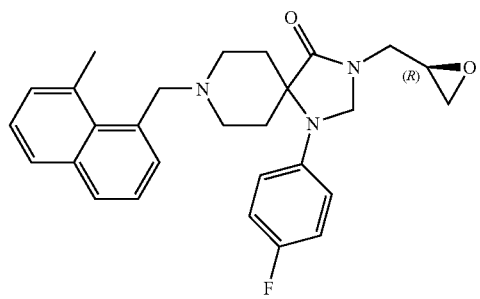

1-(4-Fluoro-phenyl)-8-(8-methyl-naphthalen-1-ylmethyl)-1,3,8-triaza-spiro[4.5]-decan-4-one (0.91 g, 2.25 mmol) was dissolved in N,N-dimethylformamide (10.5 mL). To the reaction mixture was then added at 0° C. sodium hydride (60% in mineral oil, 117 mg, 2.93 mmol) under nitrogen atmosphere and the reaction mixture was stirred at 0° C. for one hour, then warmed to room temperature. To the reaction mixture was then added (S)-epichlorhydrin (0.53 mL, 6.76 mmol). The reaction mixture was stirred at room temperature under nitrogen atmosphere for 18 hours and partitioned with water and ethyl acetate. The organic layer was washed with brine, dried with Na₂SO₄, filtered and the solvent evaporated in vacuo to yield a crude oil. The crude oil was purified via flash chromatography (2.5% methanol/dichloromethane) to yield the title compound as a foam.
¹H NMR (300 MHz, CDCl₃) δ7.78-7.75 (1H, m), 7.71-7.68 (1H, m), 7.39-7.30 (4H, m), 6.99-6.92 (2H, m), 6.88-6.83 (2H, m), 4.76 (1H, d, J=4.8 Hz), 4.64 (1H, d, J=4.8 Hz), 4.0 (2H, s), 3.21-3.11 (6H, m), 2.86-2.78 (5H, m), 2.60-2.58 (1H, m), 2.30-2.22 (2H, m), 1.70-1.62 (2H, m) MS (ES⁺) m/z 460.2 (M+H)⁺.

EXAMPLE 21

3-{3-[8-Acenaphthen-1-yl-1-(4-fluoro-phenyl)-4-oxo-1,3,8-triaza-spiro[4.5]dec-3-yl}-2-(R)-hydroxypropylsulfanyl]-2-acetylamino-(R)-propionic Acid Compound #100

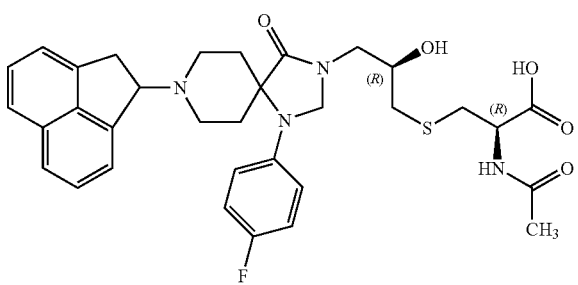

8-Acenaphthen-1-yl-1-(4-fluoro-phenyl)-3-(R)-oxiranyl-methyl-1,3,8-triaza-spiro[4.5]decan-4-one (0.022 g, 0.048 mmol) and N-acetyl-L-cysteine (0.03 g, 0.184 mmol) were dissolved in ethanol (1 mL). The reaction mixture was heated at 80° C. for 18 hours, then cooled to room temperature and the solvent evaporated in vacuo to yield an oil. The oil was partitioned with water and ethyl acetate. The organic layer was dried with Na$_2$SO$_4$, filtered and the solvent evaporated in vacuo to yield a crude oil. The crude oil was purified via preparative TLC plate (10% methanol/dichloromethane) to yield the title compound as an oil.

EXAMPLE 22

8-Cyclooctylmethyl-1-(4-fluoro-phenyl)-1,3,8-triaza-spiro[4.5]decan-4-one Compounds #582

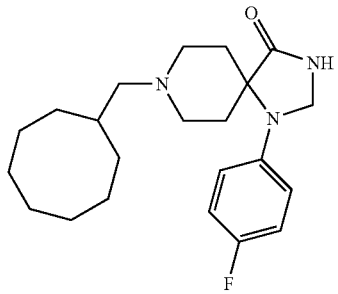

Cyclooctanecarbaldehyde (0.676 g, 4.8 mmol) synthesized according to the procedure described in Kawamoto, H. et al. *Tetrahedron* 2001, 57, 981-986 was reacted with 1-(4-fluoro-phenyl)-1,3,8-triaza-spiro[4.5]decan-4-one (1 g, 4 mmol) in tetrahydrofuran (anhydrous, 100 mL), with the addition of sodium triacetoxyborohydride (1.2 g, 6 mmol) at 0° C. The reaction was then stirred overnight at room temperature. The organic layer was partitioned with 1N sodium hydroxide, water and brine. The organic layer was dried with sodium sulfate and filtered to yield a clear residue. Purification of the residue by flash chromatography yielded the title compound as a white powder.

MS (electrospray)=374.1 (MH+) $^1$H NMR (300 MHz, CDCl$_3$) δ1.1-1.9 (m, 15H), 2.1 (d, 2H), 2.2-2.4 (m, 2H), 2.7 (d, 4H), 3.3 (d, 2H), 4.7 (s, 2H), 6.4 (s, 1H), 6.8-7.0 (m, 4H).

EXAMPLE 23

8-Cyclooctylmethyl-1-(4-fluoro-phenyl)-(R)-3-oxiranylmethyl-1,3,8-triaza-spiro[4.5]decan-4-one Compound #540

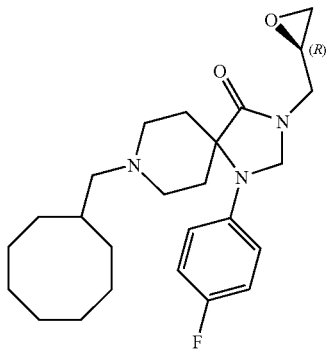

8-Cyclooctylmethyl-1-(4-fluoro-phenyl)-1,3,8-triaza-spiro[4.5]decan-4-one (4, 3 g, 8 mmol) was dissolved with NMP (150 mL) and stirred at 0° C. Sodium hydride (60% dispersion in oil, 0.75 g, 18.7 mmol) was added to the reaction mixture which was then stirred an additional 30 minutes at 0° C. S-(+)-epichlorohydrin (1.88 ml, 24 mmol) was added and the reaction was stirred overnight at room temperature. The reaction was then partitioned with water and ethyl acetate. The organic was dried with sodium sulfate and filtered. The solvent was evaporated to yield the title compound as an oil.

MS (electrospray)=430.5 (MH+) $^1$H NMR (300 MHz, CDCl$_3$) δ1.1-1.9 (m, 17H), 2.15 (d, 2H), 2.2-2.4 (m, 2H), 2.5-2.85 (m, 4H), 3.1 (m, 2H), 4.0 (m, 1H), 4.65 (d, 1H), 4.75 (d, 1H), 6.8-7.0(m, 4H)

EXAMPLE 24

3-[3-(Benzyl-butyl-amino)-2-(S)-hydroxy-propyl]-8-cyclooctylmethyl-1-(4-fluoro-phenyl)-1,3,8-triaza-spiro[4.5]decan-4-one Compound #64

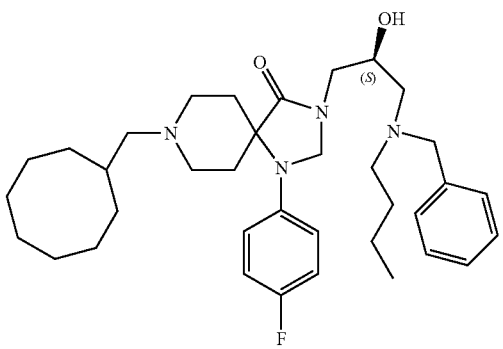

Cyclooctylmethyl-1-(4-fluoro-phenyl)-3-(R)-oxiranylmethyl-1,3,8-triaza-spiro[4.5]decan-4-one (3.4 g, 8 mmol) was dissolved in absolute ethanol (75 mL), mixed with N-butyl-benzylamine (3.1 mL, 17.6 mmol) and heated at reflux overnight. The solvent was evaporated and the resulting residue was purified by column chromatography (5% MeOH/CH$_2$Cl$_2$) to yield the free base as an oil. The oil (2.2 g, 3.7 mmol) was dissolved in diethyl ether (10 mL) and reacted with HCl (11 mL, [1M in diethylether]) at 0° C. He resulting crystals were collected by filtration and recrystallized with ethanol to yield 1 g the title compound white powder.

MS (electrospray)=593.5 (MH+), 592.6 $^1$H NMR (300 MHz, CD$_3$OD) δ1.1 (m, 3H), 1.3-1.9 (m, 15H), 2.1 (m, 2H), 2.4 (m, 2H), 2.9-3.6 (m, 14H), 3.65-3.8 (m, 2H), 4.2 (m, 1H), 4.3-4.3 (m, 3H), 4.8 (m, 2H), 7.0-7.2 (m, 4H), 7.4-7.7 (m, 5H)

EXAMPLE 25

8-Cyclooctylmethyl-3-{3-[2-(3,4-dimethoxy-phenyl)-ethoxy]-2-(R)-hydroxy-propyl}-1-(4-fluoro-phenyl)-1,3,8-triaza-spiro[4.5]decan-4-one Compound #105

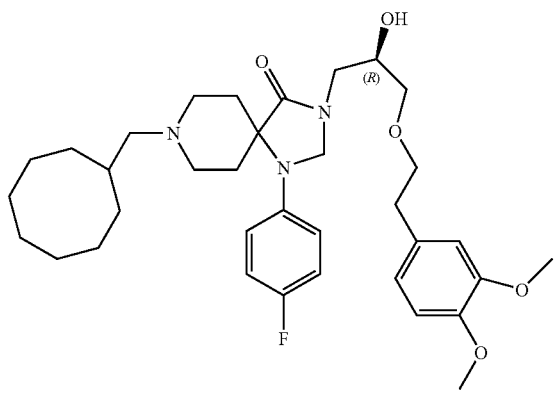

3,4-Dimethoxyphenethylalcohol was dissolved in NMP (2 mL) and stirred for 30 min. NaH (60% dispersion in oil) was added and the mixture was stirred for thirty minutes. 8-Cyclooctylmethyl-1-(4-fluoro-phenyl)-3-(S)-oxiranylmethyl-1,3,8-triaza-spiro[4.5]decan-4-one (0.2 g, 0.46 mmol) was added and the reaction was stirred overnight at room temperature. The reaction was partitioned with saturated NaHCO$_3$ solution and ethyl acetate. The organic layer was dried with MgSO$_4$, filtered and the solvent evaporated in vacuo to yield crude product. Purification by reverse phase chromatography (AcCN/water) yielded the title compound as a trifluoroacetate salt as a solid.

MS (electrospray)=612.1 (MH+), 522.0, 402.2 $^1$H NMR (300 MHz, CD$_3$OD) δ1.3-1.8 (m, 14H), 2.0-2.1 (m, 4H), 2.2-2.4 (m, 2H), 2.8 (t, 2H), 3.0 (d, 2H), 3.35-3.8 (m, 13H), 3.9 (m, 4H), 4.7 (m, 2H), 6.8 (m, 3H), 7.1 (m, 4H)

EXAMPLE 26

2-Acetylamino-3-{3-[8-cyclooctylmethyl-1-(4-fluoro-phenyl)-4-oxo-1,3,8-triaza-spiro[4.5]dec-3-yl]-2-(R)-hydroxy-propylsulfanyl}-propionic Acid Compound #100

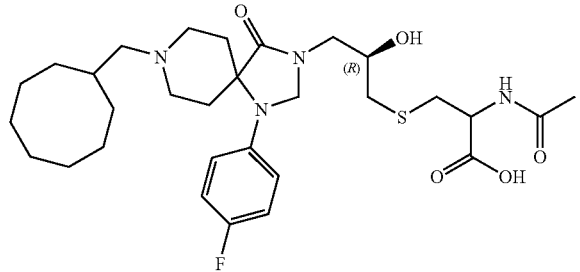

1-(4fluorophenyl)-3R-oxarinyl-methyl-8-cyclooctylmethyl-1,3,8-triaza-spiro[4.5]decan-4-one (0.06 g, 0.14 mmol) was dissolved in absolute ethanol (1 mL), mixed with N-acetylcysteine (68 mg, 0.42 mmol) and heated to 70° C. overnight. The solvent was evaporated and the resulting residue was purified by reverse phase chromatography (AcCN/water) to yield the title compounds as a trifluoroacetate salt as a solid.

MS (electrospray)=593.8 (MH+).

EXAMPLE 27

1-(4-Fluoro-phenyl)-8-pentamethylphenylmethyl-1,3,8-triaza-spiro[4.5]decan-4-one Compound #583

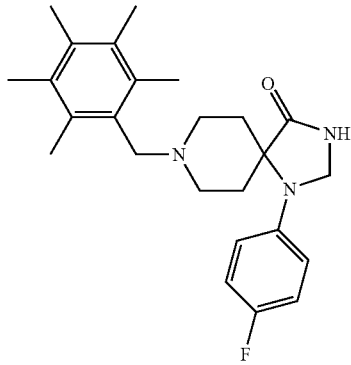

Pentamethylbenzaldehyde (4 g, 23 mmol, commercially available) was reacted with 1-(4-Fluoro-phenyl)-1,3,8-triaza-spiro[4.5]decan-4-one (5.5 g, 20 mmol) in tetrahydrofuran (anhydrous, 250 mL), with addition of sodium triacetoxyborohydride (8.2 g, 42 mmol) at 0° C. The reaction was then stirred overnight at room temperature. The organic layer was partitioned with 1N sodium hydroxide, water and brine. The organic layer was dried with sodium sulfate and filtered to yield the title compound as a white powder.

MS (electrospray)=410.5 (MH+), 250.0 $^1$H NMR (300 MHz, DMSO-d$_6$) δ1.6 (d, 2H), 2.2-2.3 (m, 17 H), 2.6-2.8 (m, 4H), 3.55 (s, 2H), 4.5 (s, 2H), 6.8 (m, 2H), 7.1 (t, 2H), 8.65 (s, 1H).

EXAMPLE 28

1-(4-Fluoro-phenyl)-3R-oxiranylmethyl-8-pentamethylphenylmethyl-1,3,8-triaza-spiro[4.5]decan-4-one Compound #584

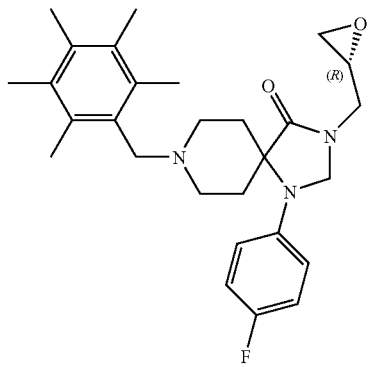

1-(4-Fluoro-phenyl)-8-pentamethylphenylmethyl-1,3,8-triaza-spiro[4.5]decan-4-one (0.6 g, 1.46 mmol) was dissolved with NMP (5 mL) and stirred at room temperature. Sodium hydride (60% dispersion in oil, 0.11 g, 1.6 mmol) was added and the mixture stirred an additional 30 minutes. S-(+)-epichlorohydrin (0.3 ml, 3.2 mmol) was added and the reaction was stirred overnight at room temperature. The reaction was then partitioned with water and ethyl acetate. The organic was dried with sodium sulfate and filtered. The solvent was evaporated to yield the title compounds as an oil.

MS (electrospray)=466.1 (MH+)

EXAMPLE 29

3-[3-(Benzyl-butyl-amino)-2-(S)-hydroxy-propyl]-1-(4-fluoro-phenyl)-8-pentamethylphenylmethyl-1,3,8-triaza-spiro[4.5]decan-4-one Compound #280

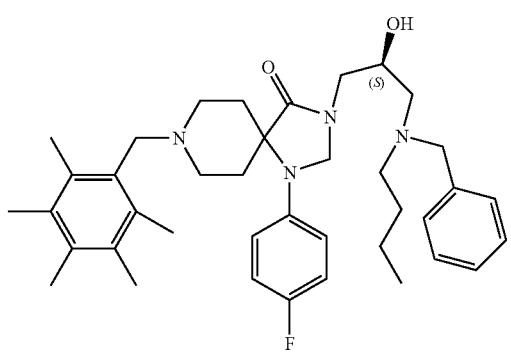

1-(4-Fluoro-phenyl)-3R-oxiranylmethyl-8-pentamethylphenylmethyl-1,3,8-triaza-spiro[4.5]decan-4-one (0.1 g, 0.21 mmol) was dissolved in absolute ethanol (75 mL), mixed with N-butylbenzylamine (0.1 mL, 0.6 mmol) and heated at reflux overnight. The solvent was evaporated and the resulting residue was purified by reverse phase chromatography (AcCN/water) to yield the title compound as an oil.

MS (electrospray)=629.2 (MH+), 468.9, 315.3, 311.9, 161.1 $^1$H NMR (300 MHz, CD$_3$OD) δ1.0 (m, 3H), 1.3 (m, 2 H), 1.8 (m, 2H), 1.9 (m, 2H), 2.25 (d, 9H), 2.3(s, 6H), 3.2 (m, 3H), 3.4 (m, 4H), 3.9 (m, 3H), 4.15 (m, 1H), 4.4 (m, 4H), 4.8 (m, 2H), 7.0 (m, 3H), 7.5 (m, 9H).

EXAMPLE 30

8-(2-Chloro-6-trifluoromethyl-benzyl)-1-(4-fluoro-phenyl)-3R-oxiranylmethyl-1,3,8-triaza-spiro[4.5]decan-4-one Compound #578

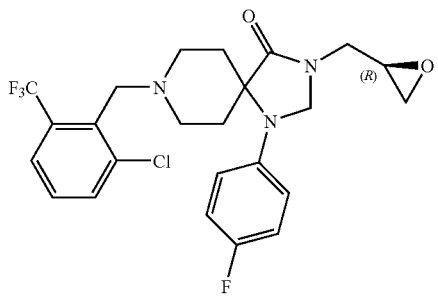

8-(2-Chloro-6-trifluoromethyl-benzyl)-1-(4-fluoro-phenyl)-1,3,8-triaza-spiro[4.5]decan-4-one (0.3 g, 0.68 mmol) was dissolved with NMP (20 mL) and stirred at room temperature. Sodium hydride (60% dispersion in oil, 0.066 g, 0.95 mmol) was added and the mixture was stirred an additional 30 minutes. S-(+)-epichlorohydrin (0.14 ml, 1.5 mmol) was added and the reaction was stirred overnight at room temperature. The reaction was then partitioned with water and ethyl acetate. The organic was dried with sodium sulfate and filtered. The solvent was evaporated to yield the title compound as an oil.

$^1$H NMR (300 MHz, CDCl$_3$) δ1.6 (m, 2H), 2.3 (m, 2H), 2.7 (m, 2H), 2.9 (bt, 2H), 3.1 (m, 1H), 3.8 (s, 2H), 4.0 (d, 1H), 4.6 (d, 1H), 4.8 (d, 2H), 6.8 (m, 2H), 6.95 (m, 2H), 7.2 (t, 1H), 7.6 (t, 2H).

EXAMPLE 31

3-[3-(Benzyl-butyl-amino)-2-(S)-hydroxy-propyl]-8-(2-chloro-6-trifluoromethyl-benzyl)-1-(4-fluoro-phenyl)-1,3,8-triaza-spiro[4.5]decan-4-one Compound #456)

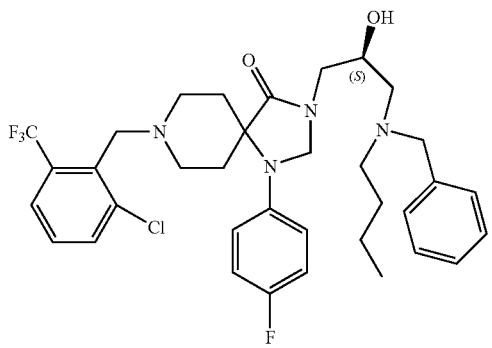

8-(2-Chloro-6-trifluoromethyl-benzyl)-1-(4-fluoro-phenyl)-3-(R)-oxiranylmethyl-1,3,8-triaza-spiro[4.5]decan-4-one (0.05 g, 0.1 mmol) was dissolved in absolute ethanol (0.5 mL), mixed with N-butylbenzylamine (0.05 mL, 0.4 mmol) and heated at reflux overnight. The solvent was evaporated and the resulting residue was purified by reverse column chromatography (AcCN/water) to yield the title compound as an oil.

MS (electrospray)=661.0 (MH+), 571.1, 331.4

EXAMPLE 32

{1-[{3-[8-Cyclooctylmethyl-1-(4-fluoro-phenyl)-4-oxo-1,3,8-triaza-spiro[4.5]dec-3-yl]-2-(S)-hydroxy-propyl}-(4-methyl-benzyl)-carbamoyl]-2-methyl-propyl}-carbamic Acid tert-butyl Ester Compound #79

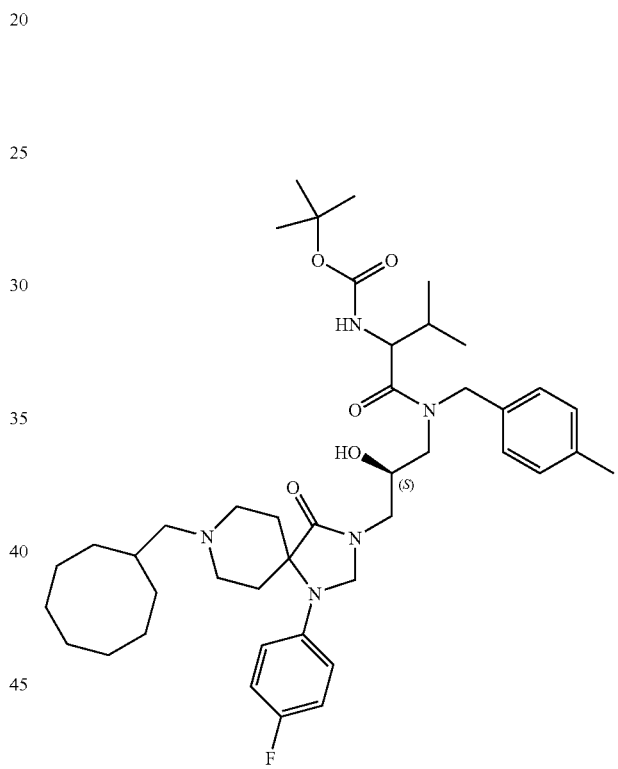

8-Cyclooctylmethyl-1-(4-fluoro-phenyl)-3-[2-hydroxy-3-(4-methyl-benzylamino)-propyl]-1,3,8-triaza-spiro[4.5]decan-4-one (0.05 g, 0.091 mmol) was dissolved in DMF (1 mL), mixed with BocD-Valine (0.02 g, 0.091 mmol), HBTU (0.035 g, 0.09 mmol) and diisopropylethylamine (0.1 mL) and stirred overnight at room temperature. The reaction mixture was partitioned with saturated NaHCO$_3$ and ethyl acetate. The organic layer dried with MgSO$_4$, filtered and the solvent evaporated in vacuo to yield the title compound as an oil.

MS (electrospray)=751.5 (MH+), 749.8, 373.6, 372.8, 203.1, 171.1

EXAMPLE 33

8-Cyclooctylmethyl-1-(4-fluoro-phenyl)-3-[2-(S)-hydroxy-3-(pyridin-4-ylamino)-propyl]-1,3,8-triaza-spiro[4.5]decan-4-one Compound #36

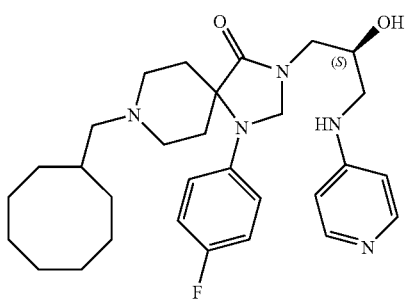

Cyclooctylmethyl-1-(4-fluoro-phenyl)-3-(R)-oxiranylmethyl-1,3,8-triaza-spiro[4.5]decan-4-one (0.5 g, 1.16 mmol) was dissolved in absolute ethanol (1 mL), mixed with 4-Aminopyridine (0.5 mL, 5.3 mmol) and heated at reflux overnight. The solvent was evaporated and the resulting residue was purified by reverse phase column chromatography (Acetonitrile/water) to yield the title compound as an oil.

$^1$H NMR (300 MHz, CD$_3$OD) δ1.35 (m, 2H), 1.5-1.7 (m, 13 H), 1.9 (s, 9H), 1.95 (m, 1H), 2.4 (m, 2H), 3.1 (d, 2H), 3.2 (m, 2H), 3.4 (m, 2H), 3.55 (d, 2H), 4.0 (m, 1H), 4.15 (m, 1H), 4.3 (m, 1H), 6.8 (d, 2H), 7.1(m, 4H), 8.1(d, 2H).

EXAMPLE 34

3-(3-Amino-2-(R)-hydroxy-propyl)-1-(4-fluoro-phenyl)-8-(8-methyl-naphthalen-1-ylmethyl)-1,3,8-triaza-spiro[4.5]decan-4-one Compound #438

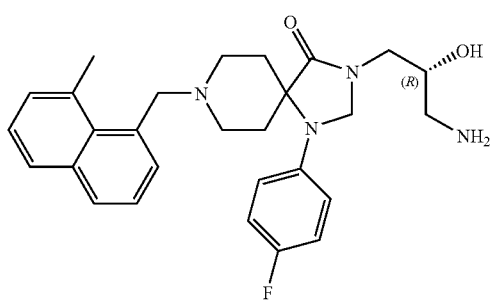

1-(4-Fluoro-phenyl)-8-(8-methyl-naphthalen-1-ylmethyl)-3-(S)-oxiranylmethyl-1,3,8-triaza-spiro[4.5]decan-4-one (0.06 g, 0.13 mmol) was dissolved in ethyl alcohol (2 mL) and methyl alcohol (0.4 mL). To the solution was then added concentrated ammonium hydroxide (1 mL) and the reaction mixture was stirred at 40° C. for two hours in a pressure flask. The solvent was then evaporated in vacuo to yield a crude oil. The crude oil was purified via flash chromatography (5.0% ammonia 2.0 M in methanol/dichloromethane) to yield the title compound as a foam.

$^1$H NMR (400 MHz, CDCl$_3$) δ7.77-7.75 (1H, m), 7.71-7.68 (1H, m), 7.37-7.30 (4H, m), 6.97-6.91 (2H, m), 6.87-6.83 (2H, m), 4.74 (2H, s), 4.0 (2H, s), 3.79-3.74 (1H, m), 3.57-3.52 (1H, m), 3.41-3.36 (1H, m), 3.11 (3H, s), 2.91-2.74 (4H, m), 2.66-2.61 (1H, m), 2.30-2.23 (2H, m), 1.66 (2H, d, J=13.7 Hz) MS (ES$^+$) m/z 477.1 (M+H)$^+$.

EXAMPLE 35

(R)-8-Acenaphthen-1-yl-3-(3-amino-2-hydroxy-(S)-propyl)-1-(4-fluoro-phenyl)-1,3,8-triaza-spiro[4.5]decan-4-one Compound #424

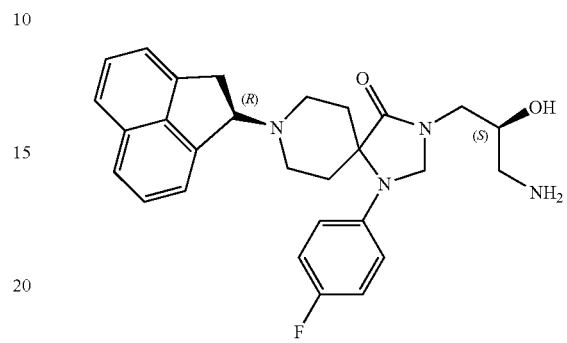

(R)-8-Acenaphthen-1-yl-1-(4-fluoro-phenyl)-3-(R)oxiranylmethyl-1,3,8-triaza-spiro[4.5]decan-4-one (0.514 g, 1.123 mmol) was dissolved in ethyl alcohol (16 mL). To the solution was then added concentrated ammonium hydroxide (8 mL) and the reaction mixture was stirred at 40° C. for two hours and a half in a pressure flask. The solvent was then evaporated in vacuo to yield the title compound as a foam.

$^1$H NMR (400 MHz, CDCl$_3$) δ7.68-7.65 (1H, m), 7.60 (1H, d, J=8.2 Hz), 7.52-7.49 (2H, m), 7.43 (1H, t), 7.26 (1H, d), 7.03-6.94 (4H, m), 4.97-4.94 (1H, m), 4.76-4.72 (2H, m), 3.74 (1H, br s), 3.55-3.48 (2H, m), 3.38-3.32 (2H, m), 3.16-3.03 (2H, m), 2.88-2.82 (2H, m), 2.59 (1H, br s), 2.44-2.41 (2H, m), 2.31-2.24 (1H, m), 1.76-1.62 (2H, m) MS (ES$^+$) m/z 475.2 (M+H)$^+$.

EXAMPLE 36

(R)8-Acenaphthen-1-yl-1-(4-fluoro-phenyl)-3-(2-hydroxy-3-methylamino-(S)-propyl)-1,3,8-triaza-spiro[4.5]decan-4-one Compound #437

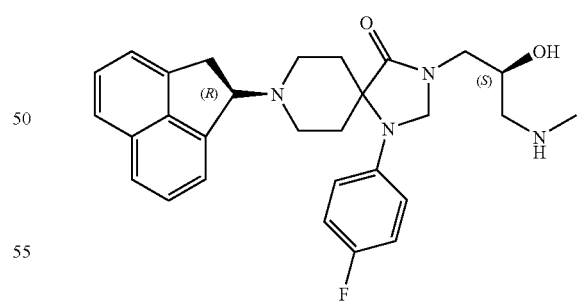

(R)-8-Acenaphthen-1-yl-1-(4-fluoro-phenyl)-3-(R)oxiranylmethyl-1,3,8-triaza-spiro[4.5]decan-4-one (0.045 g, 0.098 mmol) was dissolved in ethyl alcohol (2 mL). To the solution was then added a solution of 2.0M methylamine in THF (1 mL) and the reaction mixture was stirred at 40° C. for two hours and a half in a pressure flask. The solvent was then evaporated in vacuo to yield the title compound as a foam.

$^1$H NMR (400 MHz, CDCl$_3$) δ7.68-7.64 (1H, m), 7.59 (1H, d, J=8.2 Hz), 7.53-7.49 (2H, m), 7.45 (1H, t), 7.26-7.24 (1H, m), 7.03-6.94 (4H, m), 4.96-4.93 (1H, m), 4.78-4.73 (2H, m), 3.86-3.83 (1H, m), 3.55-3.47 (2H, m), 3.37-3.30 (2H, m), 3.16-2.99 (2H, m), 2.87-2.79 (2H, m), 2.70-2.66 (1H, m), 2.52-2.23 (6H, m), 1.75-1.61 (2H, m) MS (ES$^+$) m/z 489.3 (M+H)$^+$.

EXAMPLE 37

8-Acenaphthen-1-yl-1-(4-fluoro-phenyl)-3-[2-hydroxy-3-(pyridin-4-ylamino)-propyl]-1,3,8-triaza-spiro[4.5]decan-4-one Compound #327

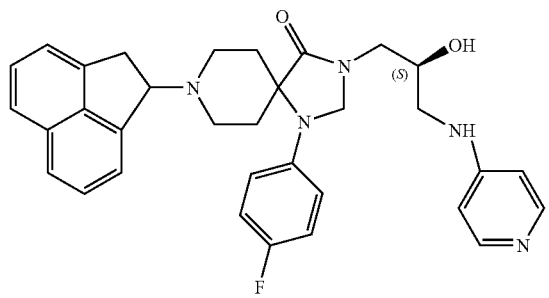

8-Acenaphthen-1-yl-1-(4-fluoro-phenyl)-3-(R)oxiranylmethyl-1,3,8-triaza-spiro[4.5]decan-4-one (0.100 g, 0.21 mmol) was dissolved in absolute ethyl alcohol (0.5 mL), mixed with 4-aminopyridine (0.2 mL) and heated at reflux overnight. The solvent was evaporated and the resulting residue was purified by reverse phase chromatography (MeCN/water) to yield the title compound as an oil.

EXAMPLE 38

(R)-8-Acenaphthen-1-yl-1-(4-fluoro-phenyl)-3-[2-hydroxy-3-(pyridin-2-ylamino)-(R)-propyl]-1,3,8-triaza-spiro[4.5]decan-4-one Compound #421

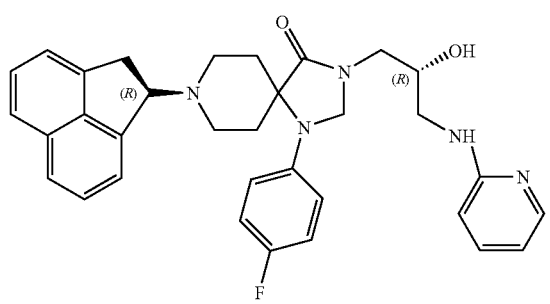

Sodium amide (0.0085 g, 0.21 mmol) and 2-aminopyridine (0.0165 g, 0.17 mmol) were suspended in toluene (0.25 mL) and benzene (0.15 mL). To the reaction mixture was then added (R)-8-Acenaphthen-1-yl-1-(4-fluoro-phenyl)-3-(S)oxiranylmethyl-1,3,8-triaza-spiro[4.5]decan-4-one (0.100 g, 0.21 mmol). The mixture was refluxed overnight under nitrogen, cooled down to room temperature and partitioned with brine and dichloromethane. The organic layer was washed with brine, dried with Na$_2$SO$_4$, filtered and the solvent evaporated in vacuo to yield a crude oil. The crude oil was purified via flash chromatography (3.25% ammonia 2.0 M in methanol/dichloromethane) to yield the title compound as an oil.

$^1$H NMR (300 MHz, CDCl$_3$) δ7.98-7.96 (1H, m), 7.69-7.65 (1H, m), 7.60 (1H, d, J=8.2 Hz), 7.53-7.51 (2H, m), 7.47-7.40 (1H, m), 7.28-7.26 (1H, m), 7.03-6.92 (4H, m), 6.66-6.47 (3H, m), 5.08-5.04 (1H, m), 4.98-4.94 (1H, m), 4.79-4.73 (2H, m), 4.0-3.94 (1H, m), 3.72-3.61 (2H, m), 3.57-3.49 (1H, m), 3.40-3.28 (2H, m), 3.14-3.02 (2H, m), 2.85-2.81 (1H, m), 2.44-2.26 (3H, m), 1.74-1.25 (2H, m) MS (ES$^+$) m/z 552.3 (M+H)$^+$.

EXAMPLE 39

1-(4-Fluoro-phenyl)-4-oxo-1,3,8-triaza-spiro[4.5]decane-8-carboxylic Acid tert-butyl Ester Compound #535

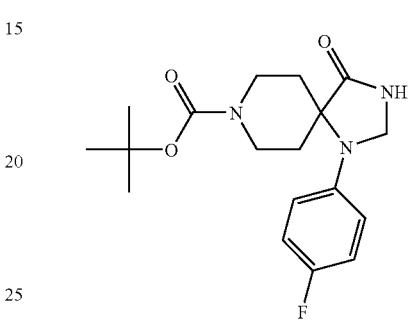

Di-tert-butyl dicarbonate (2.2 g, 10.0 mmol) and 1-(4-fluoro-phenyl)-1,3,8-triaza-spiro[4.5]decan-4-one (2.5 g, 10.0 mmol) were dissolved in dioxane (50 mL) and water (100 mL). Sodium hydrogeno carbonate (1.7 g, 20 mmol) was then added and the reaction mixture was stirred at room temperature under nitrogen atmosphere for 18 hours. The reaction mixture was concentrated in vacuo and partitioned with water and ethyl acetate. The organic layer was washed with brine, dried with Na$_2$SO$_4$, filtered and the solvent evaporated in vacuo to yield a solid. Recrystallization from hot ethyl acetate yielded the title compound as a white solid.

$^1$H NMR (300 MHz, CDCl$_3$) δ8.25 (1H, br s), 7.0-6.95 (2H, m), 6.82-6.77 (2H, m), 4.71 (2H, s), 4.08-3.8 (2H, m), 3.65-3.40 (2H, m), 2.35-2.15 (2H, m), 1.8-1.65 (2H, m), 1.48 (9H, s) MS (ES$^+$) m/z 372.1 (MNa)$^+$.

EXAMPLE 40

8-Ethyl-1-(4-fluoro-phenyl)-1,3,8-triaza-spiro[4.5]decan-4-one Compound #536

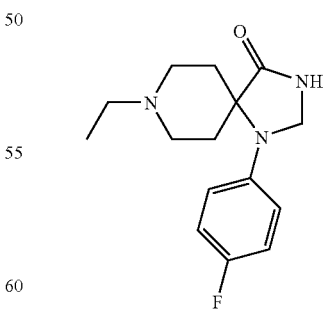

2-iodoethane (0.47 g, 3.0 mmol) and 1-(4-fluoro-phenyl)-1,3,8-triaza-spiro[4.5]decan-4-one (0.6 g, 2.4 mmol) were dissolved in acetonitrile (15 mL). Potassium carbonate (0.66 g, 4.8 mmol) was then added and the reaction mixture was stirred at room temperature under nitrogen atmosphere for 18 hours. The reaction mixture was partitioned with water and diethyl ether. The organic layer was washed with brine, dried with Na$_2$SO$_4$, filtered and the solvent evaporated in vacuo to yield a crude oil. The crude oil was purified via flash chromatography (30-50% ethyl acetate/hexane) to yield the title compound as an oil.

$^1$H NMR (300 MHz, CDCl$_3$) δ7.03-6.93 (4H, m), 6.46 (1H, br s), 4.67 (2H, s), 2.82-2.69 (4H, m), 2.48 (2H, q), 2.31-2.21 (2H, m), 1.81-1.76 (2H, m), 1.08 (3H, t) MS (ES$^+$) m/z 278.2 (M+H)$^+$.

EXAMPLE 41

8-(4-Chloro-benzyl)-1-(4-fluoro-phenyl)-1,3,8-triaza-spiro[4.5]decan-4-one Compound #508

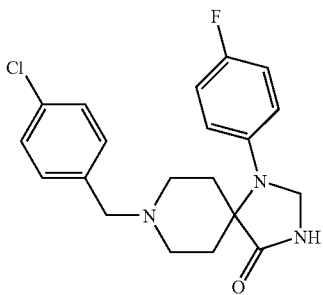

1-(4-Fluoro-phenyl)-1,3,8-triaza-spiro[4.5]decan-4-one (3.0 g, 12.03 mmol) and 4-chloro-benzaldehyde (2.03 g, 14.44 mmol) were dissolved in dry tetrahydrofuran (120 mL). To the reaction mixture was then added at 0° C. sodium triacetoxyborohydride (3.82 g, 18.05 mmol) under nitrogen atmosphere and the reaction mixture was stirred at room temperature for 18 hours. The reaction mixture was then partitioned with 1N NaOH and ethyl acetate. The organic layer was washed with brine, dried with Na$_2$SO$_4$, filtered and the solvent evaporated in vacuo to yield a crude oil. The crude oil was purified via flash chromatography (3.5% methanol/dichloromethane) to yield the title compound as a white foam.

$^1$H NMR (300 MHz, CDCl$_3$) δ7.30-7.15 (4H, m), 7.01-6.87 (4H, m), 4.63 (2H, s), 3.47 (2H, s), 2.78-2.65 (4H, m), 2.31-2.0 (2H, m), 1.73-1.68 (2H, m) MS (ES$^+$) m/z 374.1 (M+H)$^+$.

EXAMPLE 42

8-(4-Chloro-benzyl)-1-(4-fluoro-phenyl)-3-(R)-oxiranylmethyl-1,3,8-triaza-spiro[4.5]decan-4-one Compound #513

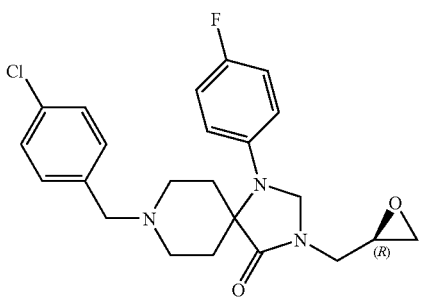

8-(4-Chloro-benzyl)-1-(4-fluoro-phenyl)-1,3,8-triaza-spiro[4.5]decan-4-one (0.220 g, 0.588 mmol) was dissolved in N,N-dimethylformamide (2.2 mL). To the reaction mixture was then added at 0° C. sodium hydride (60% in mineral oil, 31 mg, 0.765 mmol) under nitrogen atmosphere and the reaction mixture was stirred at 0° C. for 40 minutes. To the reaction mixture was then added (S)-epichlorhydrin (0.14 mL, 1.765 mmol) at 0° C. The reaction mixture was stirred at room temperature under nitrogen atmosphere for 18 hours and partitioned with water and ethyl acetate. The organic layer was washed with brine, dried with Na$_2$SO$_4$, filtered and the solvent evaporated in vacuo to yield a crude oil. The crude oil was purified via flash chromatography (2% methanol/dichloromethane) to yield the title compound as a foam.

$^1$H NMR (300 MHz, CDCl$_3$) δ7.32-7.26 (4H, m), 7.04-6.91 (4H, m), 4.77 (H, d, J=4.9Hz), 4.66 (1H, d, J=4.9Hz), 4.06-3.99 (1H, m), 3.52 (3H, s), 3.20-3.14 (2H, m), 2.85-2.68 (5H, m), 2.60-2.58 (1H, m), 2.33-2.23 (2H, m), 1.73-1.60 (2H, m) MS (ES$^+$) m/z 430.2 (M+H)$^+$.

EXAMPLE 43

1-(4-Fluoro-phenyl)-3-(S)-[2-hydroxy-3-(2-morpholin-4-1-ethylamino)-propyl]-8-(5-phenyl-thien-2-yl-methyl)-1,3,8-triaza-spiro[4.5]decan-4-one Compound #293

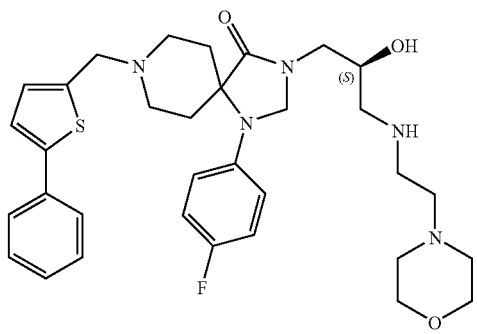

(R)-1-(4-Fluoro-phenyl)-3-oxiranylmethyl-8-(5-phenyl-thien-2-yl-methyl)-1,3,8-triaza-spiro[4.5]decan-4-one (0.02 g, 0.041 mmol) was dissolved in absolute ethanol (1 mL), mixed with 2-morpholin-4-yl-ethylamine (16.3 mg, 0.125 mmol) and heated under stirring at 70° C. overnight. The solvent was evaporated and the resulting residue was purified via flash chromatography (9% methanol/dichloromethane) to yield the title compound as an oil.

$^1$H NMR (300 MHz, CDCl$_3$) δ7.59-7.56 (2H, m), 7.38-7.33 (2H, m), 7.28-7.25 (2H, m), 7.14 (1H, d, J=3.6 Hz), 7.04-6.91 (3H, m), 6.87 (1H, d, J=3.5 Hz), 4.80-4.76 (2H, m), 3.86-3.69 (6H, m), 3.61-3.55 (1H, m), 3.36-3.29 (1H, m), 2.85-2.71 (7H, m), 2.58-2.32 (1OH, m), 1.72 (2H, d, J=13.7 Hz) MS (ES$^+$) m/z 608.3 (M+H)$^+$.

EXAMPLE 44

1-(4-Fluoro-phenyl)-8-quinoline-8-ylmethyl-1,3,8-triaza-spiro[4.5]decan-4-one Compound #522

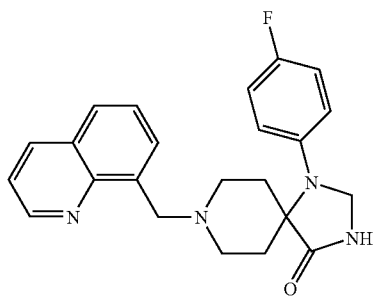

1-(4-Fluoro-phenyl)-1,3,8-triaza-spiro[4.5]decan-4-one (0.15 g, 0.601 mmol) and quinoline-8-carbaldehyde (0.113 g, 0.722 mmol) were dissolved in dry tetrahydrofuran (12 mL). To the reaction mixture was then added at 0° C. sodium triacetoxyborohydride (0.192 g, 0.902 mmol) under nitrogen atmosphere and the reaction mixture was stirred at room temperature for 18 hours. The reaction mixture was then partitioned with 1N NaOH and ethyl acetate. The organic layer was washed with brine, dried with $Na_2SO_4$, filtered and the solvent evaporated in vacuo to yield a crude oil. The crude oil was purified via flash chromatography (5% methanol/dichloromethane) to yield the title compound as a white solid.
$^1$H NMR (300 MHz, $CDCl_3$) δ 8.93-8.91 (1H, m), 8.14 (1H, d, J=8.3 Hz), 7.89 (1H, br s), 7.71 (1H, m), 7.55 (1H, t, J=7.7 Hz), 7.41-7.38 (1H, m), 7.05-7.01 (4H, m), 6.79 (1H, br s), 4.69 (2H, s), 4.35 (2H, s), 3.01-2.90 (4H, m), 2.41 (2H, br s), 1.80 (2H, d, J=13.8 Hz) MS ($ES^+$) m/z 391.0 (M+H)$^+$.

EXAMPLE 45

(R)-8-Acenaphthen-1-yl-3-(R)-(3-ethoxy-2-hydroxy-propyl)-1-(4-fluoro-phenyl)-1,3,8-triaza-spiro[4.5]decan-4-one Compound #571

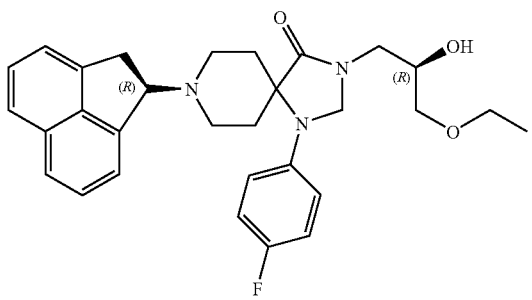

(R)-8-Acenaphthen-1-yl-1-(4-fluoro-phenyl)-3-(R)oxiranylmethyl-1,3,8-triaza-spiro[4.5]decan-4-one (0.084 g, 0.183 mmol) was dissolved in ethanol (4 mL). The reaction mixture was heated at 80° C. for 18 hours, then cooled to room temperature and the solvent evaporated in vacuo to yield an oil. The oil was partitioned with water and ethyl acetate. The organic layer was dried with $Na_2SO_4$, filtered and the solvent evaporated in vacuo to yield a crude oil. The crude oil was purified via flash chromatography (4% [methanol in ammonia 2.0M]/dichloromethane) to yield the title compound as an oil.

$^1$H NMR (300 MHz, $CDCl_3$) δ 7.69-7.66 (1H, m), 7.61 (1H, d, J=8.2 Hz), 7.54-7.50 (2H, m), 7.44 (1H, t), 7.27-7.25 (1H, m), 7.05-6.90 (4H, m), 4.98-4.90 (1H, m), 4.77-4.71 (2H, m), 4.03-3.98 (1H, m), 3.57-3.31 (8H, m), 3.16-3.01 (3H, m), 2.88-2.85 (1H, m), 2.43 (2H, br s), 2.32-2.24 (1H, m), 1.77-1.62 (2H, m), 1.18 (3H, t); MS ($ES^+$) m/z 504.3 (M+H)$^+$.

EXAMPLE 46

3-[3-(Ethyl-methyl-amino)-2-hydroxy-(S)-propyl]-1-(4-fluoro-phenyl)-8-(8-methyl-naphthalen-1-ylmethyl)-1,3,8-triaza-spiro[4.5]decan-4-one Compound #440

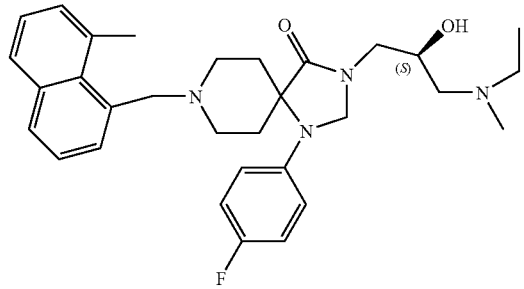

1-(4-Fluoro-phenyl)-8-(8-methyl-naphthalen-1-ylmethyl)-3-(R)-oxiranylmethyl-1,3,8-triaza-spiro[4.5]decan-4-one (0.02 g, 0.043 mmol) was dissolved in ethyl alcohol (2 mL). To the solution was then added N-methylethylamine (0.2 mL) and the reaction mixture was stirred at 40° C. for 3 hrs in a pressure flask. The solvent was then evaporated in vacuo to yield a crude oil. The crude oil was purified via flash chromatography (5.0% ammonia 2.0 M in methanol/dichloromethane) to yield the title compound as an oil.
$^1$H NMR (400 MHz, $CDCl_3$) δ 7.77-7.75 (1H, m), 7.71-7.68 (1H, m), 7.38-7.30 (4H, m), 6.96-6.91 (2H, m), 6.88-6.84 (2H, m), 4.82-4.75 (2H, m), 4.08-3.98 (3H, m), 3.61-3.57 (1H, m), 3.34-3.29 (1H, m), 3.11 (3H, s), 2.83-2.54 (8H, m), 2.44 (3H, s), 2.32-2.23 (2H, m), 1.68-1.63 (2H, m); 1.15 (3H, t, J=7.2 Hz) MS ($ES^+$) m/z 519.3 (M+H)$^+$.

EXAMPLE 47

(R)-Acenaphthen-1-yl-3-(3-dimethylamino-2-hydroxy-(R)-propyl)-1-(4-fluoro-phenyl)-1,3,8-triaza-spiro[4.5]decan-4-one Compound #423

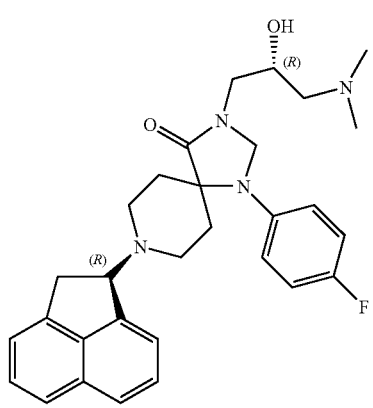

(R)-8-Acenaphthen-1-yl-1-(4-fluoro-phenyl)-3-(S) oxiranylmethyl-1,3,8-triaza-spiro[4.5]decan-4-one (0.057 g, 0.124 mmol) was dissolved in ethyl alcohol (2 mL). To the solution was then added a solution of 2.0M dimethylamine in THF (1 mL) and the reaction mixture was stirred at 40° C. for 2.5 hrs in a pressure flask. The solvent was then evaporated in vacuo to yield a crude oil. The crude oil was purified via flash chromatography (6.0% ammonia 2.0 M in methanol/dichloromethane) to yield the title compound as a foam.

$^1$H NMR (400 MHz, CDCl$_3$) δ 7.68-7.65 (1H, m), 7.59 (1H, d, J=8.2 Hz), 7.52-7.49 (2H, m), 7.44 (1H, t), 7.26-7.25 (1H, m), 7.03-6.94 (4H, m), 4.97-4.94 (1H, m), 4.83-4.80 (2H, m), 4.77-4.75 (1H, m), 3.87-3.81 (1H, m), 3.60-3.03 (7H, m), 2.85-2.82 (1H, m), 2.49-2.42 (2H, m), 2.32-2.24 (8H, m), 1.75-1.62 (2H, m) MS (ES$^+$) m/z 503.3 (M+H)$^+$.

EXAMPLE 48

1-(4-Fluoro-phenyl)-8-(8-methyl-naphthalen-1-ylmethyl)-3-(S)-oxiranylmethyl-1,3,8-triaza-spiro[4.5]decan-4-one Compound #550

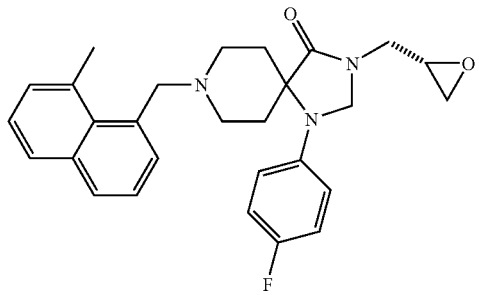

1-(4-Fluoro-phenyl)-8-(8-methyl-naphthalen-1-ylmethyl)-1,3,8-triaza-spiro[4.5]-decan-4-one (2.0 g, 4.95 mmol) was dissolved in N,N-dimethylformamide (25.0 mL). To the reaction mixture was then added at 0° C. sodium hydride (60% in mineral oil, 238 mg, 5.94 mmol) under nitrogen atmosphere and the reaction mixture was stirred at 0° C. for one hour. To the reaction mixture was then added at 0° C. (2R)-(−)-glycidyl-3-nitrobenzenesulfonate (1.54 g, 5.94 mmol). The reaction mixture was stirred at 0° C. for one hour, then at room temperature under nitrogen atmosphere for 18 hours and partitioned with water and ethyl acetate. The organic layer was washed with brine, dried with Na$_2$SO$_4$, filtered and the solvent evaporated in vacuo to yield a crude oil. The crude oil was purified via flash chromatography (2.5% methanol/dichloromethane) to yield the title compound as a foam.

$^1$H NMR (300 MHz, CDCl$_3$) δ 7.78-7.76 (1H, m), 7.73-7.69 (1H, m), 7.38-7.31 (4H, m), 6.99-6.91 (2H, m), 6.89-6.84 (2H, m), 4.76 (1H, d, J=4.8 Hz), 4.65 (1H, d, J=4.8 Hz), 4.01 (2H, s), 3.20-3.11 (6H, m), 2.86-2.77 (5H, m), 2.61-2.59 (1H, m), 2.31-2.21 (2H, m), 1.69-1.63 (2H, m) MS (ES$^+$) m/z 460.2 (M+H)$^+$.

EXAMPLE 49

3,3,3-Trifluoro-N-{3-[1-(4-fluoro-phenyl)-8-(8-methyl-naphthalen-1-ylmethyl)-4-oxo-1,3,8-triaza-spiro[4.5]dec-3-yl]-2-(R)-hydroxy-propyl}-2-methoxy-2-phenyl-(R)-propionamide Compound #615

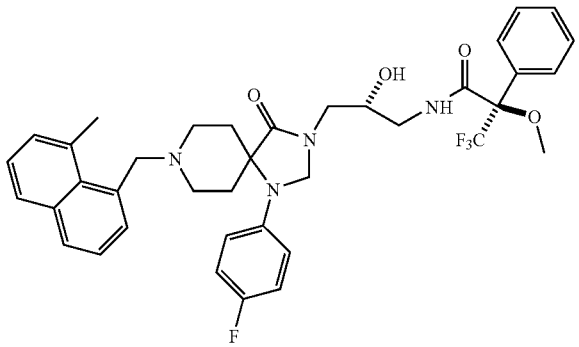

3-(3-Amino-2-(R)-hydroxy-propyl)-1-(4-fluoro-phenyl)-8-(8-methyl-naphthalen-1-ylmethyl)-1,3,8-triaza-spiro[4.5]decan-4-one (0.0118 g, 0.024 mmol) was dissolved in dichloromethane (1.0 mL) and pyridine (0.15 mL). To the reaction mixture was then added at 0° C. (S)-(+)-α-methoxy-α-(trifluoro methyl)phenyl acetyl chloride (8.7 mg, 0.034 mmol) under nitrogen atmosphere. The reaction mixture was stirred at 0° C. for one hour, then the solvent was evaporated in vacuo to yield a crude foam. The crude foam was dissolved in ethyl acetate and successively washed twice with aqueous 0.5N HCl, twice with aqueous NaHCO$_3$, brine, dried with Na$_2$SO$_4$, filtered and the solvent evaporated in vacuo to yield a white foam.

$^1$H NMR (300 MHz, CDCl$_3$) δ 7.78-7.75 (1H, m), 7.71-7.68 (1H, m), 7.64-7.61 (1H, m), 7.56-7.54 (2H, m), 7.42-7.40 (3H, m), 7.39-7.30 (3H, m), 6.97-6.93 (2H, m), 6.87-6.83 (2H, m), 4.70 (1H, d, J=4.9 Hz), 4.64 (1H, d, J=4.9 Hz), 3.99 (3H, s), 4.01 (1H, s), 3.60-3.54 (1H, m), 3.45-3.32 (5H, m), 3.1 (3H, s), 2.82-2.74 (4H, m), 2.24-2.20 (2H, m), 1.70-1.63 (4H, m) MS (ES$^+$) m/z 693.0 (M+H)$^+$.

EXAMPLE 50

3-(3-Dimethylamino-2-(R)-hydroxy-propyl)-1-(4-fluoro-phenyl)-8-(8-methyl-naphthalen-1-ylmethyl)-1,3,8-triaza-spiro[4.5]decan-4-one Compound #441

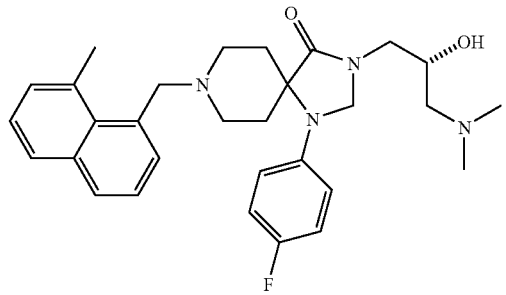

1-(4-Fluoro-phenyl)-8-(8-methyl-naphthalen-1-ylmethyl)-3-(S)-oxiranylmethyl-1,3,8-triaza-spiro[4.5]decan-4- one (0.035 g, 0.07mmol) was dissolved in ethyl alcohol (2 mL). To the solution was then added a 2.0M solution of dimethylamine in methanol (1.0 mL, 2.0 mmol) and the reaction mixture was stirred at 45° C. for 3 hrs in a pressure flask. The solvent was then evaporated in vacuo to yield a crude oil. The crude oil was purified via flash chromatography (5.0% ammonia 2.0 M in methanol/dichloromethane) to yield the title compound as a foam.

$^1$H NMR (400 MHz, CDCl$_3$) δ7.78-7.75 (1H, m), 7.71-7.68 (1H, m), 7.38-7.31 (4H, m), 6.96-6.91 (2H, m), 6.88-6.84 (2H, m), 4.80 (1H, d, J=5.1 Hz), 4.77 (1H, d, J=5.1 Hz), 4.01 (2H, m), 3.95-3.87 (1H, m), 3.62-3.58 (1H, m), 3.31-3.26 (1H, m), 3.11 (3H, s), 2.86-2.78 (6H, m), 2.36-2.22 (9H, m), 1.68-1.63 (2H, m). MS (ES$^+$) m/z 505.4 (M+H)$^+$.

EXAMPLE 51

1-(4-Fluoro-phenyl)-3-(2-(R)-hydroxy-3-methylamino-propyl)-8-(8-methyl-naphthalen-1-ylmethyl)-1,3,8-triaza-spiro[4.5]decan-4-one Compound #660

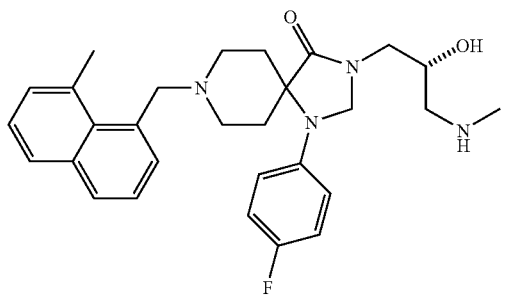

1-(4-Fluoro-phenyl)-8-(8-methyl-naphthalen-1-ylmethyl)-3-(S)-oxiranylmethyl-1,3,8-triaza-spiro[4.5]decan-4-one (0.05 g, 0.109 mmol) was dissolved in methanol (3 mL). To the solution was then added a 2.0M solution of methylamine in methanol (1.0 mL, 2.0 mmol) and the reaction mixture was stirred at 40° C. for 3 hrs in a pressure flask. The solvent was then evaporated in vacuo to yield a crude oil. The crude oil was purified via flash chromatography (5.0% ammonia 2.0 M in methanol/dichloromethane) to yield the title compound as a foam.

$^1$H NMR (400 MHz, CDCl$_3$) δ7.78-7.75 (1H, m), 7.71-7.68 (1H, m), 7.38-7.31 (4H, m), 6.96-6.91 (2H, m), 6.88-6.84 (2H, m), 4.80 (1H, d, J=5.1 Hz), 4.77 (1H, d, J=5.1 Hz), 4.00 (2H, m), 3.97-3.86 (1H, m), 3.58-3.53 (1H, m), 3.43-3.35 (1H, m), 3.12 (3H, s), 2.84-2.69 (7H, m), 2.56-2.49 (1H, m), 2.44 (3H, s), 2.31-2.24 (2H, m), 1.67-1.64 (2H, m) MS (ES$^+$) m/z 491.1 (M+H)$^+$.

EXAMPLE 52

1-(4-Fluoro-phenyl)-3-[2-(R)-hydroxy-3-(3-methylamino-propylamino)-propyl]-8-(8-methyl-naphthalen-1-ylmethyl)-1,3,8-triaza-spiro[4.5]decan-4-one Compound #656

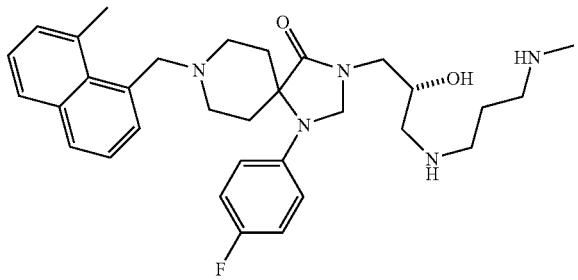

1-(4-Fluoro-phenyl)-8-(8-methyl-naphthalen-1-ylmethyl)-3-(S)-oxiranylmethyl-1,3,8-triaza-spiro[4.5]decan-4-one (0.035 g, 0.07 mmol) was dissolved in methanol (4 mL). To the solution was then added N-methyl-1-3-propanediamine (0.027 g, 0.35 mmol) and the reaction mixture was stirred at 45° C. for 12 hrs in a pressure flask. The solvent was then evaporated in vacuo to yield a crude oil. The crude oil was purified via flash chromatography (5.0% ammonia 2.0 M in methanol/dichloromethane) to yield the title compound as a foam.

$^1$H NMR (400 MHz, CDCl$_3$) δ7.78-7.75 (1H, m), 7.71-7.68 (1H, m), 7.38-7.30 (4H, m), 6.95-6.91 (2H, m), 6.87-6.84 (2H, m), 4.80 (1H, d, J=5.05 Hz), 4.77 (1H, d, J=5.05 Hz), 4.00 (2H, s), 3.96-3.89 (1H, m), 3.58-3.54 (1H, m), 3.32-3.30 (1H, m), 3.12 (3H, s), 2.85-2.77 (6H, m), 2.65-2.58 (1H, m), 2.49-2.12 (10H, m), 1.68-1.63 (4H, m) MS (ES$^+$) m/z 548.3 (M+H)$^+$.

EXAMPLE 53

3-[3-(3-Dimethylamino-propylamino)-2-(R)-hydroxy-propyl]-1-(4-fluoro-phenyl)-8-(8-methyl-naphthalen-1-ylmethyl)-1,3,8-triaza-spiro[4.5]decan-4-one Compound #666

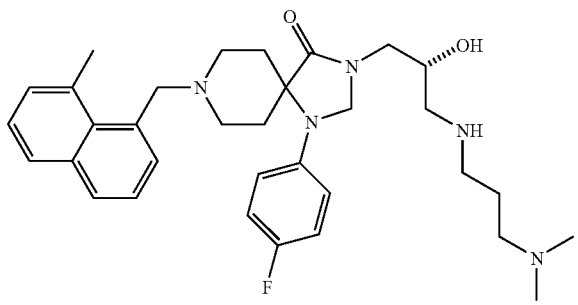

1-(4-Fluoro-phenyl)-8-(8-methyl-naphthalen-1-ylmethyl)-3-(S)-oxiranylmethyl-1,3,8-triaza-spiro[4.5]decan-4-one (0.037 g, 0.07 mmol) was dissolved in ethanol (2 mL). To the solution was then added dimethylaminopropylamine (0.03 g, 0.3 mmol) and the reaction mixture was stirred at 45° C. for 12 hrs in a pressure flask. The solvent was then evaporated in vacuo to yield a crude oil. The crude oil was purified via flash chromatography (5.0% ammonia 2.0 M in methanol/dichloromethane) to yield the title compound as a foam.

¹H NMR (300 MHz, CDCl₃) δ7.78-7.75 (1H, m), 7.71-7.68 (1H, m), 7.38-7.30 (4H, m), 6.97-6.90 (2H, m), 6.87-6.82 (2H, m), 4.78-4.73 (2H, m), 4.00 (2H, s), 3.96-3.82 (1H, m), 3.59-3.53 (1H, m), 3.37-3.30 (1H, m), 3.12 (3H, s), 2.86-2.50 (9H, m), 2.35-2.11 (11H, m), 1.68-1.59 (4H, m) MS (ES⁺) m/z 562.2 (M+H)⁺.

EXAMPLE 54

1-(4-Fluoro-phenyl)-3-[2-(R)-hydroxy-3-(3-hydroxy-propylamino)-propyl]-8-(8-methyl-naphthalen-1-ylmethyl)-1,3,8-triaza-spiro[4.5]decan-4-one Compound #651

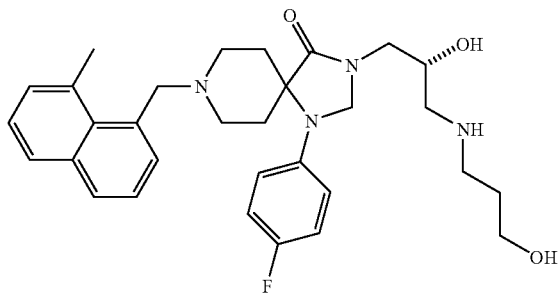

1-(4-Fluoro-phenyl)-8-(8-methyl-naphthalen-1-ylmethyl)-3-(S)-oxiranylmethyl-1,3,8-triaza-spiro[4.5]decan-4-one (1.16 g, 2.5 mmol) was dissolved in methanol (20 mL). To the solution was then added 3-amino-1-propanol (0.375 g, 5.0 mmol,) and the reaction mixture was stirred at 40° C. for 12 hrs in a pressure flask. The solvent was then evaporated in vacuo to yield a crude oil. The crude oil was purified via flash chromatography (5.0% ammonia 2.0 M in methanol/dichloromethane) to yield the title compound as a foam.

¹H NMR (300 MHz, CDCl₃) δ7.78-7.75 (1H, m), 7.71-7.68 (1H, m), 7.38-7.30 (4H, m), 6.97-6.90 (2H, m), 6.87-6.82 (2H, m), 4.74-4.70 (2H, m), 3.99 (2H, s), 3.96-3.90 (1H, m), 3.81-3.77 (2H, m), 3.47-3.42 (3H, m), 3.11 (3H, s), 2.91-2.56 (10H, m), 2.30-2.20 (2H, m), 1.76-1.63 (4H, m) MS (ES⁺) m/z 535.2 (M+H)⁺.

EXAMPLE 55

11-(4-Fluoro-phenyl)-8-(8-methyl-1,2,3,4-tetrahydro-naphthalen-1-ylmethyl)-1,3,8-triaza-spiro[4.5]decan-4-one Compound #728

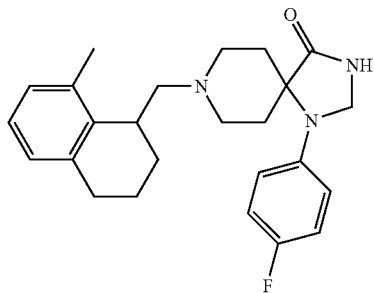

Step A:

8-Methyl-1,2,3,4-tetrahydro-naphthalene-1-carboxylic acid (J. Org. Chem. 1982, 47, 2590-2593) (0.066 g, 0.34 mmol) was dissolved in tetrahydrofuran (3 mL). To the solution was then added at 0° C. a 1.0M solution of borane-methyl sulfide complex in dichloromethane (0.7 mL, 0.69 mmol). The reaction mixture was stirred at room temperature for 15 minutes, refluxed for 2 hrs, then cooled down to 0° C. and quenched with methanol. The solvent was then evaporated in vacuo to yield a crude oil. The crude oil was partitioned with water and diethyl ether. The organic layer was dried with Na₂SO₄, filtered and the solvent evaporated in vacuo to yield crude (8-methyl-1,2,3,4-tetrahydro-naphthalen-1-yl)-methanol as an oil which was used directly to the next step.

¹H NMR (400 MHz, CDCl₃) δ 7.05-6.92 (3H, m), 3.70-3.59 (2H, m), 3.15-3.10 (1H, m), 2.83-2.71 (2H, m), 2.34 (3H, s), 2.21-2.16 (1H, m), 1.95-1.83 (1H, m), 1.79.1.67 (2H, m), 1.52 (1H, br s)

Step B:

(8-Methyl-1,2,3,4-tetrahydro-naphthalen-1-yl)-methanol (0.03 g, 0.17 mmol) was dissolved in dichloromethane (0.5 mL). To the solution was then added 1,1,1-triacetoxy-1,1-dihydro-1,2-benziodoxol-3(1H)-one, also known as Dess-Martin periodinane (0.087 g, 0.20 mmol). The reaction mixture was stirred for 2 hrs then partitioned with an aqueous saturated solution of thiosulfate and dichloromethane. The organic layer was washed with an aqueous saturated solution of thiosulfate, an aqueous saturated solution of sodium bicarbonate, brine, dried with Na₂SO₄, filtered and the solvent evaporated in vacuo to yield 8-methyl-1,2,3,4-tetrahydro-naphthalene-1-carbaldehyde as a solid.

¹H NMR (400 MHz, CDCl₃) δ 9.66 (1H, d, J=1.8 Hz), 7.13-6.99 (3H, m), 3.74-3.72 (1H, m), 2.81-2.77 (2H, m), 2.37-2.31 (1H, m), 2.2 (3H, s), 1.95-1.61 (3H, m).

Step C:

1-(4-Fluoro-phenyl)-1,3,8-triaza-spiro[4.5]decan-4-one (0.035 g, 0.14 mmol) and 8-methyl-1,2,3,4-tetrahydro-naphthalene-1-carbaldehyde (0.03 g, 0.17 mmol) were dissolved in dry tetrahydrofuran (2 mL) and dry dichloromethane (0.5 mL). To the reaction mixture was then added at 0° C. sodium triacetoxyborohydride (0.045 g, 0.21 mmol) under nitrogen atmosphere and the reaction mixture was stirred at room temperature for 18 hours. The reaction mixture was then partitioned with 1N NaOH and ethyl acetate. The organic layer was washed with brine, dried with Na₂SO₄, filtered and the solvent evaporated in vacuo to yield a crude oil. The crude oil was purified via flash chromatography (5% methanol/dichloromethane) to yield the title compound as an oil.

¹H NMR (400 MHz, CDCl₃) δ 7.06-6.90 (7H, m), 6.56 (1H, br s), 4.68 (2H, s), 3.12-2.33 (12H, m), 1.91-1.53 (6H, m), 1.25-1.21 (2H, m) MS (ES⁺) m/z 408.1 (M+H)⁺.

EXAMPLE 56

(R)-8-Acenaphthen-1-yl-1-(4-fluoro-phenyl)-3-[2-hydroxy-3-(3-hydroxymethyl-piperidin-1-yl)-(R)-propyl]-1,3,8-triaza-spiro[4.5]decan-4-one Compound #695

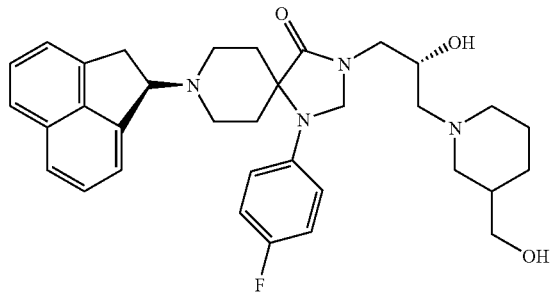

(R)-8-Acenaphthen-1-yl-1-(4-fluoro-phenyl)-3-(S)oxiranylmethyl-1,3,8-triaza-spiro[4.5]decan-4-one (0.02 g, 0.04 mmol) was dissolved in ethyl alcohol (1.5 mL). To the solution was then added 3-piperidinemethanol (0.01 g, 0.08 mmol) and the reaction mixture was stirred at 60° C. for 12 hrs in a pressure flask. The solvent was evaporated in vacuo to yield a crude oil. The crude oil was purified via flash chromatography (6.0% ammonia 2.0 M in methanol/dichloromethane) to yield the title compound as a foam.

$^1$H NMR (400 MHz, CDCl$_3$) δ 7.69-7.49 (4H, m), 7.46-7.41 (1H, m), 7.26-7.25 (1H, m), 7.04-6.95 (4H, m), 4.97-4.94 (1H, m), 4.81-4.74 (2H, m), 3.97-3.90 (1H, m), 3.58-1.6 (27H, m) MS (ES$^+$) m/z 573.3 (M+H)$^+$.

EXAMPLE 57

N-{3-[(R)-8-Acenaphthen-1-yl-1-(4-fluoro-phenyl)-4-oxo-1,3,8-triaza-spiro[4.5]dec-3-yl]-2-hydroxy-(R)-propyl}-3,3,3-trifluoro-2-methoxy-2-phenyl-(R)-propionamide Compound #645

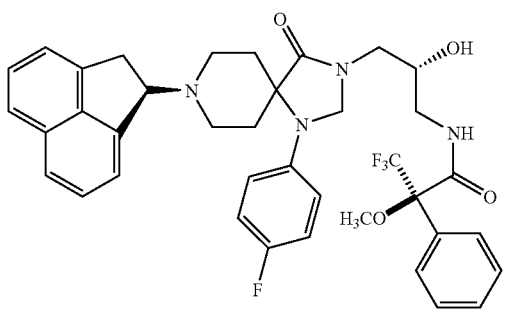

(R)-8-Acenaphthen-1-yl-3-(3-amino-2-hydroxy-(R)-propyl)-1-(4-fluoro-phenyl)-1,3,8-triaza-spiro[4.5]decan-4-one (0.02 g, 0.042 mmol) was dissolved in dichloromethane (3 mL) and pyridine (0.3 mL). To the reaction mixture was then added at 0° C. (S)-(+)-(α-methoxy-(α-(trifluoromethyl)phenyl acetyl chloride (13.8 mg, 0.055 mmol) under nitrogen atmosphere. The reaction mixture was stirred at 0° C. for one hour, then and the solvent evaporated in vacuo to yield a crude foam. The crude foam was dissolved in ethyl acetate and successively washed twice with aqueous 0.5N HCl, twice with aqueous NaHCO$_3$, brine, dried with Na$_2$SO$_4$, filtered and the solvent evaporated in vacuo to yield the title compounds as a white foam.

$^1$H NMR (400 MHz, CDCl$_3$) δ 7.68-7.59 (3H, m), 7.55-7.39 (8H, m), 7.03-6.99 (2H, m), 6.98-6.93 (2H, m), 4.95-4.92 (1H, m), 4.70 (1H, d, J=4.8 Hz), 4.65 (1H, d, J=4.9 Hz), 3.99-3.97 (1H, s), 3.76 (1H, s), 3.57-3.29 (5H, m), 3.08-3.00 (2H, m), 2.79-2.76 (1H, m), 2.46-2.37 (1H, m), 2.37-2.29 (1H, m), 2.24-2.16 (1H, m), 2.00 (3H, s), 1.74-1.60 (4H, m) MS (ES$^+$) m/z 691.3 (M+H)$^+$.

EXAMPLE 58

1-(4-Fluoro-phenyl)-8-(8-hydroxymethyl-naphthalen-1-ylmethyl)-1,3,8-triaza-spiro[4.5]decan-4-one Compound #734

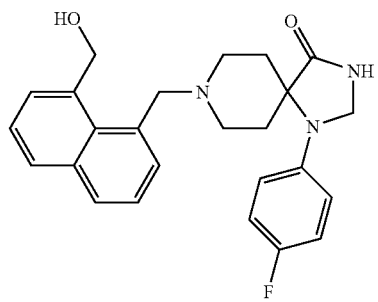

Step A:

[8-(tert-Butyl-dimethyl-silanyloxymethyl)-naphthalen-1-yl]-methanol (*Aust. J. Chem.* 1996, 49, 793-800) (0.2 g, 0.66 mmol) was dissolved in dichloromethane (8 mL). To the solution was then added 1,1,1-triacetoxy-1,1-dihydro-1,2-benziodoxol-3(1H)-one, also known as Dess-Martin periodinane (0.56 g, 1.32 mmol). The reaction mixture was stirred for 1 hr then partitioned with an aqueous saturated solution of thiosulfate and dichloromethane. The organic layer was washed with an aqueous saturated solution of thiosulfate, an aqueous saturated solution of sodium bicarbonate, brine, dried with Na$_2$SO$_4$, filtered and the solvent evaporated in vacuo to yield a crude oil. The crude oil was purified via flash chromatography (6.0% ammonia 2.0 M in methanol/dichloromethane) to yield 8-(tert-butyl-dimethyl-silanyloxymethyl)-naphthalene-1-carbaldehyde as a clear oil.

$^1$H NMR (400 MHz, CDCl$_3$) δ 10.73 (1H, s), 8.05-7.98 (2H, m), 7.86-7.84 (1H, m), 7.65-7.63 (1H, m), 7.55-7.48 (2H, m), 5.07 (2H, s), 0.83 (9H, s), 0.01 (6H, s)

Step B:

1-(4-Fluoro-phenyl)-1,3,8-triaza-spiro[4.5]decan-4-one (0.056 g, 0.22 mmol) and 8-(tert-butyl-dimethyl-silanyloxymethyl)-naphthalene-1-carbaldehyde (0.067 g, 0.22 mmol) were dissolved in dry 1,2-dichloroethane (5 mL). To the reaction mixture was added crashed 4A Molecular Sieve (0.028 g), a catalytic amount of glacial acetic acid. The reaction mixture was stirred at room temperature for 1 hr and it was then added at room temperature sodium triacetoxyborohydride (0.071 g, 0.33 mmol) under nitrogen atmosphere and the reaction mixture was stirred at room temperature for 18 hours. The reaction mixture was then partitioned with water and dichloromethane. The organic layer was washed with brine, dried with Na$_2$SO$_4$, filtered and the solvent evaporated in vacuo to yield a crude oil. The crude oil was purified via semi-preparative HPLC (aqueous 0.5% TFA/acetonitrile) to yield crude 8-[8-(tert-butyl-dimethyl-silanyloxymethyl)-naphthalen-1-ylmethyl]-1-(4-fluoro-phenyl)-1,3,8-triaza-spiro[4.5]decan-4-one which was directly used to the next step.

Step C:

To the crude intermediate prepared as in STEP B was added acetonitrile (5 mL) and aqueous 5% TFA (5 mL). The reaction mixture was stirred at room temperature for 6 hrs. The solvent was then evaporated in vacuo to yield the title compound as a solid.

$^1$H NMR (400 MHz, CDCl$_3$) δ 8.85 (1H, br s), 7.86-7.81 (2H, m), 7.53-7.51 (1H, m), 7.43-7.33 (3H, m), 6.98-6.92 (2H, m), 6.84-6.79 (2H, m), 6.55 (1H, s), 5.12 (2H, br s), 4.66 (2H, s), 4.33 (1H, br s), 3.03-2.93 (4H, m), 2.38-2.31 (2H, m), 1.79-1.75 (2H, m) MS (ES$^+$) m/z 420.1 (M+H)$^+$.

EXAMPLE 59

1-(4-Fluoro-phenyl)-8-(8-methoxymethyl-naphthalen-1-ylmethyl)-1,3,8-triaza-spiro[4.5]decan-4-one Compound #733

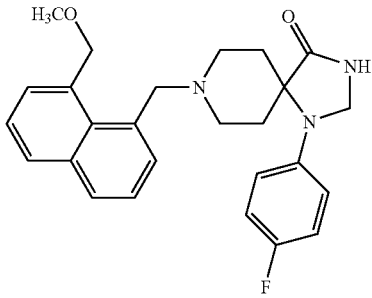

Step A:

(8-Methoxymethyl-naphthalen-1-yl)-methanol (*Tetrahedron Lett.* 1997; 38, 8161-8164) (0.36 g, 1.8 mmol) was dissolved in dichloromethane (10 mL). To the solution was then added 1,1,1-triacetoxy-1,1-dihydro-1,2-benziodoxol-3 (1H)-one, also known as Dess-Martin periodinane (1.5 g, 3.6 mmol). The reaction mixture was stirred for 1 hr, then partitioned with an aqueous saturated solution of thiosulfate and dichloromethane. The organic layer was washed with an aqueous saturated solution of thiosulfate, an aqueous saturated solution of sodium bicarbonate, brine, dried with Na$_2$SO$_4$, filtered and the solvent evaporated in vacuo to yield crude 8-methoxymethyl-naphthalene-1-carbaldehyde which was used directly into the next step.

Step B:

1-(4-Fluoro-phenyl)-1,3,8-triaza-spiro[4.5]decan-4-one (0.45 g, 1.8 mmol) and crude 8-methoxymethyl-naphthalene-1-carbaldehyde (0.35 g, 1.8 mmol) were dissolved in dry dichloromethane (25 mL), dry 1,2-dichloroethane (5 mL) and glacial acetic acid (0.5 mL). The reaction mixture was stirred at room temperature for 1 hr. To the reaction mixture was then added, at room temperature, sodium triacetoxyborohydride (0.57 g, 2.7 mmol) under nitrogen atmosphere and the reaction mixture was stirred at room temperature for 4 days. The reaction mixture was partitioned with water and dichloromethane. The organic layer was washed with brine, dried with Na$_2$SO$_4$, filtered and the solvent evaporated in vacuo to yield a crude oil. The crude oil was purified via flash chromatography (40% ethyl acetate in hexanes) to yield the title compound as a solid.

$^1$H NMR (400 MHz, CDCl$_3$) δ 7.85-7.80 (2H, m), 7.60-7.58 (1H, m), 7.49-7.37 (3H, m), 6.94-6.83 (4H, m), 6.12 (1H, s), 5.23 (2H, s), 4.64 (2H, s), 4.10 (2H, s), 3.38 (3H, s), 2.91-2.81 (4H, m), 2.30-2.23 (2H, m), 1.73-1.70 (2H, m) MS (ES$^+$) m/z 434.2 (M+H)$^+$.

EXAMPLE 60

(R)-8-Acenaphthen-1-yl-1-(4-fluoro-phenyl)-3-(2-(R)--oxiranyl-ethyl)-1,3,8-triaza-spiro[4.5]decan-4-one Compound #723

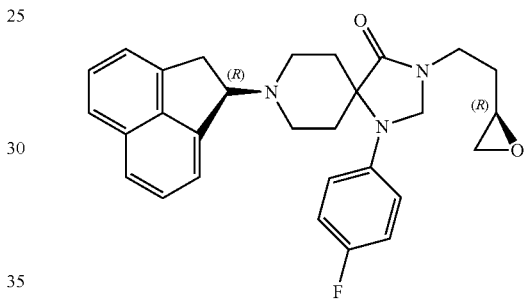

(R)-8-Acenaphthen-1-yl-1-(4-fluoro-phenyl)-1,3,8-triaza-spiro[4.5]decan-4-one (0.25 g, 0.62 mmol) was dissolved in N,N-dimethylformamide (2.0 mL). To the reaction mixture was then added at 0° C. sodium hydride (60% in mineral oil, 0.03 g, 0.80 mmol) under nitrogen atmosphere. The reaction mixture was stirred at 0° C. for 30 minutes. To the reaction mixture was then added, at 0° C., 2-(R)-(2-bromo-ethyl)-oxirane (0.14 g, 0.93 mmol). The reaction mixture was stirred at 0° C. under nitrogen atmosphere for 1 hr, then room temperature for 18 hours and then partitioned with water and ethyl acetate. The organic layer was dried with Na$_2$SO$_4$, filtered and the solvent evaporated in vacuo to yield a crude oil. The crude oil was purified via flash chromatography (6% methanol/dichloromethane) to yield the title compound as a foam.

$^1$H NMR (400 MHz, CDCl$_3$) δ 7.70-7.65 (1H, m), 7.59 (1H, d, J=8.2 Hz), 7.54-7.50 (2H, m), 7.43 (1H, t), 7.26 (1H, d), 7.04-6.93 (4H, m), 4.95 (1H, dd, J=3.4 and 7.8 Hz), 4.64 (2H, dd, J=4.3 and 10.7 Hz), 3.64-3.50 (3H, m), 3.38-3.31 (1H, m), 3.19-3.03 (2H, m), 2.97-2.92 (1H, m), 2.83-2.80 (1H, m), 2.75-2.73 (1H, m), 2.48-2.39 (3H, m), 2.29-2.21 (1H, m), 2.03-1.95 (1H, m), 1.75-1.62 (3H, m) MS (ES$^+$) m/z 472.2 (M+H)$^+$.

EXAMPLE 61

(R)-8-Acenaphthen-1-yl-3-(4-amino-3-(S)-hydroxy-butyl)-1-(4-fluoro-phenyl)-1,3,8-triaza-spiro[4.5]decan-4-one Compound #722

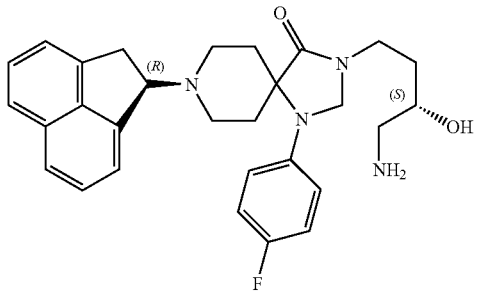

(R)-8-Acenaphthen-1-yl-1-(4-fluoro-phenyl)-3-(2-(R)-(oxiranyl-ethyl)-1,3,8-triaza-spiro[4.5]decan-4-one (0.03 g, 0.06 mmol) was dissolved in ethyl alcohol (1.0 mL). To the solution was then added concentrated ammonium hydroxide (1.0 mL) and the reaction mixture was stirred at 40° C. for 7 hrs in a pressure flask. The solvent was then evaporated in vacuo to yield a crude oil. The crude oil was purified via flash chromatography (6.0% ammonia 2.0 M in methanol/dichloromethane) to yield the title compound as a foam.

$^1$H NMR (400 MHz, CDCl$_3$) δ 7.70-7.65 (1H, m), 7.59 (1H, d, J=8.2 Hz), 7.54-7.50 (2H, m), 7.43 (1H, t), 7.26 (1H, d), 7.04-6.93 (4H, m), 4.96-4.94 (1H, m), 4.64 (2H, dd, J=4.3 and 10.7 Hz), 3.86-3.76 (1H, m), 3.57-3.45 (2H, m), 3.39-2.98 (4H, m), 2.85-2.76 (2H, m), 2.65-2.58 (1H, m), 2.52-2.40 (2H, m), 2.32-2.24 (1H, m), 2.10-1.90 (3H, m), 1.76-1.51 (4H, m) MS (ES$^+$) m/z 489.1 (M+H)$^+$.

EXAMPLE 62

8-(S)-Acetonaphthen-1-yl-1-(4-fluoro-phenyl)-3-[2-(R)-hydroxy-3-(1-phenyl-ethylamino)-propyl]-1,3,8-triaza-spiro[4.5]decan-4-one Compound #663

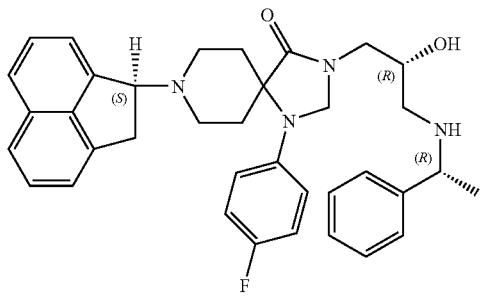

8-Acenaphthen-1-yl-1-(4-fluoro-phenyl)-3-(S)-oxiranyl-methyl-1,3,8-triaza-spiro[4.5]decan-4-one (0.45 g, 0.98 mmol) and R-(+)-α-methylbenzyl amine (0.178 g, 1.47 mmol) were dissolved in ethanol (3 mL). The reaction mixture was heated at 120° C. and microwaved for 600 sec. The solvent was evaporated in vacuo to yield an oil. The crude oil was purified via flash chromatography (80% ethyl acetate/heptane) to yield the title compound as a solid.

$^1$H NMR (300 MHz, CDCl$_3$) δ 7.65 (1H, t), 7.60 (1H, d, J=8.2 Hz), 7.50-7.54 (2H, d, J=5.1 Hz), 7.44 (1H, t), 7.07-7.28 (6H, m), 6.8-7.0 (4H, m), 4.9 (1H, m), 4.6 (2H, s), 3.8 (2H, m), 3.25-3.55 (5H, m), 2.95-3.1 (2H, m), 2.78-2.82 (1H, m), 2.6 (1H, m), 2.1-2.4 (5H, m), 1.5 (2H, m), 1.3 (3H, d) MS (ES$^+$) m/z 579.2 (MH+), 427.2

EXAMPLE 63

3-(3-Amino-2-(R)-hydroxy-propyl)-8-cyclooctylmethyl-1-(4-fluoro-phenyl)-1,3,8-triaza-spiro[4.5]decan-4-one Compound #620

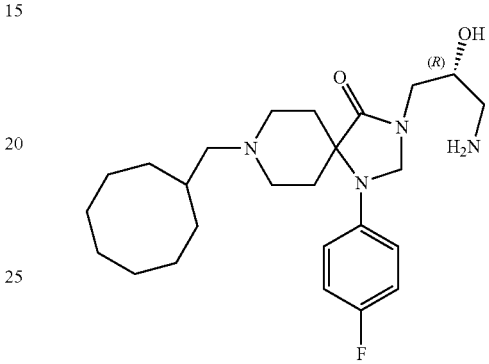

Cyclooctylmethyl-1-(4-fluoro-phenyl)-3-(S)-oxiranylmethyl-1,3,8-triaza-spiro[4.5]decan-4-one (0.71 g, 1.65 mmol) was dissolved in absolute ethanol (5 mL), then mixed with ammonium hydroxide (2 mL, 14.4 mmol) and heated to 120° C. and microwaved for 600 sec. The solvent was evaporated and the resulting residue was purified by column chromatography (80% ethyl acetate/heptane) to yield the title compound as an oil.

MS (electrospray)=447.4 (MH+) $^1$H NMR (300 MHz, CDCl$_3$) δ 1.1-1.3 (m, 2H), 1.4-1.8 (m, 16 H), 2.1 (d, 2H), 2.2-2.38 (m, 2H), 2.6-2.8 (m, 5H), 2.8-3.0 (m, 2H), 3.3-3.6 (m, 2H), 3.7-3.8 (m, 2H), 4.7 (s, 2H), 6.8-7.0 (m, 4H).

EXAMPLE 64

3-(3-Amino-2-(R)-hydroxy-propyl)-1-(4-fluoro-phenyl)-8-(2,3,3a,4,5,6-hexahydro-1H-phenalen-1-yl)-1,3,8-triaza-spiro[4.5]decan-4-one dihydrochloride Compound #640

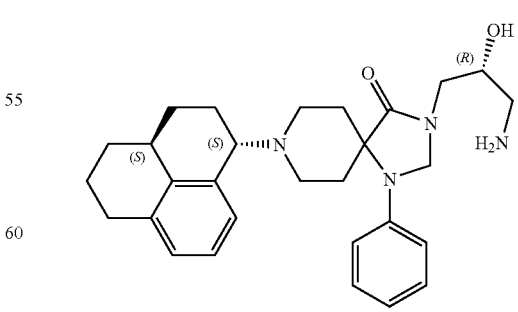

1-(4-Fluoro-phenyl)-8-(2,3,3a,4,5,6-hexahydro-1H-phenalen-1-yl)-3-(S)-oxiranylmethyl-1,3,8-triaza-spiro[4.5]decan-4-one (60 mg, 0.131 mmol) was dissolved in absolute ethanol (1 mL), then mixed with ammonium hydroxide (0.3 mL) and heated to 120° C. and microwaved for 480 sec. The solvent was evaporated. The resulting residue was dissolved in ethyl acetate and then treated with HCl in diethyl ether (1M, 1 mL) to yield the title compound as a solid.

MS (electrospray)=475.2 (MH+), 305.1 $^1$H NMR (300 MHz, CD$_3$OD) δ 0.9-1.0 (m, 1H), 1.1-1.5 (m, 5H) 1.7-1.8 (m, 1H), 2.0-2.25 (m, 6H), 2.3-2.7 (m, 4H), 2.7-3.2 (m, 7H), 3.32-3.7 (m, 2H), 3.85-4.2 (m, 2H), 4.9 (m, 2H), 6.9-7.4 (m, 8H)

EXAMPLE 65

1-(4-Fluoro-phenyl)-8-(8-methyl-naphthalen-1-ylmethyl)-1,3,8-triaza-spiro[4.5]-decan-4-one Compound #547

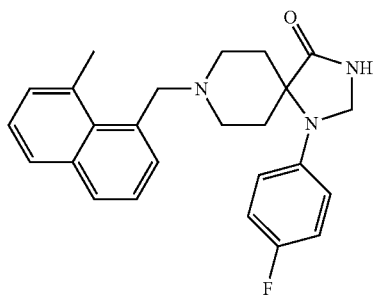

Step A: (8-Hydroxymethyl-naphthalen-1-yl)-methanol

A 12-L 4-neck flask equipped with a thermocouple, an overhead stirrer, a 2-L addition funnel, and a condenser under N$_2$ was charged with 1,8-naphthalic anhydride (200 g, 1.0 mol) in toluene (2.5 L) at room temperature. The reaction mixture was agitated while adding DIBAL-H (1.5 M in toluene, 2.664 L, 4 mol) via the addition funnel over 1.5 h. The solution was then heated to 95° C. overnight, cooled to 15° C. and then slowly diluted with ethyl acetate (2.2 L) and H$_2$O (2 L) followed by addition of concentrated HCl (320 mL). The resulting suspension was stirred for 30 min at room temperature, filtered, and air dried on the filter for 2 h. The resultant material was in 95% ethanol (1.2 L), stirred at 70° C. for 2 h, and filtered to yield a wet solid which was air dried overnight on the filter and then dried at 70° C. in a vacuum oven to yield (8-hydroxymethyl-naphthalen-1-yl)-methanol as a solid;

$^1$H NMR (400 MHz, CD$_3$OD) δ7.85 (2H, dd, J=1.3 and 8.2 Hz), 7.61 (2H, dd, J=1.0 and 7.0 Hz), 7.46-7.42 (2H, m), 5.22 (2H, s), 4.82 (4H, s).

Step B: 1H,3H-Benzo[de]isochromene

A 1-L 3-neck flask equipped with an overhead stirrer, a condenser, and a thermocouple was charged with (8-hydroxymethyl-naphthalen-1-yl)-methanol (33.0 g, 0.175 mol), concentrated phosphoric acid (225 mL), and water (5 mL). The reaction mixture was stirred at 140° C. for 3 h, cooled to room temperature, diluted with CH$_2$Cl$_2$ (800 mL) and transferred to a 2-L separatory funnel. After washing the organic layer with water and saturated NaHCO$_3$ it was dried over MgSO$_4$ and evaporated to yield 1H,3H-Benzo[de]isochromene as a solid.

$^1$H NMR (400 MHz, DMSO-d$_6$): δ 6.96-6.92 (2H, m), 6.62-6.58 (2H, m), 6.39-6.37 (2H, m), 4.17 (3H, s).

Step C: (8-Methyl-naphthalen-1-yl)-methanol (See *Tetrahedron,* 2000, 56, 8375-8382)

A 3-L 4-neck flask equipped with an overhead stirrer, a thermocouple, a condenser, a nitrogen inlet, and a 1-L addition funnel was charged with potassium (30 g, 0.764 mol) and THF (1 L). The metal suspension was heated to 60° C. for 30 min and then stirred to room temperature. To the reaction mixture was then added naphthalene (2 g, 0.015 mol), the suspension was stirred at room temperature for 10 min and then cooled to –20° C. to afford a blue suspension. A solution of 1H,3H-Benzo[de]isochromene (26 g, 0.153 mol) in THF (500 ml) was slowly added via the addition funnel, with addition controlled so that the reaction temperature did not exceed –15° C. After stirring for 5 h at –20° C., the suspension was removed from the cooling bath, warmed with stirring to 0° C., and then allowed to stand without stirring (potassium metal settling). The solution was decanted and the residual potassium was cooled and carefully decomposed with isopropyl alcohol (IPA) under N$_2$. The decanted solution was carefully treated with water (20 mL) under nitrogen and stirring was continued for 20 min. Additional water and ether were added and the organic layer was separated. The aqueous layer was extracted with CH$_2$Cl$_2$ and the combined organics were dried over MgSO$_4$ and condensed in vacuo to yield a crude material. The crude material was purified by flash chromatography (7.5/2.5 hexane/EtOAc) to yield 8-methyl-1-napthalenemethanol as a solid.

$^1$H NMR (300 MHz, DMSO-d$_6$): δ 7.82-7.80 (1H, m), 7.73-7.69 (1H, m), 7.52-7.50 (1H, m), 7.41-7.32 (3H, m), 5.17 (2H, bs), 3.01 (3H, s).

Step D: 8-Methyl-naphthalene-1-carbaldehyde

A 1-L 4-neck equipped with an overhead stirrer, a condenser and a thermocouple was charged with 8-methyl-1-napthalenemethanol (18.5 g, 0.107 mol) in CH$_2$Cl$_2$ (500 mL) and stirred at room temperature under N$_2$. Solid Mn$_{(IV)}$O$_2$ (61 g, 0.7 mol) was carefully added and the reaction was stirred at room temperature for 3 h, then at 40° C. for 6 h and then at room temperature overnight. The reaction mixture was diluted with CH$_2$Cl$_2$ (500 mL), filtered and the filtrate was washed with 1N HCl and then dried over MgSO$_4$. The resulting crude material was purified using silica gel chromatography (8/2 hexane/ethyl acetate) to yield 8-methyl-naphthalene-1-carbaldehyde as a solid.

$^1$H NMR (400 MHz, CDCl$_3$) δ 10.92 (1H, s), 8.04 (1H, dd, J=1.3 and 8.1 Hz), 7.96 (1H, dd, J=1.4 and 7.1 Hz), 7.82-7.73 (1H, m), 7.55-7.51 (1H, m), 7.49-7.44 (2H, m), 2.82 (3H, s)

Step E: 1-(4-Fluoro-phenyl)-8-(8-methyl-naphthalen-1-ylmethyl)-1,3,8-triaza-spiro[4.5]-decan-4-one.

A 1-L 3-neck flask equipped with an overhead stirrer and a thermocouple was charged with 8-methyl-naphthalene-1-carbaldehyde (13.75 g, 0.08 mol) and 1-(4-fluoro-phenyl)-1,3,8-triaza-spiro[4.5]decan-4-one (21.5 g, 0.085 mol) under N$_2$ in CH$_2$Cl$_2$ (500 mL). After stirring for 20 min, HOAc (1 mL) was added followed by careful addition of solid NaBH(OAc)$_3$ (33.4 g, 0.157 mol). The mixture was stirred for 16 h at room temperature (suspension becomes a solution). The reaction was then warmed at 50° C. for 2 h, cooled down to room temperature and then treated with 0.5 N NaOH (50 mL), stirred for 10 min and then diluted with CH$_2$Cl$_2$ (100 mL). The organic layer was isolated and dried over MgSO$_4$. The solvent was evaporated to yield a residue, which was suspended in diethyl ether, stirred for 20 min, filtered and dried in a 60° C. vacuum oven to yield 1-(4-fluoro-phenyl)-8-(8-methyl-naphthalen-1-ylmethyl)-1,3,8-triaza-spiro[4.5]-decan-4-one as a white solid;

¹H NMR (400 MHz, CDCl₃) δ 7.79-7.76 (1H, m), 7.72-7.69 (1H, m), 7.39-7.30 (4H, m), 6.98-6.92 (2H, m), 6.87-6.82 (2H, m), 6.24 (1H, br s), 4.66 (2H, s), 4.01 (2H, s), 3.12 (3H, s), 2.86-2.78 (4H, m), 2.33-2.23 (2H, m), 1.72 (2H, d, J=14.1 Hz); MS (ES⁺) m/z 404.2 (M+H)⁺. Elemental Analysis Calculated: C: 69.26%, H: 7.06%, N: 11.34%, F: 3.91%, $H_2O$: 1.85%.

Measured: C: 68.96%, H: 6.83%, N: 11.38%, F: 4.00%, $H_2O$: 0.58%.

EXAMPLE 66

Production of Cells Expressing the ORL-1, Delta, Kappa or Mu Receptor

HEK293 cells were transfected with nociceptin receptor (ORL-1, human mRNA GenBank #AF348323) or any of the opioid receptor subtype delta (δ, human mRNA Genbank #U07882) kappa (κ, human mRNA Genbank #U17298) and mu (μ, human mRNA Genbank #L29301). The vector used was pCi-neo (G418 selection). The transfections were performed with LipofectAMINE 2000 (Life Technologies Cat. # 11668-019) using the following procedure.

The day before transfection, a 24 well plate was inoculated with 2×10⁵ cells per well in 0.5 ml of normal growth medium (MEM+EBSS+NEAA+10% BCS). Two wells were prepared for each specialty along with a no DNA control. For each well transfected, 0.8 μg of DNA was diluted into 50 μl (total volume) of OPTI-MEM I Reduced Serum Medium (Life Technologies Cat. # 51985-034). For each well transfected, 2 μl of LipofectAMINE 2000 (LF2000) was diluted into 50 μl (total volume) of OPTI-MEM I medium and incubated for 5 minutes at room temperature. The diluted DNA and LF2000 were combined and incubated at room temperature for 20 minutes. The growth medium was aspirated from each well and replaced with 1 ml of OPTI-MEM I. A total of 100 μl of the DNA-LF2000 complexes were added to each well and mixed with gentle swirling. The plate was incubated at 37° C., 5% $CO_2$ for 5 hours. The OPTI-MEM I medium was aspirated from each transfected well and replaced with 1 ml growth medium. The plate was returned to the incubator for 24 hours. The wells were trypsinized and cells added to 100 mm tissue culture dishes (2 dishes per well). The dishes were incubated for 24 hours. The medium was aspirated from each dish and replaced with growth medium containing 400 μg/ml Geneticin (G418) selective antibiotic. The plates were refer every 3-4 days.

Distinct colonies appeared in approximately 3 weeks. One week later, 48 out of approximately 100 colonies per dish were subcultures to 1 well each of two 24 well plates containing 1 ml of selective medium per well.

Confluent wells were expanded to 6 well plates, then T25 flasks and T75 flasks. Cell lines showing poor growth patterns were eliminated. Membranes were prepared from each cell line and receptor activity determined by a receptor binding assay.

EXAMPLE 67

Method for Measuring Affinity for the ORL-1 Receptor

The nociceptin receptor binding assay measures the binding of ¹²⁵I-Tyr¹⁴-nociceptin (2200 Ci/mmol, New England Nuclear) to human nociceptin receptor (ORL-1) on HEK293 cell membranes.

HEK293 cell membrane (prepared as described in Pulito, V. L. et al., 2000, *J. Pharmacol. Exp. Ther.* 294, 224-229), with the exception that the buffer used was a mixture of 50 mM Tris-HCl pH7.8, 5 mM $MgCl_2$ and 1 mM EGTA), was added to PEI treated WGA FlashPlates (New England Nuclear) at 1 μg/well in binding buffer of 50 mM Tris-HCl pH 7.8, 5 mM $MgCl_2$ and 1 mM EGTA. ¹²⁵I-Tyr¹⁴-nociceptin was added at a final concentration of 0.5 nM and the volume adjusted to 50 μl with binding buffer. The plate was incubated for two hours at room temperature, the reactions were aspirated and the wells washed two times with 200 μl binding buffer and then filled with 200 μl binding buffer. The plates were then sealed and counted on a Packard Top Count to determine radioactivity bound to the membranes.

For each test compound, the total binding (% Inh) was measured at several concentrations and the $IC_{50}$ (the concentration at which 50% of the binding is inhibited) was determined from the graphical display of X=logarithm of concentration versus Y=response, using the following calculation:

$$Y = (\text{Minimum}) + \frac{(\text{Maximum} - \text{Minimum})}{(1 + 10^{\log(EC_{50} - X)})}$$

For some of the test compound, Ki was determined, using the following calculation:

Ki values were calculated using Graphpad Prizm software, where $$Ki = (IC_{50})/(+[\text{radioligand}]/Kd)$$

For the ORL-1 binding, the Kd was 0.5 nM. The [radioligand] used was the same as the Kd.

The ability of representative compounds of the present invention to bind to the ORL-1 receptor in a HEK cell line using a radio-labelled nociceptin as the displaceable ligand was determine according to the procedure described above with results as listed in Table 12. (Note that for the compounds which were tested more than once, the value listed in Table 12 is the calculated mean.)

TABLE 12

| ID# | ORL-1 IC₅₀ (nM) | ORL-1 Ki (nM) |
|---|---|---|
| 1 | 8.10 | |
| 2 | 8.49 | |
| 3 | 173.0 | |
| 4 | 3.63 | |
| 5 | 20.1 | |
| 6 | 4.66 | |
| 7 | 13.4 | |
| 8 | 4.86 | |
| 9 | 233.0 | |
| 10 | 10.5 | |
| 11 | 22.3 | |
| 12 | 21.0 | |
| 13 | 10.6 | |
| 14 | 25.2 | |
| 15 | 31.8 | |
| 16 | 122.0 | |
| 17 | 10.8 | |
| 18 | 10.3 | |
| 19 | 15.0 | |
| 20 | 15.8 | |
| 21 | 9.22 | |
| 22 | 20.7 | |
| 23 | 80.5 | |
| 24 | 34.8 | |
| 25 | 33.0 | |
| 26 | 20.3 | |
| 27 | 11.0 | |

TABLE 12-continued

| ID# | ORL-1 IC$_{50}$ (nM) | ORL-1 Ki (nM) |
|---|---|---|
| 28 | 7.74 | |
| 29 | 121.0 | |
| 30 | 23.2 | |
| 31 | 44.5 | |
| 32 | 13.7 | |
| 33 | 95.3 | |
| 34 | 26.9 | |
| 35 | 30.3 | |
| 36 | 8.73 | |
| 38 | 8.88 | |
| 39 | 149.0 | |
| 40 | 9.40 | |
| 41 | 8.32 | |
| 42 | 19.2 | |
| 43 | 19.9 | |
| 44 | 43.1 | |
| 45 | 6.45 | |
| 46 | 16.2 | |
| 47 | 0.86 | |
| 48 | 1.28 | |
| 49 | 14.8 | |
| 50 | 298.0 | |
| 51 | 259.0 | |
| 52 | 0.48 | |
| 53 | 0.47 | |
| 54 | 3.03 | |
| 55 | 2.75 | |
| 56 | 4.70 | |
| 57 | 20.0 | |
| 58 | 476.0 | |
| 59 | 94.5 | |
| 60 | 396.0 | |
| 61 | 1.09 | |
| 62 | 0.78 | |
| 63 | 19.2 | |
| 64 | 33.9 | |
| 65 | 88.5 | |
| 66 | 39.2 | |
| 67 | 12.2 | |
| 68 | 10.4 | |
| 69 | 20.5 | |
| 70 | 72.9 | |
| 71 | 59.3 | |
| 72 | 82.6 | |
| 73 | 14.0 | |
| 74 | 8.08 | |
| 75 | 21.1 | |
| 76 | 16.1 | |
| 78 | 18.0 | |
| 79 | 18.2 | |
| 100 | 4.10 | |
| 101 | 1.79 | |
| 102 | 199.0 | |
| 103 | 18.5 | |
| 104 | 0.72 | |
| 105 | 81.6 | |
| 106 | 55.4 | |
| 107 | 57.7 | |
| 108 | 36.9 | |
| 110 | 45.0 | |
| 111 | 25.2 | |
| 112 | 18.0 | |
| 113 | 27.4 | |
| 114 | 15.1 | |
| 115 | 14.0 | |
| 116 | 17.0 | |
| 117 | 99.7 | |
| 119 | 2.8 | |
| 121 | 39.9 | |
| 122 | 32.4 | |
| 123 | 61.2 | |
| 124 | 41.6 | |
| 125 | 44.1 | |
| 126 | 38.6 | |
| 127 | 61.0 | |
| 128 | 38.6 | |
| 129 | 160.0 | |
| 130 | 48.8 | |
| 131 | 17.0 | |
| 132 | 33.9 | |
| 133 | 108.0 | |
| 134 | 329.0 | |
| 135 | 17.3 | |
| 136 | 1330.0 | |
| 137 | 101.0 | |
| 138 | 31.9 | |
| 139 | 139.0 | |
| 140 | 108.0 | |
| 141 | 26.0 | |
| 142 | 49.9 | |
| 143 | 39.7 | |
| 144 | 40.0 | |
| 145 | 12.8 | |
| 146 | 85.6 | |
| 147 | 34.3 | |
| 148 | 81.1 | |
| 149 | 40.9 | |
| 150 | 28.5 | |
| 151 | 10.9 | |
| 152 | 37.6 | |
| 153 | 60.4 | |
| 154 | 6.96 | |
| 155 | 98.9 | |
| 156 | 21.8 | |
| 157 | 43.5 | |
| 158 | 41.9 | |
| 159 | 298.0 | |
| 160 | 53.5 | |
| 161 | 90.7 | |
| 162 | 46.0 | |
| 163 | 539.0 | |
| 164 | 252.0 | |
| 165 | 54.5 | |
| 166 | 52.2 | |
| 167 | 45.5 | |
| 168 | 151.0 | |
| 169 | 219.0 | |
| 170 | >10,000 | |
| 171 | 19.9 | |
| 173 | 31.8 | |
| 174 | 68.7 | |
| 175 | 86.3 | |
| 176 | 51.3 | |
| 177 | 166.0 | |
| 178 | 62.2 | |
| 179 | 33.0 | |
| 180 | 116.0 | |
| 181 | 67.3 | |
| 182 | 7.7 | |
| 183 | 40.0 | |
| 187 | 17.1 | |
| 188 | 7.1 | |
| 189 | 7.6 | |
| 190 | 41.0 | |
| 191 | 10.7 | |
| 192 | 4.2 | |
| 193 | 14.0 | |
| 194 | 7.00 | |
| 197 | 2.00 | |
| 198 | 46.0 | |
| 203 | 1.3 | |
| 204 | 30.9 | |
| 205 | 17.5 | |
| 206 | 8.0 | |
| 208 | 10.7 | |
| 209 | 33.00 | |
| 210 | 3.10 | |
| 211 | 2.90 | |
| 215 | 9.35 | |
| 217 | 12.7 | |
| 218 | 6.6 | |
| 219 | 6.6 | |
| 220 | 100.0 | |
| 224 | 9.00 | |

TABLE 12-continued

| ID# | ORL-1 IC$_{50}$ (nM) | ORL-1 Ki (nM) |
|---|---|---|
| 225 | 7.3 | |
| 227 | 25.0 | |
| 228 | 3.3 | |
| 229 | 7.6 | |
| 230 | 105.0 | |
| 250 | 59.7 | |
| 251 | 10.5 | |
| 252 | 35.2 | |
| 253 | 20.4 | |
| 254 | 16.3 | |
| 255 | 66.5 | |
| 256 | 23.5 | |
| 257 | 14.9 | |
| 258 | 343.0 | |
| 259 | 199.0 | |
| 260 | 560.0 | |
| 261 | 54.1 | |
| 262 | 182.0 | |
| 263 | 86.7 | |
| 264 | 283.0 | |
| 265 | 366.0 | |
| 266 | 471.0 | |
| 267 | 178.0 | |
| 268 | 147.0 | |
| 269 | 157.0 | |
| 270 | 148.0 | |
| 271 | 0.70 | |
| 275 | 1.19 | |
| 276 | 7.97 | |
| 280 | 118.0 | |
| 281 | 8.90 | |
| 282 | 6.35 | |
| 283 | 13.9 | |
| 284 | 7.86 | |
| 285 | 78.3 | |
| 289 | 7.05 | |
| 290 | 14.2 | |
| 291 | 17.5 | |
| 292 | 462.5 | |
| 293 | 279.0 | |
| 294 | 1360.0 | |
| 295 | 0.52 | |
| 296 | 1.78 | |
| 298 | 0.87 | |
| 299 | 3.06 | |
| 300 | 0.89 | |
| 305 | 0.996 | |
| 307 | 2.22 | |
| 308 | 1.99 | |
| 309 | 0.36 | |
| 310 | 10.7 | |
| 311 | 0.83 | |
| 312 | 1.16 | |
| 313 | 6.03 | |
| 314 | 1.37 | |
| 315 | 0.78 | |
| 316 | 1.01 | |
| 317 | 1.06 | |
| 318 | 0.87 | |
| 319 | 3.44 | |
| 320 | 1.70 | |
| 321 | 0.65 | |
| 322 | 0.51 | |
| 323 | 0.82 | |
| 324 | 2.51 | |
| 325 | 1.64 | |
| 326 | 0.74 | |
| 327 | 0.23 | |
| 328 | 4.55 | |
| 329 | 2.02 | |
| 330 | 0.91 | |
| 331 | 0.90 | |
| 332 | 0.41 | |
| 333 | 1.68 | |
| 334 | 0.53 | |
| 335 | 0.40 | |
| 336 | 0.50 | |
| 337 | 1.40 | |
| 338 | 0.82 | |
| 339 | 0.75 | |
| 340 | 0.12 | |
| 341 | 0.30 | |
| 342 | 135.0 | |
| 343 | 1.05 | |
| 344 | 1.92 | |
| 345 | 0.24 | |
| 346 | 0.72 | |
| 347 | 2.72 | |
| 348 | 0.66 | |
| 349 | 0.90 | |
| 350 | 0.58 | |
| 351 | 0.81 | |
| 352 | 1.55 | |
| 353 | 0.42 | |
| 354 | 0.92 | |
| 355 | 2.13 | |
| 356 | 0.57 | |
| 358 | 0.10 | |
| 360 | 0.25 | |
| 362 | 2.37 | |
| 364 | 1.67 | |
| 365 | 1.30 | |
| 366 | 1.59 | |
| 367 | 4.05 | |
| 368 | 5.54 | |
| 370 | 2.10 | |
| 371 | 2.96 | |
| 372 | 1.13 | |
| 373 | 3.48 | |
| 374 | 20.9 | |
| 375 | 3.93 | |
| 376 | 0.85 | |
| 377 | 0.82 | |
| 378 | 0.56 | |
| 379 | 0.17 | |
| 380 | 1.03 | |
| 381 | 0.28 | |
| 382 | 0.80 | |
| 383 | 0.32 | |
| 385 | 135.0 | |
| 386 | 111.0 | |
| 387 | 37.8 | |
| 388 | 30.5 | |
| 389 | 106.0 | |
| 390 | 69.7 | |
| 391 | 51.5 | |
| 392 | 121.0 | |
| 393 | 6.68 | |
| 394 | 198.0 | |
| 395 | 130.0 | |
| 396 | 23.1 | |
| 398 | 77.5 | |
| 399 | 65.8 | |
| 418 | 79.5 | |
| 419 | 1.17 | |
| 420 | 0.33 | |
| 421 | 0.26 | |
| 422 | 13.6 | |
| 423 | 0.34 | |
| 424 | 0.23 | |
| 425 | 1.01 | |
| 426 | 2.19 | |
| 427 | 3.23 | |
| 428 | 2.48 | |
| 429 | 2.53 | |
| 430 | 2.64 | |
| 431 | 2.07 | |
| 432 | 3.41 | |
| 433 | 1.95 | |
| 434 | 1.02 | |
| 435 | 0.78 | |
| 436 | 0.99 | |
| 437 | 1.24 | |
| 438 | 49.6 | |

TABLE 12-continued

| ID# | ORL-1 IC$_{50}$ (nM) | ORL-1 Ki (nM) |
|---|---|---|
| 439 | 34.2 | |
| 440 | 22.7 | |
| 441 | 70.5 | |
| 442 | 27.4 | |
| 443 | 1.19 | |
| 444 | 1.18 | |
| 445 | 1.78 | |
| 446 | 1.98 | |
| 447 | 17.9 | |
| 448 | 2.02 | |
| 451 | 6.35 | |
| 452 | 29.0 | |
| 453 | 39.4 | |
| 454 | 4.71 | |
| 455 | 183.0 | |
| 456 | 462.0 | |
| 457 | 377.0 | |
| 458 | 35.9 | |
| 459 | 128.0 | |
| 460 | 42.7 | |
| 461 | 1.32 | |
| 462 | 1.54 | |
| 463 | 1.44 | |
| 464 | 0.81 | |
| 465 | 0.16 | |
| 500 | 0.74 | |
| 501 | 567.0 | |
| 502 | 3920.0 | |
| 503 | 563.0 | |
| 504 | 39.3 | |
| 505 | 9770 | |
| 506 | 493.6 | |
| 507 | 23.9 | |
| 508 | 383.0 | |
| 509 | 0.36 | |
| 510 | 165.0 | |
| 511 | 35.7 | |
| 512 | 1.02 | |
| 513 | 254.0 | |
| 514 | 20.8 | |
| 516 | >10,000 | |
| 517 | >10,000 | |
| 518 | 19.0 | |
| 519 | 24.4 | |
| 520 | 84.0 | |
| 521 | >10,000 | |
| 522 | 213.4 | |
| 523 | >10,000 | |
| 524 | >10,000 | |
| 525 | >10,000 | |
| 526 | >10,000 | |
| 527 | >10,000 | |
| 528 | >10,000 | |
| 529 | >10,000 | |
| 530 | >10,000 | |
| 531 | >10,000 | |
| 532 | >10,000 | |
| 533 | >10,000 | |
| 534 | >10,000 | |
| 535 | 5720 | |
| 536 | 4300 | |
| 537 | 569. | |
| 538 | >10,000 | |
| 539 | >10,000 | |
| 541 | 897 | |
| 542 | 283 | |
| 543 | 2640 | |
| 544 | 204.0 | |
| 546 | 3530 | |
| 547 | 42.6 | |
| 548 | 132.0 | |
| 549 | 1220 | |
| 550 | 13.5 | |
| 551 | 37.4 | |
| 552 | 92.0 | |
| 553 | 11.0 | |
| 554 | 80.4 | |
| 555 | 0.25 | |
| 556 | 1.27 | |
| 564 | 0.22 | |
| 565 | 0.38 | |
| 566 | 0.77 | |
| 567 | 1.41 | |
| 568 | 1.36 | |
| 569 | 0.83 | |
| 570 | 0.24 | |
| 571 | 0.23 | |
| 572 | 5600 | |
| 573 | 896 | |
| 576 | 0.46 | |
| 578 | 164.0 | |
| 579 | 0.83 | |
| 581 | 9.00 | |
| 582 | 40.00 | |
| 600 | 1.11 | |
| 601 | 7.59 | |
| 602 | 1.11 | |
| 603 | 1.98 | |
| 604 | 2.06 | |
| 605 | 0.81 | |
| 606 | 1.03 | |
| 607 | 3.05 | |
| 608 | 10.00 | |
| 609 | 10.00 | |
| 610 | 10.00 | |
| 611 | 0.37 | |
| 612 | 1.85 | |
| 613 | 0.83 | |
| 614 | 1.69 | |
| 616 | | 17.95 |
| 617 | | 5.83 |
| 618 | | 6.23 |
| 619 | | 30.21 |
| 620 | | 6.16 |
| 621 | | 5.05 |
| 623 | | 19.77 |
| 624 | | 5.83 |
| 625 | | 5.50 |
| 626 | | 158.30 |
| 627 | | 4.66 |
| 628 | | 20.21 |
| 629 | | 19.58 |
| 633 | | 18.87 |
| 634 | | 6.49 |
| 635 | | 4.80 |
| 636 | | 6.08 |
| 637 | | 2.26 |
| 638 | | 4.30 |
| 639 | | 0.11 |
| 640 | | 0.61 |
| 641 | | 0.28 |
| 642 | | 0.43 |
| 643 | | 0.47 |
| 644 | | 0.42 |
| 647 | | 0.44 |
| 648 | | 320.4 |
| 649 | | 35.44 |
| 650 | | 21.43 |
| 651 | | 5.87 |
| 652 | | 17.34 |
| 653 | | 177.1 |
| 654 | | 1.10 |
| 655 | | 26.55 |
| 656 | | 8.17 |
| 657 | | 2.18 |
| 658 | | 0.32 |
| 659 | | 0.75 |
| 660 | | 19.2 |
| 661 | | 25.74 |
| 662 | | 29.86 |
| 663 | | 1.60 |
| 664 | | 117.90 |
| 665 | | 44.36 |
| 666 | | 8.02 |

TABLE 12-continued

| ID# | ORL-1 IC$_{50}$ (nM) | ORL-1 Ki (nM) |
|---|---|---|
| 667 | | 0.04 |
| 668 | 3.25 | |
| 669 | 1.40 | |
| 670 | 10.00 | |
| 671 | 10.00 | |
| 672 | 10.00 | |
| 673 | 10.00 | |
| 674 | 10.00 | |
| 675 | | 25.49 |
| 677 | | 56.99 |
| 678 | | 6.73 |
| 679 | | 0.53 |
| 680 | | 115.7 |
| 681 | | 7.54 |
| 682 | 10.00 | |
| 683 | 10.00 | |
| 684 | 10.00 | |
| 685 | 10.00 | |
| 686 | 10.00 | |
| 687 | | 18.68 |
| 688 | | 76.33 |
| 689 | | 25.05 |
| 690 | | 23.51 |
| 691 | 0.35 | |
| 692 | | 0.48 |
| 693 | 0.37 | |
| 694 | 0.46 | |
| 695 | 0.19 | |
| 696 | 0.29 | |
| 697 | 0.34 | |
| 698 | 0.26 | |
| 699 | 0.55 | |
| 700 | 0.94 | |
| 701 | 0.52 | |
| 702 | 0.84 | |
| 703 | 0.72 | |
| 704 | | 20.11 |
| 705 | | 11.78 |
| 706 | | 15.04 |
| 707 | | 13.72 |
| 708 | | 9.42 |
| 709 | | 17.45 |
| 710 | | 23.32 |
| 711 | | 17.87 |
| 712 | | 27.59 |
| 713 | | 4.87 |
| 714 | | 27.61 |
| 715 | | 5.16 |
| 716 | | 5.76 |
| 717 | | 5.25 |
| 718 | | 4.41 |
| 719 | | 4.34 |
| 720 | | 5.21 |
| 721 | | 17.62 |
| 722 | 0.57 | |
| 723 | 0.88 | |
| 726 | | 10.58 |
| 727 | | 75.12 |
| 728 | | 104.9 |
| 729 | | 476.6 |
| 733 | | 3.77 |
| 734 | | 72.8 |

EXAMPLE 68

Filtration Binding Assay: ORL-1, Mu, Kappa and Delta Opioid Receptors

The assay used to measure the binding of representative test compounds to the ORL-1, delta, kappa and mu opioid receptors was run similarly, with appropriate selection and substitution of cell membrane and radiolabeled ligand. The following cell membranes and ligands were used for the determination of binding to the respective opioid receptors.

| | |
|---|---|
| ORL-1 (Nociceptin) | 1 µg/well of 3C4 cell line membrane and 0.5 nM final concentration of $^{125}$I nociceptin |
| Delta (δ) opioid: | 1 µg/well of 2D4 cell line membrane and a final concentration of 2.44 nM DPDPE-$^3$H ligand. |
| Mu (µ) opioid: | 5 µg/well of 1D4 cell line membrane and a final concentration 0.8993 nM DAMGO-$^3$H ligand. |
| Kappa (κ) opioid: | 7 µg/well of 2C2 cell line membrane and a final concentration of 2.76 nM U-69,593-$^3$H ligand. |

Both membrane and ligand were diluted such that a 25 µl addition delivered the necessary amount per well, as noted above. Both membrane and ligand were diluted in 1× ORL-1 buffer. The ORL-1 buffer was composed of 50 mM Tris-HCl, pH=7.4, 5 mM MgCl$_2$ and 1 mM EGTA. Each test compound was diluted to a concentration in the range of from 100 µM to 10 µM (half-log curve) with 100% DMSO. To each well of a 96 well plate was added 25 µL cell membrane (as listed above), 1 µL of the diluted test compound, and 25 µL labeled ligand (as listed above) for the mu, delta, kappa or ORL-1 opioid receptor, as desired.

The plate was incubated on a rotating shaker for 2 hours at room temperature. The plate was filtered over GF/C Filterplates, prewetted in 0.03% polyethyleneimine, in Filtermate 196 apparatus (Packard). The plate was then washed 6 times with ORL-1 buffer in the filtration apparatus and dried in vacuum oven for 1 hour at a temperature of 50° C.

To each well was then added 25 µL Microscint 20 (Packard) (to solubilize bound radioactivity) and each well counted in a Packard TopCount for 1 minute/well using counting parameters optimized for the particular radioligand/opioid receptor being tested. Percent radioactive ligand bound in each reaction was calculated relative to a control using DMSO for maximum binding (no inhibition). Curves were fitted and K$_i$'s determined using Graphpad Prizm software (v3.0). The K$_i$s were calculated using the following formula by Graphpad Prizm software, where $$K_i = (IC_{50})/(1+[radioligand]/K_d)$$

For the ORL-1, the K$_d$ is 0.5nM, for Mu it is 0.8993 nM, for kappa it is 2.76 nM and for delta it is 2.44 nM. Note that the [radioligand] (concentration of radioligand) was equivalent to the K$_d$.

Representative compounds of the present invention were tested for binding to the mu, kappa and delta opioid receptors using the procedure, cell membranes and ligands as described above, with results as listed in Table 13. The values listed below correspond to IC$_{50}$ measurements, unless followed with the notation "Ki" which denotes that for the listed value is a Ki measurement. (Note that for the compounds which were tested more than once, the value listed in Table 13 is the calculated mean.)

TABLE 13

| ID# | Delta IC$_{50}$ (µM) | Kappa IC$_{50}$ (µM) | Mu IC$_{50}$ (µM) |
|---|---|---|---|
| 1 | >10 | 0.13 | 0.62 |
| 2 | >10 | 0.19 | 1.20 |
| 3 | 9.16 | 0.44 | 4.05 |
| 4 | >10 | 0.11 | 0.16 |
| 5 | >10 | 0.12 | 0.78 |
| 6 | >10 | 0.23 | 0.42 |
| 7 | 7.11 | 0.13 | 1.38 |
| 8 | | 0.05 | 0.83 |

TABLE 13-continued

| ID# | Delta IC$_{50}$ (μM) | Kappa IC$_{50}$ (μM) | Mu IC$_{50}$ (μM) |
|---|---|---|---|
| 9 |  | 1.40 | 0.94 |
| 10 |  | 0.08 | 0.85 |
| 11 |  | 0.29 | 0.82 |
| 12 |  | 0.20 | 0.52 |
| 13 |  | 0.12 | 0.62 |
| 14 |  | 0.40 | 1.20 |
| 15 |  | 0.33 | 0.85 |
| 16 |  | 0.55 | 1.12 |
| 17 | >10 | 0.25 | 0.65 |
| 18 | >10 | 0.28 | 0.45 |
| 19 |  | 0.09 | 0.59 |
| 20 | >10 | 0.44 | 1.28 |
| 21 | >10 | 0.32 | 0.80 |
| 22 |  | 0.30 | 0.60 |
| 23 |  | 0.49 | 9.20 |
| 24 | >10 | 0.75 | 1.25 |
| 25 |  | 0.45 | 1.10 |
| 26 |  | 0.29 | 0.79 |
| 27 |  | 0.03 | 0.40 |
| 28 | >10 | 0.18 | 0.41 |
| 29 |  | 0.41 | 5.41 |
| 30 | >10 | 0.71 | 2.73 |
| 31 |  | 0.28 | 2.93 |
| 32 | >10 | 0.27 | 0.45 |
| 33 |  | 1.16 | >10 |
| 34 |  | 0.27 | 0.68 |
| 35 | >10 | 0.66 | 0.82 |
| 36 | 1.76 | 0.23 | 1.76 |
| 38 | >10 | 0.20 | 0.99 |
| 39 | >10 | 3.25 | 8.83 |
| 40 | >10 | 0.40 | 1.22 |
| 41 | >10 | 0.25 | 2.10 |
| 42 |  | 0.26 | 0.54 |
| 43 |  | 0.32 | 0.54 |
| 44 |  | 0.16 | 1.13 |
| 45 | 1.18 | 0.10 | 0.51 |
| 46 | 9.87 | 0.19 | 1.32 |
| 47 | >10 | 0.09 | 0.21 |
| 48 | >10 | 0.17 | 0.54 |
| 49 |  |  | 0.08 |
| 50 |  |  | 1.04 |
| 51 |  |  | 0.18 |
| 52 | 4.41 | 0.05 | 0.29 |
| 53 | 4.74 | 0.03 | 0.07 |
| 54 | >10 | 0.11 | 0.35 |
| 55 | 3.90 | 0.37 | 0.60 |
| 56 | 1.25 | 0.50 | 0.08 |
| 57 |  |  | 0.07 |
| 58 |  |  | 1.12 |
| 59 |  |  | 0.10 |
| 60 |  |  | 0.35 |
| 61 | 0.64 | 0.08 | 0.32 |
| 62 | 0.90 | 0.10 | 0.06 |
| 63 | 8.78 | 0.23 | 3.43 |
| 64 | 7.34 | 0.24 | 1.19 |
| 65 |  | 0.51 | 0.58 |
| 66 | 5.93 | 0.13 | 0.55 |
| 67 | >10 | 0.04 | 0.71 |
| 68 | >10 | 0.02 | 0.26 |
| 69 | >10 | 0.04 | 0.51 |
| 70 |  |  | 0.63 |
| 71 |  |  | 0.57 |
| 72 |  | 0.79 | 1.84 |
| 73 | >10 | 0.25 | 0.68 |
| 74 | 8.02 | 0.09 | 0.89 |
| 75 | >10 | 0.30 | 0.98 |
| 76 | >10 | 0.02 | 0.51 |
| 78 |  |  | 0.82 |
| 79 |  | 1.04 | 3.11 |
| 100 | >10 | 0.28 | 0.23 |
| 101 | 3.93 | 0.78 | 0.076 |
| 102 |  |  | 0.18 |
| 103 |  |  | 0.02 |
| 104 | 0.52 | 0.08 | 0.02 |
| 105 |  |  | 2.26 |
| 106 |  |  | 0.016 |
| 107 |  |  | 0.003 |
| 108 |  |  | 0.54 |
| 115 |  |  | 0.012 |
| 116 |  |  | 0.022 |
| 117 |  |  | 0.036 |
| 124 |  |  | 0.023 |
| 127 |  |  | 0.029 |
| 129 |  |  | 0.029 |
| 130 |  |  | 0.061 |
| 131 |  |  | 0.051 |
| 132 |  |  | 0.043 |
| 133 |  |  | 0.087 |
| 137 |  |  | 0.100 |
| 138 |  |  | 0.066 |
| 139 |  |  | 0.103 |
| 140 |  |  | 0.074 |
| 142 |  |  | 0.104 |
| 143 |  |  | 0.048 |
| 144 |  |  | 0.049 |
| 145 |  |  | 0.104 |
| 146 |  |  | 0.038 |
| 147 |  |  | 0.044 |
| 148 |  |  | 0.037 |
| 149 |  |  | 0.057 |
| 152 |  |  | 0.044 |
| 153 |  |  | 0.057 |
| 155 |  |  | 0.050 |
| 156 |  |  | 0.016 |
| 158 |  |  | 0.066 |
| 159 |  |  | 0.068 |
| 160 |  |  | 0.021 |
| 161 |  |  | 0.049 |
| 164 |  |  | 0.082 |
| 165 |  |  | 0.011 |
| 166 |  |  | 0.022 |
| 167 |  |  | 0.053 |
| 168 |  |  | 0.010 |
| 169 |  |  | 0.057 |
| 171 |  |  | 0.037 |
| 173 |  |  | 0.038 |
| 174 |  |  | 0.022 |
| 175 |  |  | 0.030 |
| 176 |  |  | 0.055 |
| 177 |  |  | 0.047 |
| 178 |  |  | 0.018 |
| 179 |  |  | 0.020 |
| 180 |  |  | 0.045 |
| 181 |  |  | 0.034 |
| 183 |  |  | 0.047 |
| 192 | 2.51 | 0.01 |  |
| 203 | 3.08 | 0.02 | 0.04 |
| 228 |  |  | 0.070 |
| 229 |  |  | 0.060 |
| 230 |  |  | 0.152 |
| 250 | >10 | 0.38 | 1.20 |
| 251 | >10 | 0.45 | 1.58 |
| 252 | >10 | 1.34 | 3.70 |
| 253 | 2.16 | 0.40 | 0.76 |
| 254 | >10 | 0.80 | 2.83 |
| 255 | >10 | 0.62 | 2.49 |
| 256 | >10 | 1.18 | 5.45 |
| 257 | >10 | 0.38 | 0.88 |
| 259 |  |  | 0.50 |
| 261 | >10 | 0.27 | 1.56 |
| 262 |  |  | 0.85 |
| 263 |  |  | 0.59 |
| 267 |  |  | 0.77 |
| 268 |  |  | 0.95 |
| 269 |  |  | 2.49 |
| 270 |  |  | 0.41 |
| 271 | >10 | 0.07 | 0.37 |
| 275 | 5.01 | 0.09 | 0.45 |
| 276 | >10 | 0.70 | 0.86 |
| 280 | 1.08 |  | 2.52 |
| 281 | 0.96 |  | 0.58 |
| 282 |  | 0.77 | 0.324 |
| 283 |  | 1.15 | 3.24 |
| 284 |  | 0.42 | 3.20 |

TABLE 13-continued

| ID# | Delta IC$_{50}$ (μM) | Kappa IC$_{50}$ (μM) | Mu IC$_{50}$ (μM) |
|---|---|---|---|
| 285 | | 2.69 | 4.78 |
| 289 | | 0.19 | 1.39 |
| 290 | | | 0.93 |
| 291 | | 0.57 | 4.56 |
| 298 | 6.06 | 0.05 | 0.38 |
| 299 | >10 | 1.98 | 0.43 |
| 300 | 4.84 | 0.13 | 0.51 |
| 305 | 8.27 | 0.171 | 0.592 |
| 307 | | 0.21 | 0.75 |
| 308 | | 0.05 | 0.20 |
| 309 | | 0.09 | 0.04 |
| 310 | | 1.63 | 1.09 |
| 311 | 1.70 | 0.28 | 0.27 |
| 312 | | 0.33 | 0.32 |
| 313 | | 0.50 | 0.33 |
| 314 | | 0.16 | 0.13 |
| 315 | | 0.28 | 0.30 |
| 316 | | 0.19 | 0.49 |
| 317 | | 0.22 | 0.92 |
| 318 | | 0.08 | 0.23 |
| 319 | | 0.58 | 0.32 |
| 320 | | 0.12 | 0.34 |
| 321 | | 0.15 | 0.16 |
| 322 | | 0.22 | 0.13 |
| 323 | | 0.10 | 0.72 |
| 324 | | 0.23 | 0.11 |
| 325 | | 0.21 | 0.73 |
| 326 | | 0.01 | 0.25 |
| 327 | >10 | 0.11 | 0.13 |
| 328 | | 0.30 | 1.03 |
| 330 | >10 | 0.48 | 0.19 |
| 331 | | 0.12 | 0.46 |
| 332 | | 0.02 | 0.08 |
| 333 | | 0.39 | 0.24 |
| 334 | | 0.03 | 0.06 |
| 335 | | 0.07 | 0.13 |
| 336 | | 0.04 | 0.06 |
| 337 | | 0.25 | 0.55 |
| 338 | | 0.14 | 0.74 |
| 339 | >10 | 0.18 | 0.21 |
| 340 | 7.34 | 0.495 | 1.29 |
| 341 | >10 | 0.29 | 0.81 |
| 342 | >10 | 0.29 | 0.35 |
| 343 | 2.70 | 0.42 | 0.55 |
| 344 | 4.81 | 0.23 | 0.55 |
| 345 | 9.27 | 0.668 | 0.37 |
| 346 | 1.10 | 0.14 | 0.17 |
| 347 | 9.13 | 0.62 | 5.4 |
| 348 | >10 | 0.93 | 5.42 |
| 349 | >10 | 0.38 | 1.4 |
| 350 | 3.16 | 0.078 | 0.25 |
| 351 | 8.00 | 0.081 | 0.38 |
| 352 | >10 | 0.27 | 0.94 |
| 353 | 8.89 | 0.24 | 0.47 |
| 354 | >10 | 0.15 | 0.30 |
| 355 | 4.15 | 0.16 | 0.18 |
| 356 | >10 | 0.08 | 0.63 |
| 358 | 2.46 | 0.13 | 0.17 |
| 360 | 2.51 | 0.03 | 0.15 |
| 362 | | 0.82 | 0.20 |
| 364 | | 0.18 | 0.21 |
| 365 | | 0.79 | 1.75 |
| 366 | | 0.34 | 0.26 |
| 367 | | 0.36 | 1.86 |
| 368 | | 0.43 | 1.08 |
| 370 | | 0.29 | 0.35 |
| 371 | | 0.73 | 0.57 |
| 372 | | 0.26 | 0.70 |
| 373 | | 1.24 | 0.37 |
| 374 | | 0.73 | 1.96 |
| 376 | | 0.14 | 0.07 |
| 377 | 2.61 | 0.093 | 0.16 |
| 378 | | 0.20 | 0.64 |
| 379 | | 0.14 | 0.16 |
| 380 | | 0.23 | 0.07 |
| 381 | | 0.10 | 0.22 |
| 382 | | 0.21 | 0.15 |
| 383 | | 0.06 | 0.54 |
| 386 | | 3.69 | >10 |
| 388 | | 0.23 | >10 |
| 389 | | 9.84 | 7.06 |
| 390 | | 1.22 | 1.79 |
| 391 | | 2.18 | >10 |
| 392 | | 1.39 | >10 |
| 393 | | 1.04 | >10 |
| 395 | | >10 | 1.10 |
| 396 | | 0.81 | >10 |
| 398 | >10 | 0.25 | >10 |
| 399 | | 0.75 | >10 |
| 418 | >10 | >10 | >10 |
| 419 | | 0.16 | 0.13 |
| 420 | >10 | 0.42 | 0.41 |
| 421 | | 0.13 | 0.04 |
| 422 | | >10 | >10 |
| 423 | >1 | 0.59 | 0.31 |
| 424 | 0.28 | 0.60 | 0.28 |
| 425 | | 0.82 | 0.29 |
| 426 | >10 | 1.06 | 2.74 |
| 427 | | 1.45 | 2.37 |
| 428 | | 0.75 | 0.90 |
| 429 | | 0.67 | 0.80 |
| 430 | >10 | 0.89 | 2.47 |
| 431 | | 0.58 | 1.74 |
| 432 | | 0.37 | 1.00 |
| 433 | | 0.42 | 1.26 |
| 434 | | 0.88 | 0.24 |
| 435 | | 0.60 | 0.22 |
| 436 | | 0.83 | 0.25 |
| 437 | | 1.40 | 0.36 |
| 438 | | >10 | >10 |
| 439 | | >10 | >10 |
| 440 | | >10 | >10 |
| 441 | | >10 | >10 |
| 442 | | >10 | >10 |
| 443 | | 1.75 | 0.17 |
| 444 | | 1.71 | 0.25 |
| 445 | >10 | 0.10 | 0.06 |
| 446 | 4.12 | 0.13 | 0.45 |
| 447 | 0.48 | | 0.48 |
| 448 | | 0.17 | 1.14 |
| 451 | | 0.77 | 0.32 |
| 452 | | 1.52 | 0.57 |
| 453 | | 0.39 | 1.70 |
| 454 | | 0.12 | 0.51 |
| 455 | | 0.38 | 5.16 |
| 456 | | >10 | >10 |
| 457 | | 9.43 | >10 |
| 458 | | 1.45 | >10 |
| 459 | | 3.21 | >10 |
| 460 | | 0.83 | 0.90 |
| 461 | >10 | 0.25 | 1.03 |
| 462 | 5.62 | 0.15 | 0.12 |
| 463 | | 1.77 | 0.17 |
| 464 | | 0.34 | 2.38 |
| 465 | | 0.10 | 0.38 |
| 505 | >10 | >10 | >10 |
| 506 | | 0.67 | 0.529 |
| 507 | >10 | 0.277 | 1.29 |
| 508 | | 0.874 | 0.156 |
| 509 | 0.50 | 0.11 | 0.02 |
| 510 | 5.77 | 0.24 | 0.69 |
| 511 | 3.91 | 0.42 | 0.14 |
| 512 | 0.82 | 0.98 | 0.086 |
| 513 | | 0.46 | 0.05 |
| 514 | | 0.21 | 0.26 |
| 516 | | 0.77 | >10 |
| 517 | | 0.45 | >10 |
| 541 | 9.28 | 2.14 | 0.48 |
| 542 | >10 | 0.53 | 0.16 |
| 543 | >10 | 0.71 | 2.09 |
| 544 | >10 | 0.379 | 0.582 |
| 546 | >10 | 2.13 | 1.29 |
| 547 | >10 | >10 | >10 |
| 548 | >10 | 0.07 | 0.54 |

TABLE 13-continued

| ID# | Delta IC$_{50}$ (μM) | Kappa IC$_{50}$ (μM) | Mu IC$_{50}$ (μM) |
|---|---|---|---|
| 549 | >10 | 4.37 | >10 |
| 550 | 2.61 | 0.09 | 0.16 |
| 551 | | | 1.51 |
| 552 | >10 | 1.22 | 0.066 |
| 553 | >10 | 0.75 | 3.4 |
| 554 | 10.0 | 9.47 | >10 |
| 555 | 0.1 | 0.56 | 0.10 |
| 556 | >10 | 0.438 | 0.382 |
| 564 | | 0.49 | 0.04 |
| 565 | | 0.41 | 0.03 |
| 566 | | 0.98 | 0.27 |
| 567 | | 1.00 | 0.17 |
| 568 | | 0.72 | 0.11 |
| 569 | | 0.29 | 0.14 |
| 570 | | 0.79 | 0.05 |
| 571 | 0.05 | 0.20 | 0.04 |
| 572 | 3.87 | 9.85 | |
| 573 | 2.09 | 7.22 | |
| 576 | 1.4 | 0.185 | 0.03 |
| 578 | | >10 | 2.86 |
| 579 | | 2.75 | 0.17 |
| 600 | | 0.49 | 0.04 |
| 601 | | 1.77 | 0.77 |
| 602 | | 0.88 | 0.07 |
| 603 | | 1.32 | 0.08 |
| 604 | | 0.79 | 0.08 |
| 605 | | 0.33 | 2.38 |
| 606 | | 0.58 | 0.09 |
| 607 | | 10.0 | 10.0 |
| 608 | | 10.0 | 10.0 |
| 609 | | 10.0 | 10.0 |
| 610 | | 9.02 | 10.0 |
| 611 | | 0.18 | 0.05 |
| 612 | | 0.44 | 0.28 |
| 613 | | 0.51 | 0.27 |
| 614 | | 1.58 | 0.56 |
| 616 | >5 Ki | 0.09 Ki | 0.20 Ki |
| 617 | >5 Ki | 0.02 Ki | 0.09 Ki |
| 618 | >5 Ki | 0.04 Ki | 0.08 Ki |
| 619 | >5 Ki | 0.17 Ki | 0.14 Ki |
| 620 | >5 Ki | 0.19 Ki | 0.28 Ki |
| 621 | >5 Ki | 0.02 Ki | 0.04 Ki |
| 623 | >5 Ki | 0.03 Ki | 0.14 Ki |
| 624 | >5 Ki | 0.006 Ki | 0.07 Ki |
| 625 | 0.35 Ki | 0.003 Ki | 0.01 Ki |
| 626 | 1.45 Ki | 0.05 Ki | 0.05 Ki |
| 627 | >5 Ki | 0.01 Ki | 0.06 Ki |
| 628 | 1.43 Ki | 0.008 Ki | 0.03 Ki |
| 629 | >5 Ki | 0.01 Ki | 0.07 Ki |
| 633 | >5 Ki | 0.04 Ki | 0.44 Ki |
| 634 | >5 Ki | 0.03 Ki | 0.12 Ki |
| 635 | >5 Ki | 0.03 Ki | 0.13 Ki |
| 636 | 3.40 Ki | 0.01 Ki | 0.23 Ki |
| 637 | >5 Ki | 0.08 Ki | 0.10 Ki |
| 638 | >5 Ki | 0.07 Ki | 0.40 Ki |
| 639 | 1.60 Ki | 0.03 Ki | 0.01 Ki |
| 640 | >5 Ki | 0.21 Ki | 0.12 Ki |
| 641 | 1.58 Ki | 0.02 Ki | 0.01 Ki |
| 642 | 3.06 Ki | 0.08 Ki | 0.02 Ki |
| 643 | 4.42 Ki | 0.04 Ki | 0.01 Ki |
| 644 | 2.28 Ki | 0.03 Ki | 0.03 Ki |
| 647 | >5 Ki | 0.02 Ki | 0.05 Ki |
| 648 | >5 Ki | 2.87 Ki | 5.00 Ki |
| 649 | >5 Ki | 0.68 Ki | 0.89 Ki |
| 650 | >5 Ki | 0.46 Ki | 0.74 Ki |
| 651 | >5 Ki | 0.31 Ki | 0.67 Ki |
| 652 | >5 Ki | 0.75 Ki | 1.06 Ki |
| 653 | >5 Ki | 1.58 Ki | 5.00 Ki |
| 654 | >5 Ki | 0.06 Ki | 0.13 Ki |
| 655 | >5 Ki | 0.43 Ki | 2.19 Ki |
| 656 | >5 Ki | 0.42 Ki | 1.52 Ki |
| 657 | >5 Ki | 0.04 Ki | 0.09 Ki |
| 658 | >5 Ki | 0.13 Ki | 0.17 Ki |
| 659 | >5 Ki | 0.42 Ki | 0.13 Ki |
| 660 | | | 0.87 Ki |
| 661 | | | 0.80 Ki |
| 662 | | | 1.60 Ki |
| 663 | >5 Ki | 0.018 Ki | 0.071 Ki |
| 664 | >5 Ki | 0.72 Ki | 0.26 Ki |
| 665 | >5 Ki | 0.29 Ki | 2.71 Ki |
| 666 | >5 Ki | 0.14 Ki | 2.59 Ki |
| 667 | 4.14 Ki | 0.45 Ki | 0.77 Ki |
| 668 | | 1.25 | 0.19 |
| 669 | | 1.36 | 0.13 |
| 670 | | 10.00 | 10.00 |
| 671 | | 10.00 | 10.00 |
| 672 | | 10.00 | 10.00 |
| 673 | | 10.00 | 10.00 |
| 674 | | 10.00 | 10.00 |
| 675 | 3.10 Ki | 0.01 Ki | 0.04 Ki |
| 677 | 0.53 Ki | 0.10 Ki | 0.08 Ki |
| 678 | 5.0 Ki | 0.04 Ki | 0.14 Ki |
| 679 | 1.52 Ki | 0.03 Ki | 0.05 Ki |
| 680 | >5 Ki | 0.66 Ki | 3.02 Ki |
| 681 | >5 Ki | 0.58 Ki | 0.71 Ki |
| 682 | | 10.00 | 10.00 |
| 683 | | 10.00 | 10.00 |
| 684 | | 5.90 | 10.00 |
| 685 | | 10.00 | 10.00 |
| 686 | | 2.52 | 10.00 |
| 687 | 0.51 Ki | 0.01 Ki | 0.01 Ki |
| 688 | >5 Ki | 0.16 Ki | 0.11 Ki |
| 689 | 1.46 Ki | 0.005 Ki | 0.01 Ki |
| 690 | 1.07 Ki | 0.004 Ki | 0.03 Ki |
| 691 | | 0.25 | 0.03 |
| 692 | 3.36 Ki | 0.06 Ki | 0.02 Ki |
| 693 | | 0.03 | 0.17 |
| 694 | | 0.01 | 0.85 |
| 695 | | 0.16 | 0.18 |
| 696 | | 0.05 | 0.04 |
| 697 | | 0.16 | 0.20 |
| 698 | | 0.19 | 0.17 |
| 699 | | 0.07 | 0.19 |
| 700 | | 0.03 | 0.92 |
| 701 | | 0.05 | 0.20 |
| 702 | | 0.41 | 0.30 |
| 703 | | 0.45 | 0.11 |
| 704 | >5 Ki | 0.34 Ki | 1.33 Ki |
| 705 | >5 Ki | 0.71 Ki | 1.50 Ki |
| 706 | | | 0.48 Ki |
| 707 | | | 0.55 Ki |
| 708 | | | 0.49 Ki |
| 709 | | | 0.89 Ki |
| 710 | >5 Ki | 0.36 Ki | 1.09 Ki |
| 711 | | | 0.82 Ki |
| 712 | | | 1.95 Ki |
| 713 | | | 0.23 Ki |
| 714 | >5 Ki | | 0.59 Ki |
| 715 | >5 Ki | 0.15 Ki | 0.56 Ki |
| 716 | >5 Ki | 0.47 Ki | 1.31 Ki |
| 717 | >5 Ki | 0.33 Ki | 1.32 Ki |
| 718 | >5 Ki | 0.03 Ki | 0.48 Ki |
| 719 | >5 Ki | 0.17 Ki | 0.64 Ki |
| 720 | >5 Ki | 0.16 Ki | 0.57 Ki |
| 721 | >5 Ki | 0.17 Ki | 0.59 Ki |
| 722 | | 0.44 | 0.48 |
| 723 | | 0.83 | 0.08 |
| 726 | 0.53 Ki | 0.005 Ki | 0.04 Ki |
| 727 | >5 Ki | 0.21 Ki | 0.12 Ki |
| 728 | >5 Ki | 0.14 Ki | 0.08 Ki |
| 729 | 0.35 Ki | 0.01 Ki | 0.003 Ki |
| 733 | >5 Ki | 0.07 Ki | 0.08 Ki |
| 734 | >5 Ki | 1.93 Ki | >5 Ki |

EXAMPLE 69

In Vitro Assay—Filtration Binding Assay, Dopamine

The assay was used to measure the binding of representative compounds to D2 receptor, with appropriate selection and substitution of cell membrane and radiolabeled ligand.

The following cell membranes and ligands were used for the determination of binding to the respective D2 receptor.

Dopamine: 0.4 μg/well of membrane from cos-7 cell which has been transfected with cloned human Dopamine, Spiperone-I125 ligand at 150 μM final Both membrane and ligand were diluted such that a 25 μl addition delivered the necessary amount per well, as noted above. Both membrane and ligand were diluted in TNE buffer. The TNE buffer was a mixture of 50 mM Tris-HCl pH=7.4, 5 mM EDTA and 50 mM NaCl. Each test compound was diluted to a concentration from 10 μM to 1 μM with 100% DMSO. To each well of a 96 well plate was added 140 μL of TNE buffer, 10 μL of the diluted test compound in DMSO, 25 μL of spiperone and 25 μL of membrane.

The plate was incubated on a rotating shaker for 1 hour at room temperature. The plate was filtered over GF/C Filter-plates, prewetted in 0.03% polyethleneimine, in Filtermate 196 apparatus (Packard). The plate was then washed 6 times with ORL-1 buffer in the filtration apparatus and dried in vacuum oven for 1 hour at a temperature of 50° C.

To each well was then added 25 μL Microscint 20 (Packard) (to solubilize bound radioactivity) and each well counted in a Packard TopCount for 1 minute/well using counting parameters optimized for the particular radioligand/opioid receptor being tested. Percent radioactive ligand bound in each reaction was calculated relative to a control using DMSO for maximum binding (no inhibition). Curves were fitted and Ki determined using Graphpad Prizm software (v3.0).

Representative compounds of the present invention were tested according to the procedure outlined above with results as listed in Table 14.

TABLE 14

| ID # | $IC_{50}$ (nM) |
| --- | --- |
| 422 | 2208 |
| 424 | 278.2 |
| 426 | >10,000 |
| 430 | >10,000 |
| 433 | 3520 |
| 439 | 2334 |
| 440 | 1517 |
| 442 | 3229 |
| 327 | 387.5 |

EXAMPLE 70

Elevated Plus Maze (EPM) and Spontaneous Locomotor Activity (SMA) (Pellow, S., Chopin, P., File. S. E. and Briley, M., *J Neurosci Methods*, (1985) 14, 149-167)

The procedure used in the EPM was based on the natural aversion of rodents to explore brightly illuminated open and high places, as well as their innate tendency for thigmotaxis. When rats are placed on the elevated-plus maze, they have a normal tendency to remain in the enclosed arms of the maze and avoid venturing into the open arms. Animals treated with typical or atypical anxiolytics show an increase in the percentage of time spent (% Time) and/or the percentage of entries made (% Entries) into the open arms.

The spontaneous locomotor activity test (SMA) was an automated procedure for measuring the effect of a test compound on spontaneous motor activity in an open-field. A drug-induced decrease in spontaneous horizontal or vertical motor activity is regarded as an indication of sedation.

Animals

Male Long-Evans Hooded rats weighing 180 to 200 grams were purchased from Charles River Inc (Portage Mich.). The rats were housed in groups of four at an ambient temperature of 21 to 23° C. in a room with an automated 12/12 hour light/dark cycle, and access to water and a commercial rodent food ad libitum.

EPM Test Apparatus

Each black plastic maze had two open arms and two arms with 40 cm high walls (enclosed arms) of equal 50 cm length extending from the center at right angles, such that arms of similar type are opposite each other. Each plus-maze was elevated approximately 60 cm above the floor. Infrared photo-beams that cross the entrance of each arm and the center of the maze detected the exploratory activity of an animal in the maze. Rats were divided into groups (N=8 to 12) and test compound or vehicle was administered either orally (p.o.) by gavage in a dose volume equivalent to 5 mL/kg or intraperitoneally (i.p.) in a dose volume of 1 mL/kg. One hour after dosing (for p.o. administration) or 30 minutes after dosing (for i.p. administration), rats were placed on an open arm of the plus-maze facing the center. The 10 minute test was initiated when the rat enters the center of the apparatus. Data collection was automated.

SMA Test Apparatus

The test apparatus consisted of a plastic cubicle (42.0 cm in length; 42.0 cm in width and 30.5 cm height) that was placed in the center of a main frame. Photocell sensors (16 beams from front to back and 16 beams from side to side) were built into the sides of the frame for monitoring horizontal movement. The photocells were located at right angles to each other, projecting horizontal infrared beams of light 2.5 cm apart and 3 cm above the floor to measure horizontal activity, and 2.5 cm apart and 14 cm above the floor to measure vertical activity. Rats were divided into groups (N=8 to 12). Test compound or vehicle was administered either orally (p.o.) by gavage in a dose volume equivalent to 5 mL/kg or intraperitoneally (i.p.) in a dose volume of 1 mL/kg. At 50 minutes after p.o. administration or at 20 minutes after i.p. administration, each rat was placed into a separate plastic cubicle, and spontaneous exploratory activity was recorded for 10 minutes. Horizontal activity and vertical movements of the rats were recorded by counting the number of times the beams of light were interrupted (horizontal and vertical counts). Collection of the data and preliminary data analysis was automated.

Combined SMA/EPM Test Procedure

All animals were tested in the SMA 50 minutes after drug administration, for a 10 minute test session. Upon completion of the SMA test, the same animals were immediately placed on the EPM for a 10 minute test session.

Test Compounds

The test compound was dissolved in polyethylene glycol, molecular weight 200 (PEG-200) for i.p. administration. Test compound was suspended in an aqueous vehicle (MC) comprised of 0.5% Methylcellulose for p.o. administration.

Derivation and Analysis of EPM Data

Anxiolytic activity of a test compound in the EPM was quantified using two parameters. The percent of total time spent by a rat in one of the two open arms of the apparatus (% open arm time) was calculated as 100× (time on open arms)/ (total time of test session)

The number of times a rat entered the open arms relative to the total entries into all arms and the center area (% open arm entries) was calculated as 100× (entries into open arms)/(entries into open and closed arms, plus center)

A test compound was considered active in rats whose % open arm time or % open arm entries was significantly greater than in rats that received vehicle. Data was analyzed for statistical significance between drug and vehicle-treated groups via one tailed Mann-Whitney T-Test. If the probability was less than 5% (p<0.05) that an increase in the % open arm time and/or % open arm entries in the drug-treated group compared to the vehicle-treated group was due to chance, then the dose of the test compound was considered active.

The total number of entries into all arms and the center of the EPM was recorded as part of the automated data collection in this test. This information (total entries) served as a measure of spontaneous motor activity on the EPM. Compounds with sedative activity reduced the total number of entries in the EPM test. A test compound was considered to have sedative activity in rats whose total entries were significantly less than in rats that received vehicle. Data was analyzed for statistical significance between drug and vehicle-treated groups via one tailed Mann-Whitney T-Test. If the probability was less than 5% (p<0.05) that a decrease in the total entries in the drug-treated group compared to the vehicle-treated group was due to chance, then the dose of the test compound was considered to be a dose at which the compound produces sedation.

Derivation and Analysis of SMA Data

A test compound was considered sedative in rats whose horizontal activity (HA) or vertical movements (VM, rearing) counts were significantly less than that in vehicle-treated rats. HA data was analyzed for statistical significance between drug and vehicle-treated groups that were administered either the vehicle or each dose of the test compound by a one-way analysis of variance. Then Dunnett's multiple comparison method was used to test for a reduction (p<0.05, 1-tailed) in the average number of HA counts or VM counts in drug-treated groups, compared to a concurrently run vehicle-treated group. If the probability was less than 5% (p<0.05) that a decrease in HA and/or VM in the drug-treated group compared to a concurrently run vehicle-treated group was due to chance, then the dose of the test compound was considered to have sedative activity. Mann-Whitney T-Test was used in cases where the distribution of the data was non-gaussian.

Representative compounds of the present invention were tested according to the EPM and SMA procedures described above, with results as listed in Table 15-19, below. Statistical significance (P<0.05) was determined using a Mann-Whitney U Test (one-tailed); NS indicates results were not statistically significant.

TABLE 15

EPM and SMA Assay Results
Acute (30 min) Intraperitoneal Administration
Compound #64(*)

| Dosage mg/kg, i.p. (# Animals) | Statistics | % Open Arm Time (EPM) | % Open Arm Entries (EPM) | Total Entries (EPM) | Horizontal Activity (SMA) | Vertical Movement (SMA) |
|---|---|---|---|---|---|---|
| Vehicle (PEG-200) (40) | Mean | 8.92 | 5.50 | 94.8 | 3210 | 50.0 |
| | S.E.M. | ±1.65 | ±0.86 | ±4.11 | ±158 | ±2.82 |
| | % Change | 0.0% | 0.0% | 0.0% | 0.0% | 0.0% |
| 0.03 Mg/Kg (28) | Mean | 9.21 | 5.92 | 95.7 | 3259 | 49.8 |
| | S.E.M. | ±2.14 | ±1.17 | ±2.73 | ±169 | ±2.37 |
| | % Change | 3.2% | 7.6% | 0.95% | 1.5% | −0.4% |
| | P-value | NS | NS | NS | NS | NS |
| 0.1 Mg/Kg (32) | Mean | 15.3 | 10.6 | 95.4 | 3845 | 55.7 |
| | S.E.M. | ±1.97 | ±1.17 | ±3.91 | ±200 | ±2.72 |
| | % Change | 71.5% | 92.7% | 0.63% | 19.8% | 11.4% |
| | P-value | 0.0053 | 0.0004 | NS | 0.0091 | NS |
| 0.3 Mg/Kg (32) | Mean | 13.7 | 7.86 | 99.7 | 3561 | 58.0 |
| | S.E.M. | ±1.96 | ±0.87 | ±3.60 | ±181 | ±2.69 |
| | % Change | 53.6% | 42.9% | 5.2% | 10.9% | 16.0% |
| | P-value | 0.0159 | 0.0146 | NS | NS | 0.0270 |
| 1 Mg/Kg (32) | Mean | 14.0 | 7.78 | 94.8 | 3611 | 53.8 |
| | S.E.M. | ±2.11 | ±0.89 | ±3.73 | ±184 | ±1.83 |
| | % Change | 57.0% | 41.4% | 0.0% | 12.5% | 7.6% |
| | P-value | 0.0155 | 0.0099 | NS | NS | NS |
| 3 Mg/Kg (28) | Mean | 11.2 | 7.38 | 90.8 | 3449 | 51.1 |
| | S.E.M. | ±1.86 | ±1.00 | ±3.90 | ±172 | ±2.14 |
| | % Change | 25.6% | 34.2% | −4.2% | 7.4% | 2.2% |
| | P-value | NS | NS | NS | NS | NS |
| 10 Mg/Kg (8) | Mean | 11.8 | 7.36 | 86.8 | 2803 | 46.9 |
| | S.E.M. | ±4.03 | ±1.85 | ±6.91 | ±165 | ±3.72 |
| | % Change | 32.3% | 38.8% | −8.4% | −12.7% | −6.2% |
| | P-value | NS | NS | NS | NS | NS |

(*)Compound #64 was also tested in the SMA and EPM assays, using oral administration, but found to be inactive.

TABLE 16

EPM and SMA Assay Results
Acute (1 hr) Oral Administration - Mixture 3 Parts
Compound #422(*): 1
Part Compound #438

| Dosage mg/kg, p.o. (# Animals) | Statistics | % Open Arm Time (EPM) | % Open Arm Entries (EPM) | Total Entries (EPM) | Horizontal Activity (SMA) | Vertical Movement (SMA) |
|---|---|---|---|---|---|---|
| Vehicle (0.5% Methylcellulose) (80) | Mean | 9.61 | 6.59 | 102.0 | 3085 | 50.7 |
| | S.E.M. | ±1.04 | ±0.59 | ±3.02 | ±129 | ±1.27 |
| | % Change | 0.0% | 0.0% | 0.0% | 0.0% | 0.0% |
| 0.03 Mg/Kg (16) | Mean | 7.80 | 5.53 | 88.3 | 3307 | 53.6 |
| | S.E.M. | ±1.82 | ±1.00 | ±5.25 | ±240 | ±2.41 |
| | % Change | −18.8% | −16.1% | 13.4% | 7.2% | 5.7% |
| | P-value | NS | NS | 0.0235 | NS | NS |
| 0.1 Mg/Kg (32) | Mean | 11.5 | 7.73 | 101 | 3467 | 59.4 |
| | S.E.M. | ±1.97 | ±1.04 | ±3.56 | ±165 | ±2.50 |
| | % Change | 19.7% | 17.3% | −1.0% | 12.4% | 17.2% |
| | P-value | NS | NS | NS | 0.0077 | 0.0011 |
| 0.3 Mg/Kg (56) | Mean | 12.1 | 7.85 | 98.7 | 3397 | 53.7 |
| | S.E.M. | ±1.38 | ±0.64 | ±2.26 | ±150 | ±1.68 |
| | % Change | 25.9% | 19.1% | −3.2% | 10.1% | 5.9% |
| | P-value | NS | 0.0444 | NS | 0.0227 | 0.0408 |
| 1 Mg/Kg (48) | Mean | 14.0 | 9.55 | 99.7 | 3645 | 55.7 |
| | S.E.M. | ±1.68 | ±0.75 | ±3.34 | ±164 | ±1.83 |
| | % Change | 45.7% | 44.9% | −2.3% | 18.2% | 9.9% |
| | P-value | 0.0082 | 0.0009 | NS | 0.0015 | 0.0180 |
| 3 Mg/Kg (48) | Mean | 14.0 | 8.88 | 102.0 | 3621 | 55.0 |
| | S.E.M. | ±1.44 | ±0.70 | ±2.23 | ±188 | ±1.81 |
| | % Change | 45.7% | 34.7% | 0.0% | 17.4% | 8.5% |
| | P-value | 0.0032 | 0.0043 | NS | 0.0051 | 0.0338 |
| 10 Mg/Kg (56) | Mean | 17.0 | 10.3 | 97.6 | 3207 | 51.5 |
| | S.E.M. | ±1.51 | ±0.77 | ±3.06 | ±124 | ±1.51 |
| | % Change | 76.9% | 56.3% | −4.3% | 4.0% | 1.6% |
| | P-value | P < 0.0001 | P < 0.0001 | NS | NS | NS |
| 30 Mg/Kg (24) | Mean | 10.6 | 8.90 | 80.7 | 2741 | 46.3 |
| | S.E.M. | ±1.55 | ±1.16 | ±4.20 | ±171 | ±2.39 |
| | % Change | 10.3% | 35.1% | −20.9% | −11.2% | −8.7% |
| | P-value | NS | 0.0197 | P < 0.0001 | NS | 0.0091 |

(*)Compound #422 was also tested in the SMA and EPM assays, using oral administration, but was found to be inactive.

TABLE 17

EPM and SMA Assay Results
Acute (1 hr) Oral Administration
Compound #424(†)

| Dosage mg/kg, p.o. (# Animals) | Statistics | % Open Arm Time (EPM) | % Open Arm Entries EPM | Total Entries (EPM) | Horizontal Activity (SMA) | Vertical Movement (SMA) |
|---|---|---|---|---|---|---|
| Vehicle (0.5% Methylcellulose) (24) | Mean | 5.76 | 5.48 | 96.7 | 2881 | 49.1 |
| | S.E.M. | ±1.50 | ±1.21 | ±4.65 | ±208 | ±3.28 |
| | % Change | 0.0% | 0.0% | 0.0% | 0.0% | 0.0% |
| 0.3 Mg/Kg (24) | Mean | 9.80 | 7.33 | 90.0 | 3033 | 54.6 |
| | S.E.M. | ±2.09 | ±1.09 | ±4.90 | ±232 | ±3.11 |
| | % Change | 70.1% | 33.8% | −6.9% | 5.3% | 11.2% |
| | P-value | 0.0206 | NS | NS | NS | NS |
| 1 Mg/Kg (24) | Mean | 9.76 | 7.49 | 91.5 | 2752 | 50.3 |
| | S.E.M. | ±1.83 | ±1.28 | ±3.11 | ±188 | ±3.65 |
| | % Change | 69.4% | 36.7% | −5.3% | −4.5% | 2.4% |
| | P-value | NS | NS | NS | NS | NS |
| 3 Mg/Kg (24) | Mean | 10.1 | 7.92 | 96.3 | 3300 | 56.8 |
| | S.E.M. | ±1.83 | ±1.15 | ±3.43 | ±145 | ±2.35 |
| | % Change | 75.3% | 44.5% | −0.4% | 14.5% | 15.7% |
| | P-value | 0.0426 | 0.0398 | NS | 0.0239 | NS |

TABLE 17-continued

EPM and SMA Assay Results
Acute (1 hr) Oral Administration
Compound #424(†)

| Dosage mg/kg, p.o. (# Animals) | Statistics | % Open Arm Time (EPM) | % Open Arm Entries EPM | Total Entries (EPM) | Horizontal Activity (SMA) | Vertical Movement (SMA) |
|---|---|---|---|---|---|---|
| 10 Mg/Kg (24) | Mean | 7.54 | 7.49 | 102.6 | 2588 | 44.2 |
| | S.E.M. | ±1.75 | ±1.32 | ±4.63 | ±215 | ±3.32 |
| | % Change | 30.9% | 36.7% | 6.1% | −10.2% | −10.1% |
| | P-value | NS | NS | NS | NS | NS |

(†)Compound #424 was also tested in the SMA and EPM assays, using intraperotineal administration, with the following results.

In the rat EPM, at doses of 0.1 mg/kg, 0.3 mg/kg and 3.0 mg/kg, Compound #424 produced significant increases in percent open arm time (P<0.04) with peak activity occurring at doses 0.1 mg/kg and 3 mg/kg (97.5% increase as compared to vehicle). At doses of 0.1 mg/kg, 0.3 mg/kg, 3.0 mg/kg, and 10.0 mg/kg Compound #424 also produced significant increases in percent open arm entries (P<0.03) with peak activity occurring at 3.0 mg/kg and 10.0 mg/kg doses (205% and 237% increase as compared to from vehicle, respectively). Compound #424 significantly reduced the total number of entries into various zones of the maze at doses 1.0 mg/kg, 3.0 mg/kg and 10.0 mg/kg (18.6%, 60.3%, and 76.7% reductions, respectively).

In the rat SMA, at doses of 3.0 mg/kg and 10.0 mg/kg, Compound #424 produced significant reductions (55% and 83.7% reductions, respectively) in horizontal activity (P<0.001; Dunnett's multiple comparison test). At doses of 1.0 mg/kg, 3.0 mg/kg and 10.0 mg/kg (17.8%, 73.4%, 93.9% reductions, respectively) Compound #424 produced significant reductions (P<0.05; Dunnett's multiple comparison test) in the number of vertical movements (rearing behavior).

TABLE 18

EPM and SMA Assay Results
Acute (1 hr) Oral Administration of Compound #438

| Dosage mg/kg, p.o. (# Aminals) | Statistics | % Open Arm Time (EPM) | % Open Arm Entries (EPM) | Total Entries (EPM) | Horizontal Activity (SMA) | Vertical Movement (SMA) |
|---|---|---|---|---|---|---|
| Vehicle 0.5% Methylcellulose (40) | Mean | 8.21 | 5.78 | 101.0 | 3244 | 48.7 |
| | S.E.M. | ±1.18 | ±0.532 | ±3.81 | ±168 | ±1.85 |
| | % Change | 0.0% | 0.0% | 0.0% | 0.0% | 0.0% |
| 0.03 Mg/Kg (24) | Mean | 6.67 | 5.14 | 102.0 | 3565 | 54.8 |
| | S.E.M. | ±1.59 | ±0.984 | ±3.67 | ±216 | ±2.75 |
| | % Change | −18.8% | −11.1% | 1.0% | 9.9% | 12.5% |
| | P-value | NS | NS | NS | NS | NS |
| 0.1 Mg/Kg (24) | Mean | 12.1 | 7.77 | 103 | 3435 | 53.1 |
| | S.E.M. | ±1.92 | ±0.913 | ±3.81 | ±160 | ±2.25 |
| | % Change | 47.4% | 34.4% | 2.0% | 5.9% | 9.0% |
| | P-value | 0.0434 | 0.0352 | NS | NS | NS |
| 0.3 Mg/Kg (24) | Mean | 13.8 | 8.95 | 99.8 | 3450 | 51.7 |
| | S.E.M. | ±1.56 | ±0.891 | ±3.64 | ±155 | ±2.36 |
| | % Change | 68.1% | 54.8% | −1.2% | 6.4% | 6.2% |
| | P-value | 0.0038 | 0.0010 | NS | NS | NS |
| 1 Mg/Kg (24) | Mean | 14.8 | 9.95 | 103.0 | 3772 | 56.6 |
| | S.E.M. | ±2.13 | ±1.23 | ±4.08 | ±170 | ±2.32 |
| | % Change | 80.3% | 72.1% | 2.0% | 16.3% | 16.2% |
| | P-value | 0.0053 | 0.0025 | NS | NS | NS |
| 3 Mg/Kg (24) | Mean | 12.4 | 8.34 | 101.0 | 3502 | 55.3 |
| | S.E.M. | ±1.73 | ±1.02 | ±4.75 | ±223 | ±2.17 |
| | % Change | 51.0% | 44.3% | 0.0% | 8.0% | 13.6% |
| | P-value | 0.0170 | 0.0336 | NS | NS | NS |
| 10 Mg/Kg (24) | Mean | 8.14 | 6.4 | 94.5 | 3115 | 54.5 |
| | S.E.M. | ±1.30 | ±0.856 | ±3.41 | ±168 | ±1.73 |
| | % Change | 0.9% | 11.1% | −6.4% | −4.0% | 11.9% |
| | P-value | 0.3644 | NS | NS | NS | NS |
| 30 Mg/Kg (7/8) | Mean | 3.21 | 6.65 | 86.3 | 2730 | 45.3 |
| | S.E.M. | ±1.76 | ±2.28 | ±6.40 | ±185 | ±3.34 |
| | % Change | −60.9% | 15.1% | −14.6% | −15.8% | −7.0% |
| | P-value | 0.0486 | NS | NS | NS | NS |

TABLE 19

EPM and SMA Assay Results
Sub-Chroinc (8-day/once a day) Oral Administration
Compound #438

| Dosage mg/kg, p.o. # Aminals | Statistics | % Open Arm Time (EPM) | % Open Arm Entries (EPM) | Total Entries (EPM) | Horizontal Activity (SMA) | Vertical Movement (SMA) |
|---|---|---|---|---|---|---|
| Vehicle | Mean | 7.96 | 6.53 | 101.0 | 3451 | 54.6 |
| (0.5% methylcellulose) | S.E.M. | ±1.87 | ±1.05 | ±4.72 | ±196 | ±3.35 |
| (16) | % Change | 0.0% | 0.0% | 0.0% | 0.0% | 0.0% |
| 0.1 Mg/Kg | Mean | 17.2 | 9.17 | 102 | 3813 | 62.9 |
| (16) | S.E.M. | ±1.84 | ±0.931 | ±4.82 | ±170 | ±1.75 |
| | % Change | 116.1% | 40.4% | 1.0% | 10.5% | 15.2% |
| | P-value | 0.0012 | 0.0338 | NS | NS | NS |
| 0.3 Mg/Kg | Mean | 21.8 | 11.8 | 99.1 | 4390 | 61.1 |
| (16) | S.E.M. | ±1.8 | ±0.891 | ±5.56 | ±253 | ±3.61 |
| | % Change | 173.9% | 80.7% | −1.9% | 27.2% | 11.9% |
| | P-value | P < 0.0001 | 0.0007 | NS | P < 0.05 | NS |
| 1 Mg/Kg | Mean | 15.1 | 9.57 | 99.6 | 3979 | 59.5 |
| (16) | S.E.M. | ±1.96 | ±1.12 | ±3.42 | ±151 | ±2.53 |
| | % Change | 89.7% | 46.6% | −1.4% | 15.3% | 9.0% |
| | P-value | 0.0064 | 0.0007 | NS | NS | NS |
| 3 Mg/Kg | Mean | 16.9 | 9.0 | 106.0 | 4253 | 59.9 |
| (16) | S.E.M. | ±2.9 | ±1.21 | ±4.42 | ±306 | ±3.47 |
| | % Change | 112.3% | 37.8% | 5.0% | 23.2% | 9.7% |
| | P-value | 0.0047 | 0.0367 | NS | P < 0.05 | NS |

EXAMPLE 71

In Vivo Study—Vogel Rat Conflict Assay (Vogel, J. R., et al., *Psychopharmacology*, (1971), 21, 1)

This behavioral assay assesses the anxiolytic activity of a test compound by determining the ability of rats to release (disinhibit) behavior that has been suppressed by punishment.

Method

Male adult rats were deprived of water for 48 hours and were deprived of food for 24 hours prior to testing. After the first 24 hours of water deprivation, the rats were placed in the conflict chamber for a training period; during which time the rats were allowed 200 unpunished licks from a bottle containing tap water. The experiment was run the following day. The rats were dosed with the test compound orally by gavage or intraperitoneally (i.p.). At the expected time of peak activity (30 minutes for i.p administration and 60 min for oral administration), the rats were placed in the conflict chamber and were allowed access to tap water. If they failed to drink, the experiment was terminated in 5 min, and the animals were evaluated for signs of CNS depression. The first lick initiated a 3min test session. Subsequently, every $20^{th}$ lick was punished with an 0.2 sec, 0.6 milliampere (RMS) shock delivered via the stainless steel drinking tube. Vehicle treated control animals were generally willing to accept a median of 3 to 8 shocks per test session. Animals treated with an active anxiolytic drug tolerated significantly more shocks than control animals. The Wilcoxon rank-sum test (Mann-Whitney U-test) was used to test for an increase (p<0.05, 1 tailed) in the median number of shocks in the drug treated group compared with a concurrently run control treated group. The assay was considered to be valid if the effects of a known anxiolytic (a positive control) were detected within the same experiment. A test compound was considered active if there was a significant difference in the median number of shocks tolerated between the drug treated and the control group.

Compound #64 and a mixture of three parts Compound #422 to one part Compound 438 (denoted as "CMPD mix" in the table below) were tested according to the procedure described above, with results as listed in Table 20, below. No./Group indicates the number of animals tested for the listed dosage. % increase in mean no of shock is as compared with vehicle. Statistically significant results were those with a Mann-Whitney U Test (one tailed) p value of <0.05.

TABLE 20

| | No/ Group | % Increase Mean No. of Shocks | P Value |
|---|---|---|---|
| Dose (mg/kg, i.p.) | | | |
| PEG-200 (Vehicle) | 25 | 0 | — |
| Compound #64 0.3 | 8 | −10% | 0.3294 |
| Compound #64 1 | 24 | 25% | 0.3480 |
| Compound #64 3 | 24 | 96% | 0.0692 |
| Compound #64 10 | 22 | 150% | 0.0002 |
| Compound #64 30 | 8 | −26% | 0.5000 |
| Dose (mg/kg, p.o.) | | | |
| 0.5% Methylcellulose (Vehicle) | 17 | 0 | — |
| CMPD mix 0.3 | 8 | 8% | 0.3304 |
| CMPD mix 1 | 8 | 39% | 0.4418 |
| CMPD mix 3 | 8 | 47% | 0.0425 |
| CMPD mix 10 | 18 | 54% | 0.1634 |
| CMPD mix 30 | 12 | 47% | 0.0327 |

EXAMPLE 72

Stress Induced Hyperthermia in Vivo Assay

Procedure

Male Long-Evans Hooded rats weighing 180 to 200 grams at the time of purchase were obtained from Charles River Laboratories (Raleigh, N.C.). Upon arrival, the animals were group housed four per cage in quarantine for 5 days in wire-mesh cages at an ambient temperature of 21 to 23° C. with an automated 12/12 hour light/dark cycle and ad libitum access to water and a commercial rodent chow. The rats were then transferred to a general housing room for a one-week acclimation with housing and environmental conditions, and 12/12 hour light/dark cycle conditions. Animals were fasted overnight (18 hours) prior to experiment.

On the day of experiment, group-housed (4/group) Long-Evans Hooded rats were divided into various treatment groups (N=8 to 32) and test compound at 0.03-3.0 mg/kg or vehicle was administered orally (p.o.) by gavage in a dose volume equivalent to 5 mL/kg. One hour after dosing, baseline rectal temperatures were recorded for each rat. Rats were then immediately isolated in shoebox cages with ALPHA-DRY bedding. Rectal temperatures were then recorded at 15 min, 30 min, and 45 min after isolation (i.e., 1 hr 15 min, 1 hr 30 min, and 1 hr 45 minutes after test compound or vehicle administration). All experiments were conducted during the light cycle. After completion of the behavioral portion of the study, each animal was killed via decapitation using a guillotine and trunk blood was collected in 5 mL vacutainer tube containing EDTA and placed on ice. The samples were then centrifuged at 3800 RPM for 10 minutes and plasma was removed and placed on dry ice in an Eppendorff sample tube. Plasma samples were stored at −80° C. and later used for determining ACTH, corticosterone, and glucose levels. Plasma samples were outsourced to Anilytics, Inc. for determination of plasma levels of ACTH, coricosterone, and glucose. A Mann-Whitney U t-test (one-tailed) was used for statistical analysis of behavioral data and an unpaired t-test (one-tailed) was used for analysis of plasma ACTH, corticosterone, and glucose levels.

Results

Compound #438 was suspended in an aqueous vehicle comprised of 0.5% (w/v) methylcellulose (15 centipoises) solution.

Rats treated with Compound #438 showed an attenuation of rectal temperature in the SIH model as described above, at 0.03 mg/kg, 0.01 mg/kg, 0.3 mg/kg, 1.0 mg/kg and 3.0 mg/kg, with measured temperatures and p values as listed in Table 21. In the Table below, the abbreviation "S.E.M." represents the standard error of the mean and the abbreviation "N.S." indicates that the p value indicated that any measured difference in temperature was not statistically significant.

Plasma stress hormone levels for rats treated with Compound #438 showed a 25% reduction in plasma ACTH levels at 0.3 mg/kg, the reduction calculated to be statistically significant (P=0.0170). Changes in the plasma levels of corticosterone were not statistically significant.

EXAMPLE 73

Tissue Distribution Assay

Procedure

Male Long-Evans Hooded rats weighing 180 to 200 grams at the time of purchase were obtained from Charles River Laboratories (Portage, Mich.). Upon arrival, the animals were group housed four per cage in quarantine for 5 days in wire-mesh cages at an ambient temperature of 21 to 23° C. with an automated 12/12 hour light/dark cycle and ad libitum access to water and a commercial rodent chow. The rats were then transferred to a general housing room for a one-week acclimation with housing and environmental conditions, and 12/12 hour light/dark cycle conditions. Animals were fasted overnight (18 hours) prior to experiment.

On the day of experiment, two Long-Evans Hooded rats were treated orally with a vehicle (0.5% methylcellulose) and eight rats were treated orally with 10.0 mg/kg of Compound #438. Five hours after drug administration, each treated animal was killed via decapitation using a guillotine, trunk blood was collected and the following tissues were harvested for analysis of compound distribution in the following tissues/systems: (1) brain regions including the cortex, cerebellum, hypothalamus and hippocampus, (2) heart, (3) lung, (4) kidney, (5) liver, (6) spleen, (7) adrenal glands, (8) small intestines, (9) large intestines, (10) muscle, as well as (11) whole blood and (12) plasma.

Whole blood and plasma samples were prepared for analysis as follows. 400 µL of acetonitrile containing 1 µM internal standard (propranolol) was added to 200 µL of plasma or whole blood to precipitate proteins. Samples were centrifuged at 5000 g for 5 minutes and supernatant removed for analysis by LC-MS. 400 µL of water was added to adjust sample solvent strength and prevent peak splitting. Calibration standards were prepared by adding appropriate volumes of stock solution directly into plasma and treated identically to collected plasma samples. LC-MS analysis was performed

TABLE 21

| Compound (dose) | | Temp. ° C. 0 (Basal) | Temp. ° C. 15 min | Temp. ° C. 30 min | Temp. ° C. 45 min |
| --- | --- | --- | --- | --- | --- |
| Vehicle | Mean | 37.4 | 38.7 | 38.9 | 38.9 |
| | S.E.M. | ±0.12 | ±0.062 | ±0.053 | ±0.049 |
| | P-value | | | | |
| Cmpd #438 | Mean | 37.5 | 38.7 | 38.6 | 38.4 |
| (0.03 mg/kg) | S.E.M. | 0.166 | ±0.0707 | ±0.139 | ±0.128 |
| | P-value | NS | NS | 0.0188 | 0.0018 |
| Cmpd #438 | Mean | 37.2 | 38.4 | 38.5 | 38.5 |
| (0.1 Mg/Kg) | S.E.M. | ±0.119 | ±0.093 | ±0.101 | ±0.125 |
| | P-value | NS | 0.0139 | 0.0011 | 0.0098 |
| Cmpd #438 | Mean | 37.4 | 38.4 | 38.5 | 38.3 |
| (0.3 Mg/Kg) | S.E.M. | ±0.121 | ±0.0873 | ±0.0782 | ±0.0853 |
| | P-value | NS | 0.0068 | <0.0001 | <0.0001 |
| Cmpd #438 | Mean | 37.1 | 38.4 | 38.5 | 38.2 |
| (1.0 Mg/Kg) | S.E.M. | ±0.105 | ±0.108 | ±0.0856 | ±0.109 |
| | P-value | 0.0280 | 0.0148 | <0.0001 | <0.0001 |
| Cmpd #438 | Mean | 37.0 | 38.2 | 38.4 | 38.2 |
| (3.0 Mg/Kg) | S.E.M. | ±0.0949 | ±0.146 | ±0.124 | ±0.131 |
| | P-value | 0.0121 | 0.0011 | 0.0002 | <0.0001 | using MRM for detection of characteristic ions for each test compound and internal standard.

Tissue samples were prepared for analysis as follows. Individual tissue samples were extracted with 2 mLs of ethanol if the tissue weight was 1 gram or less. A volume of ethanol in milliliters equal to twice the weight in grams was added if the tissue weight was greater than 1 gram. The extracts were centrifuged to precipitate solids and the supernatant was transferred to clean Eppendorf tubes. 200 μL of this was transferred to autosampler vials and 20 μL of acetonitrile containing 1 μM internal standard (propranolol) was added for analysis by LC/MS. Calibration standards were prepared using an equivalent volume of tissue extract at 2 ml per gram from undosed or vehicle dosed animals. The extracts from brain tissue were concentrated in order to achieve lower detection limits (<1 nM). For these, 20 μL of 1 uM propranolol in acetonitrile was added to 700 μL of extract and blown to dryness under nitrogen. These were then reconstituted in 100 μL of 1:1::acetonitrile:water and analyzed by LC/MS. Calibration standards were prepared in blank extract and treated exactly as samples.

Measured values within the various samples were as listed in Table 22 and 23, for vehicle and Compound #438 treated rats, respectively. Results are reported in μmoles/kg or ng/g as appropriate converting the sample concentrations based on extraction solvent/tissue ratio. These units are on the same scale as μmoles/l or ng/ml as typically reported for plasma and can be used for comparison. Detection of analytes down to 0.005 μmoles/kg were typical for the LC-MS used.

TABLE 22

| | Vehicle (Control) | | | |
|---|---|---|---|---|
| | Animal 9 (Vehicle) | | Animal 10 (Vehicle) | |
| | μM | μM/kg | μM | μM/kg |
| Cortex | 0.000 | 0.000 | 0.000 | 0.000 |
| Cerebellum | 0.000 | 0.000 | 0.000 | 0.000 |
| Hypothalamus | 0.000 | 0.000 | 0.000 | 0.000 |
| Hippocampus | 0.000 | 0.000 | 0.000 | 0.000 |
| Heart | 0.000 | 0.000 | 0.000 | 0.000 |
| Lung | 0.000 | 0.000 | 0.000 | 0.000 |
| Liver | 0.000 | 0.000 | 0.000 | 0.000 |
| Spleen | 0.000 | 0.000 | 0.000 | 0.000 |
| Kidney | 0.000 | 0.000 | 0.000 | 0.000 |
| Adrenal Glands | 0.000 | 0.000 | 0.000 | 0.000 |
| Lr intestine | 0.000 | 0.000 | 0.000 | 0.000 |
| Sm Intestine | 0.011 | 0.027 | 0.000 | 0.000 |
| Muscle | 0.000 | 0.000 | 0.000 | 0.000 |
| Plasma | 0.000 | | 0.000 | |
| Whole Blood | 0.000 | | 0.000 | |

TABLE 23

| | Compound #438 Tissue Concentration | | | | | | | |
|---|---|---|---|---|---|---|---|---|
| | μM | μM/kg | μM | μM/kg | μM | μM/kg | μM | μM/kg |
| | Animal 1 | | Animal 2 | | Animal 3 | | Animal 4 | |
| Cortex | 0.0062 | 0.030 | 0.0047 | 0.020 | 0.0047 | 0.030 | 0.0026 | 0.0130 |
| Cerebellum | 0.0402 | 0.161 | 0.014 | 0.090 | 0.0189 | 0.140 | 0.0045 | 0.0350 |
| Hypothalamus | 0.0124 | 0.413 | 0.0055 | 0.367 | 0.0064 | 0.427 | 0.0062 | 1.2400 |
| Hippocampus | 0.0195 | 0.650 | 0.0021 | 0.070 | 0.0009 | 0.030 | 0.0140 | 0.2550 |
| Heart | 2.036 | 4.072 | 2.485 | 5.144 | 2.346 | 4.692 | 1.664 | 3.328 |
| Lung | 5.821 | 15.119 | 4.737 | 12.632 | 5.153 | 13.741 | 4.361 | 11.629 |
| Liver | 6.664 | 13.257 | 6.409 | 12.785 | 4.632 | 9.294 | 3.879 | 7.758 |
| Spleen | 9.140 | 25.389 | 7.232 | 17.857 | 7.163 | 23.106 | 5.207 | 13.703 |
| Kidney | 3.747 | 7.546 | 4.031 | 8.062 | 4.123 | 8.027 | 3.841 | 7.570 |
| Adrenal Glands | 0.967 | 24.175 | 0.988 | 28.229 | 1.289 | 28.644 | 1.088 | 31.086 |
| Lg intestine | 4.518 | 9.036 | 12.478 | 29.019 | 30.593 | 59.694 | 2.231 | 6.562 |
| Sm Intestine | 21.836 | 53.916 | 27.120 | 84.750 | 17.359 | 48.219 | 13.898 | 38.077 |
| Muscle | 0.919 | 1.814 | 0.688 | 1.371 | 0.791 | 1.560 | 0.651 | 1.280 |
| Plasma | 0.419 | | 0.426 | | 0.360 | 0.289 | | |
| Whole Blood | 0.166 | | 0.147 | | 0.135 | 0.088 | | |
| | Animal 5 | | Animal 6 | | Animal 7 | | Animal 8 | |
| Cortex | 0.0038 | 0.017 | 0.0023 | 0.010 | 0.0055 | 0.025 | 0.0139 | 0.062 |
| Cerebellum | 0.0026 | 0.019 | 0.0101 | 0.067 | 0.0138 | 0.095 | 0.0102 | 0.068 |
| Hypothalamus | 0.0030 | 0.200 | 0.0036 | 0.360 | 0.0101 | 0.673 | 0.0027 | 0.180 |
| Hippocampus | 0.05 | 0.200 | 0.002 | 0.010 | 0.0065 | 0.217 | 0.0019 | 0.190 |
| Heart | 1.785 | 3.471 | 2.478 | 4.878 | 1.572 | 2.977 | 2.083 | 4.261 |
| Lung | 3.533 | 7.438 | 5.290 | 20.346 | 5.655 | 15.930 | 6.189 | 11.902 |
| Liver | 4.006 | 7.861 | 5.090 | 10.180 | 5.887 | 10.398 | 5.677 | 11.120 |
| Spleen | 6.730 | 19.229 | 7.742 | 26.697 | 8.062 | 29.859 | 9.205 | 28.766 |
| Kidney | 3.993 | 7.791 | 4.718 | 9.523 | 4.109 | 7.645 | 4.750 | 8.782 |
| Adrenal Glands | 1.075 | 26.875 | 1.487 | 59.480 | 1.267 | 42.233 | 1.946 | 64.867 |
| Lr intestine | 24.916 | 56.627 | 9.584 | 26.622 | 33.756 | 68.194 | 5.070 | 9.941 |
| Sm Intestine | 16.743 | 41.858 | 14.131 | 56.524 | 25.408 | 72.594 | 13.018 | 39.448 |
| Muscle | 0.917 | 1.754 | 0.977 | 1.954 | 0.882 | 1.707 | 1.509 | 3.006 |
| Plasma | 0.183 | | 0.174 | | 0.268 | | 0.470 | |
| Whole Blood | 0.469 | | 0.266 | | 0.061 | | 0.093 | |

EXAMPLE 74

Oral Formulation

As a specific embodiment of an oral composition, 100 mg of the compound #438 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A pharmaceutical dosage form selected from the group consisting of tablets, pills, capsules, powders, granules, sterile parenteral solutions, parenteral suspensions, metered aerosol or liquid spray, drops, ampoules and suppositories comprising a compound of the formula (I)

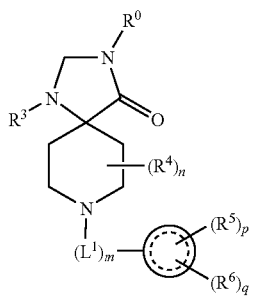

wherein
$R^0$ is selected from the group consisting of

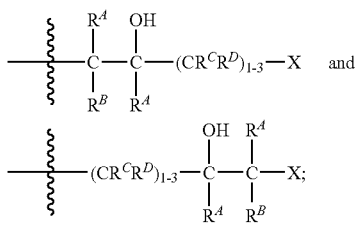

each $R^A$ and $R^B$ is independently selected from the group consisting of hydrogen and $C_{1-4}$alkyl;
each $R^C$ and $R^D$ is independently selected from the group consisting of hydrogen and $C_{1-4}$alkyl;
each $R^E$ is independently selected from the group consisting of hydrogen and $C_{1-4}$alkyl;
X is $—NR^1R^2$;
each $R^1$ and $R^2$ is independently selected from the group consisting of hydrogen, $C_{1-8}$alkyl, $C_{1-8}$alkoxy, $C_{1-8}$alkoxycarbonyl, cycloalkyl, cycloalkyl-$C_{1-4}$alkyl, partially unsaturated carbocylyl, partially unsaturated carbocylyl-$C_{1-4}$alkyl, aryl, ar$C_{1-4}$alkyl, ar$C_{1-4}$alkoxy, —C(O)—$C_{1-6}$alkyl, —C(O)-aryl, —C(O)-ar$C_{1-4}$alkyl, —C(O)O-cycloalkyl, —C(O)O-aryl, —C(O)O-ar$C_{1-4}$alkyl and —C(O)O-(partially unsaturated carbocyclyl); wherein the $C_{1-8}$alkyl, cycloalkyl, partially unsaturated carbocyclyl, aryl or ar$C_{1-8}$alkyl group, whether alone or part of a substituent group, is optionally substituted with one or more substituents independently selected from halogen, hydroxy, carboxy, $C_{1-4}$alkyl, $C_{1-4}$alkoxy, trifluoromethyl, trifluoromethoxy, nitro, cyano, —C(O)—$C_{1-4}$alkyl, $C_{1-4}$alkoxycarbonyl, $N(R^E)_2$, $N(R^E)_2$—$C_{1-4}$alkyl, $N(R^E)$—$C(O)C(CH_3)_3$, —$C_{1-4}$alkyl-$N(R^E)$—C(O)O—$C_{1-4}$alkyl and —$N(R^E)$—C(O)O—$C_{1-4}$alkyl, aryl, aryloxy, cycloalkyl, heteroaryl, aryl substituted heteroarylaminosulfonyl or $C_{1-6}$alkylthio;

$R^3$ is aryl; wherein the aryl is optionally substituted with one or more substituents independently selected from halogen, hydroxy, carboxy, $C_{1-4}$alkyl, $C_{1-4}$alkoxy, trifluoromethyl, trifluoromethoxy, nitro, cyano or $N(R^E)_2$;
n is an integer from 0 to 2;
$R^4$ is selected from the group consisting of hydroxy, $C_{1-4}$alkyl and hydroxy substituted $C_{1-4}$alkyl;
m is an integer from 0 to 1;
$L^1$ is selected from the group consisting of $C_{1-6}$alkyl and $C_{3-6}$alkenyl; wherein the double bond of the $C_{3-6}$alkenyl group is at least one carbon atom removed from the attachment point to the N atom; and wherein the $C_{1-6}$alkyl or $C_{3-6}$alkenyl group is optionally substituted with one to two substituents independently selected from hydroxy, fluoro, $C_{1-6}$alkyl, fluorinated $C_{1-6}$alkyl or $C_{1-6}$alkoxy;

is selected from the group consisting of phenyl, naphthyl and acenaphthyl;
p is an integer from 0 to 5;
$R^5$ is selected from the group consisting of hydroxy, carboxy, halogen, $C_{1-6}$alkyl, hydroxy substituted $C_{1-6}$alkyl, $C_{1-6}$alkoxy, nitro, cyano, $NR^1R^2$, trifluoromethyl, trifluoromethoxy, $C_{1-4}$alkoxycarbonyl, —SO—$NR^1R^2$, —$SO_2$—$NR^1R^2$ and —C(O)—$NR^1R^2$;
q is 0;
$R^6$ selected from the group consisting of -$(L^2)_{0-1}$-$R^7$;
$L^2$ is selected from the group consisting of —$C_{1-6}$alkyl-, -$C_{2-4}$alkenyl-, -$C_{2-6}$alkynyl-, —O—, —S—, —NH—, —N($C_{1-4}$alkyl)-, —$C_{1-6}$alkyl-O—, —$C_{1-6}$alkyl-S—, —O—$C_{1-6}$alkyl-, —S—$C_{1-6}$alkyl-, —O—$C_{2-6}$alkyl—O—, —S—$C_{2-6}$alkyl-S—, —$SO_2$—, —$SO_2$NH—, —$SO_2$N($C_{1-4}$alkyl)-, —NH—$SO_2$—, —N($C_{1-4}$alkyl)-$SO_2$—, —C(O)—O— and —O—C(O)—;
$R^7$ is selected from the group consisting of aryl, partially unsaturated carbocyclyl, cycloalkyl, heteroaryl and heterocycloalkyl; wherein the aryl, partially unsaturated carbocyclyl, cycloalkyl, heteroaryl or heterocycloalkyl group is optionally substituted with one or more substituents independently selected from hydroxy, carboxy, halogen, $C_{1-6}$alkyl, $C_{1-6}$alkoxy, nitro, cyano, $N(R^E)_2$, trifluoromethyl, trifluoromethoxy, $C_{1-4}$alkoxycarbonyl, —$SO_2$—$N(R^E)_2$ and —C(O)—$N(R^E)_2$;

or a pharmaceutically acceptable salt thereof and a pharmaceutically acceptable carrier.

2. The pharmaceutical dosage form of claim 1 wherein in the compound of formula (I)
$R^0$ is selected from the group consisting of

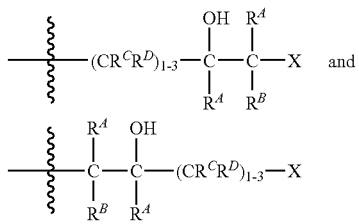

each $R^C$ and $R^D$ is independently selected from hydrogen and $C_{1-4}$alkyl;

X is —NR$^1$R$^2$;

R$^1$ is selected from the group consisting of hydrogen, C$_{1-4}$alkyl, C$_{1-4}$alkoxy, C$_{1-4}$alkoxycarbonyl, aryl, arC$_{1-4}$alkyl, arC$_{1-4}$alkyloxy, cycloalkyl-alkyl and C(O)—C$_{1-4}$alkyl;

wherein the C$_{1-4}$alkyl, aryl, arC$_{1-4}$alkyl or cycloalkyl group, whether alone or part of a substituent group, is optionally substituted with one to three substituents independently selected from halogen, hydroxy, carboxy, C$_{1-4}$alkyl, C$_{1-4}$alkoxy, C$_{1-4}$alkoxycarbonyl, N(R$^E$)$_2$, N(R$^E$)$_2$—C$_{1-4}$alkyl, N(R$^E$)—C(O)OC(CH$_3$)$_3$, nitro, trifluoromethyl, trifluoromethoxy, phenyl, phenoxy, heteroaryl, cycloalkyl, 1-phenyl-pyrazol-2-yl-aminosulfonyl or C$_{1-4}$alkylthio;

R$^2$ is selected from the group consisting of hydrogen, C$_{1-4}$alkyl, C$_{1-4}$alkoxy, cycloalkyl, cycloalkyl-C$_{1-4}$alkyl, aryl, arC$_{1-4}$alkyl, arC$_{1-4}$alkyloxy, partially unsaturated carbocyclyl, partically unsaturated carbocyclyl-C$_{1-4}$alkyl, —C(O)—C$_{1-4}$alkyl, —C(O)-aryl, —C(O)—arC$_{1-4}$alkyl, —C(O)O-cycloalkyl and —C(OO)—C$_{1-4}$alkyl;

wherein the C$_{1-4}$alkyl, aryl, arC$_{1-4}$alkyl, partially unsaturated carbocyclyl or cycloalkyl group, whether alone or part of a substituent group, is optionally substituted with one to three substituents independently selected from halogen, hydroxy, carboxy, C$_{1-4}$alkyl, C$_{1-4}$alkoxy, C$_{1-4}$alkoxycarbonyl, N(R$^E$)$_2$, N(R$^E$)$_2$—C$_{1-4}$alkyl, (CH$_3$)$_3$COC(O)—N(R$^E$)—C$_{1-4}$-alkyl, nitro, cyano, trifluoromethyl, trifluoromethoxy, phenyl, phenoxy, heteroaryl, cycloalkyl, 1-phenyl substituted heteroaryl-aminosulfonyl, —C(O)—C$_{1-4}$alkyl or C$_{1-4}$alkylthio;

R$^3$ is aryl; wherein the aryl is optionally substituted with one to three substituents independently selected from halogen, hydroxy, carboxy, C$_{1-4}$alkyl, C$_{1-4}$alkoxy, trifluoromethyl, trifluoromethoxy, nitro, cyano or N(R$^E$)$_2$;

n is an integer from 0 to 1;

L$^1$ is C$_{1-4}$alkyl; wherein the C$_{1-4}$alkyl group is optionally substituted with one to two substituents independently selected from hydroxy, fluoro, C$_{1-4}$alkyl, fluorinated C$_{1-4}$alkyl or C$_{1-4}$alkoxy;

R$^5$ is selected from the group consisting of hydroxy, carboxy, halogen, C$_{1-4}$alkyl, C$_{1-4}$alkoxy, nitro, cyano, N(R$^E$)$_2$, trifluoromethyl, trifluoromethoxy, C$_{1-4}$alkoxycarbonyl, —SO—N(R$^E$)$_2$, —SO$_2$— N(R$^E$)$_2$ and —C(O)— N(R$^E$)$_2$;

or a pharmaceutically acceptable salt thereof.

3. The pharmaceutical dosage form of claim 1 wherein in the compound of formula (I)

R$^0$ is selected from the group consisting of

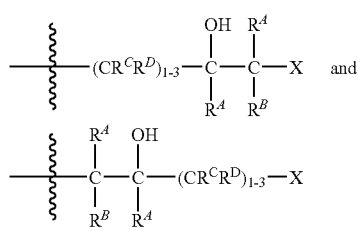

each R$^A$, R$^B$, R$^C$ and R$^D$ is hydrogen;

X is —NR$^1$R$^2$;

R$^1$ is selected from the group consisting of hydrogen, C$_{1-4}$alkyl, C$_{1-4}$alkoxycarbonyl, arC$_{1-4}$alkyl and C(O)—C$_{1-4}$alkyl;

wherein the C$_{1-4}$alkyl or aryl group, whether alone or part of a substituent group, is optionally substituted with one to two substituents independently selected from carboxy, C$_{1-4}$alkyl, C$_{1-4}$alkoxy, C$_{1-4}$alkoxycarbonyl, N(R$^E$)$_2$ or N(R$^E$)—C(O)OC(CH$_3$)$_3$;

R$^2$ is selected from the group consisting of hydrogen, C$_{1-4}$alkyl, C$_{1-4}$alkoxy, cycloalkyl, aryl, arC$_{1-4}$alkyl, arC$_{1-4}$alkyloxy, partially unsaturated carbocyclyl, partially unsaturated carbocyclyl-C$_{1-4}$alkyl, cycloalkyl-C$_{1-4}$alkyl, —C(O)arC$_{1-4}$alkyl, —C(OO)-cycloalkyl and —C(O)O—C$_{1-4}$alkyl;

wherein the C$_{1-4}$alkyl, aryl, arC$_{1-4}$alkyl, partially unsaturated carbocyclyl-or cycloalkyl group, whether alone or part of a substituent group, is optionally substituted with one to three substituents independently selected from halogen, hydroxy, carboxy, C$_{1-4}$alkyl, C$_{1-4}$alkoxy, C$_{1-4}$alkoxycarbonyl, N(R$^E$)$_2$, N(R$^E$)$_2$—C$_{1-4}$alkyl, (CH$_3$)$_3$CO—C(O)—N(R$^E$)—C$_{1-4}$alkyl, nitro, trifluoromethyl, trifluoromethoxy, phenyl, phenoxy, heteroaryl, cycloalkyl, 1-phenyl-pyrazol-2-yl-aminosulfonyl or C$_{1-4}$alkylthio;

R$^3$ is aryl; wherein the aryl group is optionally substituted with one or more substituents independently selected from halogen;

n is 0;

L$^1$ is C$_{1-4}$alkyl;

R$^5$ is selected from the group consisting of halogen, C$_{1-4}$alkyl and trifluoromethyl;

or a pharmaceutically acceptable salt thereof.

4. The pharmaceutical dosage form of claim 1 wherein in the compound of formula (I)

R$^0$ is selected from the group consisting of —CH$_2$—CH(OH)—CH$_2$—X and —CH$_2$—CH$_2$—CH(OH)—CH$_2$—X;

X is —NR$^1$R$^2$;

R$^1$ is selected from the group consisting of hydrogen, methyl, ethyl, n-propyl, n-butyl, t-butyl, amino-n-propyl, dimethylaminoethyl, benzyl, phenylethyl, 4-methyl-benzyl,

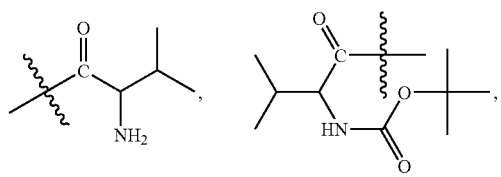

2-(3,4-dimethoxy-phenyl)ethyl, 3-methyl-phenyl, ethoxycarbonyl-methyl, 2-amino-2-methoxycarbonyl-ethyl, t-butoxycarbonyl and

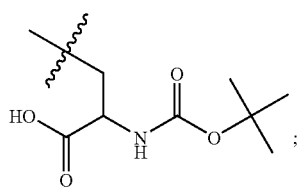

R$^2$ is selected from the group consisting of hydrogen, methyl, methoxy, ethyl, carboxy-methyl, ethoxycarbonylmethyl, 2,2,2,-triluoroethyl, ethoxy, dimethylaminoethyl, t-butoxycarbonylamino-ethyl, n-butyl, t-butyl, n-propyl, 3-hydroxy-n-propyl, 3-methoxy-n-propyl, methylamino-n-propyl, dimethylamino-n-propyl, di(n-butyl)amino-n-propyl, t-butoxycarbonylamino-n-propyl, 3-phenyl-n-propyl, 3-(2-pyridyl)-n-propyl, t-butoxycarbonyl, cyclopropyl, phenyl, 4-fluorophenyl, 4-methylphenyl, 3,4-dimethoxyphenyl, 2-aminophenyl, 4-biphenyl, 2-ethoxyphenyl, 4-((1-phenyl-pyrazol-2-yl)-aminosulfonyl)-phenyl, 4-cyclohexylphenyl, 4-(aminoethyl)phenyl, 4-(t-butoxycarbonylamino-ethyl)-phenyl, —CH(CH$_3$)-phenyl, benzyl, benzyloxy, 2-methylbenzyl, 3-methylbenzyl, 4-methylbenzyl, 2-methoxybenzyl, 3-methoxybenzyl, 4-methoxybenzyl, 2-ethoxybenzyl, 3-ethoxybenzyl, 2-bromobenzyl, 3-bromobenzyl, 4-bromobenzyl, 3-chlorobenzyl, 4-chlorobenzyl), 3-iodobenzyl, 2-fluorobenzyl, 3-fluorobenzyl, 4-fluorobenzyl, 2-trifluoromethylbenzyl, 3-trifluoromethylbenzyl, 4-trifluoromethylbenzyl, 4-trifluoromethoxybenzyl, 4-methoxycarbonylbenzyl, 2,3-dimethoxybenzyl, 2,4-dichlorobenzyl, 3,4-dichlorobenzyl, 2,4-difluorobenzyl, 2,5-difluorobenzyl, 3,4-difluorobenzyl, 3,4,5-trimethoxybenzyl, 2,4,6-trimethoxybenzyl, 4-carboxybenzyl, 3-nitrobenzyl, 4-nitrobenzyl, 2,4-dimethoxybenzyl, 3,4-dimethoxybenzyl, 3,5-dimethoxybenzyl, 3,4-difluorobenzyl, 3,5-di(trifluoromethyl)benzyl, 4-(dimethylamino)benzyl, 2-phenylethyl, 2-(4-bromophenyl)ethyl, 2-(3-methoxyphenyl)ethyl, 2-(4-methoxyphenyl)ethyl, 2-(3,4-dimethoxyphenyl)ethyl, 2-(2-nitro-4,5-dimethoxy-phenyl)ethyl, 1-adamantanyl, 1-adamantanyl-methyl, 1-naphthyl, 1-naphthyl-methyl, 1-phenyl-2-(t-butoxycarbonyl)ethyl, —C(O)—C(OCH$_3$)(CF$_3$)-phenyl, —C(O)O-(2-isopropyl-5-methyl-cyclohexyl),

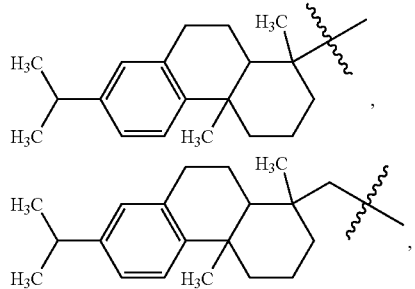

2S-hydroxy-S-cyclopentyl-methyl, 2S-hydroxy-S-cyclohexyl-methyl, 2S-hydroxy-S-cycloheptyl-methyl, 2-phenoxy-ethyl and 2-phenyl-cyclopropyl;

$R^3$ is selected from the group consisting of phenyl and 4-fluorophenyl;

$L^1$ is selected from the group consisting of —CH$_2$—, —CH(CH$_3$)— and —CH$_2$CH$_2$—;

is selected from the group consisting of 1-acenaphthenyl, R-1-acenaphthenyl, S-1-acenaphthenyl, phenyl, 1-naphthyl, 2-naphthyl and 1,2,3,4-tetrahydro-naphthyl;

$R^5$ is selected from the group consisting of chloro, methyl, n-propyl and trifluoromethyl;

or a pharmaceutically acceptable salt thereof.

5. The pharmaceutical dosage form of claim 4 wherein in the compound of formula (1)

X is —NR$^1$R$^2$;

$R^1$ is selected from the group consisting of hydrogen, methyl, ethyl, n-propyl, n-butyl, t-butyl, dimethylaminoethyl, benzyl, phenylethyl,

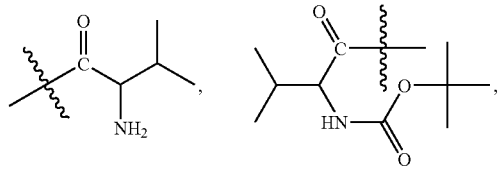

3-methyl-phenyl, 2-(3,4-dimethoxyphenyl)-ethyl, ethoxycarbonyl-methyl, dimethylamino-ethyl and 2-amino-2-methoxycarbonyl-ethyl;

$R^2$ is selected from the group consisting of hydrogen, methyl, methoxy, ethyl, ethoxycarbonyl-methyl, 2,2,2-triluoroethyl, ethoxy, dimethylaminoethyl, n-butyl, t-butyl, n-propyl, di(n-butyl)amino-n-propyl, 3-phenyl-n-propyl, cyclopropyl, phenyl, 4-fluorophenyl, 4-methylphenyl, 2-aminophenyl, 4-(t-butoxycarbonylamino-ethyl)-phenyl, 3,4-dimethoxyphenyl, 4-biphenyl, 2-ethoxyphenyl, 4-(aminoethyl)-phenyl, benzyl, benzyloxy, 2-methylbenzyl, 3-methylbenzyl, 4-methylbenzyl, 2-methoxybenzyl, 3-methoxybenzyl, 4-methoxybenzyl, 2-ethoxybenzyl, 3-ethoxybenzyl, 2-bromobenzyl, 3-bromobenzyl, 4-bromobenzyl, 3-chlorobenzyl, 4-chlorobenzyl, 3-iodobenzyl, 2-fluorobenzyl, 3-fluorobenzyl, 4-fluorobenzyl, 2-trifluoromethylbenzyl, 3-trifluoromethylbenzyl, 4-trifluoromethylbenzyl, 4-trifluoromethoxybenzyl, 4-methoxycarbonyl-benzyl, 2,3-dimethoxybenzyl, 2,4-dichlorobenzyl, 3,4-dichlorobenzyl, 2,4-difluorobenzyl, 2,5-difluorobenzyl, 3,4-difluorobenzyl, 3,4,5-trimethoxybenzyl, 2,4,6-trimethoxybenzyl, 4-carboxybenzyl, 3-nitrobenzyl, 4-nitrobenzyl, 2,4-dimethoxybenzyl, 3,4-dimethoxybenzyl, 3,5-dimethoxybenzyl, 3,4-difluorobenzyl, 3,5-di(trifluoromethyl)-benzyl, 2-phenylethyl, 2-(4-bromophenyl)ethyl, 2-(3-methoxyphenyl)ethyl, 2-(4-methoxyphenyl)ethyl, 2-(3,4-dimethoxyphenyl)ethyl, 2-(2-nitro-4,5-dimethoxy-phenyl)ethyl, adamantanyl, 1-adamantanyl-methyl, 1-naphthyl, 1-naphthyl-methyl,

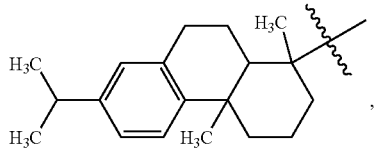

2S-hydroxy-S-cyclopentyl-methyl, 2S-hydroxy-S-cyclohexyl-methyl, 2S-hydroxy-S-cycloheptyl-methyl and 2-phenoxy-ethyl;

$L^1$ is selected from the group consisting of —CH$_2$— and —CH$_2$—CH$_2$—;

is selected from the group consisting of 1-acenaphthenyl, R-1-acenaphthenyl, S-1-acenaphthenyl, phenyl-and 1-naphthyl;

p is an integer from 0 to 2;
or a pharmaceutically acceptable salt thereof.

6. The pharmaceutical dosage form of claim 5 wherein in the compound of formulate (I)

R¹ is selected from the group consisting of hydrogen, methyl, ethyl, n-propyl, n-butyl, t-butyl, dimethylaminoethyl, benzyl, phenylethyl, 2-(3,4-dimethoxyphenyl)-ethyl, dimethylamino-ethyl, ethoxycarbonyl-methyl,

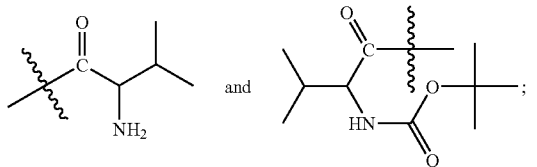

R² is selected from the group consisting of hydrogen, methyl, methoxy, ethyl, ethoxycarbonyl-methyl, ethoxy, dimethylaminoethyl, n-butyl, n-propyl, di(n-butyl)amino-n-propyl, 3-phenyl-n-propyl, 3-(2-pyridyl)-n-propyl, cyclopropyl, phenyl, 4-fluorophenyl, 4-methylphenyl, 2-aminophenyl, 3,4-dimethoxyphenyl, 4-(t-butoxycarbonylamino-ethyl)-phenyl, 4-biphenyl, 2-ethoxyphenyl, 4-(aminoethyl)-phenyl, benzyl, benzyloxy, 2-methylbenzyl, 3-methylbenzyl, 4-methylbenzyl, 2-methoxybenzyl, 3-methoxybenzyl, 4-methoxybenzyl, 2-ethoxybenzyl, 3-ethoxybenzyl, 2-bromobenzyl, 3-bromobenzyl, 4-bromobenzyl, 3-chlorobenzyl, 4-chlorobenzyl, 3-iodobenzyl, 2-fluorobenzyl, 3-fluorobenzyl, 4-fluorobenzyl, 2-trifluoromethylbenzyl, 3-trifluoromethylbenzyl, 4-trifluoromethylbenzyl, 4-trifluoromethoxybenzyl, 4-methoxycarbonyl-benzyl, 2,3-dimethoxybenzyl, 2,4-dichlorobenzyl, 3,4-dichlorobenzyl, 2,4-difluorobenzyl, 2,5-difluorobenzyl, 3,4,5-trimethoxybenzyl, 2,4,6-trimethoxybenzyl, 3-nitrobenzyl, 4-nitrobenzyl, 2,4-dimethoxybenzyl, 3,4-dimethoxybenzyl, 3,5-dimethoxybenzyl, 3,4-difluorobenzyl, 3,5-di(trifluoromethyl)-benzyl, 2-phenyl-ethyl, 2-(4-bromophenyl)ethyl, 2-(3-methoxyphenyl)ethyl, 2-(4-methoxyphenyl)ethyl, 2-(3,4-dimethoxyphenyl)ethyl, 2-(2-nitro-4,5-dimethoxyphenyl)ethyl, 1-adamantanyl, 1-adamantanyl-methyl, 1-naphthyl, 1-naphthyl-methyl

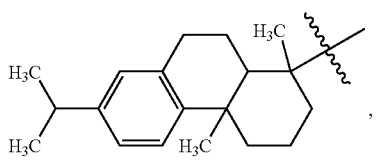

2S-hydroxy-S-cyclopentyl-methyl, 2S-hydroxy-S-cyclohexyl-methyl, 2S-hydroxy-S-cycloheptyl-methyl and 2-phenoxy-ethyl;

p is an integer from 0 to 1;
R⁵ is selected from the group consisting of methyl, n-propyl and trifluoromethyl;
or a pharmaceutically acceptable salt thereof.

7. The pharmaceutical dosage form of claim 4 wherein in the compound of formula (I)
R⁰ —CH₂—CH(OH)—CH₂—X;
X is —NR¹R²;

R¹ is selected from the group consisting of hydrogen, 2-(3,4-dimethoxyphenyl)-ethyl, 1-(3,4-dimethoxyphenyl)-n-ethyl and amino-n-propyl;
R² is selected from the group consisting of hydrogen, methyl, n-butyl, 3-hydroxy-n-propyl, 3-methoxy-n-propyl, methylamino-n-propyl, dimethylamino-n-propyl, t-butoxycarbonylamino-n-propyl, N-methyl-N-t-butoxycarbonyl-amino-n-ethyl, 3-nitrobenzyl, 4-methoxycarbonyl-benzyl and —CH(CH₃)-phenyl;
R³ is selected from the group consisting of phenyl and 4-fluorophenyl;
L¹ selected from the group consisting of —CH₂— and —CH₂CH₂—;

is selected from the group consisting 1-naphthyl, 1-acenaphthenyl, R-1-acenaphthenyl and S-1-acenaphthenyl;
p is an integer from 0 to 1;
R⁵ is methyl;
or a pharmaceutically acceptable salt thereof.

8. The pharmaceutical dosage form of claim 7 wherein in the compound of formula (I)
R¹ is selected from the group consisting of hydrogen, 1-(3,4-dimethoxyphenyl)-n-ethyl and amino-n-propyl;
R² is selected from the group consisting of hydrogen, methyl, n-butyl, 3-hydroxy-n-propyl, 3-methoxy-n-propyl, methylamino-n-propyl, dimethylamino-n-propyl, N-methyl-N-t-butoxycarbonyl-amino-n-ethyl, 3-nitrobenzyl, 4-methoxycarbonyl-benzyl and —CH(CH₃)-phenyl;

is selected from the group consisting 1-naphthyl, 1-acenaphthenyl, R-1-acenaphthenyl and S-1-acenaphthenyl;
or a pharmaceutically acceptable salt thereof.

9. The pharmaceutical dosage form of claim 7 wherein the compound is selected from the group consisting of 8-(R) acenaphthen-1-yl-3-(3-amino-2-(S)-hydroxy-propyl)-1-(4-fluoro-phenyl)-1,3,8-triaza-spiro [4.5]decan-4-one;

8-(R) acenaphthen-1-yl-3-(3-amino-2-(R)-hydroxy-propyl)-1-(4-fluoro-phenyl)-1,3,8-triaza-spiro[4.5]decan-4-one;

8-(R)-Acenaphthen-1-yl-3-(3-dimethylamino-2-(R)-hydroxy-propyl)-1-(4-fluoro-phenyl)-1,3,8-triaza-spiro [4.5]decan-4-one;

3-(3-Amino-2-(R)-hydroxy-propyl)-1-(4-fluoro-phenyl)-8-(8-methyl-naphthalen-1-ylmethyl)-1,3,8-triaza-spiro [4.5]decan-4-one;

3-(3-Dimethylamino-2-(R)-hydroxy-propyl)-1-(4-fluoro-phenyl)-8-(8-methyl-naphthalen-1-ylmethyl)-1,3,8-triaza-spiro[4.5]decan-4-one;

1-(4-Fluoro-phenyl)-3-[2-(R)-hydroxy-3-(3-hydroxy-propylamino)-propyl]-8-(8-methyl-naphthalen-1-ylmethyl)-1,3,8-triaza-spiro[4.5]decan-4-one;

1-(4-Fluoro-phenyl)-3-[2-(R)-hydroxy-3-(3-methylamino-propylamino)-propyl]-8-(8-methyl-naphthalen-1-ylmethyl)-1,3,8-triaza-spiro[4.5]decan-4-one;

3-[3-(3-Dimethylamino-propylamino)-2-(R)-hydroxy-propyl]-1-(4-fluoro-phenyl)-8-(8-methyl-naphthalen-1-ylmethyl)-1,3,8-triaza-spiro[4.5]decan-4-one and pharmaceutically acceptable salts thereof.

10. The pharmaceutical dosage form of claim 1 wherein the compound is 3-(3-amino-2-(R)-hydroxy-propyl)-1-(4-fluoro-phenyl)-8-(8-methyl-naphthalen-1-ylmethyl)-1,3,8-triaza-spiro[4.5]decan-4-one and pharmaceutically acceptable salts thereof.

11. A pharmaceutical composition suitable for oral administration comprising 3-(3-amino-2-(R)-hydroxy-propyl)-1-(4-fluoro-phenyl)-8-(8-methyl-naphthalen-1-ylmethyl)-1,3,8-triaza-spiro[4.5]decan-4-one and pharmaceutically acceptable salts thereof and pharmaceutically acceptable carriers.

12. The pharmaceutical composition of claim 11 wherein the dosage form is a solid dosage form.

13. The pharmaceutical composition of claim 12 where in the solid dosage form is selected from the group consisting of pills, tablet, caplet, capsule granules and powders.

14. The pharmaceutical composition of claim 11 wherein the dosage form is a liquid dosage form selected from the group consisting of solution, syrups, elixirs, emulsions and suspensions.

* * * * *

UNITED STATES PATENT AND TRADEMARK OFFICE
CERTIFICATE OF CORRECTION

PATENT NO. : 7,582,649 B2  Page 1 of 1
APPLICATION NO. : 11/242654
DATED : September 1, 2009
INVENTOR(S) : Battista et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 674 days.

Signed and Sealed this

Fourteenth Day of September, 2010

David J. Kappos
*Director of the United States Patent and Trademark Office*